US009850268B2

(12) United States Patent
Hoveyda et al.

(10) Patent No.: US 9,850,268 B2
(45) Date of Patent: Dec. 26, 2017

(54) METATHESIS CATALYSTS AND METHODS THEREOF

(71) Applicants: Massachusetts Institute of Technology, Cambridge, MA (US); Trustees of Boston College, Chestnut Hill, MA (US)

(72) Inventors: Amir H. Hoveyda, Lincoln, MA (US); Hanmo Zhang, Chestnut Hill, MA (US); Ming Joo Koh, Chestnut Hill, MA (US); Richard Royce Schrock, Winchester, MA (US)

(73) Assignees: Trustees of Boston College, Chestnut Hill, MA (US); Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 14/933,741

(22) Filed: Nov. 5, 2015

(65) Prior Publication Data

US 2016/0194343 A1    Jul. 7, 2016

Related U.S. Application Data

(60) Provisional application No. 62/075,315, filed on Nov. 5, 2014.

(51) Int. Cl.

| | | |
|---|---|---|
| C07C 17/275 | (2006.01) | |
| C07C 45/63 | (2006.01) | |
| C07C 37/62 | (2006.01) | |
| B01J 31/22 | (2006.01) | |
| C07F 11/00 | (2006.01) | |
| C07D 333/54 | (2006.01) | |
| C07D 209/10 | (2006.01) | |
| C07D 209/48 | (2006.01) | |
| C07F 5/02 | (2006.01) | |
| C07F 7/18 | (2006.01) | |
| C07C 17/266 | (2006.01) | |
| C07C 17/269 | (2006.01) | |
| C07C 17/278 | (2006.01) | |
| C07C 17/10 | (2006.01) | |
| C07C 17/14 | (2006.01) | |
| C07C 17/361 | (2006.01) | |
| C07B 37/04 | (2006.01) | |
| C07C 17/02 | (2006.01) | |
| C07J 9/00 | (2006.01) | |
| C07J 51/00 | (2006.01) | |
| C07C 67/307 | (2006.01) | |
| C07C 67/333 | (2006.01) | |
| C07C 41/30 | (2006.01) | |

(52) U.S. Cl.
CPC ............ *C07F 11/00* (2013.01); *B01J 31/2265* (2013.01); *C07B 37/04* (2013.01); *C07C 17/02* (2013.01); *C07C 17/10* (2013.01); *C07C 17/14* (2013.01); *C07C 17/266* (2013.01); *C07C 17/269* (2013.01); *C07C 17/275* (2013.01); *C07C 17/278* (2013.01); *C07C 17/361* (2013.01); *C07C 37/62* (2013.01); *C07C 41/30* (2013.01); *C07C 45/63* (2013.01); *C07C 67/307* (2013.01); *C07C 67/333* (2013.01); *C07D 209/10* (2013.01); *C07D 209/48* (2013.01); *C07D 333/54* (2013.01); *C07F 5/025* (2013.01); *C07F 7/1844* (2013.01); *C07F 7/1852* (2013.01); *C07J 9/00* (2013.01); *C07J 51/00* (2013.01); *B01J 2231/543* (2013.01); *B01J 2531/64* (2013.01); *B01J 2531/66* (2013.01); *C07C 2601/14* (2017.05); *C07C 2603/26* (2017.05)

(58) Field of Classification Search
CPC ....... C07C 17/275; C07C 45/63; C07C 37/62; B01J 2231/543; B01J 2531/64; B01J 2531/66; B01J 31/2265
USPC .................................. 548/402; 514/408, 184
See application file for complete search history.

(56) References Cited

U.S. PATENT DOCUMENTS

2012/0323000 A1    12/2012  Hoveyda et al.
2014/0309388 A1    10/2014  Schrock et al.

FOREIGN PATENT DOCUMENTS

EP           0585887         3/1994
WO      WO 2011008258 A2 *  1/2011  .......... B01J 31/1805
WO         2011097642        8/2011
(Continued)

OTHER PUBLICATIONS

Dobereiner, et al., "Catalytic Synthesis of n-Alkyl Arenes Through Alkyl Group Cross-Metathesis", JACS, 135, 2013, 12572-12575.

(Continued)

*Primary Examiner* — Matthew Coughlin
*Assistant Examiner* — Sagar Patel
(74) *Attorney, Agent, or Firm* — Stoel Rives LLP

(57) ABSTRACT

The present application provides, among other things, compounds and methods for metathesis reactions. In some embodiments, the present disclosure provides methods for preparing alkenyl halide with regioselectivity and/or stereoselectivity. In some embodiments, the present disclosure provides methods for preparing alkenyl halide with regioselectivity and Z-selectivity. In some embodiments, the present disclosure provides methods for preparing alkenyl halide with regioselectivity and E-selectivity. In some embodiments, provided technologies are particularly useful for preparing alkenyl fluorides. In some embodiments, a provided compound useful for metathesis reactions has the structure of formula II-a. In some embodiments, a provided compound useful for metathesis reactions has the structure of formula II-b.

16 Claims, No Drawings

(56) References Cited

FOREIGN PATENT DOCUMENTS

| WO | 2014172534 | 10/2014 |
| WO | 2015136093 | 9/2015 |

OTHER PUBLICATIONS

Fomine, et al., "Metathesis of Fluorinated Olefins by Ruthenium Alkylidene Catalysts. Fluorine Substituent Effects on a Ru-Carbene (Alkylidene) Complex Stability: A Computational Study", Applied Catalysis A: General, 355, 2009, 148-155.

MacNaughtan, et al., "Cross-Metathesis of Vinyl Halides. Scope and Limitations of Ruthenium-Based Catalysts", Organometallics, 28, 2009, 2880-2887.

PCT/US2015/059286, International Search Report and Written Opinion, dated Mar. 14, 2016, 15 pages.

Zhang, et al., "Preparation of Macrocyclic Z-Enoates and (E,Z)- or (Z,E)-Dienoates Through Catalytic Stereoselective Ring-Closing Metathesis", JACS, 136, 2014, 16493-16496.

\* cited by examiner

METATHESIS CATALYSTS AND METHODS THEREOF

CROSS-REFERENCE TO RELATED APPLICATIONS

The present application claims priority to the U.S. Provisional Application No. 62/075,315, filed Nov. 5, 2014, the entirety of which is incorporated herein by reference.

STATEMENT REGARDING FEDERALLY SPONSORED RESEARCH OR DEVELOPMENT

This invention was made with government support under Grant No. GM59426 awarded by the National Institute of Health and Grant No. CHE-1362763 awarded by the National Science Foundation. The U.S. government has certain rights in the invention.

FIELD OF THE INVENTION

The present invention generally relates to metathesis reactions.

BACKGROUND

Catalytic metathesis has transformed chemical synthesis and offers exceptionally efficient pathways for the synthesis of many commercially important chemicals including biologically active molecules, oleochemicals, renewables, fine chemicals, and polymeric materials. There remains an unmet need for improved methods and catalysts for metathesis reactions, for example, in terms of better catalyst stability and/or activity, efficiency and stereoselectivity.

SUMMARY

Among other things, the present disclosure recognizes that it is particularly challenging to use alkenyl halides as metathesis substrates to provide alkenyl halides efficiently and selectively. The present disclosure, among other things, provides technologies, e.g., compounds, compositions, methods, etc. for preparing alkenyl halides through metathesis reactions with high efficiency, high regioselectivity and high Z- or E-selectivity.

DETAILED DESCRIPTION OF CERTAIN EMBODIMENTS

1. General Description of Certain Embodiments of the Invention

In some embodiments, a provided catalyst or metal complex is of formula II-a:

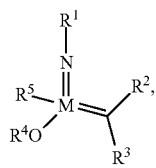

II-a wherein:

M is molybdenum or tungsten;

$R^1$ is an optionally substituted group selected from $C_{1-20}$ aliphatic, $C_{1-20}$ heteroaliphatic having 1-3 heteroatoms independently selected from nitrogen, oxygen, or sulfur, phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 4-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-10 membered bicyclic heteroaryl ring having 1-5 heteroatoms independently selected from nitrogen, oxygen, or sulfur; or $R^1$ is optionally substituted

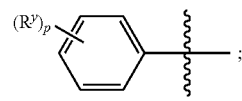

each of $R^2$ and $R^3$ is independently R', —OR', —SR', —N(R')$_2$, —OC(O)R', —SOR', —SO$_2$R', —SO$_2$N(R')$_2$, —C(O)N(R')$_2$, —NR'C(O)R', or —NR'SO$_2$R', provided that $R^2$ and $R^3$ are not simultaneously hydrogen;

$R^4$ is $R^7$, or an optionally substituted group selected from —Ar, $C_{1-20}$ aliphatic, $C_{1-20}$ heteroaliphatic having 1-3 heteroatoms independently selected from nitrogen, oxygen, or sulfur, phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 4-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-14 membered bicyclic or tricyclic heteroaryl ring having 1-5 heteroatoms independently selected from nitrogen, oxygen, or sulfur;

Ar is of the following formula:

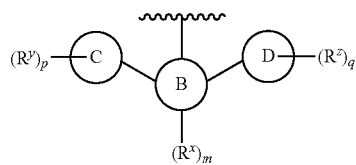

wherein:

m is 0-3;

Ring B is an optionally substituted group selected from phenyl or a 5-6 membered monocyclic heteroaryl ring having 1-4 heteroatoms independently selected from nitrogen, oxygen, or sulfur;

p and q are independently 0-6;

each of Ring C and Ring D is independently optionally substituted groups selected from phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 4-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-10 membered bicyclic heteroaryl ring having 1-5 heteroatoms independently selected from nitrogen, oxygen, or sulfur;

each of $R^x$, $R^y$, and $R^z$ is independently $R^s$;

$R^5$ is halogen, —$OR^6$, —$OR^7$, —$N(R')_2$, —NR'C(O)R', —NR'C(O)OR', —NR'C(O)N(R')_2, —NR'SO_2R', —NR'SO_2N(R')_2, or —NR'OR', or an optionally substituted group selected from a 5-6 membered monocyclic heteroaryl ring having at least one nitrogen and 0-3 heteroatoms independently selected from nitrogen, oxygen, or sulfur, a 4-7 membered saturated or partially unsaturated heterocyclic ring having at least one nitrogen and 0-2 heteroatoms independently selected from nitrogen, oxygen, or sulfur, a 7-10 membered bicyclic saturated or partially unsaturated heterocyclic ring having at least one nitrogen and 0-4 heteroatoms independently selected from nitrogen, oxygen, or sulfur, or an 8-10 membered bicyclic heteroaryl ring having at least one nitrogen and 0-4 heteroatoms independently selected from nitrogen, oxygen, or sulfur;

$R^6$ is an optionally substituted group selected from $C_{1-20}$ aliphatic, $C_{1-20}$ heteroaliphatic having 1-3 heteroatoms independently selected from nitrogen, oxygen, or sulfur, phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 4-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-14 membered bicyclic or tricyclic heteroaryl ring having 1-5 heteroatoms independently selected from nitrogen, oxygen, or sulfur; and each R' is independently hydrogen or an optionally substituted group selected from $C_{1-20}$ aliphatic, phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 4-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-10 membered bicyclic heteroaryl ring having 1-5 heteroatoms independently selected from nitrogen, oxygen, or sulfur, wherein:

two R' groups on the same nitrogen atom are optionally taken together with the nitrogen atom to form an optionally substituted 3-8 membered, saturated, partially unsaturated, or aryl ring having 1-4 heteroatoms independently selected from nitrogen, oxygen, or sulfur;

each $R^7$ is independently an optionally substituted group selected from —Ar', $C_{1-20}$ aliphatic, $C_{1-20}$ heteroaliphatic having 1-3 heteroatoms independently selected from nitrogen, oxygen, or sulfur, phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 4-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-14 membered bicyclic or tricyclic heteroaryl ring having 1-5 heteroatoms independently selected from nitrogen, oxygen, or sulfur; and two $R^7$ are optionally taken together with the oxygen atoms they are bound to form a bidentate ligand; and Ar' is of the following formula:

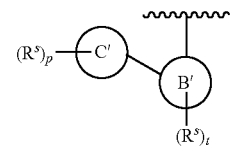

wherein:
t is 0-4;
p is 0-6;
each Ring B' and Ring C' is independently an optionally substituted group selected from phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 4-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-10 membered bicyclic heteroaryl ring having 1-5 heteroatoms independently selected from nitrogen, oxygen, or sulfur; and each $R^s$ is independently halogen, R', —OR', —SR', —S(O)R', —S(O)_2R', —OSi(R')_3, —N(R')_2, —NR'C(O)R', —NR'C(O)OR', —NR'C(O)N(R')_2, —NR'SO_2R', —NR'SO_2N(R')_2, or —NR'OR'.

In some embodiments, a provided catalyst or metal complex is of formula II-a, wherein:
M is molybdenum or tungsten;
$R^1$ is an optionally substituted group selected from $C_{1-20}$ aliphatic, $C_{1-20}$ heteroaliphatic having 1-3 heteroatoms independently selected from nitrogen, oxygen, or sulfur, phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 4-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-10 membered bicyclic heteroaryl ring having 1-5 heteroatoms independently selected from nitrogen, oxygen, or sulfur;

each of $R^2$ and $R^3$ is independently R', —OR', —SR', —N(R')$_2$, —OC(O)R', —SOR', —SO$_2$R', —SO$_2$N(R')$_2$, —C(O)N(R')$_2$, —NR'C(O)R', or —NR'SO$_2$R', provided that $R^2$ and $R^3$ are not simultaneously hydrogen;

$R^4$ is $R^7$, or an optionally substituted group selected from —Ar, C$_{1-20}$ aliphatic, C$_{1-20}$ heteroaliphatic having 1-3 heteroatoms independently selected from nitrogen, oxygen, or sulfur, phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 4-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-14 membered bicyclic or tricyclic heteroaryl ring having 1-5 heteroatoms independently selected from nitrogen, oxygen, or sulfur;

Ar is of the following formula:

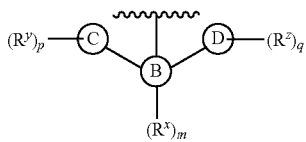

wherein:
m is 0-3;
Ring B is an optionally substituted group selected from phenyl or a 5-6 membered monocyclic heteroaryl ring having 1-4 heteroatoms independently selected from nitrogen, oxygen, or sulfur;
p and q are independently 0-6;
each of Ring C and Ring D is independently optionally substituted groups selected from phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 4-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-10 membered bicyclic heteroaryl ring having 1-5 heteroatoms independently selected from nitrogen, oxygen, or sulfur;
each of $R^x$, $R^y$, and $R^z$ is independently halogen, —OR', —N(R')$_2$, —NR'C(O)R', —NR'C(O)OR', —NR'C(O)N(R')$_2$, —NR'SO$_2$R', —NR'SO$_2$N(R')$_2$, —NR'OR', or an optionally substituted group selected from C$_{1-20}$ aliphatic, C$_{1-20}$ heteroaliphatic having 1-3 heteroatoms independently selected from nitrogen, oxygen, or sulfur;
$R^5$ is halogen, —OR$^6$, —OR$^7$, —N(R')$_2$, —NR'C(O)R', —NR'C(O)OR', —NR'C(O)N(R')$_2$, —NR'SO$_2$R', —NR'SO$_2$N(R')$_2$, or —NR'OR', or an optionally substituted group selected from a 5-6 membered monocyclic heteroaryl ring having at least one nitrogen and 0-3 heteroatoms independently selected from nitrogen, oxygen, or sulfur, a 4-7 membered saturated or partially unsaturated heterocyclic ring having at least one nitrogen and 0-2 heteroatoms independently selected from nitrogen, oxygen, or sulfur, a 7-10 membered bicyclic saturated or partially unsaturated heterocyclic ring having at least one nitrogen and 0-4 heteroatoms independently selected from nitrogen, oxygen, or sulfur, or an 8-10 membered bicyclic heteroaryl ring having at least one nitrogen and 0-4 heteroatoms independently selected from nitrogen, oxygen, or sulfur;

$R^6$ is an optionally substituted group selected from C$_{1-20}$ aliphatic, C$_{1-20}$ heteroaliphatic having 1-3 heteroatoms independently selected from nitrogen, oxygen, or sulfur, phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 4-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-14 membered bicyclic or tricyclic heteroaryl ring having 1-5 heteroatoms independently selected from nitrogen, oxygen, or sulfur; and each R' is independently hydrogen or an optionally substituted group selected from C$_{1-6}$ aliphatic, phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 4-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-10 membered bicyclic heteroaryl ring having 1-5 heteroatoms independently selected from nitrogen, oxygen, or sulfur, wherein:

two R' groups on the same nitrogen atom are optionally taken together with the nitrogen atom to form an optionally substituted 3-8 membered, saturated, partially unsaturated, or aryl ring having 1-4 heteroatoms independently selected from nitrogen, oxygen, or sulfur; and each $R^7$ is independently an optionally substituted group selected from —Ar', C$_{1-20}$ aliphatic, C$_{1-20}$ heteroaliphatic having 1-3 heteroatoms independently selected from nitrogen, oxygen, or sulfur, phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 4-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-14 membered bicyclic or tricyclic heteroaryl ring having 1-5 heteroatoms independently selected from nitrogen, oxygen, or sulfur; and two $R^7$ are optionally taken together with the oxygen atoms they are bound to form a bidentate ligand; and Ar' is of the following formula:

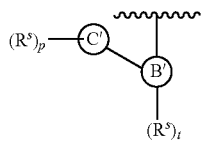

wherein:
t is 0-4;
p is 0-6;
each Ring B' and Ring C' is independently an optionally substituted group selected from phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 4-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-10 membered bicyclic heteroaryl ring having 1-5 heteroatoms independently selected from nitrogen, oxygen, or sulfur; and
each $R^s$ is independently halogen, R', —OR', —SR', —S(O)R', —S(O)$_2$R', —OSi(R')$_3$, —N(R')$_2$, —NR'C(O)R', —NR' C(O)OR', —NR' C(O)N(R')$_2$, —NR'SO$_2$R', —NR'SO$_2$N(R')$_2$, or —NR'OR'.

In some embodiments, a provided catalyst or metal complex is of formula II-b:

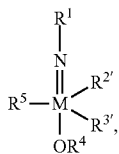

II-b wherein:
$R^{2'}$ and $R^{3'}$ are taken together with their intervening metal atom to form an optionally substituted 3-8 membered saturated or partially unsaturated ring having, in addition to the intervening metal atom, 0-4 heteroatoms independently selected from nitrogen, oxygen, or sulfur; and
each of the other variables is independently as defined and described for formula II-a.

In some embodiments, a provided catalyst or metal complex is of formula II-b, wherein:
M is molybdenum or tungsten;
$R^1$ is an optionally substituted group selected from $C_{1-20}$ aliphatic, $C_{1-20}$ heteroaliphatic having 1-3 heteroatoms independently selected from nitrogen, oxygen, or sulfur, phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 4-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-10 membered bicyclic heteroaryl ring having 1-5 heteroatoms independently selected from nitrogen, oxygen, or sulfur;
each of $R^2$ and $R^3$ is independently R', —OR', —SR', —N(R')$_2$, —OC(O)R', —SOR', —SO$_2$R', —SO$_2$N(R')$_2$, —C(O)N(R')$_2$, —NR'C(O)R', or —NR'SO$_2$R', provided that $R^2$ and $R^3$ are not simultaneously hydrogen;
$R^4$ is $R^7$, or an optionally substituted group selected from —Ar, $C_{1-20}$ aliphatic, $C_{1-20}$ heteroaliphatic having 1-3 heteroatoms independently selected from nitrogen, oxygen, or sulfur, phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 4-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-14 membered bicyclic or tricyclic heteroaryl ring having 1-5 heteroatoms independently selected from nitrogen, oxygen, or sulfur;
Ar is of the following formula:

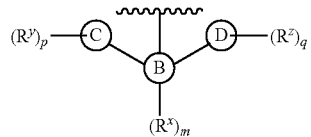

wherein:
m is 0-3;
Ring B is an optionally substituted group selected from phenyl or a 5-6 membered monocyclic heteroaryl ring having 1-4 heteroatoms independently selected from nitrogen, oxygen, or sulfur;
p and q are independently 0-6;
each of Ring C and Ring D is independently optionally substituted groups selected from phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 4-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-10 membered bicyclic heteroaryl ring having 1-5 heteroatoms independently selected from nitrogen, oxygen, or sulfur;
each of $R^x$, $R^y$, and $R^z$ is independently halogen, —OR', —N(R')$_2$, —NR'C(O)R', —NR'C(O)OR', —NR'C(O)N(R')$_2$, —NR'SO$_2$R', —NR'SO$_2$N(R')$_2$, —NR'OR', or an optionally substituted group selected from $C_{1-20}$ aliphatic, $C_{1-20}$ heteroaliphatic having 1-3 heteroatoms independently selected from nitrogen, oxygen, or sulfur;
$R^5$ is halogen, —OR$^6$, —OR$^7$, —N(R')$_2$, —NR'C(O)R', —NR'C(O)OR', —NR'C(O)N(R')$_2$, —NR'SO$_2$R', —NR'SO$_2$N(R')$_2$, or —NR'OR', or an optionally substituted group selected from a 5-6 membered monocyclic heteroaryl ring having at least one nitrogen and 0-3 heteroatoms independently selected from nitrogen, oxygen, or sulfur, a 4-7 membered saturated or partially unsaturated heterocyclic ring having at least one nitrogen and 0-2 heteroatoms independently selected from nitrogen, oxygen, or sulfur, a 7-10 membered bicyclic saturated or partially unsaturated heterocyclic ring having at least one nitrogen and 0-4 heteroatoms independently selected from nitrogen, oxygen, or sulfur, or an 8-10 membered bicyclic heteroaryl ring having at least one nitrogen and 0-4 heteroatoms independently selected from nitrogen, oxygen, or sulfur;

$R^6$ is an optionally substituted group selected from $C_{1-20}$ aliphatic, $C_{1-20}$ heteroaliphatic having 1-3 heteroatoms independently selected from nitrogen, oxygen, or sulfur, phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 4-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-14 membered bicyclic or tricyclic heteroaryl ring having 1-5 heteroatoms independently selected from nitrogen, oxygen, or sulfur; and each R' is independently hydrogen or an optionally substituted group selected from $C_{1-6}$ aliphatic, phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 4-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-10 membered bicyclic heteroaryl ring having 1-5 heteroatoms independently selected from nitrogen, oxygen, or sulfur, wherein:

two R' groups on the same nitrogen atom are optionally taken together with the nitrogen atom to form an optionally substituted 3-8 membered, saturated, partially unsaturated, or aryl ring having 1-4 heteroatoms independently selected from nitrogen, oxygen, or sulfur; and each $R^7$ is independently an optionally substituted group selected from —Ar', $C_{1-20}$ aliphatic, $C_{1-20}$ heteroaliphatic having 1-3 heteroatoms independently selected from nitrogen, oxygen, or sulfur, phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 4-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-14 membered bicyclic or tricyclic heteroaryl ring having 1-5 heteroatoms independently selected from nitrogen, oxygen, or sulfur; and two $R^7$ are optionally taken together with the oxygen atoms they are bound to form a bidentate ligand; and Ar' is of the following formula:

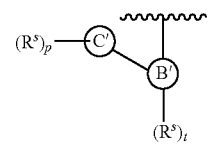

wherein:
t is 0-4;
p is 0-6;
each Ring B' and Ring C' is independently an optionally substituted group selected from phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 4-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-10 membered bicyclic heteroaryl ring having 1-5 heteroatoms independently selected from nitrogen, oxygen, or sulfur; and each $R^s$ is independently halogen, R', —OR', —SR', —S(O)R', —S(O)$_2$R', —OSi(R')$_3$, —N(R')$_2$, —NR' C(O)R', —NR' C(O)OR', —NR' C(O)N(R')$_2$, —NR'SO$_2$R', —NR'SO$_2$N(R')$_2$, or —NR'OR'.

In some embodiments, a provided catalyst or metal complex, such as a compound of formula II-a or II-b, is useful for metathesis reactions. In some embodiments, a provided catalyst or metal complex, such as a compound of formula II-a or II-b, is useful for olefin metathesis. In some embodiments, a provided catalyst or metal complex is useful for enyne metathesis.

In some embodiments, the present disclosure provides methods for metathesis reactions. In some embodiments, the present disclosure provides a method, comprising:

reacting a first species comprising an olefin with a second species comprising an olefin in the presence of a catalyst or metal complex to provide at least one product comprising an olefin, wherein:
each carbon atom of the olefin in the first species is substituted with at least one halogen; and
the olefin in the at least one product comprises a carbon atom from the first species and a carbon atom from the second species.

In some embodiments, the present disclosure provides a method, comprising:

reacting a first species comprising an olefin with a second species comprising an alkyne in the presence of a catalyst or metal complex to provide at least one product comprising an olefin, wherein:
each carbon atom of the olefin in the first species is substituted with at least one halogen; and
the olefin in the at least one product comprises a carbon atom from the first species and a carbon atom from the second species.

2. Definitions

Compounds of the present disclosure include those described generally herein, and are further illustrated by the classes, subclasses, and species disclosed herein. As used herein, the following definitions shall apply unless otherwise indicated. For purposes of this disclosure, the chemical elements are identified in accordance with the Periodic Table of the Elements, CAS version, Handbook of Chemistry and Physics, 75$^{th}$ Ed. Additionally, general principles of organic chemistry are described in "Organic Chemistry", Thomas Sorrell, University Science Books, Sausalito: 1999, and "March's Advanced Organic Chemistry", 5$^{th}$ Ed., Ed.: Smith, M. B. and March, J., John Wiley & Sons, New York: 2001, the entire contents of which are hereby incorporated by reference.

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon, bicyclic hydrocarbon, or tricyclic hydrocarbon that is completely saturated or that contains one or more units of unsaturation, but which is not aromatic (also referred to herein as "carbocycle," "cycloaliphatic" or "cycloalkyl"), that has a single point of attachment to the rest of the molecule. Unless otherwise specified, aliphatic groups contain 1-30 aliphatic carbon atoms. In some embodiments, aliphatic groups contain 1-20 aliphatic carbon atoms. In other embodiments, aliphatic groups contain 1-10 aliphatic carbon atoms. In still other embodiments, aliphatic groups contain 1-5 aliphatic carbon atoms, and in yet other embodiments, aliphatic groups contain 1, 2, 3, or 4 aliphatic carbon atoms. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

The term "cycloaliphatic," as used herein, refers to saturated or partially unsaturated cyclic aliphatic monocyclic, bicyclic, or polycyclic ring systems, as described herein, having from 3 to 14 members, wherein the aliphatic ring system is optionally substituted as defined above and described herein. Cycloaliphatic groups include, without limitation, cyclopropyl, cyclobutyl, cyclopentyl, cyclopentenyl, cyclohexyl, cyclohexenyl, cycloheptyl, cycloheptenyl, cyclooctyl, cyclooctenyl, norbornyl, adamantyl, and cyclooctadienyl. In some embodiments, the cycloalkyl has 3-6 carbons. The terms "cycloaliphatic," may also include aliphatic rings that are fused to one or more aromatic or nonaromatic rings, such as decahydronaphthyl or tetrahydronaphthyl, where the radical or point of attachment is on the aliphatic ring. In some embodiments, a carbocyclic group is bicyclic. In some embodiments, a carbocyclic group is tricyclic. In some embodiments, a carbocyclic group is polycyclic. In some embodiments, "cycloaliphatic" (or "carbocycle" or "cycloalkyl") refers to a monocyclic $C_3$-$C_6$ hydrocarbon, or a $C_8$-$C_{10}$ bicyclic hydrocarbon that is completely saturated or that contains one or more units of unsaturation, but which is not aromatic, that has a single point of attachment to the rest of the molecule, or a $C_9$-$C_{16}$ tricyclic hydrocarbon that is completely saturated or that contains one or more units of unsaturation, but which is not aromatic, that has a single point of attachment to the rest of the molecule.

As used herein, the term "alkyl" is given its ordinary meaning in the art and may include saturated aliphatic groups, including straight-chain alkyl groups, branched-chain alkyl groups, cycloalkyl (alicyclic) groups, alkyl substituted cycloalkyl groups, and cycloalkyl substituted alkyl groups. In certain embodiments, a straight chain or branched chain alkyl has about 1-20 carbon atoms in its backbone (e.g., $C_1$-$C_{20}$ for straight chain, $C_2$-$C_{20}$ for branched chain), and alternatively, about 1-10. In some embodiments, a cycloalkyl ring has from about 3-10 carbon atoms in their ring structure where such rings are monocyclic or bicyclic, and alternatively about 5, 6 or 7 carbons in the ring structure. In some embodiments, an alkyl group may be a lower alkyl group, wherein a lower alkyl group comprises 1-4 carbon atoms (e.g., $C_1$-$C_4$ for straight chain lower alkyls).

As used herein, the term "alkenyl" refers to an alkyl group, as defined herein, having one or more double bonds.

As used herein, the term "alkynyl" refers to an alkyl group, as defined herein, having one or more triple bonds.

The term "heteroalkyl" is given its ordinary meaning in the art and refers to alkyl groups as described herein in which one or more carbon atoms is replaced with a heteroatom (e.g., oxygen, nitrogen, sulfur, and the like). Examples of heteroalkyl groups include, but are not limited to, alkoxy, poly(ethylene glycol)-, alkyl-substituted amino, tetrahydrofuranyl, piperidinyl, morpholinyl, etc.

The term "aryl" used alone or as part of a larger moiety as in "aralkyl," "aralkoxy," or "aryloxyalkyl," refers to monocyclic or bicyclic ring systems having a total of five to fourteen ring members, wherein at least one ring in the system is aromatic and wherein each ring in the system contains 3 to 7 ring members. The term "aryl" may be used interchangeably with the term "aryl ring." In certain embodiments of the present disclosure, "aryl" refers to an aromatic ring system which includes, but not limited to, phenyl, biphenyl, naphthyl, binaphthyl, anthracyl and the like, which may bear one or more substituents. Also included within the scope of the term "aryl," as it is used herein, is a group in which an aromatic ring is fused to one or more non-aromatic rings, such as indanyl, phthalimidyl, naphthimidyl, phenanthridinyl, or tetrahydronaphthyl, and the like.

The terms "heteroaryl" and "heteroar-," used alone or as part of a larger moiety, e.g., "heteroaralkyl," or "heteroaralkoxy," refer to groups having 5 to 10 ring atoms (i.e., monocyclic or bicyclic), in some embodiments 5, 6, 9, or 10 ring atoms. In some embodiments, such rings have 6, 10, or 14 π electrons shared in a cyclic array; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. In some embodiments, a heteroaryl is a heterobiaryl group, such as bipyridyl and the like. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Non-limiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group may be mono- or bicyclic. The term "heteroaryl" may be used interchangeably with the terms "heteroaryl ring," "heteroaryl group," or "heteroaromatic," any of which terms include rings that are optionally substituted. The term "heteroaralkyl" refers to an alkyl group substituted by a heteroaryl, wherein the alkyl and heteroaryl portions independently are optionally substituted.

As used herein, the terms "heterocycle," "heterocyclyl," "heterocyclic radical," and "heterocyclic ring" are used interchangeably and refer to a stable 5- to 7-membered monocyclic or 7-10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or $^{+}$NR (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothienyl, pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle," "heterocyclyl," "heterocyclyl ring," "heterocyclic group," "heterocyclic moiety," and "heterocyclic radical," are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl. A heterocyclyl group may be mono- or bicyclic. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or NR$^{+}$ (as in N-substituted pyrrolidinyl)).

The term "unsaturated," as used herein, means that a moiety has one or more units of unsaturation.

The term "halogen" means F, Cl, Br, or I.

As described herein, compounds of the disclosure may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this disclosure are preferably those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently halogen; —(CH$_2$)$_{0-4}$R°; —(CH$_2$)$_{0-4}$OR°; —O(CH$_2$)$_{0-4}$R°, —O—(CH$_2$)$_{0-4}$C(O)OR°; —(CH$_2$)$_{0-4}$CH(OR°)$_2$; —(CH$_2$)$_{0-4}$Ph, which may be substituted with R°; —(CH$_2$)$_{0-4}$O(CH$_2$)$_{0-1}$Ph which may be substituted with R°; —CH=CHPh, which may be substituted with R°; —(CH$_2$)$_{0-4}$O(CH$_2$)$_{0-1}$-pyridyl which may be substituted with R°; —NO$_2$; —CN; —N$_3$; —(CH$_2$)$_{0-4}$N(R°)$_2$; —(CH$_2$)$_{0-4}$N(R°)C(O)R°; —N(R°)C(S)R°; —(CH$_2$)$_{0-4}$N(R°)C(O)NR°$_2$; —N(R°)C(S)NR°$_2$; —(CH$_2$)$_{0-4}$N(R°)C(O)OR°; —N(R°)N(R°)C(O)R°; —N(R°)N(R°)C(O)NR°$_2$; —N(R°)N(R°)C(O)OR°; —(CH$_2$)$_{0-4}$C(O)R°; —C(S)R°; —(CH$_2$)$_{0-4}$C(O)OR°; —(CH$_2$)$_{0-4}$C(O)SR°; —(CH$_2$)$_{0-4}$C(O)OSiR°$_3$; —(CH$_2$)$_{0-4}$C(O)R°; —OC(O)(CH$_2$)$_{0-4}$SR—, SC(S)SR°; —(CH$_2$)$_{0-4}$SC(O)R°; —(CH$_2$)$_{0-4}$C(O)NR°$_2$; —C(S)NR°$_2$; —C(S)SR°; —SC(S)SR°, —(CH$_2$)$_{0-4}$OC(O)NR°$_2$; —C(O)N(OR°)R°; —C(O)C(O)R°; —C(O)CH$_2$C(O)R°; —C(NOR°)R°; —(CH$_2$)$_{0-4}$SSR°; —(CH$_2$)$_{0-4}$S(O)$_2$R°; —(CH$_2$)$_{0-4}$S(O)$_2$OR°; —(CH$_2$)$_{0-4}$OS(O)$_2$R°; —S(O)$_2$NR°$_2$; —(CH$_2$)$_{0-4}$S(O)R°; —N(R°)S(O)$_2$NR°$_2$; —N(R°)S(O)$_2$R°; —N(OR°)R°; —C(NH)NR°$_2$; —P(O)$_2$R°; —P(O)R°$_2$; —OP(O)R°$_2$; —OP(O)(OR°)$_2$; —SiR°$_3$; —OSiR°$_3$; —(C$_{1-4}$ straight or branched alkylene)O—N(R°)$_2$; or —(C$_{1-4}$ straight or branched alkylene)C(O)O—N(R°)$_2$, wherein each R° may be substituted as defined below and is independently hydrogen, C$_{1-6}$ aliphatic, —CH$_2$Ph, —O(CH$_2$)$_{0-1}$Ph, —CH$_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of R°, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on R° (or the ring formed by taking two independent occurrences of R° together with their intervening atoms), are independently halogen, —(CH$_2$)$_{0-2}$R$^{•}$, -(haloR$^{•}$), —(CH$_2$)$_{0-2}$OH, —(CH$_2$)$_{0-2}$OR$^{•}$, —(CH$_2$)$_{0-2}$CH(OR$^{•}$)$_2$; —O(haloR$^{•}$), —CN, —N$_3$, —(CH$_2$)$_{0-2}$C(O)R$^{•}$, —(CH$_2$)$_{0-2}$C(O)OH, —(CH$_2$)$_{0-2}$C(O)OR$^{•}$, —(CH$_2$)$_{0-2}$SR$^{•}$, —(CH$_2$)$_{0-2}$SH, —(CH$_2$)$_{0-2}$NH$_2$, —(CH$_2$)$_{0-2}$NHR$^{•}$, —(CH$_2$)$_{0-2}$NR$^{•}$$_2$, —NO$_2$, —SiR$^{•}$$_3$, —OSiR$^{•}$$_3$, —C(O)SR$^{•}$, —(C$_{1-4}$ straight or branched alkylene)C(O)OR$^{•}$, or —SSR$^{•}$ wherein each R$^{•}$ is unsubstituted or where preceded by "halo" is substituted only with one or more halogens, and is independently selected from C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur. Suitable divalent substituents on a saturated carbon atom of R° include =O and =S.

Suitable divalent substituents on a saturated carbon atom of an "optionally substituted" group include the following: =O, =S, =NNR*$_2$, =NNHC(O)R*, =NNHC(O)OR*, =NNHS(O)$_2$R*, =NR*, =NOR*, —O(C(R*$_2$))$_{2-3}$O—, or —S(C(R*$_2$))$_{2-3}$S—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR*$_2$)$_{2-3}$O—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, —R˙, -(haloR˙), —OH, —OR˙, —O(haloR˙), —CN, —C(O)OH, —C(O)OR˙, —NH$_2$, —NHR˙, —NR˙$_2$, or —NO$_2$, wherein each R˙ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —R†, —NR†$_2$, —C(O)R†, —C(O)OR†, —C(O)C(O)R†, —C(O)CH$_2$C(O)R†, —S(O)$_2$R†, —S(O)$_2$NR†$_2$, —C(S)NR†$_2$, —C(NH)NR†$_2$, or —N(R†)S(O)$_2$R†; wherein each R† is independently hydrogen, C$_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of R†, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of R† are independently halogen, —R˙, -(haloR˙), —OH, —OR˙, —O(haloR˙), —CN, —C(O)OH, —C(O)OR˙, —NH$_2$, —NHR˙, —NR˙$_2$, or —NO$_2$, wherein each R˙ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

As used herein, the term "stereogenic metal atom" is given its ordinary meaning, and refers to a metal atom coordinated by at least two ligands (e.g., at least four ligands), wherein the ligands are arranged about the metal atom such that the overall structure (e.g., metal complex) lacks a plane of symmetry with respect to the metal atom. In some cases, the stereogenic metal atom may be coordinated by at least three ligands, at least four ligands, at least five ligands, at least six ligands, or more. In certain embodiments, the stereogenic metal atom may be coordinated by four ligands. Metal complexes comprising a stereogenic metal center may provide sufficient space specificity at a reaction site of the metal complex, such that a molecular substrate having a plane of symmetry may be reacted at the reaction site to form a product that is free of a plane of symmetry. That is, the stereogenic metal center of the metal complex may impart sufficient shape specificity to induce stereogenicity effectively, producing a chiral product. Such metal complexes may exhibit improved catalytic activity and stereoselectivity, relative to previous systems, and may reduce undesired side reactions (e.g., dimerization or oligomerization of the metal complex).

The term "chiral" is given its ordinary meaning in the art and refers to a molecule that is not superimposable with its mirror image, wherein the resulting nonsuperimposable mirror images are known as "enantiomers" and are labeled as either an (R) enantiomer or an (S) enantiomer. Typically, chiral molecules lack a plane of symmetry.

The term "achiral" is given its ordinary meaning in the art and refers to a molecule that is superimposable with its mirror image. Typically, achiral molecules possess a plane of symmetry.

As used herein, a ligand may be either monodentate or polydentate. In some embodiments, a ligand is monodentate. In some embodiments, a ligand is bidentate. In some embodiments, a ligand is tridentate. In some embodiments, two or more monodentate ligands are taken together to form a polydentate ligand. A ligand may have hapticity of more than one. In some cases, a ligand has a hapticity of 1 to 10. In some embodiments, a ligand has a hapticity of 1. In some embodiments, a ligand has a hapticity of 2. In some embodiments, a ligand has a hapticity of 3. In some embodiments, a ligand has a hapticity of 4. In some embodiments, a ligand has a hapticity of 5. In some embodiments, a ligand has a hapticity of 6. For a ligand having hapticity greater than one, as sometimes done in the art, a single bond may be drawn between the ligand and the metal. In some cases, a ligand is alkylidene. In some cases, a ligand is a nitrogen-containing ligand. In some cases, a ligand is an oxygen-containing ligand. In some cases, a ligand is a phosphorus-containing ligand. In some embodiments, a ligand comprises an unsaturated bond, and the unsaturated bond is coordinated to a metal. In some embodiments, a ligand comprises a carbon-carbon double bond, and the double bond is coordinated to a metal. In some embodiments, a ligand is an olefin. When an olefin double bond is coordinated to a metal, the chemical bonding between the olefin and the metal can either be depicted as a 3-membered ring wherein the ring members comprises the metal and both carbon atoms of the double bond, or as a single bond between the metal and the double bond.

As used herein, a "nitrogen-containing ligand" may be any species comprising a nitrogen atom. In some cases, the nitrogen atom may bind to the metal atom. In some cases, the nitrogen-containing ligand may bind the metal center via a different atom. In some cases, the nitrogen atom may be a ring atom of a heteroaryl or heteroalkyl group. In some cases, the nitrogen atom may be a substituted amine group. It should be understood that, in catalyst precursors described herein, the nitrogen-containing ligand may have sufficiently ionic character to coordinate a metal center, such as a Mo or W metal center. Examples of nitrogen-containing ligands include, but are not limited to, pyrrolyl, pyrazolyl, pyridinyl, pyrazinyl, pyrimidinyl, imidazolyl, triazolyl, tetrazolyl, oxazolyl, isoxazolyl, thiazolyl, isothiazolyl, indolyl, indazolyl, carbazolyl, morpholinyl, piperidinyl, oxazinyl, substituted derivatives thereof, and the like. For example, the nitrogen-containing ligand may be pyrrolide or 2,5-dimethylpyrrolide. The nitrogen-containing ligand may be selected to interact with an oxygen-containing ligand such that the oxygen-containing ligand can readily replace the nitrogen-containing ligand in a precatalyst to generate a catalyst. In cases where the catalyst composition may be generated in situ in order to carry out a chemical reaction, the first, nitrogen-containing ligand may be selected such that, upon replacement by an oxygen-containing ligand, the nitrogen-containing ligands or protonated versions thereof do not interfere with the chemical reaction. In some embodiments, the nitrogen-containing ligand may be chiral and the precatalyst may be provided as a racemic mixture or a purified stereoisomer.

In some embodiments, a nitrogen-containing ligand may also describe a ligand precursor comprising at least one hydrogen atom directly bonded to a nitrogen atom, wherein deprotonation of the at least one hydrogen atom results in a negatively charged nitrogen atom, which may coordinate to a metal atom. Exemplary such precursors include but are not limited to amines, amides, and pyrrole and its derivatives thereof. A nitrogen-containing ligand may be a heteroaryl or heteroalkyl group comprising at least one nitrogen ring atom. In some cases, the nitrogen atom may be positioned on a substituent of an alkyl, heteroalkyl, aryl, or heteroaryl group. For example, a nitrogen-containing ligand may be an amine- or amide-substituted aryl group, wherein the amine or amide group is deprotonated upon coordination to the metal center.

As used herein, the term "oxygen-containing ligand" may be used to refer to ligands comprising at least one oxygen atom. In some cases, the oxygen atom binds to the metal atom thereby forming an ether-linkage. In other cases, the oxygen-containing ligand may bind the metal center via a different atom. The term "oxygen-containing ligand" may also describe ligand precursors comprising at least one hydroxyl group (e.g., a hydroxyl-containing ligand), wherein deprotonation of the hydroxyl group results in a negatively charged oxygen atom, which may coordinate to a metal atom. The oxygen-containing ligand may be a heteroaryl or heteroalkyl group comprising at least one oxygen ring atom. In some cases, the oxygen atom may be positioned on a substituent of an alkyl, heteroalkyl, aryl, or heteroaryl group. For example, the oxygen-containing ligand may be a hydroxy-substituted aryl group, wherein the hydroxyl group is deprotonated upon coordination to the metal center.

In some embodiments, an oxygen-containing ligand may also describe a ligand precursor comprising at least one hydroxyl group (e.g., a hydroxyl-containing ligand), wherein deprotonation of the hydroxyl group results in a negatively charged oxygen atom, which may coordinate to a metal atom. An oxygen-containing ligand may be a heteroaryl or heteroalkyl group comprising at least one oxygen ring atom. In some cases, the oxygen atom may be positioned on a substituent of an alkyl, heteroalkyl, aryl, or heteroaryl group. For example, an oxygen-containing ligand may be a hydroxy-substituted aryl group, wherein the hydroxyl group is deprotonated upon coordination to the metal center. In some embodiments, an oxygen-containing ligand is a neutral ligand.

As used herein, the term "phosphorus-containing ligand" may be used to refer to ligands comprising at least one phosphorus atom. In some cases, the phosphorus atom binds to the metal. In other cases, the phosphorus-containing ligand may bind to the metal center via a different atom (i.e., an atom other than the phosphorous). The phosphorus-containing ligand may have phosphorus atom of various oxidation states. In some cases the phosphorus-containing ligand is phosphine. In some cases the phosphorus-containing ligand is phosphite. In some cases the phosphorus-containing ligand is phosphate. The phosphorus-containing ligand may be either monodentate or polydentate. In some cases, two or more phosphorus atoms bind to the metal. In some cases, one or more phosphorus atoms together with one or more non-phosphorus atoms bind to the metal. In some embodiments, a phosphorus-containing ligand is a neutral ligand.

The phrase "protecting group," as used herein, refers to temporary substituents which protect a potentially reactive functional group from undesired chemical transformations. Examples of such protecting groups include esters of carboxylic acids, silyl ethers of alcohols, and acetals and ketals of aldehydes and ketones, respectively. A "Si protecting group" is a protecting group comprising a Si atom, such as Si-trialkyl (e.g., trimethylsilyl, tributylsilyl, t-butyldimethylsilyl), Si-triaryl, Si-alkyl-diphenyl (e.g., t-butyldiphenylsilyl), or Si-aryl-dialkyl (e.g., Si-phenyldialkyl). Generally, a Si protecting group is attached to an oxygen atom. The field of protecting group chemistry has been reviewed (Greene, T. W.; Wuts, P. G. M. Protective Groups in Organic Synthesis, 2nd ed.; Wiley: New York, 1991). Such protecting groups (and associated protected moieties) are described in detail below.

Protected hydroxyl groups are well known in the art and include those described in detail in *Protecting Groups in Organic Synthesis*, T. W. Greene and P. G. M. Wuts, $3^{rd}$ edition, John Wiley & Sons, 1999, the entirety of which is incorporated herein by reference. Examples of suitably protected hydroxyl groups further include, but are not limited to, esters, carbonates, sulfonates, allyl ethers, ethers, silyl ethers, alkyl ethers, arylalkyl ethers, and alkoxyalkyl ethers. Examples of suitable esters include formates, acetates, proprionates, pentanoates, crotonates, and benzoates. Specific examples of suitable esters include formate, benzoyl formate, chloroacetate, trifluoroacetate, methoxyacetate, triphenylmethoxyacetate, p-chlorophenoxyacetate, 3-phenylpropionate, 4-oxopentanoate, 4,4-(ethylenedithio) pentanoate, pivaloate (trimethylacetate), crotonate, 4-methoxy-crotonate, benzoate, p-benzylbenzoate, 2,4,6-trimethylbenzoate. Examples of suitable carbonates include 9-fluorenylmethyl, ethyl, 2,2,2-trichloroethyl, 2-(trimethylsilyl)ethyl, 2-(phenylsulfonyl)ethyl, vinyl, allyl, and p-nitrobenzyl carbonate. Examples of suitable silyl ethers include trimethylsilyl, triethylsilyl, t-butyldimethylsilyl, t-butyldiphenylsilyl, triisopropylsilyl ether, and other trialkylsilyl ethers. Examples of suitable alkyl ethers include methyl, benzyl, p-methoxybenzyl, 3,4-dimethoxybenzyl, trityl, t-butyl, and allyl ether, or derivatives thereof. Alkoxyalkyl ethers include acetals such as methoxymethyl, methylthiomethyl, (2-methoxyethoxy)methyl, benzyloxymethyl, beta-(trimethylsilyl)ethoxymethyl, and tetrahydropyran-2-yl ether. Examples of suitable arylalkyl ethers include benzyl, p-methoxybenzyl (MPM), 3,4-dimethoxybenzyl, O-nitrobenzyl, p-nitrobenzyl, p-halobenzyl, 2,6-dichlorobenzyl, p-cyanobenzyl, 2- and 4-picolyl ethers.

Protected amines are well known in the art and include those described in detail in Greene (1999). Suitable mono-protected amines further include, but are not limited to, aralkylamines, carbamates, allyl amines, amides, and the like. Examples of suitable mono-protected amino moieties include t-butyloxycarbonylamino (—NHBOC), ethyloxycarbonylamino, methyloxycarbonylamino, trichloroethyloxycarbonylamino, allyloxycarbonylamino (—NHAlloc), benzyloxocarbonylamino (—NHCBZ), allylamino, benzylamino (—NHBn), fluorenylmethylcarbonyl (—NHFmoc), formamido, acetamido, chloroacetamido, dichloroacetamido, trichloroacetamido, phenylacetamido, trifluoroacetamido, benzamido, t-butyldiphenylsilyl, and the like. Suitable di-protected amines include amines that are substituted with two substituents independently selected from those described above as mono-protected amines, and further include cyclic imides, such as phthalimide, maleimide, succinimide, and the like. Suitable di-protected amines also include pyrroles and the like, 2,2,5,5-tetramethyl-[1,2,5] azadisilolidine and the like, and azide.

Protected aldehydes are well known in the art and include those described in detail in Greene (1999). Suitable protected aldehydes further include, but are not limited to, acyclic acetals, cyclic acetals, hydrazones, imines, and the like. Examples of such groups include dimethyl acetal, diethyl acetal, diisopropyl acetal, dibenzyl acetal, bis(2-nitrobenzyl) acetal, 1,3-dioxanes, 1,3-dioxolanes, semicarbazones, and derivatives thereof.

Protected carboxylic acids are well known in the art and include those described in detail in Greene (1999). Suitable protected carboxylic acids further include, but are not limited to, optionally substituted $C_{1-6}$ aliphatic esters, optionally substituted aryl esters, silyl esters, activated esters, amides, hydrazides, and the like. Examples of such ester groups include methyl, ethyl, propyl, isopropyl, butyl, isobutyl, benzyl, and phenyl ester, wherein each group is optionally substituted. Additional suitable protected carboxylic acids include oxazolines and ortho esters.

Protected thiols are well known in the art and include those described in detail in Greene (1999). Suitable protected thiols further include, but are not limited to, disulfides, thioethers, silyl thioethers, thioesters, thiocarbonates, and thiocarbamates, and the like. Examples of such groups include, but are not limited to, alkyl thioethers, benzyl and substituted benzyl thioethers, triphenylmethyl thioethers, and trichloroethoxycarbonyl thioester, to name but a few.

Unless otherwise stated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the disclosure.

Unless otherwise stated, all tautomeric forms of the compounds of the disclosure are within the scope of the disclosure.

Additionally, unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a $^{11}$C- or $^{13}$C- or $^{14}$C-enriched carbon are within the scope of this disclosure. Such compounds are useful, for example, as analytical tools or probes in biological assays.

As used herein, the term "electron-withdrawing group" is given its ordinary meaning in the art and refers to an atom or group that draws electron density from a neighboring atom or group, usually by resonance and/or inductive effects. In some embodiments, an electron-withdrawing group withdraws electron density from an aromatic ring system by resonance and/or inductive effects. In some embodiments, an electron-withdrawing group withdraws electron density from an aromatic ring system by resonance and inductive effects. In some embodiments, an electron-withdrawing group lowers the electron density of an aromatic ring system such as phenyl. Exemplary electron-withdrawing groups are extensively described in the art, including but not limited to halogen, carbonyl moieties (e.g., aldehyde and ketone groups), —COOH and its derivatives (e.g., ester and amide moieties), protonated amines, quaternary ammonium groups, —CN, —NO$_2$, —S(O)—, and —S(O)$_2$—. In some embodiments, an electron-withdrawing group is halogen. In some embodiments, an electron-withdrawing group is —F. In some embodiments, an electron-withdrawing group is —Cl. In some embodiments, an electron-withdrawing group is —Br. In some embodiments, an electron-withdrawing group is —I. In some embodiments, hydrogen is used as reference and regarded as having no effect.

As used herein and in the claims, the singular forms "a", "an", and "the" include the plural reference unless the context clearly indicates otherwise. Thus, for example, a reference to "a compound" includes a plurality of such compounds.

3. Description of Certain Embodiments of the Invention

In some embodiments, M is molybdenum. In some embodiments, M is tungsten.

As defined generally above, $R^1$ is an optionally substituted group selected from $C_{1-20}$ aliphatic, $C_{1-20}$ heteroaliphatic, phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 3-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-10 membered bicyclic heteroaryl ring having 1-5 heteroatoms independently selected from nitrogen, oxygen, or sulfur; or $R^1$ is optionally substituted

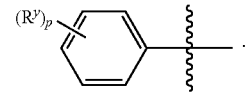

In some embodiments, $R^1$ is an optionally substituted group selected from $C_{1-20}$ aliphatic, $C_{1-20}$ heteroaliphatic, phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 3-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-10 membered bicyclic heteroaryl ring having 1-5 heteroatoms independently selected from nitrogen, oxygen, or sulfur; or $R^1$ is optionally substituted

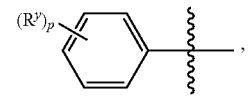

wherein each $R^y$ is independently an electron-withdrawing group. In some embodiments, $R^1$ is an optionally substituted group selected from $C_{1-20}$ aliphatic, $C_{1-20}$ heteroaliphatic, phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 3-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-10 membered bicyclic heteroaryl ring having 1-5 heteroatoms independently selected from nitrogen, oxygen, or sulfur. In some embodiments, $R^1$ is optionally substituted

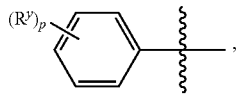

wherein each $R^y$ is independently an electron-withdrawing group. In some embodiments, $R^1$ is an optionally substituted

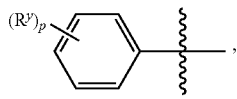

wherein each $R^y$ is independently an electron-withdrawing group, and wherein each =CH— of the depicted phenyl ring, if any, is independent optionally substituted.

In some embodiments, $R^1$ is optionally substituted $C_{1-20}$ aliphatic. In some embodiments, $R^1$ is optionally substituted $C_{1-20}$ cycloaliphatic. In some embodiments, $R^1$ is optionally substituted $C_{1-12}$ aliphatic. In some embodiments, $R^1$ is optionally substituted $C_{1-12}$ cycloaliphatic. In some embodiments, $R^1$ is optionally substituted $C_{1-12}$ cycloalkyl. In some embodiments, $R^1$ is optionally substituted adamantyl. In some embodiments, $R^1$ is adamantyl. In some embodiments, $R^1$ is optionally substituted $C_{1-6}$ aliphatic. In some embodiments, $R^1$ is optionally substituted $C_{1-6}$ alkyl. In some embodiments, $R^1$ is optionally substituted hexyl, pentyl, butyl, propyl, ethyl or methyl. In some embodiments, $R^1$ is optionally substituted hexyl. In some embodiments, $R^1$ is optionally substituted pentyl. In some embodiments, $R^1$ is optionally substituted butyl. In some embodiments, $R^1$ is optionally substituted propyl. In some embodiments, $R^1$ is optionally substituted ethyl. In some embodiments, $R^1$ is optionally substituted methyl. In some embodiments, $R^1$ is hexyl. In some embodiments, $R^1$ is pentyl. In some embodiments, $R^1$ is butyl. In some embodiments, $R^1$ is propyl. In some embodiments, $R^1$ is ethyl. In some embodiments, $R^1$ is methyl. In some embodiments, $R^1$ is isopropyl.

In certain embodiments, $R^1$ is optionally substituted phenyl. In some embodiments, $R^1$ is substituted phenyl. In some embodiments, $R^1$ is mono-, di-, tri-, tetra- or penta-substituted phenyl. In some embodiments, $R^1$ is mono-substituted phenyl. In certain embodiments, $R^1$ is 2,6-disubstituted phenyl. In some embodiments, $R^1$ is tri-substituted phenyl. In some embodiments, $R^1$ is tetra-substituted phenyl. In some embodiments, $R^1$ is penta-substituted phenyl. In some embodiments, a substituent is a halogen. In some embodiments, a substituent is —F, and $R^1$ is phenyl substituted with one or more —F. In some embodiments, $R^1$ is pentafluorophenyl. In some embodiments, a substituent is optionally substituted $C_{1-4}$ aliphatic. In some embodiments, $R^1$ is phenyl disubstituted with halogen or $C_{1-4}$ aliphatic. Such $R^1$ groups include but are not limited to 2,6-dichlorophenyl, 2,6-dibromophenyl, 2,6-dimethylphenyl, 2,6-di-tert-butylphenyl, and 2,6-diisopropylphenyl. In some embodiments, $R^1$ is not 2,6-dichlorophenyl. In some embodiments, $R^1$ is not —$C_6F_5$. In some embodiments, $R^1$ is not 2,6-dichlorophenyl or —$C_6F_5$. In some embodiments, $R^1$ is substituted phenyl, wherein at least one substituent is an electron-withdrawing group. In some embodiments, $R^1$ is substituted with at least one $R^y$ group. In some embodiments, a substituent is a small group such as halogen. In some embodiments, each substituent at the 2'- and 6'-positions, if any, is a small group such as halogen.

In some embodiments, $R^1$ is R', wherein R' is not hydrogen.

In some embodiments, $R^1$ is optionally substituted

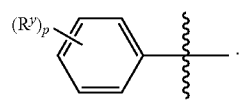

In some embodiments, $R^1$ is

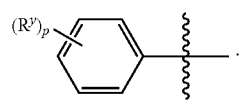

In some embodiments, $R^1$ is

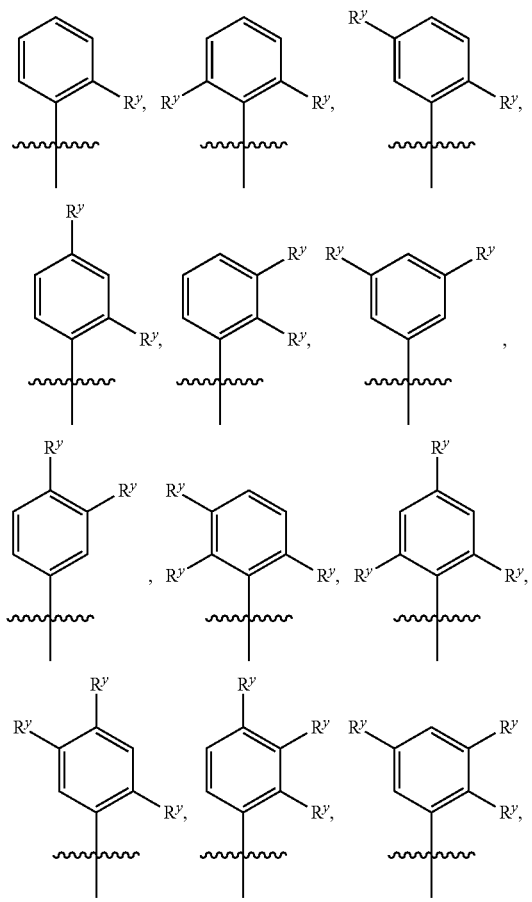

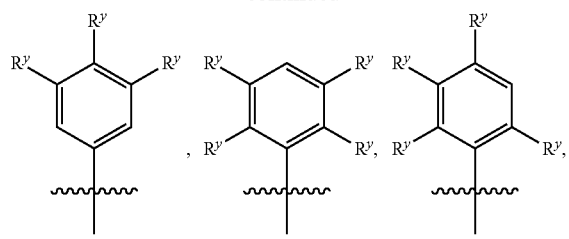

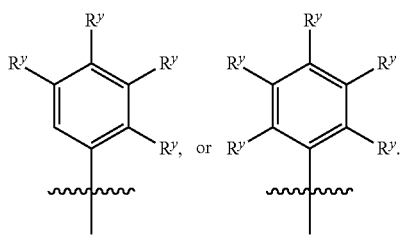

In some embodiments, at least one $R^y$ is halogen or —CF$_3$. In some embodiments, at least one $R^y$ is —F. In some embodiments, at least one $R^y$ is —CF$_3$. In some embodiments, each $R^y$ is —F. In some embodiments, $R^1$ is other than

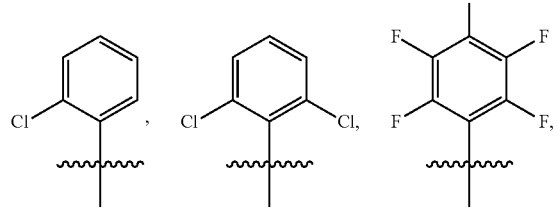

In some embodiments, $R^1$ is other than

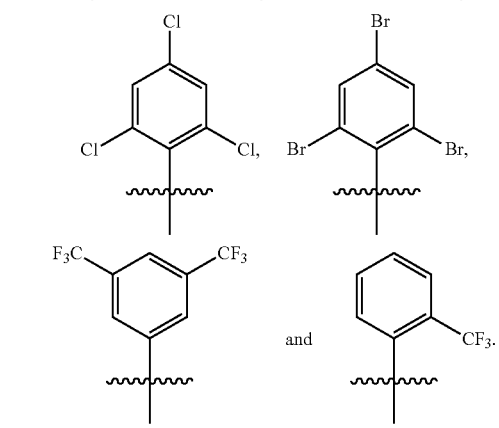

In some embodiments, $R^1$ is other than

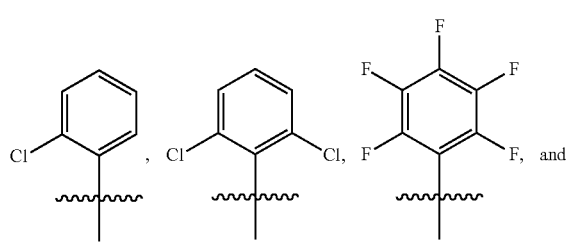

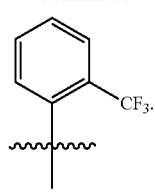

In some embodiments, $R^1$ is other than

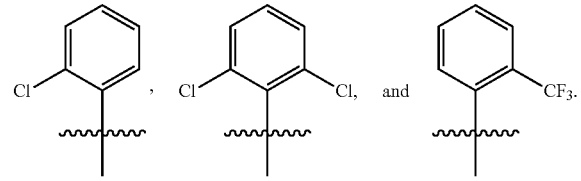

In some embodiments, $R^1$ is other than

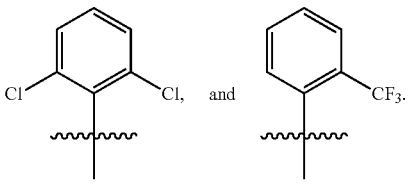 [SMILES: *c1c(Cl)cccc1Cl ; "and" ; *c1ccccc1C(F)(F)F]

In some embodiments, $R^1$ is other than

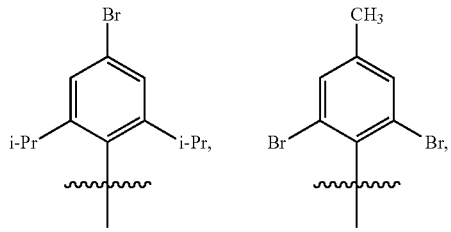

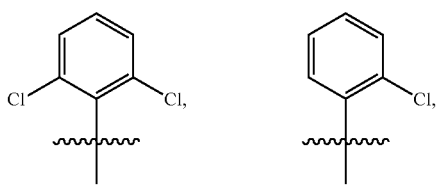

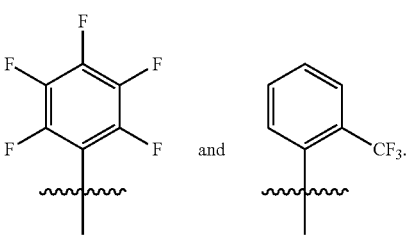

In some embodiments, $R^1$ is other than
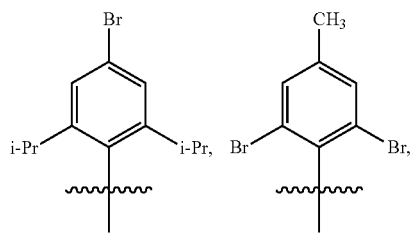
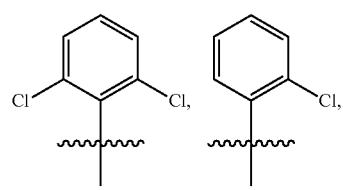
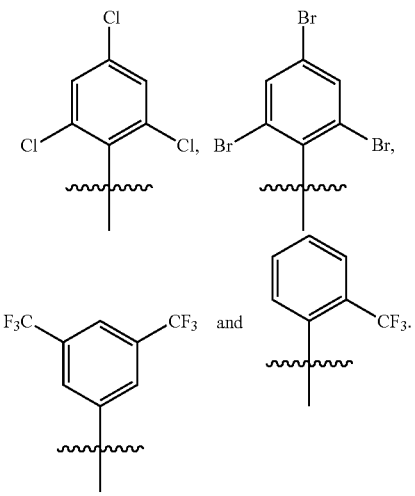
In some embodiments, $R^1$ is other than
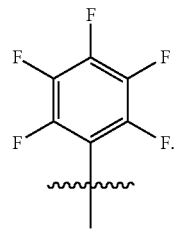
In some embodiments, $R^1$ is selected from:
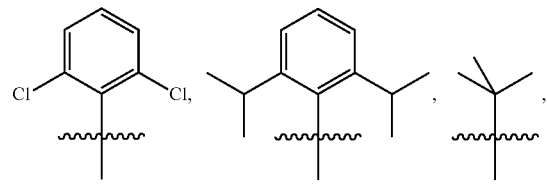
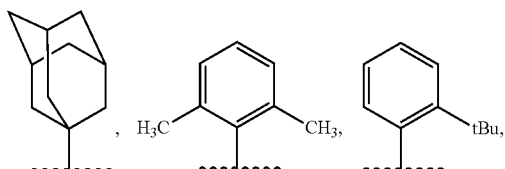
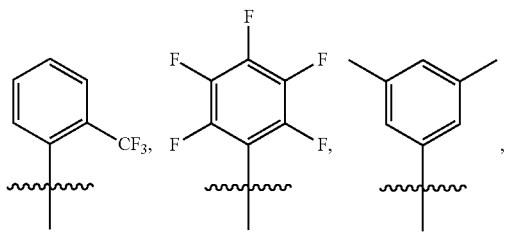
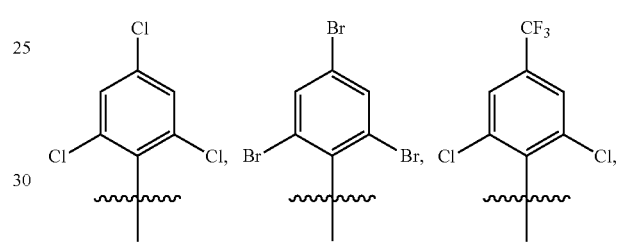
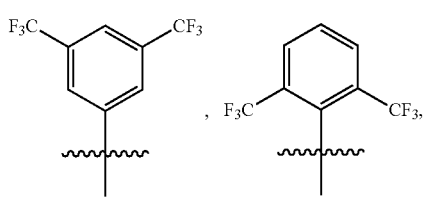
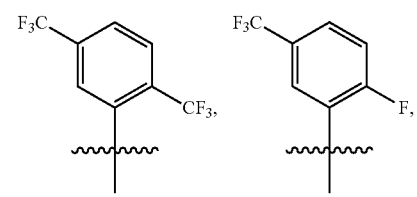
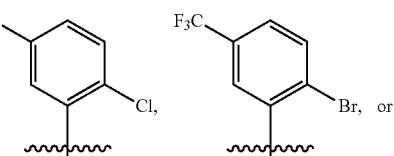
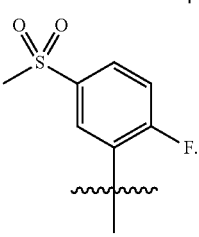

In some embodiments, $R^1$ is
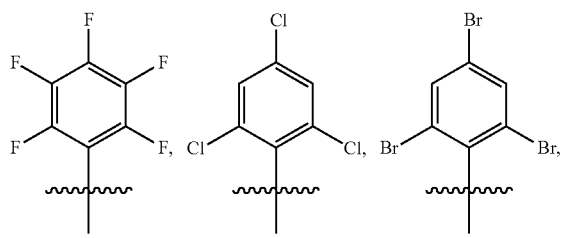
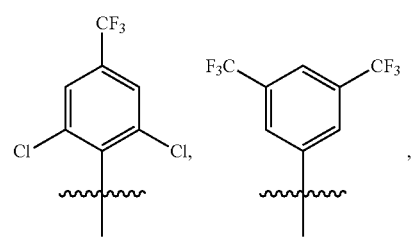
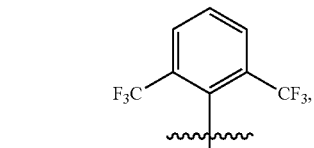
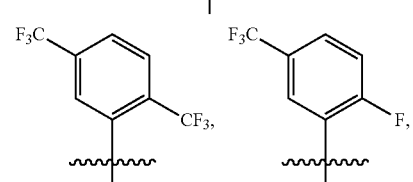
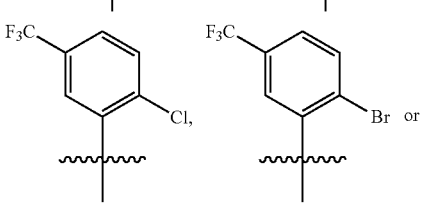
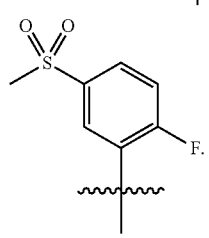
In some embodiments, $R^1$ is
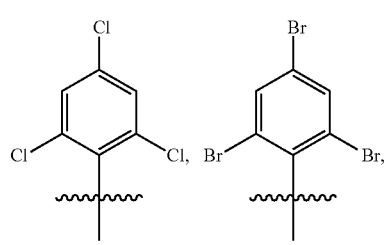
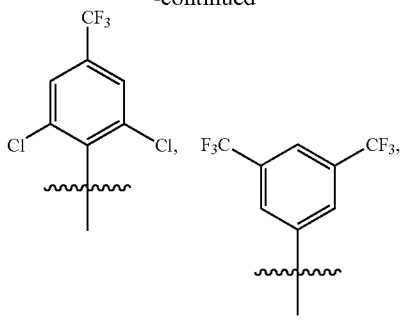
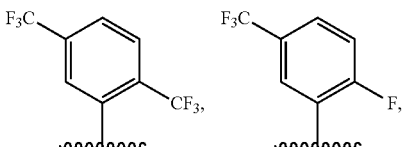
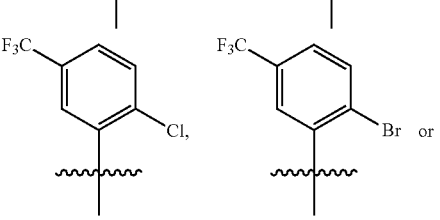
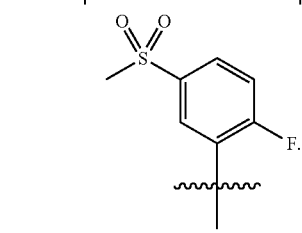
In some embodiments, $R^1$ is
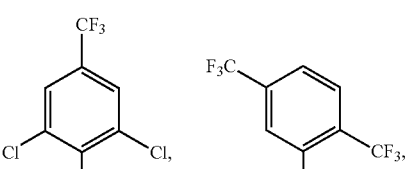
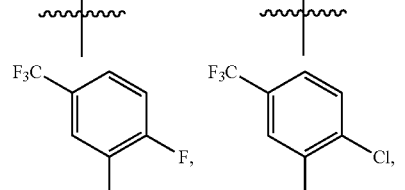
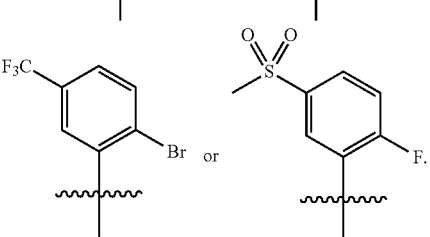

In some embodiments, $R^1$ is
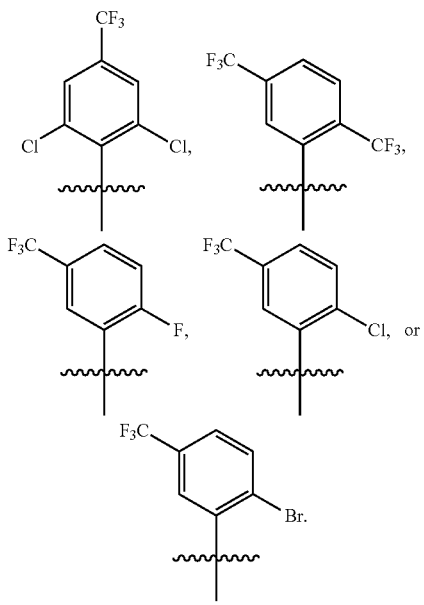
In some embodiments, $R^1$ is
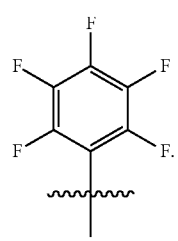
In some embodiments, $R^1$ is
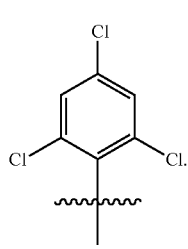 [SMILES: *c1c(Br)cc(Br)cc1Br]
In some embodiments, $R^1$ is
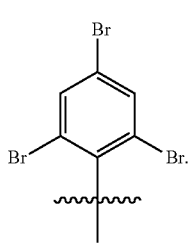
In some embodiments, $R^1$ is
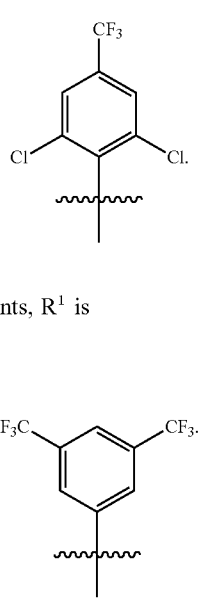
In some embodiments, $R^1$ is
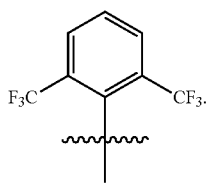
In some embodiments, $R^1$ is
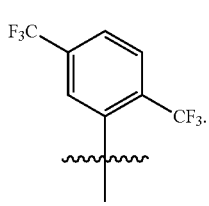
In some embodiments, $R^1$ is
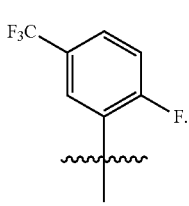

In some embodiments, R¹ is

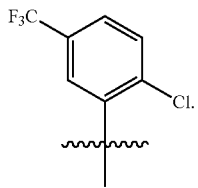 [SMILES: *c1cc(C(F)(F)F)ccc1Br]

In some embodiments, R¹ is

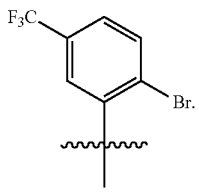

In some embodiments, R¹ is

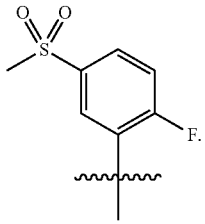 [SMILES: *c1cc(S(C)(=O)=O)ccc1F]

In some embodiments, R¹ is an optionally substituted $C_{1-20}$ aliphatic, wherein R¹ is a tertiary substituent, or R¹ is substituted phenyl wherein at least one substituent is an electron-withdrawing group. In some embodiments, R¹ is an optionally substituted $C_{1-20}$ aliphatic, wherein R¹ is a tertiary substituent, or R¹ is substituted phenyl wherein at least one substituent is an electron-withdrawing group selected from halogen and optionally substituted $C_{1-6}$ haloalkyl. In some embodiments, R¹ is an optionally substituted tertiary $C_{4-20}$ aliphatic, or R¹ is substituted phenyl wherein at least one substituent is an electron-withdrawing group selected from —F and optionally substituted $C_{1-6}$ perfluoroalkyl. In some embodiments, R¹ is an optionally substituted $C_{1-20}$ aliphatic, wherein R¹ is a tertiary substituent, or R¹ is substituted phenyl wherein each substituent is independently an electron-withdrawing group. In some embodiments, R¹ is an optionally substituted $C_{1-20}$ aliphatic, wherein R¹ is a tertiary substituent, or R¹ is substituted phenyl wherein each substituent is independently an electron-withdrawing group selected from halogen and optionally substituted $C_{1-6}$ haloalkyl. In some embodiments, R¹ is an optionally substituted tertiary $C_{4-20}$ aliphatic, or R¹ is substituted phenyl wherein each substituent is independently an electron-withdrawing group selected from —F and optionally substituted $C_{1-6}$ perfluoroalkyl. In some embodiments, R¹ is an optionally substituted adamantyl, or R¹ is substituted phenyl wherein each substituent is independently an electron-withdrawing group selected from —F and optionally substituted $C_{1-6}$ perfluoroalkyl. In some embodiments, R¹ is optionally substituted adamantyl, or substituted phenyl comprising one or more electron-withdrawing substituents, wherein each electron-withdrawing substituent is independently halogen or substituted $C_{1-6}$ alkyl comprising one or more halogen. In some embodiments, R¹ is substituted phenyl comprising one or more electron-withdrawing substituents, wherein each electron-withdrawing substituent is independently halogen or substituted $C_{1-6}$ alkyl comprising one or more halogen. In some embodiments, each electron-withdrawing substituent is independently halogen or $C_{1-6}$ haloalkyl. In some embodiments, each electron-withdrawing substituent is independently —F or $C_{1-6}$ fluoroalkyl. In some embodiments, each electron-withdrawing substituent is independently —F or $C_{1-6}$ perfluoroalkyl.

As defined generally above, each of R² and R³ is independently R', —OR', —SR', —N(R')₂, —OC(O)R', —SOR', —SO₂R', —SO₂N(R')₂, —C(O)N(R')₂, —NR'C(O)R', or —NR'SO₂R', provided that R² and R³ are not simultaneously hydrogen.

In some embodiments, one of R² and R³ is hydrogen and the other is an optionally substituted group selected from $C_{1-6}$ aliphatic, phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 4-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-10 membered bicyclic heteroaryl ring having 1-5 heteroatoms independently selected from nitrogen, oxygen, or sulfur, —OR', —SR', —N(R')₂, —OC(O)R', —SOR', —SO₂R', —SO₂N(R')₂, —C(O)N(R')₂, —NR'C(O)R', or —NR'SO₂R'. In some embodiments, one of R² and R³ is hydrogen and the other is an optionally substituted group selected from $C_{1-6}$ aliphatic, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 4-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-10 membered bicyclic heteroaryl ring having 1-5 heteroatoms independently selected from nitrogen, oxygen, or sulfur.

In certain embodiments, R² or R³ is optionally substituted $C_{1-6}$ aliphatic. In some embodiments, R² or R³ is optionally substituted $C_{1-6}$ alkyl. In certain embodiments, R² or R³ is $C_{1-6}$ alkyl substituted with phenyl and one or two additional substituents. In certain embodiments, R² or R³ is a lower alkyl group optionally substituted with one or two methyl groups and phenyl. In certain embodiments, R² or R³ is —C(Me)₂Ph. In certain embodiments, R² or R³ is —C(Me)₃.

In some embodiments, each of R² and R³ is independently R', wherein at least one of R² and R³ is not hydrogen.

In certain embodiments, R² is hydrogen and R³ is R', —OR', —SR', —N(R')₂, —OC(O)R', —SOR', —SO₂R', —SO₂N(R')₂, —C(O)N(R')₂, —NR'C(O)R', or —NR'SO₂R', wherein each R' is independently as defined above and described herein. In certain embodiments, R² is hydrogen and R³ is R', wherein R' is as defined above and described herein. In certain embodiments, R² is hydrogen and R³ is optionally substituted $C_{1-20}$ aliphatic. In some embodiments, R² is hydrogen and R³ is optionally substituted $C_{1-20}$ alkyl. In certain embodiments, R² is hydrogen and R³ is $C_{1-6}$ alkyl substituted with phenyl and one or two additional substituents. In certain embodiments, R² is hydrogen and R³ is a lower alkyl group optionally substituted with one or two methyl groups and phenyl. In certain embodiments, R² is hydrogen and R³ is —C(Me)₂Ph. In certain embodiments, R² is hydrogen and R³ is —C(Me)₃.

In some embodiments, R⁴ is R⁷. In some embodiments, R⁴ is R⁷, wherein R⁷ is optionally substituted phenyl. In some embodiments, R⁴ is R⁷, wherein R⁷ is Ar':

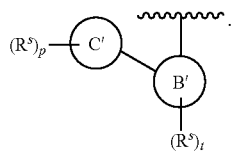

In some embodiments, p is 0-6. In some embodiments, p is 0-5. In some embodiments, p is 1-5. In some embodiments, p is 1. In some embodiments, p is 2. In some embodiments, p is 3. In some embodiments, p is 4. In some embodiments, p is 5. In some embodiments, p is 6. In some embodiments, p is 2 or 3.

In some embodiments, t is 0. In some embodiments, t is 1-4. In some embodiments, t is 1. In some embodiments, t is 2. In some embodiments, t is 3. In some embodiments, t is 4. In some embodiments, t is 0-2. In some embodiments, t is 0-3.

In some embodiments, Ring B' is optionally substituted phenyl.

In some embodiments, Ring B' is an optionally substituted 3-7 membered saturated carbocyclic ring. In some embodiments, Ring B' is an optionally substituted 5-6 membered saturated carbocyclic ring. In some embodiments, Ring B' is an optionally substituted 3-7 membered partially unsaturated carbocyclic ring. In some embodiments, Ring B' is an optionally substituted 5-6 membered partially unsaturated carbocyclic ring.

In some embodiments, Ring B' is an optionally substituted 8-10 membered bicyclic saturated carbocyclic ring. In some embodiments, Ring B' is an optionally substituted 8-10 membered bicyclic partially unsaturated carbocyclic ring. In some embodiments, Ring B' is an optionally substituted 8-10 membered bicyclic aryl ring.

In some embodiments, Ring B' is an optionally substituted 5-6 membered monocyclic heteroaryl ring having 1-4 heteroatoms independently selected from nitrogen, oxygen, or sulfur. In some embodiments, Ring B' is an optionally substituted 5-6 membered monocyclic heteroaryl ring having 1-2 heteroatoms independently selected from nitrogen, oxygen, or sulfur.

In some embodiments, Ring B' is an optionally substituted 5 membered monocyclic heteroaryl ring having 1-4 heteroatoms independently selected from nitrogen, oxygen, or sulfur. In some embodiments, Ring B' is an optionally substituted 5 membered monocyclic heteroaryl ring having 1-2 heteroatoms independently selected from nitrogen, oxygen, or sulfur.

In some embodiments, Ring B' is an optionally substituted 6 membered monocyclic heteroaryl ring having 1-4 heteroatoms independently selected from nitrogen, oxygen, or sulfur. In some embodiments, Ring B' is an optionally substituted 6 membered monocyclic heteroaryl ring having 1-2 heteroatoms independently selected from nitrogen, oxygen, or sulfur.

In some embodiments, Ring B' is an optionally substituted 3-7 membered saturated heterocyclic ring having 1-3 heteroatoms independently selected from nitrogen, oxygen, or sulfur. In some embodiments, Ring B' is an optionally substituted 5-6 membered saturated heterocyclic ring having 1-2 heteroatoms independently selected from nitrogen, oxygen, or sulfur.

In some embodiments, Ring B' is an optionally substituted 3-7 membered partially unsaturated heterocyclic ring having 1-3 heteroatoms independently selected from nitrogen, oxygen, or sulfur. In some embodiments, Ring B' is an optionally substituted 5-6 membered partially unsaturated heterocyclic ring having 1-2 heteroatoms independently selected from nitrogen, oxygen, or sulfur.

In some embodiments, Ring B' is an optionally substituted 7-10 membered bicyclic saturated heterocyclic ring having 1-5 heteroatoms independently selected from nitrogen, oxygen, or sulfur. In some embodiments, Ring B' is an optionally substituted 8-10 membered bicyclic saturated heterocyclic ring having 1-2 heteroatoms independently selected from nitrogen, oxygen, or sulfur.

In some embodiments, Ring B' is an optionally substituted 7-10 membered bicyclic partially unsaturated heterocyclic ring having 1-5 heteroatoms independently selected from nitrogen, oxygen, or sulfur. In some embodiments, Ring B' is an optionally substituted 8-10 membered bicyclic partially unsaturated heterocyclic ring having 1-2 heteroatoms independently selected from nitrogen, oxygen, or sulfur.

In some embodiments, Ring B' is an optionally substituted 8-14 membered bicyclic or tricyclic heteroaryl ring having 1-5 heteroatoms independently selected from nitrogen, oxygen, or sulfur. In some embodiments, Ring B' is an optionally substituted 8-10 membered bicyclic heteroaryl ring having 1-5 heteroatoms independently selected from nitrogen, oxygen, or sulfur. In some embodiments, Ring B' is an optionally substituted 8 membered bicyclic heteroaryl ring having 1-3 heteroatoms independently selected from nitrogen, oxygen, or sulfur. In some embodiments, Ring B' is an optionally substituted 9 membered bicyclic heteroaryl ring having 1-3 heteroatoms independently selected from nitrogen, oxygen, or sulfur.

In some embodiments, Ring B' is an optionally substituted 10 membered bicyclic heteroaryl ring having 1-3 heteroatoms independently selected from nitrogen, oxygen, or sulfur. In some embodiments, Ring B' is a 10-14 membered tricyclic heteroaryl ring having 1-5 heteroatoms independently selected from nitrogen, oxygen, or sulfur.

In some embodiments, Ring B' is an optionally substituted group selected from:

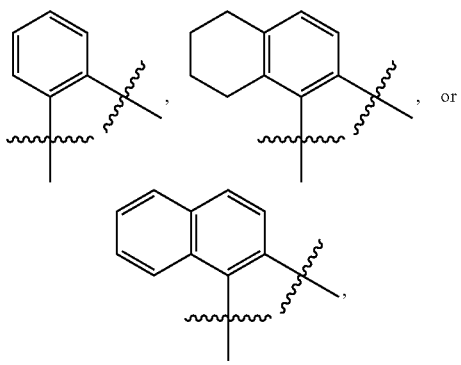

wherein each ⸹ independently represents the point of attachment to Ring C' or oxygen, and Ring B' is optionally substituted with 0-4 R$^s$.

In some embodiments, Ring C' is optionally substituted phenyl.

In some embodiments, Ring C' is an optionally substituted group selected from:

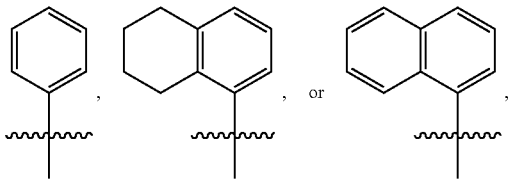

wherein each ⟊ represents the point of attachment to Ring B'; wherein Ring C' is optionally substituted with 0-6 R$^s$; and wherein each of Ring B' and R$^s$ is independently as defined above and described herein.

In some embodiments, Ring C" is optionally substituted

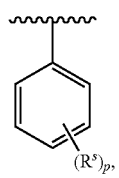

wherein R$^s$ and p is independently as defined above and described herein.

In certain embodiments, Ring C' is of the following formula:

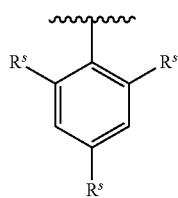

wherein each R$^s$ is independently as defined above and described herein.

In certain embodiments, Ring C' is of the following structure:

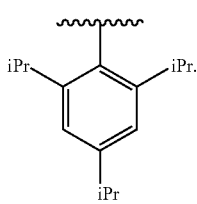 [SMILES: *c1c(C(C)C)cc(C(C)C)cc1C(C)C]

In some embodiments, Ring C' is an optionally substituted a 3-7 membered saturated carbocyclic ring. In some embodiments, Ring C' is an optionally substituted a 5-6 membered saturated carbocyclic ring. In some embodiments, Ring C' is an optionally substituted a 3-7 membered partially unsaturated carbocyclic ring. In some embodiments, Ring C' is an optionally substituted a 5-6 membered partially unsaturated carbocyclic ring.

In some embodiments, Ring C' is an optionally substituted 8-10 membered bicyclic saturated carbocyclic ring. In some embodiments, Ring C' is an optionally substituted 8-10 membered bicyclic partially unsaturated carbocyclic ring. In some embodiments, Ring C' is an optionally substituted 10 membered bicyclic aryl ring.

In some embodiments, Ring C' is an optionally substituted 5-6 membered monocyclic heteroaryl ring having 1-4 heteroatoms independently selected from nitrogen, oxygen, or sulfur. In some embodiments, Ring C' is an optionally substituted 5-6 membered monocyclic heteroaryl ring having 1-2 heteroatoms independently selected from nitrogen, oxygen, or sulfur.

In some embodiments, Ring C' is an optionally substituted 5 membered monocyclic heteroaryl ring having 1-4 heteroatoms independently selected from nitrogen, oxygen, or sulfur. In some embodiments, Ring C' is an optionally substituted 5 membered monocyclic heteroaryl ring having 1-2 heteroatoms independently selected from nitrogen, oxygen, or sulfur.

In some embodiments, Ring C' is an optionally substituted 6 membered monocyclic heteroaryl ring having 1-4 heteroatoms independently selected from nitrogen, oxygen, or sulfur. In some embodiments, Ring C' is an optionally substituted 6 membered monocyclic heteroaryl ring having 1-2 heteroatoms independently selected from nitrogen, oxygen, or sulfur.

In some embodiments, Ring C' is an optionally substituted 4-7 membered saturated heterocyclic ring having 1-3 heteroatoms independently selected from nitrogen, oxygen, or sulfur. In some embodiments, Ring C' is an optionally substituted 5-6 membered saturated heterocyclic ring having 1-2 heteroatoms independently selected from nitrogen, oxygen, or sulfur.

In some embodiments, Ring C' is an optionally substituted 4-7 membered partially unsaturated heterocyclic ring having 1-3 heteroatoms independently selected from nitrogen, oxygen, or sulfur. In some embodiments, Ring C' is an optionally substituted 5-6 membered partially unsaturated heterocyclic ring having 1-2 heteroatoms independently selected from nitrogen, oxygen, or sulfur.

In some embodiments, Ring C' is an optionally substituted 7-10 membered bicyclic saturated heterocyclic ring having 1-5 heteroatoms independently selected from nitrogen, oxygen, or sulfur. In some embodiments, Ring C' is an optionally substituted 8-10 membered bicyclic saturated heterocyclic ring having 1-2 heteroatoms independently selected from nitrogen, oxygen, or sulfur.

In some embodiments, Ring C' is an optionally substituted 7-10 membered bicyclic partially unsaturated heterocyclic ring having 1-5 heteroatoms independently selected from nitrogen, oxygen, or sulfur. In some embodiments, Ring C' is an optionally substituted 8-10 membered bicyclic partially unsaturated heterocyclic ring having 1-2 heteroatoms independently selected from nitrogen, oxygen, or sulfur.

In some embodiments, Ring C' is an optionally substituted 8-10 membered bicyclic heteroaryl ring having 1-5 heteroatoms independently selected from nitrogen, oxygen, or sulfur. In some embodiments, Ring C' is an optionally substituted 8 membered bicyclic heteroaryl ring having 1-3 heteroatoms independently selected from nitrogen, oxygen, or sulfur.

In some embodiments, Ring C' is an optionally substituted 9 membered bicyclic heteroaryl ring having 1-3 heteroatoms independently selected from nitrogen, oxygen, or sulfur. In some embodiments, Ring C' is an optionally substituted 10 membered bicyclic heteroaryl ring having 1-3 heteroatoms independently selected from nitrogen, oxygen, or sulfur.

In some embodiments, each $R^s$ is independently halogen, R', —OR', —SR', —S(O)R', —S(O)$_2$R', —OSi(R')$_3$, —N(R')$_2$, —NR'C(O)R', —NR'C(O)OR', —NR'C(O)N(R')$_2$, —NR'SO$_2$R', —NR'SO$_2$N(R')$_2$, or —NR'OR', wherein each R' is independently as defined above and described herein.

In some embodiments, $R^s$ is hydrogen. In some embodiments, $R^s$ is halogen. In some embodiments, $R^s$ is —F. In some embodiments, $R^s$ is —Cl. In some embodiments, $R^s$ is —Br. In some embodiments, $R^s$ is —I.

In some embodiments, $R^s$ is R'. In some embodiments, $R^s$ is optionally substituted $C_{1-6}$ aliphatic. In some embodiments, $R^s$ is optionally substituted $C_{1-6}$ aliphatic, wherein $R^s$ comprises one or more halogen. In some embodiments, $R^s$ is optionally substituted $C_{1-6}$ aliphatic, wherein $R^s$ comprises one or more —F. In some embodiments, $R^s$ is $C_{1-6}$ perfluoroaliphatic. In some embodiments, $R^s$ is $C_{1-6}$ perfluoroalkyl. In some embodiments, $R^s$ is —CF$_3$. In some embodiments, $R^s$ is optionally substituted $C_{1-6}$ alkyl. In some embodiments, $R^s$ is optionally substituted linear $C_{1-6}$ alkyl. In some embodiments, $R^s$ is optionally substituted branched $C_{1-6}$ alkyl. In some embodiments, $R^s$ is optionally substituted phenyl. In some embodiments, $R^s$ is phenyl. In some embodiments, $R^s$ is optionally substituted 8-10 membered bicyclic aryl. In some embodiments, $R^s$ is optionally substituted naphthyl. In some embodiments, $R^s$ is optionally substituted 1-naphthyl. In some embodiments, $R^s$ is optionally substituted 2-naphthyl. In some embodiments, $R^s$ is 1-substituted naphthyl. In some embodiments, $R^s$ is 2-substituted naphthyl. In some embodiments, $R^s$ is optionally substituted 5-6 membered monocyclic heteroaryl ring having 1-4 heteroatoms independently selected from nitrogen, oxygen, or sulfur. In some embodiments, $R^s$ is optionally substituted 8-10 membered bicyclic heteroaryl. In some embodiments, $R^s$ is an optionally substituted 4-7 membered saturated or partially unsaturated heterocyclic ring having 1-3 heteroatoms independently selected from nitrogen, oxygen, or sulfur. In some embodiments, $R^s$ is an optionally substituted 7-10 membered bicyclic saturated or partially unsaturated heterocyclic ring having 1-5 heteroatoms independently selected from nitrogen, oxygen, or sulfur. In some embodiments, $R^s$ is selected from —SR', —S(O)R', —S(O)$_2$R', wherein each R' is independently as defined above and described herein.

In certain embodiments, at least one $R^s$ is independently halogen. In certain embodiments, at least one $R^s$ is independently —F. In certain embodiments, at least one $R^s$ is independently —Cl. In certain embodiments, at least one $R^s$ is independently —Br. In certain embodiments, at least one $R^s$ is independently —I.

In certain embodiments, at least one $R^s$ is independently selected from R', —OR', —SR', —S(O)R', —S(O)$_2$R', —OSi(R')$_3$, or —N(R')$_2$, —NR'C(O)R', —NR'C(O)OR', —NR'C(O)N(R')$_2$, —NR'SO$_2$R', —NR'SO$_2$N(R')$_2$, or —NR'OR', wherein each R' is independently as defined above and described herein.

In certain embodiments, at least one $R^s$ is R', wherein R' is as defined above and described herein. In some embodiments, at least one $R^s$ is optionally substituted $C_{1-6}$ aliphatic. In some embodiments, at least one $R^s$ is optionally substituted $C_{1-6}$ alkyl. In some embodiments, at least one $R^s$ is optionally substituted $C_{1-6}$ haloalkyl. In some embodiments, at least one $R^s$ is optionally substituted $C_{1-6}$ haloalkyl, wherein one substituent is —F. In some embodiments, at least one $R^s$ is optionally substituted $C_{1-6}$ haloalkyl, wherein two or more substituents are —F. In certain embodiments, at least one $R^s$ is selected from methyl, ethyl, propyl, or butyl. In certain embodiments, at least one $R^s$ is isopropyl. In certain embodiments, at least one $R^s$ is —CF$_3$.

In some embodiments, at least one $R^s$ is hydrogen or an optionally substituted group selected from $C_{1-6}$ aliphatic, phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 4-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-10 membered bicyclic heteroaryl ring having 1-5 heteroatoms independently selected from nitrogen, oxygen, or sulfur.

In some embodiments, at least one $R^s$ is —OSi(R')$_3$, wherein each R' is independently as defined above and described herein.

In some embodiments, at least one $R^s$ is —OR', wherein each R' is independently as defined above and described herein.

In some embodiments, at least one $R^s$ is selected from —SR', —S(O)R', —S(O)$_2$R', wherein each R' is independently as defined above and described herein.

In some embodiments, $R^4$ is optionally substituted Ar, wherein Ar is of the following structure:

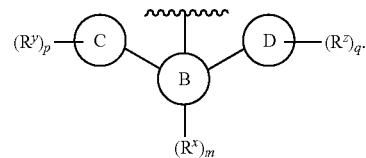

As generally defined above, m is 0-3. In some embodiments, m is 0. In some embodiments, m is 1-3. In some embodiments, m is 1. In some embodiments, m is 2. In some embodiments, m is 3. In some embodiments, m is 0-2.

In some embodiments, q is 0-6. In some embodiments, q is 0-5. In some embodiments, q is 1-5. In some embodiments, q is 1. In some embodiments, q is 2. In some embodiments, q is 3. In some embodiments, q is 4. In some embodiments, q is 5. In some embodiments, q is 6. In some embodiments, q is 2 or 3.

In some embodiments, p=q. In some embodiments, p=q=2. In some embodiments, p=q=3.

As generally defined above, Ring B is an optionally substituted group selected from phenyl or a 5-6 membered monocyclic heteroaryl ring having 1-4 heteroatoms independently selected from nitrogen, oxygen, or sulfur. In some embodiments, Ring B is of the following structure:

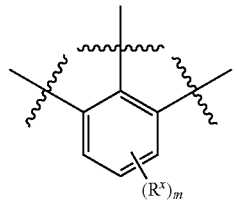

wherein $R^x$ and m are as defined above and described herein. In some embodiments, Ring B is optionally substituted phenyl. In some embodiments, m=0. In some embodiments, Ring B is

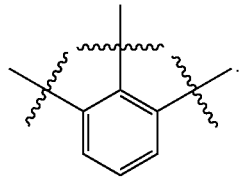 [SMILES: *c1cccc(*)c1*]

In some embodiments, Ring B is an optionally substituted 5-6 membered monocyclic heteroaryl ring having 1-4 heteroatoms independently selected from nitrogen, oxygen, or sulfur. In some embodiments, Ring B is an optionally substituted 5-membered monocyclic heteroaryl ring having 1-4 heteroatoms independently selected from nitrogen, oxygen, or sulfur, and m is 0-2. In some embodiments, Ring B is an optionally substituted 6-membered monocyclic heteroaryl ring having 1-4 heteroatoms independently selected from nitrogen, oxygen, or sulfur, and m is 0-3.

In some embodiments, Ring B is a 5-6 membered monocyclic heteroaryl ring having 1-4 heteroatoms independently selected from nitrogen, oxygen, or sulfur. In some embodiments, Ring B is a 5-6 membered monocyclic heteroaryl ring having 1-2 heteroatoms independently selected from nitrogen, oxygen, or sulfur.

In some embodiments, Ring B is a 5-membered monocyclic heteroaryl ring having 1-4 heteroatoms independently selected from nitrogen, oxygen, or sulfur. In some embodiments, Ring B is a 5-membered monocyclic heteroaryl ring having 1-2 heteroatoms independently selected from nitrogen, oxygen, or sulfur.

In some embodiments, Ring B is a 6-membered monocyclic heteroaryl ring having 1-4 heteroatoms independently selected from nitrogen, oxygen, or sulfur. In some embodiments, Ring B is a 6-membered monocyclic heteroaryl ring having 1-2 heteroatoms independently selected from nitrogen, oxygen, or sulfur.

Exemplary optionally substituted Ring B heteroaryl groups include thienylene, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, and the like.

In some embodiments, $R^x$ is $R^s$. In some embodiments, each $R^x$ is independently halogen, —OR', —N(R')$_2$, —NR' C(O)R', —NR' C(O)OR', —NR' C(O)N(R')$_2$, —NR'SO$_2$R', —NR'SO$_2$N(R')$_2$, —NR'OR', or an optionally substituted group selected from $C_{1-20}$ aliphatic and $C_{1-20}$ heteroaliphatic having 1-3 heteroatoms independently selected from nitrogen, oxygen, or sulfur.

In certain embodiments, $R^x$ is halogen. In some embodiments, $R^x$ is —F. In some embodiments, $R^x$ is —Cl. In some embodiments, $R^x$ is —Br. In some embodiments, $R^x$ is —I.

In certain embodiments, $R^x$ is independently selected from —OR', —N(R')$_2$, —NR' C(O)R', —NR' C(O)OR', —NR' C(O)N(R')$_2$, —NR'SO$_2$R', —NR'SO$_2$N(R')$_2$, —NR'OR'.

In certain embodiments, $R^x$ is optionally substituted $C_{1-20}$ aliphatic. In certain embodiments, $R^x$ is optionally substituted $C_{1-10}$ aliphatic. In certain embodiments, $R^x$ is optionally substituted $C_{1-5}$ aliphatic. In certain embodiments, $R^x$ is alkyl. In certain embodiments, $R^x$ is selected from methyl, ethyl, propyl, or butyl. In some embodiments, $R^x$ is methyl. In some embodiments, $R^x$ is ethyl. In some embodiments, $R^x$ is optionally substituted n-alkyl. In some embodiments, $R^x$ is optionally substituted isoalkyl. In certain embodiments, $R^x$ is isopropyl. In some embodiments, $R^x$ is optionally substituted tertiary aliphatic. In some embodiments, $R^x$ is optionally substituted tertiary alkyl. In some embodiments, $R^x$ is t-butyl. In some embodiments, $R^x$ is adamantyl.

In some embodiments, $R^x$ is optionally substituted cycloalkyl. In some embodiments, $R^x$ is optionally substituted heteroaliphatic. In some embodiments, $R^x$ is optionally substituted heterocyclyl.

In some embodiments, $R^x$ is substituted, and at least one substituent is halogen.

In some embodiments, $R^x$ is substituted $C_{1-20}$ aliphatic and $C_{1-20}$ heteroaliphatic, wherein one or more substituent are independently halogen. In some embodiments, $R^x$ is —CF$_3$. In some embodiments, $R^x$ is —C$_2$F$_5$. In some embodiments, $R^x$ is substituted linear, branched or cyclic aliphatic or heteroaliphatic, wherein one or more substituents are independently halogen.

In certain embodiments, $R^x$ is optionally substituted $C_{1-20}$ heteroaliphatic having 1-3 heteroatoms independently selected from nitrogen, oxygen, or sulfur.

In some embodiments, $R^x$ is optionally substituted phenyl. In some embodiments, $R^x$ is phenyl.

In some embodiments, Ring C is optionally substituted phenyl. In some embodiments, Ring C is substituted phenyl comprising a 2'-substituent. In some embodiments, Ring C is substituted phenyl comprising a 6'-substituent. In some embodiments, Ring C is substituted phenyl comprising a 2'- and a 6'-substituent. In some embodiments, Ring C is 2'- and 6'-substituted phenyl. In some embodiments, Ring C is substituted phenyl comprising a 4'-substituent. In some embodiments, Ring C is substituted phenyl comprising a 2'-, a 4'- and a 6'-substituent. In some embodiments, Ring C is 2'-, 4'- and 6'-substituted phenyl. In some embodiments, Ring C is substituted phenyl comprising a 3'-substituent. In some embodiments, Ring C is substituted phenyl comprising a 5'-substituent. In some embodiments, Ring C is substituted phenyl comprising a 3'- and a 5'-substituent. In some embodiments, Ring C is 3'- and 5'-substituted phenyl. In some embodiments, each substituent is independently an optionally substituted $C_{1-6}$ alkyl. In some embodiments, a substituent is a primary substituent, e.g., methyl, ethyl, trifluoromethyl, etc. In some embodiments, each substituent is a primary substituent. In some embodiments, a substituent is a secondary substituent, e.g., isopropyl, etc. In some embodiments, each substituent is a secondary substituent. In some embodiments, a substituent is a tertiary substituent, e.g., tert-butyl, etc. In some embodiments, each substituent is a tertiary substituent. In some embodiments, each substituent is independently an unsubstituted $C_{1-6}$ alkyl. In some embodiments, each substituent is independently an unsubstituted linear $C_{1-6}$ alkyl. In some embodiments, each substituent is methyl. In some embodiments, each substituent is ethyl. In some embodiments, each substituent is independently an unsubstituted branched $C_{1-6}$ alkyl. In some embodiments, each substituent is isopropyl. In some embodiments, each substituent is tert-butyl. In some embodiments, each substituent on Ring C is the same.

In some embodiments, Ring C is 2'- and 6'-substituted phenyl, wherein each of the 2'- and 6'-substituents is independently $C_{1-6}$ alkyl. In some embodiments, Ring C is 2'- and 6'-substituted phenyl, wherein each of the 2'- and 6'-substituents is methyl. In some embodiments, Ring C is 2'- and 6'-substituted phenyl, wherein each of the 2'- and 6'-substituents is ethyl. In some embodiments, Ring C is 2'- and 6'-substituted phenyl, wherein each of the 2'- and 6'-substituents is isopropyl. In some embodiments, Ring C is 2'-, 4'- and 6'-substituted phenyl, wherein each of the 2'-, 4'- and 6'-substituents is independently $C_{1-6}$ alkyl. In some embodiments, Ring C is 2'-, 4'- and 6'-substituted phenyl, wherein each of the 2'-, 4'- and 6'-substituents is methyl. In some embodiments, Ring C is 2'-, 4'- and 6'-substituted phenyl, wherein each of the 2'-, 4'- and 6'-substituents is ethyl. In some embodiments, Ring C is 2'-, 4'- and 6'-substituted phenyl, wherein each of the 2'-, 4'- and 6'-substituents is isopropyl. In some embodiments, Ring C is 3'- and 5'-substituted phenyl, wherein each of the 3'- and 5'-substituents is independently $C_{1-6}$ alkyl. In some embodiments, Ring C is 3'- and 5'-substituted phenyl, wherein each of the 3'- and 5'-substituents is independently tertiary $C_{1-6}$ alkyl. In some embodiments, Ring C is 3'- and 5'-substituted phenyl, wherein each of the 3'- and 5'-substituents is independently tert-butyl.

In some embodiments, Ring C is 2,4,6-trimethylphenyl. In some embodiments, Ring C is 2,4,6-triethylphenyl. In some embodiments, Ring C is 2,4,6-triisopropylphenyl. In some embodiments, Ring C is 3,5-di(tert-butyl)phenyl.

In some embodiments, Ring C is an optionally substituted group selected from phenyl, an 8-10 membered bicyclic aryl ring, a 5-6 membered monocyclic heteroaryl ring having 1-4 heteroatoms independently selected from nitrogen, oxygen, or sulfur, or an 8-10 membered bicyclic heteroaryl ring having 1-5 heteroatoms independently selected from nitrogen, oxygen, or sulfur. In some embodiments, Ring C is an optionally substituted group selected from phenyl or an 8-10 membered bicyclic aryl ring. In some embodiments, Ring C is optionally substituted phenyl. In some embodiments, Ring C is optionally substituted 8-10 membered bicyclic aryl. In some embodiments, Ring C is optionally substituted naphthyl. In some embodiments, Ring C is optionally substituted 1-naphthyl. In some embodiments, Ring C is 1-naphthyl. In some embodiments, Ring C is optionally substituted 2-naphthyl. In some embodiments, Ring C is 2-naphthyl.

In some embodiments, Ring C is an optionally substituted 3-7 membered saturated or partially unsaturated carbocyclic ring. In some embodiments, Ring C is an optionally substituted 8-10 membered bicyclic saturated, partially unsaturated or aryl ring. In some embodiments, Ring C is an optionally substituted 5-6 membered monocyclic heteroaryl ring having 1-4 heteroatoms independently selected from nitrogen, oxygen, or sulfur. In some embodiments, Ring C is an optionally substituted 4-7 membered saturated or partially unsaturated heterocyclic ring having 1-3 heteroatoms independently selected from nitrogen, oxygen, or sulfur. In some embodiments, Ring C is an optionally substituted 7-10 membered bicyclic saturated or partially unsaturated heterocyclic ring having 1-5 heteroatoms independently selected from nitrogen, oxygen, or sulfur. In some embodiments, Ring C is an optionally substituted 8-10 membered bicyclic heteroaryl ring having 1-5 heteroatoms independently selected from nitrogen, oxygen, or sulfur.

In some embodiments, $R^y$ is $R^s$. In some embodiments, each $R^y$ is independently halogen, —OR', —N(R')$_2$, —NR' C(O)R', —NR' C(O)OR', —NR' C(O)N(R')$_2$, —NR'SO$_2$R', —NR'SO$_2$N(R')$_2$, —NR'OR', or an optionally substituted group selected from $C_{1-20}$ aliphatic and $C_{1-20}$ heteroaliphatic having 1-3 heteroatoms independently selected from nitrogen, oxygen, or sulfur.

In certain embodiments, $R^y$ is halogen. In some embodiments, $R^y$ is —F. In some embodiments, $R^y$ is —Cl. In some embodiments, $R^y$ is —Br. In some embodiments, $R^y$ is —I.

In certain embodiments, $R^y$ is independently selected from —OR', —N(R')$_2$, —NR' C(O)R', —NR' C(O)OR', —NR' C(O)N(R')$_2$, —NR'SO$_2$R', —NR'SO$_2$N(R')$_2$, —NR'OR'.

In certain embodiments, $R^y$ is optionally substituted $C_{1-20}$ aliphatic. In certain embodiments, $R^y$ is optionally substituted $C_{1-10}$ aliphatic. In certain embodiments, $R^y$ is optionally substituted $C_{1-5}$ aliphatic. In certain embodiments, $R^y$ is alkyl. In certain embodiments, $R^y$ is selected from methyl, ethyl, propyl, or butyl. In some embodiments, $R^y$ is optionally substituted primary $C_{1-6}$ alkyl. In some embodiments, $R^y$ is methyl. In some embodiments, $R^y$ is ethyl. In some embodiments, $R^y$ is optionally substituted n-alkyl. In some embodiments, $R^y$ is optionally substituted secondary $C_{1-6}$ alkyl. In some embodiments, $R^y$ is optionally substituted isoalkyl. In certain embodiments, $R^y$ is isopropyl. In some embodiments, $R^y$ is optionally substituted tertiary aliphatic. In some embodiments, $R^y$ is optionally substituted tertiary $C_{1-6}$ alkyl. In some embodiments, $R^y$ is t-butyl. In some embodiments, $R^y$ is adamantyl.

In some embodiments, $R^y$ is optionally substituted cycloalkyl. In some embodiments, $R^y$ is optionally substituted heteroaliphatic. In some embodiments, $R^y$ is optionally substituted heterocyclyl.

In some embodiments, $R^y$ is substituted, and at least one substituent is halogen. In some embodiments, $R^y$ is substituted $C_{1-20}$ aliphatic and $C_{1-20}$ heteroaliphatic, wherein one or more substituent are independently halogen. In some embodiments, $R^y$ is —CF$_3$. In some embodiments, $R^y$ is —C$_2$F$_5$. In some embodiments, $R^y$ is substituted linear, branched or cyclic aliphatic or heteroaliphatic, wherein one or more substituents are independently halogen.

In certain embodiments, $R^y$ is optionally substituted $C_{1-20}$ heteroaliphatic having 1-3 heteroatoms independently selected from nitrogen, oxygen, or sulfur.

In some embodiments, $R^y$ is $C_{1-20}$ aliphatic, or heteroaliphatic having 1-3 heteroatoms independently selected from nitrogen, oxygen, or sulfur, optionally substituted with one or more halogen. In some embodiments, $R^y$ is $C_{1-10}$ aliphatic, or heteroaliphatic having 1-3 heteroatoms independently selected from nitrogen, oxygen, or sulfur, optionally substituted with one or more halogen. In some embodiments, $R^y$ is $C_{1-6}$ aliphatic, or heteroaliphatic having 1-3 heteroatoms independently selected from nitrogen, oxygen, or sulfur, optionally substituted with one or more halogen. In some embodiments, $R^y$ is $C_{1-20}$ aliphatic optionally substituted with one or more halogen. In some embodiments, $R^y$ is $C_{1-10}$ aliphatic optionally substituted with one or more halogen. In some embodiments, $R^y$ is $C_{1-6}$ aliphatic optionally substituted with one or more halogen.

In some embodiments, $R^y$ is an electron-withdrawing group. In some embodiments, each $R^y$ is independently an electron-withdrawing group. In some embodiments, $R^y$ is halogen or optionally substituted $C_{1-20}$ aliphatic. In some embodiments, $R^y$ is halogen or substituted $C_{1-20}$ aliphatic, wherein one or more substituent is halogen. In some embodiments, $R^y$ is halogen or substituted $C_{1-10}$ aliphatic, wherein one or more substituent is halogen. In some embodiments, $R^y$ is halogen. In some embodiments, $R^y$ is —F. In some embodiments, $R^y$ is —Cl. In some embodiments, $R^y$ is —Br. In some embodiments, $R^y$ is —I. In some embodiments, $R^y$ is halogen or substituted $C_{1-20}$ aliphatic, wherein one or more substituent is halogen. In some embodiments, $R^y$ is halogen or substituted $C_{1-10}$ aliphatic, wherein one or more substituent is halogen. In some embodiments, $R^y$ is $C_{1-10}$ perhaloalkyl. In some embodiments, $R^y$ is $C_{1-10}$ perfluoroalkyl. In some embodiments, $R^y$ is —$CF_3$. In some embodiments, $R^y$ is —$C_2F_5$.

In some embodiments, each $R^y$ is independently halogen or substituted $C_{1-10}$ aliphatic, wherein one or more substituent is halogen. In some embodiments, each $R^y$ is independently halogen or $C_{1-10}$ perhaloalkyl. In some embodiments, each $R^y$ is independently halogen or $C_{1-10}$ perfluoroalkyl. In some embodiments, each $R^y$ is independently halogen. In some embodiments, each $R^y$ is —F. In some embodiments, each $R^y$ is independently perfluoroalkyl.

In some embodiments, each $R^y$ is identical. In some embodiments, each $R^y$ is different. In some embodiments, two, three, four or five $R^y$ are identical, and optionally different from another $R^y$.

In some embodiments, $R^y$ is optionally substituted phenyl. In some embodiments, $R^y$ is phenyl.

In some embodiments,

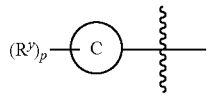

is 2,4,6-trimethylphenyl. In some embodiments,

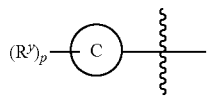

is 2,4,6-triethylphenyl. In some embodiments,

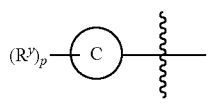

is 2,4,6-triisopropylphenyl. In some embodiments,

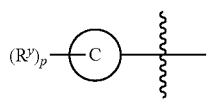

is 3,5-di(tert-butyl)phenyl. In some embodiments,

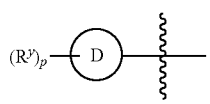

is phenyl. In some embodiments,

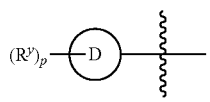

is naphthyl. In some embodiments,

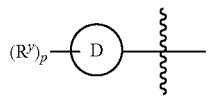

is 1-naphthyl. In some embodiments,

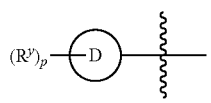

is 2-naphthyl. In some embodiments,

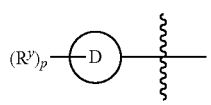

is 4-(tert-butyl)phenyl. In some embodiments,

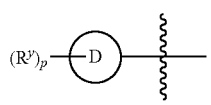

is 3,5-dimethphenyl. In some embodiments

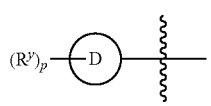

is 3,5-diphenylphenyl.

In some embodiments, Ring D is optionally substituted phenyl. In some embodiments, Ring D is substituted phenyl comprising a 2'-substituent. In some embodiments, Ring D is substituted phenyl comprising a 6'-substituent. In some embodiments, Ring D is substituted phenyl comprising a 2'- and a 6'-substituent. In some embodiments, Ring D is 2'- and 6'-substituted phenyl. In some embodiments, Ring D is substituted phenyl comprising a 4'-substituent. In some embodiments, Ring D is substituted phenyl comprising a 2'-, a 4'- and a 6'-substituent. In some embodiments, Ring D is 2'-, 4'- and 6'-substituted phenyl. In some embodiments, Ring D is substituted phenyl comprising a 3'-substituent. In some embodiments, Ring D is substituted phenyl comprising a 5'-substituent. In some embodiments, Ring D is substituted phenyl comprising a 3'- and a 5'-substituent. In some embodiments, Ring D is 3'- and 5'-substituted phenyl. In some embodiments, each substituent is independently an optionally substituted $C_{1-6}$ alkyl. In some embodiments, a substituent is a primary substituent, e.g., methyl, ethyl, trifluoromethyl, etc. In some embodiments, each substituent is a primary substituent. In some embodiments, a substituent is a secondary substituent, e.g., isopropyl, etc. In some embodiments, each substituent is a secondary substituent. In some embodiments, a substituent is a tertiary substituent, e.g., tert-butyl, etc. In some embodiments, each substituent is a tertiary substituent. In some embodiments, each substituent is independently an unsubstituted $C_{1-6}$ alkyl. In some embodiments, each substituent is independently an unsubstituted linear $C_{1-6}$ alkyl. In some embodiments, each substituent is methyl. In some embodiments, each substituent is ethyl. In some embodiments, each substituent is independently an unsubstituted branched $C_{1-6}$ alkyl. In some embodiments, each substituent is isopropyl. In some embodiments, each substituent is tert-butyl. In some embodiments, each substituent on Ring D is the same.

In some embodiments, Ring D is 2'- and 6'-substituted phenyl, wherein each of the 2'- and 6'-substituents is independently $C_{1-6}$ alkyl. In some embodiments, Ring D is 2'- and 6'-substituted phenyl, wherein each of the 2'- and 6'-substituents is methyl. In some embodiments, Ring D is 2'- and 6'-substituted phenyl, wherein each of the 2'- and 6'-substituents is ethyl. In some embodiments, Ring D is 2'- and 6'-substituted phenyl, wherein each of the 2'- and 6'-substituents is isopropyl. In some embodiments, Ring D is 2'-, 4'- and 6'-substituted phenyl, wherein each of the 2'-, 4'- and 6'-substituents is independently $C_{1-6}$ alkyl. In some embodiments, Ring D is 2'-, 4'- and 6'-substituted phenyl, wherein each of the 2'-, 4'- and 6'-substituents is methyl. In some embodiments, Ring D is 2'-, 4'- and 6'-substituted phenyl, wherein each of the 2'-, 4'- and 6'-substituents is ethyl. In some embodiments, Ring D is 2'-, 4'- and 6'-substituted phenyl, wherein each of the 2'-, 4'- and 6'-substituents is isopropyl. In some embodiments, Ring D is 3'- and 5'-substituted phenyl, wherein each of the 3'- and 5'-substituents is independently $C_{1-6}$ alkyl. In some embodiments, Ring D is 3'- and 5'-substituted phenyl, wherein each of the 3'- and 5'-substituents is independently tertiary $C_{1-6}$ alkyl. In some embodiments, Ring D is 3'- and 5'-substituted phenyl, wherein each of the 3'- and 5'-substituents is independently tert-butyl.

In some embodiments, Ring D is 2,4,6-trimethylphenyl. In some embodiments, Ring D is 2,4,6-triethylphenyl. In some embodiments, Ring D is 2,4,6-triisopropylphenyl. In some embodiments, Ring D is 3,5-di(tert-butyl)phenyl.

In some embodiments, Ring D is an optionally substituted group selected from phenyl, an 8-10 membered bicyclic aryl ring, a 5-6 membered monocyclic heteroaryl ring having 1-4 heteroatoms independently selected from nitrogen, oxygen, or sulfur, or an 8-10 membered bicyclic heteroaryl ring having 1-5 heteroatoms independently selected from nitrogen, oxygen, or sulfur. In some embodiments, Ring D is an optionally substituted group selected from phenyl or an 8-10 membered bicyclic aryl ring. In some embodiments, Ring D is optionally substituted phenyl. In some embodiments, Ring D is optionally substituted 8-10 membered bicyclic aryl. In some embodiments, Ring D is optionally substituted naphthyl. In some embodiments, Ring D is optionally substituted 1-naphthyl. In some embodiments, Ring D is 1-naphthyl. In some embodiments, Ring D is optionally substituted 2-naphthyl. In some embodiments, Ring D is 2-naphthyl.

In some embodiments, Ring D is an optionally substituted 3-7 membered saturated or partially unsaturated carbocyclic ring. In some embodiments, Ring D is an optionally substituted 8-10 membered bicyclic saturated, partially unsaturated or aryl ring. In some embodiments, Ring D is an optionally substituted 5-6 membered monocyclic heteroaryl ring having 1-4 heteroatoms independently selected from nitrogen, oxygen, or sulfur. In some embodiments, Ring D is an optionally substituted 4-7 membered saturated or partially unsaturated heterocyclic ring having 1-3 heteroatoms independently selected from nitrogen, oxygen, or sulfur. In some embodiments, Ring D is an optionally substituted 7-10 membered bicyclic saturated or partially unsaturated heterocyclic ring having 1-5 heteroatoms independently selected from nitrogen, oxygen, or sulfur. In some embodiments, Ring D is an optionally substituted 8-10 membered bicyclic heteroaryl ring having 1-5 heteroatoms independently selected from nitrogen, oxygen, or sulfur.

In some embodiments, $R^z$ is $R^s$. In some embodiments, each $R^z$ is independently halogen, —OR', —N(R')$_2$, —NR' C(O)R', —NR' C(O)OR', —NR' C(O)N(R')$_2$, —NR'SO$_2$R', —NR'SO$_2$N(R')$_2$, —NR'OR', or an optionally substituted group selected from $C_{1-20}$ aliphatic and $C_{1-20}$ heteroaliphatic having 1-3 heteroatoms independently selected from nitrogen, oxygen, or sulfur.

In certain embodiments, $R^z$ is halogen. In some embodiments, $R^z$ is —F. In some embodiments, $R^z$ is —Cl. In some embodiments, $R^z$ is —Br. In some embodiments, $R^z$ is —I.

In certain embodiments, $R^z$ is independently selected from —OR', —N(R')$_2$, —NR' C(O)R', —NR' C(O)OR', —NR' C(O)N(R')$_2$, —NR'SO$_2$R', —NR'SO$_2$N(R')$_2$, —NR'OR'.

In certain embodiments, $R^z$ is optionally substituted $C_{1-20}$ aliphatic. In certain embodiments, $R^z$ is optionally substituted $C_{1-10}$ aliphatic. In certain embodiments, $R^z$ is optionally substituted $C_{1-5}$ aliphatic. In certain embodiments, $R^z$ is alkyl. In certain embodiments, $R^z$ is selected from methyl, ethyl, propyl, or butyl. In some embodiments, $R^y$ is optionally substituted primary $C_{1-6}$ alkyl. In some embodiments, $R^z$ is methyl. In some embodiments, $R^z$ is ethyl. In some embodiments, $R^z$ is optionally substituted n-alkyl. In some embodiments, $R^y$ is optionally substituted secondary $C_{1-6}$ alkyl. In some embodiments, $R^z$ is optionally substituted isoalkyl. In certain embodiments, $R^z$ is isopropyl. In some embodiments, $R^z$ is optionally substituted tertiary aliphatic. In some embodiments, $R^z$ is optionally substituted tertiary $C_{1-6}$ alkyl. In some embodiments, $R^z$ is t-butyl. In some embodiments, $R^z$ is adamantyl.

In some embodiments, $R^z$ is optionally substituted cycloalkyl. In some embodiments, $R^z$ is optionally substituted heteroaliphatic. In some embodiments, $R^z$ is optionally substituted heterocyclyl.

In some embodiments, $R^z$ is substituted, and at least one substituent is halogen. In some embodiments, $R^z$ is substituted $C_{1-20}$ aliphatic and $C_{1-20}$ heteroaliphatic, wherein one or more substituent are independently halogen. In some embodiments, $R^z$ is —CF$_3$. In some embodiments, $R^z$ is —C$_2$F$_5$. In some embodiments, $R^z$ is substituted linear, branched or cyclic aliphatic or heteroaliphatic, wherein one or more substituents are independently halogen.

In certain embodiments, $R^z$ is optionally substituted $C_{1-20}$ heteroaliphatic having 1-3 heteroatoms independently selected from nitrogen, oxygen, or sulfur.

In some embodiments, $R^z$ is optionally substituted phenyl. In some embodiments, $R^z$ is phenyl.

In some embodiments,

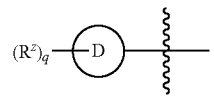

is 2,4,6-trimethylphenyl. In some embodiments,

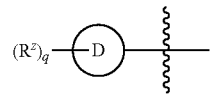

is 2,4,6-triethylphenyl. In some embodiments,

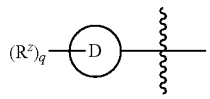

is 2,4,6-triisopropylphenyl. In some embodiments,

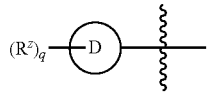

is 3,5-di(tert-butyl)phenyl. In some embodiments,

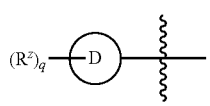

is phenyl. In some embodiments,

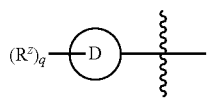

is naphthyl. In some embodiments,

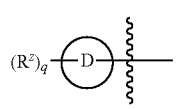

is 1-naphthyl. In some embodiments,

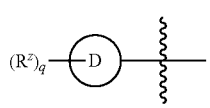

is 2-naphthyl. In some embodiments,

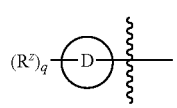

is 4-(tert-butyl)phenyl. In some embodiments,

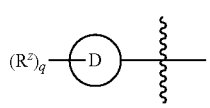

is 3,5-dimethylphenyl. In some embodiments,

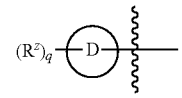

is 3,5-diphenylphenyl.

In some embodiments, each $R^x$ is identical. In some embodiments, each R is identical. In some embodiments, each $R^z$ is identical. In some embodiments, each of $R^y$ and $R^z$ is identical. In some embodiments, each of $R^x$, $R^y$ and $R^z$ is identical. In some embodiments, Ring C and Ring D are identical. In some embodiments,

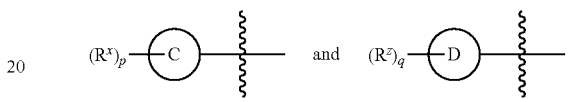

are identical.

In some embodiments, Ar is of the formula:

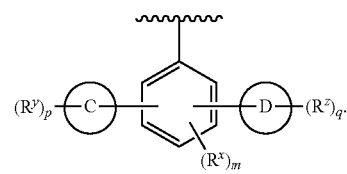

In some embodiments, Ar is of the formula:

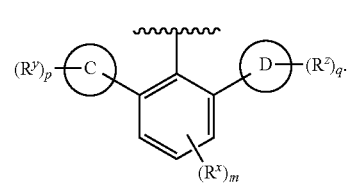

In some embodiments, Ar is of the formula:

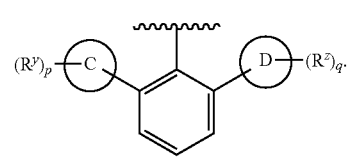

In some embodiments, Ar is of the formula:

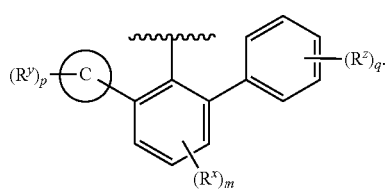

In some embodiments, Ar is of the formula:

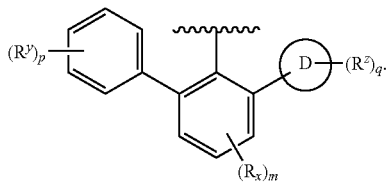

In some embodiments, Ar is of the formula:

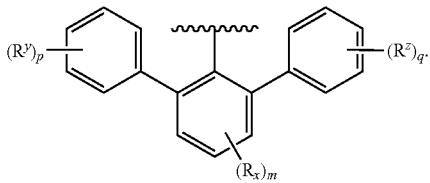

In some embodiments, Ar is of the formula:

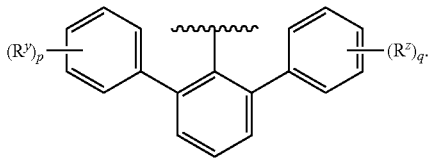

In some embodiments, Ar is of the formula:

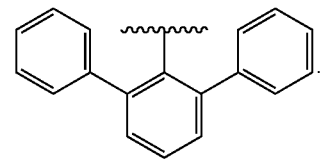 [SMILES: *c1c(-c2ccccc2)cccc1-c1ccccc1]

In some embodiments, Ar is of the formula:

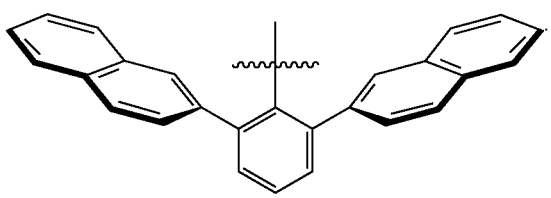

In some embodiments, Ar is of the formula

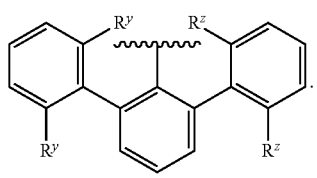

In some embodiments, Ar is of the formula

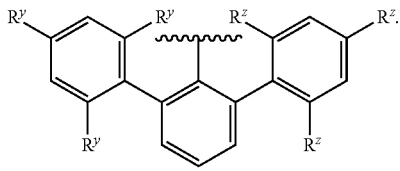

In certain embodiments wherein Ar is as depicted above, each $R^y$ and each $R^z$ is independently optionally substituted $C_{1-20}$ aliphatic. In certain embodiments wherein Ar is as depicted above, each $R^y$ and each $R^z$ is independently optionally substituted $C_{1-10}$ aliphatic. In certain embodiments wherein Ar is as depicted above, each $R^y$ and each $R^z$ is independently optionally substituted $C_{1-6}$ alkyl. In certain embodiments wherein Ar is as depicted above, each $R^y$ and each $R^z$ is independently optionally substituted primary or secondary $C_{1-6}$ alkyl. In certain embodiments wherein Ar is as depicted above, each $R^y$ and each $R^z$ is independently optionally substituted primary $C_{1-6}$ alkyl. In certain embodiments wherein Ar is as depicted above, each $R^y$ and each $R^z$ is independently optionally substituted secondary $C_{1-6}$ alkyl. In certain embodiments wherein Ar is as depicted above, each $R^y$ and each $R^z$ is independently unsubstituted primary or secondary $C_{1-6}$ alkyl. In certain embodiments wherein Ar is as depicted above, each $R^y$ and each $R^z$ is independently unsubstituted primary $C_{1-6}$ alkyl. In certain embodiments wherein Ar is as depicted above, each $R^y$ and each $R^z$ is independently unsubstituted secondary $C_{1-6}$ alkyl. Exemplary $R^y$ and $R^z$ groups include methyl, ethyl, propyl, and butyl. In some embodiments, each $R^y$ and each $R^z$ is methyl. In some embodiments, each $R^y$ and each $R^z$ is ethyl. In some embodiments, each $R^y$ and each $R^z$ is isopropyl.

In some embodiments, Ar is of the formula

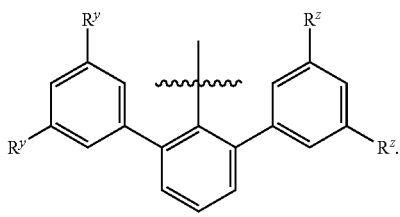

In certain embodiments wherein Ar is as depicted above, each $R^y$ and each $R^z$ is independently optionally substituted $C_{1-20}$ aliphatic. In certain embodiments wherein Ar is as depicted above, each $R^y$ and each $R^z$ is independently optionally substituted $C_{1-10}$ aliphatic. In certain embodiments wherein Ar is as depicted above, each $R^y$ and each $R^z$ is independently optionally substituted $C_{1-6}$ alkyl. In certain embodiments wherein Ar is as depicted above, each $R^y$ and each $R^z$ is independently optionally substituted primary or secondary $C_{1-6}$ alkyl. In certain embodiments wherein Ar is as depicted above, each $R^y$ and each $R^z$ is independently optionally substituted primary $C_{1-6}$ alkyl. In certain embodiments wherein Ar is as depicted above, each $R^y$ and each $R^z$ is independently optionally substituted secondary $C_{1-6}$ alkyl. In certain embodiments wherein Ar is as depicted above, each $R^y$ and each $R^z$ is independently unsubstituted primary or secondary $C_{1-6}$ alkyl. In certain embodiments wherein Ar is as depicted above, each $R^y$ and each $R^z$ is independently unsubstituted primary $C_{1-6}$ alkyl. In certain embodiments wherein Ar is as depicted above, each $R^y$ and each $R^z$ is independently unsubstituted secondary $C_{1-6}$ alkyl. Exemplary $R^y$ and $R^z$ groups include methyl, ethyl, propyl, and butyl. In some embodiments, each $R^y$ and each $R^z$ is methyl. In some embodiments, each $R^y$ and each $R^z$ is ethyl. In some embodiments, each $R^y$ and each $R^z$ is isopropyl.

In certain embodiments, Ar has the following structure:

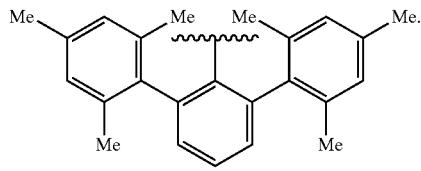 [SMILES: *c1c(-c2c(C)cc(C)cc2C)cccc1-c1c(C)cc(C)cc1C]

In certain embodiments, Ar has the following structure:

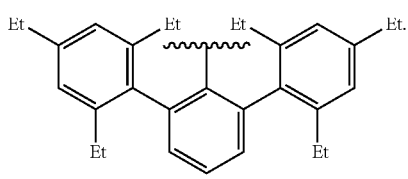 [SMILES: *c1c(-c2c(CC)cc(CC)cc2CC)cccc1-c1c(CC)cc(CC)cc1CC]

In certain embodiments, Ar has the following structure:

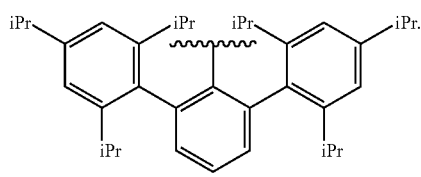 [SMILES: *c1c(-c2c(C(C)C)cc(C(C)C)cc2C(C)C)cccc1-c1c(C(C)C)cc(C(C)C)cc1C(C)C]

In certain embodiments, Ar has the following structure:

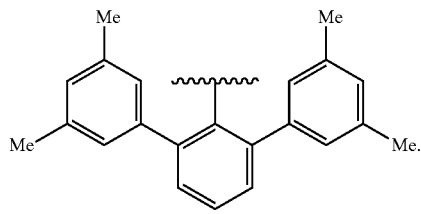 [SMILES: *c1c(-c2cc(C)cc(C)c2)cccc1-c1cc(C)cc(C)c1]

In certain embodiments, Ar has the following structure:

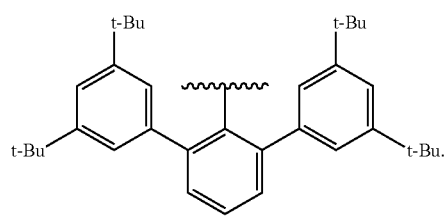 [SMILES: *c1c(-c2cc(C(C)(C)C)cc(C(C)(C)C)c2)cccc1-c1cc(C(C)(C)C)cc(C(C)(C)C)c1]

In certain embodiments, Ar has the following structure:

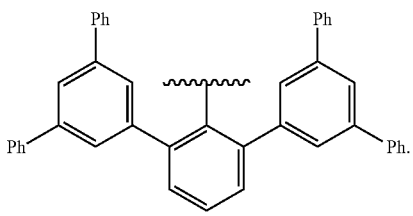 [SMILES: *c1c(-c2cc(-c3ccccc3)cc(-c3ccccc3)c2)cccc1-c1cc(-c2ccccc2)cc(-c2ccccc2)c1]

In certain embodiments, Ar has the following structure:

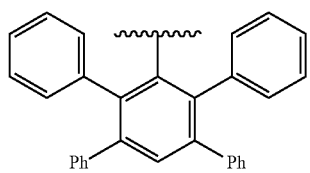

In certain embodiments, Ar has the following structure:

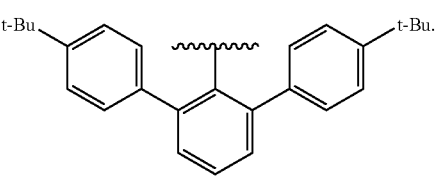 [SMILES: *c1c(-c2ccc(C(C)(C)C)cc2)cccc1-c1ccc(C(C)(C)C)cc1]

In some embodiments, $R^4$ is optionally substituted Ar, wherein Ar is

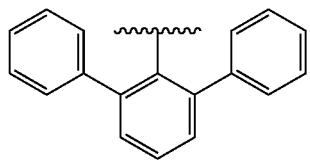

In some embodiments, $R^4$ is

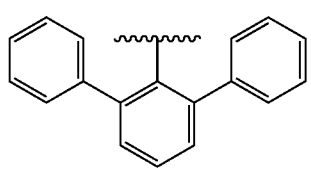

In some embodiments, $R^4$ is

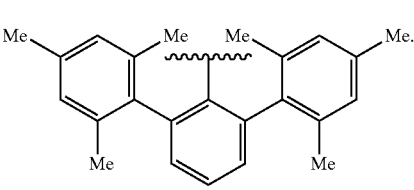 [SMILES: *c1c(-c2c(C)cc(C)cc2C)cccc1-c1c(C)cc(C)cc1C]

In some embodiments, R⁴ is

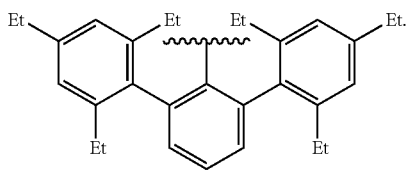 [SMILES: *c1c(-c2c(CC)cc(CC)cc2CC)cccc1-c1c(CC)cc(CC)cc1CC]

In some embodiments, R⁴ is

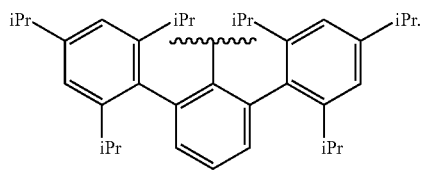 [SMILES: *c1c(-c2c(C(C)C)cc(C(C)C)cc2C(C)C)cccc1-c1c(C(C)C)cc(C(C)C)cc1C(C)C]

In some embodiments, R⁴ is

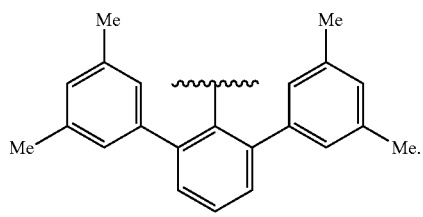 [SMILES: *c1c(-c2cc(C)cc(C)c2)cccc1-c1cc(C)cc(C)c1]

In some embodiments, R⁴ is

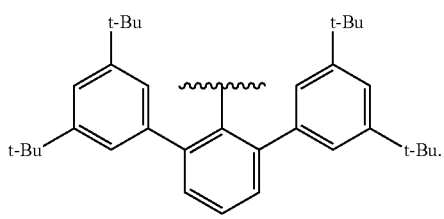

In some embodiments, R⁴ is

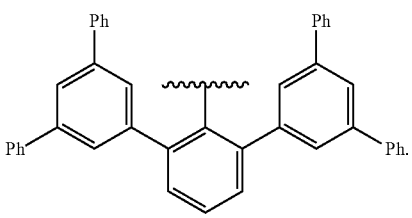 [SMILES: *c1c(-c2cc(-c3ccccc3)cc(-c3ccccc3)c2)cccc1-c1cc(-c2ccccc2)cc(-c2ccccc2)c1]

In some embodiments, R⁴ is

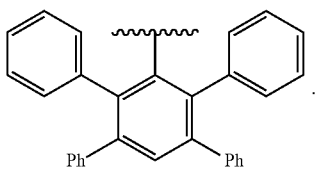 [SMILES: *c1c(-c2ccccc2)c(-c2ccccc2)cc(-c2ccccc2)c1-c1ccccc1]

In some embodiments, R⁴ is

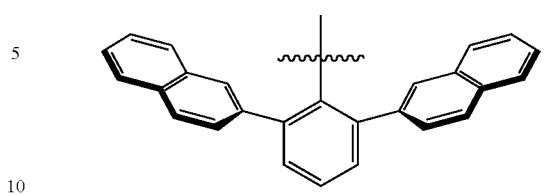

In some embodiments, R⁴ is

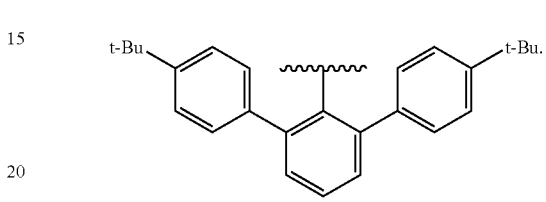

In some embodiments,

In some embodiments, R⁴ is optionally substituted $C_{1-20}$ aliphatic. In some embodiments, R⁴ is optionally substituted $C_{1-20}$ alkyl. In some embodiments, R⁴ is $C_{1-20}$ alkyl. In some embodiments, R⁴ is $C_{1-20}$ haloalkyl.

In some embodiments, R⁴ is optionally substituted $C_{1-20}$ heteroaliphatic having 1-3 heteroatoms independently selected from nitrogen, oxygen, or sulfur. In some embodiments, R⁴ is optionally substituted $C_{1-6}$ heteroaliphatic having 1-3 heteroatoms independently selected from nitrogen, oxygen, or sulfur.

In some embodiments, R⁴ is optionally substituted phenyl. In some embodiments, R⁴ is optionally substituted phenyl comprising a biphenyl moiety. In some embodiments, R⁴ is substituted phenyl comprising a 2'- and a 6'-substituent. In some embodiments, R⁴ is substituted phenyl comprising a 2'- and a 6'-substituent, each of which is independently a cyclic group. In some embodiments, R⁴ is substituted phenyl comprising a 2'- and a 6'-substituent, each of which is independently an aromatic group. In some embodiments, R⁴ is phenyl.

In some embodiments, R⁴ is an optionally substituted 3-7 membered saturated or partially unsaturated carbocyclic ring. In some embodiments, R⁴ is an optionally substituted 8-10 membered bicyclic saturated, partially unsaturated or aryl ring. In some embodiments, R⁴ is an optionally substituted 5-6 membered monocyclic heteroaryl ring having 1-4 heteroatoms independently selected from nitrogen, oxygen, or sulfur. In some embodiments, R⁴ is an optionally substituted 4-7 membered saturated or partially unsaturated heterocyclic ring having 1-3 heteroatoms independently selected from nitrogen, oxygen, or sulfur. In some embodiments, R⁴ is an optionally substituted 7-10 membered bicyclic saturated or partially unsaturated heterocyclic ring having 1-5 heteroatoms independently selected from nitrogen, oxygen, or sulfur. In some embodiments, R⁴ is an optionally substituted 8-14 membered bicyclic or tricyclic heteroaryl ring having 1-5 heteroatoms independently selected from nitrogen, oxygen, or sulfur.

In some embodiments, —OR⁴ is an optionally substituted group selected from:

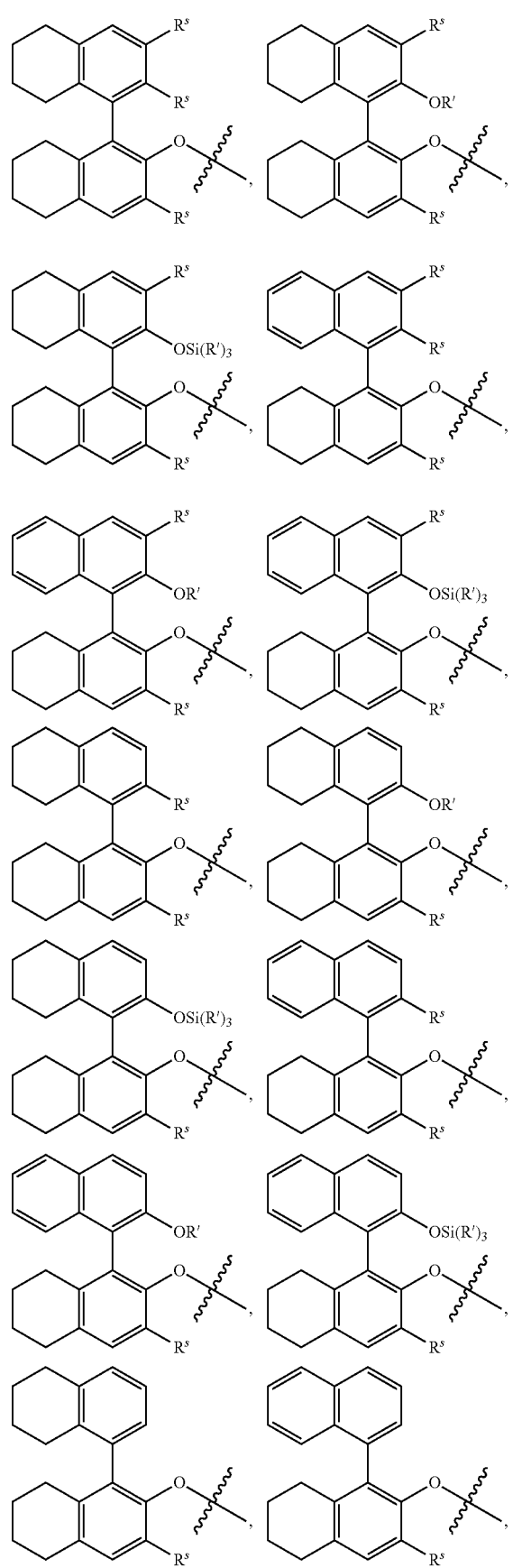
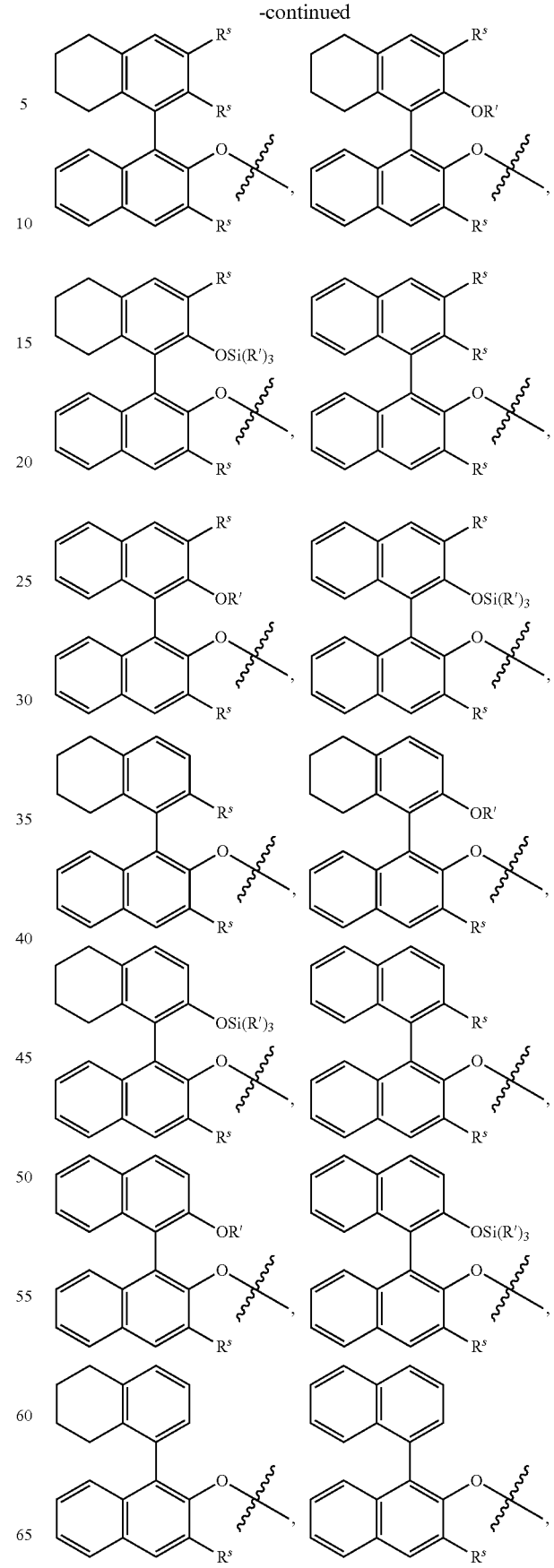

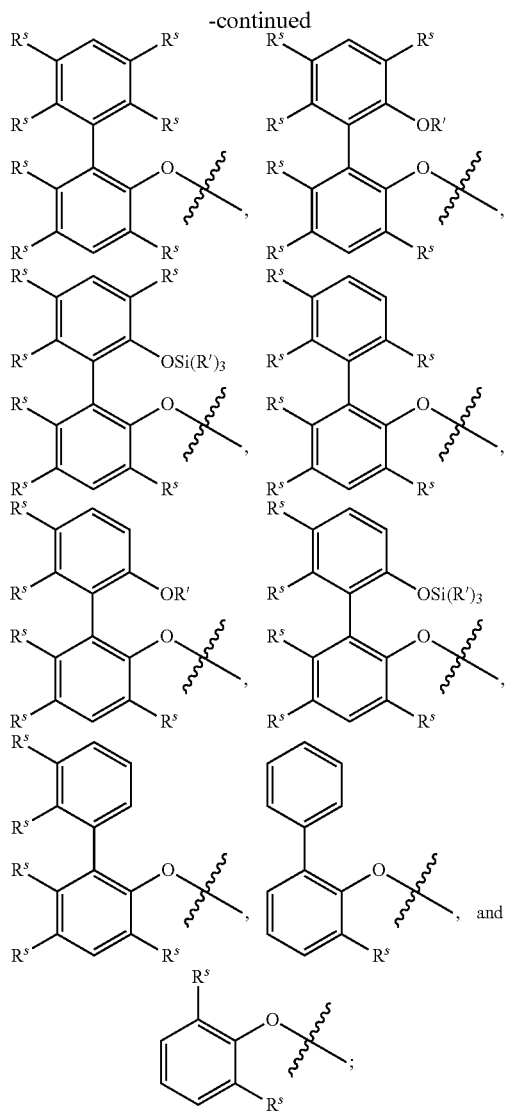

wherein each ⸺ represents the point of attachment to the metal, M, and each of $R^s$ and R' is independently as defined above and described herein. In some embodiments, $R^s$ at the o-position of the oxygen bonded to M is —Cl, —Br, —I, or R', wherein R' is not hydrogen.

In some embodiments, $R^s$ at the o-position of the oxygen bonded to M

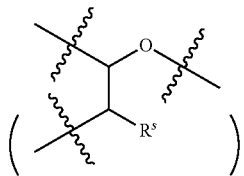

is —Cl, —Br, —I. In some embodiments, $R^s$ at the o-position of the oxygen bonded to M is —Cl. In some embodiments, $R^s$ at the o-position of the oxygen bonded to M is —Br. In some embodiments, $R^s$ at the o-position of the oxygen bonded to M is —I. In some embodiments, each $R^s$ at the o-position of the oxygen bonded to M is independently R', wherein R' is not hydrogen. In some embodiments, each $R^s$ at the o-position of the oxygen bonded to M is independently R', wherein R' is an optionally substituted cyclic group. In some embodiments, each $R^s$ at the o-position of the oxygen bonded to M is independently R', wherein R' is an optionally substituted aromatic group. In some embodiments, each $R^s$ at the o-position of the oxygen bonded to M is independently R', wherein R' is an optionally substituted tertiary group. In some embodiments, each $R^s$ at the o-position of the oxygen bonded to M is independently an optionally substituted group selected from phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 4-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-10 membered bicyclic heteroaryl ring having 1-5 heteroatoms independently selected from nitrogen, oxygen, or sulfur. In some embodiments, each $R^s$ at the o-position of the oxygen bonded to M is independently an optionally substituted group selected from phenyl, an 8-10 membered bicyclic aryl ring, a 5-6 membered monocyclic heteroaryl ring having 1-4 heteroatoms independently selected from nitrogen, oxygen, or sulfur, a 4-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-10 membered bicyclic heteroaryl ring having 1-5 heteroatoms independently selected from nitrogen, oxygen, or sulfur. In some embodiments, each $R^s$ at the o-position of the oxygen bonded to M is independently an optionally substituted group selected from phenyl, an 8-10 membered bicyclic aryl ring, a 5-6 membered monocyclic heteroaryl ring having 1-4 heteroatoms independently selected from nitrogen, oxygen, or sulfur, or an 8-10 membered bicyclic heteroaryl ring having 1-5 heteroatoms independently selected from nitrogen, oxygen, or sulfur. In some embodiments, each $R^s$ at the o-position of the oxygen bonded to M is independently optionally substituted phenyl. In some embodiments, each $R^s$ at the o-position of the oxygen bonded to M is independently optionally substituted 8-10 membered bicyclic aryl ring. In some embodiments, each $R^s$ at the o-position of the oxygen bonded to M is independently optionally substituted 1-naphthyl. In some embodiments, each $R^s$ at the o-position of the oxygen bonded to M is independently optionally substituted 2-naphthyl. In some embodiments, each $R^s$ at the o-position of the oxygen bonded to M is independently 1-substituted naphthyl. In some embodiments, each $R^s$ at the o-position of the oxygen bonded to M is independently 2-substituted naphthyl. In some embodiments, each $R^s$ at the o-position of the oxygen bonded to M is independently optionally substituted 5-6 membered monocyclic heteroaryl. In some embodiments, each $R^s$ at the o-position of the oxygen bonded to M is independently optionally substituted 4-7 membered saturated or partially unsaturated heterocyclyl. In some embodiments, each $R^s$ at the o-position of the oxygen bonded to M is independently optionally substituted 8-10 membered bicyclic heteroaryl. In some embodiments, each $R^s$ at the o-position of the oxygen bonded to M is independently optionally substituted 7-10 membered bicyclic saturated or partially unsaturated heterocyclyl. As understood by a person having ordinary in the art, an optionally substituted group, such as optionally substituted phenyl, can have one or two or more substituents. In some embodiments, the substituents are the same. In some other embodiments, the substituents are not all the same. In some embodiments, each substituent is different.

In some embodiments, there is $R^s$ at the 3- or 3'-position of $R^4$ comprising a biaryl moiety

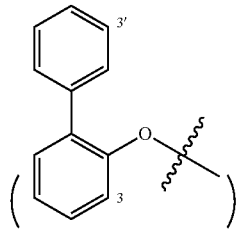

In some embodiments, there is $R^s$ at the 3-position of $R^4$ comprising a biaryl moiety. In some embodiments, there is $R^s$ at the 3'-position of $R^4$ comprising a biaryl moiety. In some embodiments, there are $R^s$ at the 3- and 3'-positions of $R^4$ comprising a biaryl moiety. In some embodiments, $R^s$ is R'. In some embodiments, $R^s$ is optionally substituted $C_{1-6}$ aliphatic. In some embodiments, $R^s$ is optionally substituted $C_{1-6}$ aliphatic, wherein $R^s$ comprises one or more halogen. In some embodiments, $R^s$ is optionally substituted $C_{1-6}$ aliphatic, wherein $R^s$ comprises one or more —F. In some embodiments, $R^s$ is $C_{1-6}$ perfluoroaliphatic. In some embodiments, $R^s$ is $C_{1-6}$ perfluoroalkyl. In some embodiments, $R^s$ is —CF$_3$. In some embodiments, $R^s$ is optionally substituted $C_{1-6}$ alkyl. In some embodiments, $R^s$ is optionally substituted linear $C_{1-6}$ alkyl. In some embodiments, $R^s$ is optionally substituted branched $C_{1-6}$ alkyl. In some embodiments, $R^s$ is optionally substituted phenyl. In some embodiments, $R^s$ is optionally substituted 8-10 membered bicyclic aryl. In some embodiments, $R^s$ is optionally substituted 1-naphthyl. In some embodiments, $R^s$ is optionally substituted 2-naphthyl. In some embodiments, $R^s$ is 1-substituted naphthyl. In some embodiments, $R^s$ is 2-substituted naphthyl. In some embodiments, $R^s$ is optionally substituted 5-6 membered monocyclic heteroaryl ring having 1-4 heteroatoms independently selected from nitrogen, oxygen, or sulfur. In some embodiments, $R^s$ is optionally substituted 8-10 membered bicyclic heteroaryl. In some embodiments, $R^s$ is an optionally substituted 4-7 membered saturated or partially unsaturated heterocyclic ring having 1-3 heteroatoms independently selected from nitrogen, oxygen, or sulfur. In some embodiments, $R^s$ is an optionally substituted 7-10 membered bicyclic saturated or partially unsaturated heterocyclic ring having 1-5 heteroatoms independently selected from nitrogen, oxygen, or sulfur. In some embodiments, $R^s$ is selected from —SR', —S(O)R', —S(O)$_2$R', wherein each R' is independently as defined above and described herein.

In some embodiments, at least one —OR$^4$ is an asymmetric ligand. In some embodiments, at least one —OR$^4$ is a symmetric ligand. In certain embodiments, at least one —OR$^4$ is a silyl-protected BINOL derivative.

In some embodiments, $R^4$ is $R^7$, wherein $R^7$ is Ar', and Ar' is an optionally substituted group selected from:

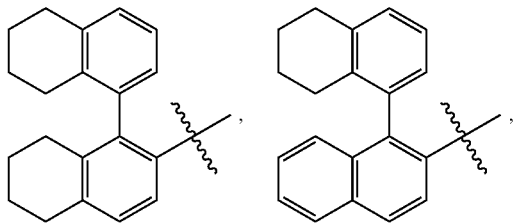

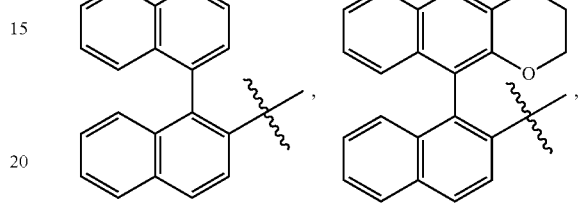

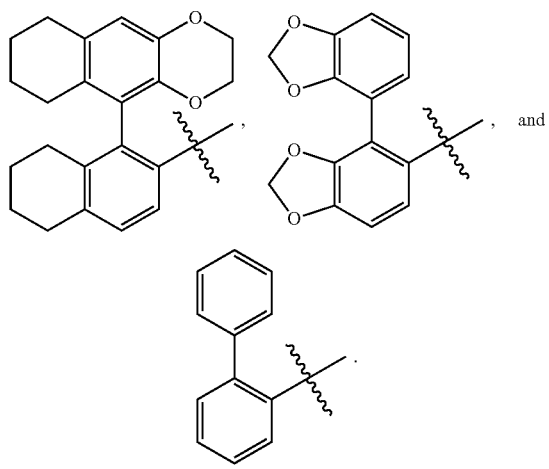

In some embodiments, $R^4$ is $R^7$, wherein $R^7$ is Ar', and Ar' is an optionally substituted group selected from:

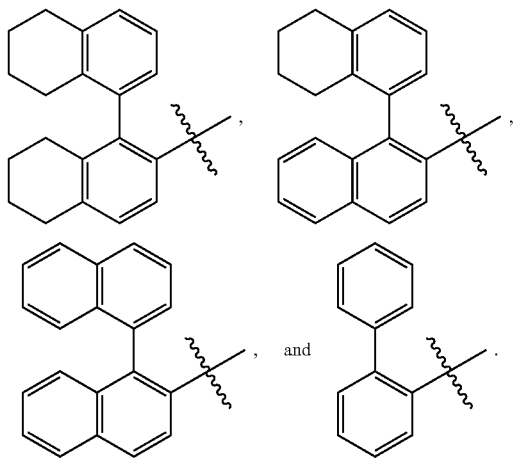

In some embodiments, R⁴ is Ar. In some embodiments, In some embodiments, R⁴ is

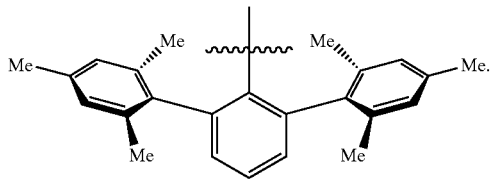

In some embodiments, R⁴ is

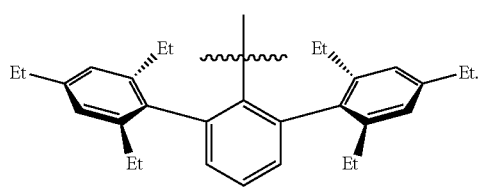

In some embodiments, R⁵ is halogen. In some embodiments, R⁵ is —OR⁶. In some embodiments, R⁵ is —OR⁷.

In some embodiments, R⁵ is —N(R')₂, —NR'C(O)R', —NR'C(O)OR', —NR'C(O)N(R')₂, —NR'SO₂R', —NR'SO₂N(R')₂, or —NR'OR', or an optionally substituted group selected from a 5-6 membered monocyclic heteroaryl ring having at least one nitrogen and 0-3 heteroatoms independently selected from nitrogen, oxygen, or sulfur, a 4-7 membered saturated or partially unsaturated heterocyclic ring having at least one nitrogen and 0-2 heteroatoms independently selected from nitrogen, oxygen, or sulfur, a 7-10 membered bicyclic saturated or partially unsaturated heterocyclic ring having at least one nitrogen and 0-4 heteroatoms independently selected from nitrogen, oxygen, or sulfur, or an 8-10 membered bicyclic heteroaryl ring having at least one nitrogen and 0-4 heteroatoms independently selected from nitrogen, oxygen, or sulfur. In some embodiments, R⁵ is —N(R')₂, —NR'C(O)R', —NR'C(O)OR', —NR'C(O)N(R')₂, —NR'SO₂R', —NR'SO₂N(R')₂, or —NR'OR', or an optionally substituted group selected from a 5-6 membered monocyclic heteroaryl ring having at least one nitrogen and 0-3 heteroatoms independently selected from nitrogen, oxygen, or sulfur, a 4-7 membered saturated or partially unsaturated heterocyclic ring having at least one nitrogen and 0-2 heteroatoms independently selected from nitrogen, oxygen, or sulfur, a 7-10 membered bicyclic saturated or partially unsaturated heterocyclic ring having at least one nitrogen and 0-4 heteroatoms independently selected from nitrogen, oxygen, or sulfur, or an 8-10 membered bicyclic heteroaryl ring having at least one nitrogen and 0-4 heteroatoms independently selected from nitrogen, oxygen, or sulfur, wherein R⁵ is bonded to M via nitrogen.

In some embodiments, R⁵ is —N(R')₂.

In some embodiments, R⁵ is an optionally substituted group selected from a 5-6 membered monocyclic heteroaryl ring having at least one nitrogen and 0-3 heteroatoms independently selected from nitrogen, oxygen, or sulfur, and an 8-10 membered bicyclic heteroaryl ring having at least one nitrogen and 0-4 heteroatoms independently selected from nitrogen, oxygen, or sulfur. In some embodiments, R⁵ is an optionally substituted group selected from a 5-6 membered monocyclic heteroaryl ring having at least one nitrogen and 0-3 heteroatoms independently selected from nitrogen, oxygen, or sulfur, and an 8-10 membered bicyclic heteroaryl ring having at least one nitrogen and 0-4 heteroatoms independently selected from nitrogen, oxygen, or sulfur, wherein the nitrogen atom is deprotonated and bonded to M. In some embodiments, R⁵ is optionally substituted 5-membered heteroaryl having at least one nitrogen and 0-3 heteroatoms independently selected from nitrogen, oxygen, or sulfur, wherein the nitrogen atom is deprotonated and bonded to M. In some embodiments, R⁵ is optionally substituted pyrrolyl wherein the nitrogen atom is deprotonated and bonded to M.

In some embodiments, R⁵ is an optionally substituted 5-membered monocyclic heteroaryl ring having 1-2 nitrogen atoms. In some embodiments, R⁵ is an optionally substituted 5-membered monocyclic heteroaryl ring having 1-2 nitrogen atoms, wherein R⁵ is bonded to M through a nitrogen atom.

In some embodiments, R⁵ is an optionally substituted 5-membered monocyclic heteroaryl ring having 1-2 nitrogen atoms. In some embodiments, R⁵ is an optionally substituted 5-membered monocyclic heteroaryl ring having one nitrogen atom. In some embodiments, R⁵ is optionally substituted pyrrolyl. In some embodiments, R⁵ is optionally substituted 1-pyrrolyl. In some embodiments, R⁵ is an optionally substituted 5-membered monocyclic heteroaryl ring having two nitrogen atoms. In some embodiments, R⁵ is optionally substituted imidazolyl. In some embodiments, R⁵ is optionally substituted pyrazolyl.

In some embodiments, R⁵ is optionally substituted pyrrolyl. In some embodiments, R⁵ is optionally substituted 1-pyrrolyl. In some embodiments, R⁵ is optionally substituted pyrrolyl having the structure of

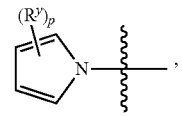

wherein each of p and Rʸ is independently as defined above and described herein. In some embodiments, R⁵ is disubstituted pyrrolyl. In some embodiments, R⁵ is disubstituted pyrrolyl having the structure of

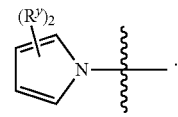

In some embodiments, R⁵ is 2,5-disubstituted pyrrolyl. In some embodiments, R⁵ is 2,5-disubstituted pyrrolyl having the structure of

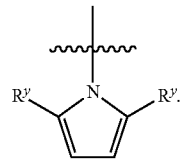

In some embodiments, R⁵ is 2,5-disubstituted pyrrolyl having the structure of

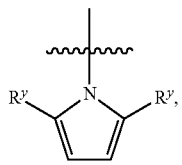

wherein each $R^y$ is independently R'. In some embodiments, $R^5$ is 2,5-disubstituted pyrrolyl having the structure of

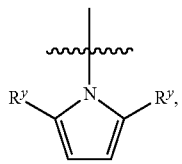

wherein each $R^y$ is independently hydrogen or $C_{1-4}$ aliphatic. In some embodiments, $R^5$ is 2,5-disubstituted pyrrolyl having the structure of

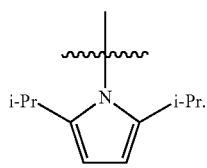

In some embodiments, $R^5$ is 2,5-disubstituted pyrrolyl having the structure of

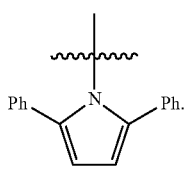

In some embodiments, $R^5$ is

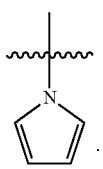

In some embodiments, $R^5$ is

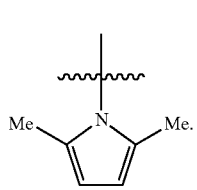

In some embodiments, $R^5$ is optionally substituted imidazolyl. In some embodiments, $R^5$ is optionally substituted imidazolyl having the structure of

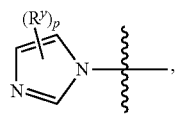

wherein each of p and $R^y$ is independently as defined above and described herein. In some embodiments, $R^5$ is disubstituted imidazolyl. In some embodiments, $R^5$ is disubstituted imidazolyl having the structure of

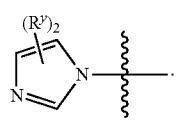

In some embodiments, $R^5$ is 2,5-disubstituted imidazolyl. In some embodiments, $R^5$ is 2,5-disubstituted imidazolyl having the structure of

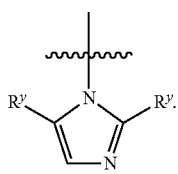

In some embodiments, $R^5$ is 2,5-disubstituted pyrrolyl having the structure of

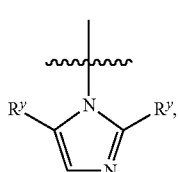

wherein each $R^y$ is independently R'. In some embodiments, $R^5$ is 2,5-disubstituted pyrrolyl having the structure of

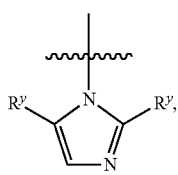

wherein each $R^y$ is independently hydrogen or $C_{1-4}$ aliphatic. In some embodiments, $R^5$ is 2,5-disubstituted pyrrolyl having the structure of

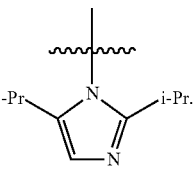

In some embodiments, $R^5$ is 2,5-disubstituted pyrrolyl having the structure of N

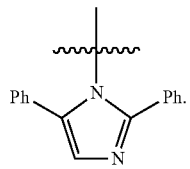

In some embodiments, $R^5$ is optionally substituted pyrazolyl. In some embodiments, $R^5$ is optionally substituted pyrazolyl having the structure of

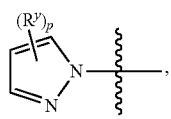

wherein each of p and $R^y$ is independently as defined above and described herein. In some embodiments, $R^5$ is disubstituted pyrazolyl. In some embodiments, $R^5$ is disubstituted pyrazolyl having the structure of

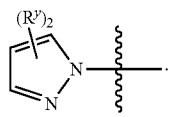

In some embodiments, $R^6$ is optionally substituted $C_{1-20}$ aliphatic. In some embodiments, $R^6$ is optionally substituted $C_{1-20}$ heteroaliphatic having 1-3 heteroatoms independently selected from nitrogen, oxygen, or sulfur. In some embodiments, $R^6$ is optionally substituted phenyl. In some embodiments, $R^6$ is an optionally substituted 3-7 membered saturated or partially unsaturated carbocyclic ring. In some embodiments, $R^6$ is an optionally substituted 8-10 membered bicyclic saturated, partially unsaturated or aryl ring. In some embodiments, $R^6$ is optionally substituted 8-10 membered aryl. In some embodiments, $R^6$ is optionally substituted 5-6 membered monocyclic heteroaryl having 1-4 heteroatoms independently selected from nitrogen, oxygen, or sulfur. In some embodiments, $R^6$ is an optionally substituted 4-7 membered saturated or partially unsaturated heterocyclic ring having 1-3 heteroatoms independently selected from nitrogen, oxygen, or sulfur. In some embodiments, $R^6$ is an optionally substituted 7-10 membered bicyclic saturated or partially unsaturated heterocyclic ring having 1-5 heteroatoms independently selected from nitrogen, oxygen, or sulfur. In some embodiments, $R^6$ is optionally substituted 8-14 membered bicyclic or tricyclic heteroaryl having 1-5 heteroatoms independently selected from nitrogen, oxygen, or sulfur.

In some embodiments, each $R^7$ is independently an optionally substituted group selected from —Ar', $C_{1-20}$ aliphatic, $C_{1-20}$ heteroaliphatic having 1-3 heteroatoms independently selected from nitrogen, oxygen, or sulfur, phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 4-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-14 membered bicyclic or tricyclic heteroaryl ring having 1-5 heteroatoms independently selected from nitrogen, oxygen, or sulfur; and two $R^7$ are optionally taken together with the oxygen atoms they are bound to form a bidentate ligand.

In some embodiments, each $R^7$ is independently an optionally substituted group selected from —Ar', $C_{1-20}$ aliphatic, $C_{1-20}$ heteroaliphatic having 1-3 heteroatoms independently selected from nitrogen, oxygen, or sulfur, phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 4-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-14 membered bicyclic or tricyclic heteroaryl ring having 1-5 heteroatoms independently selected from nitrogen, oxygen, or sulfur.

In some embodiments, $R^7$ is Ar'.

In some embodiments, $R^7$ is optionally substituted $C_{1-20}$ aliphatic. In some embodiments, $R^7$ is optionally substituted $C_{1-20}$ heteroaliphatic having 1-3 heteroatoms independently selected from nitrogen, oxygen, or sulfur. In some embodiments, $R^7$ is optionally substituted phenyl. In some embodiments, $R^7$ is an optionally substituted 3-7 membered saturated or partially unsaturated carbocyclic ring. In some embodiments, $R^7$ is an optionally substituted 8-10 membered bicyclic saturated, partially unsaturated or aryl ring. In some embodiments, $R^7$ is optionally substituted 8-10 membered aryl. In some embodiments, $R^7$ is optionally substituted 5-6 membered monocyclic heteroaryl having 1-4 heteroatoms independently selected from nitrogen, oxygen, or sulfur. In some embodiments, $R^7$ is an optionally substituted 4-7 membered saturated or partially unsaturated heterocyclic ring having 1-3 heteroatoms independently selected from nitrogen, oxygen, or sulfur. In some embodiments, $R^7$ is an optionally substituted 7-10 membered bicyclic saturated or partially unsaturated heterocyclic ring having 1-5 heteroatoms independently selected from nitrogen, oxygen, or sulfur. In some embodiments, $R^7$ is optionally substituted 8-14 membered bicyclic or tricyclic heteroaryl having 1-5 heteroatoms independently selected from nitrogen, oxygen, or sulfur.

In some embodiments, each R' is independently hydrogen or an optionally substituted group selected from $C_{1-20}$ aliphatic, phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 4-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-10 membered bicyclic heteroaryl ring having 1-5 heteroatoms independently selected from nitrogen, oxygen, or sulfur, wherein:

two R' groups on the same nitrogen atom are optionally taken together with the nitrogen atom to form an optionally substituted 3-8 membered, saturated, partially unsaturated, or aryl ring having 1-4 heteroatoms independently selected from nitrogen, oxygen, or sulfur.

In some embodiments, each R' is independently hydrogen or an optionally substituted group selected from $C_{1-6}$ aliphatic, phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 4-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-10 membered bicyclic heteroaryl ring having 1-5 heteroatoms independently selected from nitrogen, oxygen, or sulfur, wherein:

two R' groups on the same nitrogen atom are optionally taken together with the nitrogen atom to form an optionally substituted 3-8 membered, saturated, partially unsaturated, or aryl ring having 1-4 heteroatoms independently selected from nitrogen, oxygen, or sulfur.

In some embodiments, each R' is independently optionally substituted $C_{1-20}$ aliphatic. In some embodiments, each R' is independently optionally substituted $C_{1-6}$ aliphatic. In some embodiments, each R' is independently optionally substituted $C_{1-6}$ alkyl. In some embodiments, each R' is independently optionally substituted $C_{1-6}$ haloalkyl. In some embodiments, each R' is independently optionally substituted $C_{1-6}$ haloalkyl, wherein one substituent is —F. In some embodiments, each R' is independently optionally substituted $C_{1-6}$ haloalkyl, wherein two or more substituents are —F. In certain embodiments, at least one R' is independently selected from methyl, ethyl, propyl, or butyl. In certain embodiments, at least one $R^s$ is isopropyl. In certain embodiments, at least one R' is —$CF_3$.

In some embodiments, at least one R' is hydrogen. In some embodiments, at least one R' is independently selected from an optionally substituted group selected from $C_{1-6}$ aliphatic, phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 4-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-10 membered bicyclic heteroaryl ring having 1-5 heteroatoms independently selected from nitrogen, oxygen, or sulfur.

In some embodiments, at least one R' is optionally substituted $C_{1-6}$ aliphatic. In some embodiments, at least one R' is optionally substituted phenyl. In some embodiments, at least one R' is optionally substituted 3-7 membered saturated or partially unsaturated carbocyclic ring. In some embodiments, at least one R' is optionally substituted 8-10 membered bicyclic saturated, partially unsaturated or aryl ring. In some embodiments, at least one R' is optionally substituted 5-6 membered monocyclic heteroaryl ring having 1-4 heteroatoms independently selected from nitrogen, oxygen, or sulfur. In some embodiments, at least one R' is optionally substituted 4-7 membered saturated or partially unsaturated heterocyclic ring having 1-3 heteroatoms independently selected from nitrogen, oxygen, or sulfur. In some embodiments, at least one R' is optionally substituted 7-10 membered bicyclic saturated or partially unsaturated heterocyclic ring having 1-5 heteroatoms independently selected from nitrogen, oxygen, or sulfur. In some embodiments, at least one R' is optionally substituted 8-10 membered bicyclic heteroaryl ring having 1-5 heteroatoms independently selected from nitrogen, oxygen, or sulfur.

As generally defined above, $R^{2'}$ and $R^{3'}$ are taken together with their intervening metal atom to form an optionally substituted 3-8 membered saturated or partially unsaturated ring having, in addition to the intervening metal atom, 0-4 heteroatoms independently selected from nitrogen, oxygen, or sulfur. In some embodiments, $R^{2'}$ and $R^{3'}$ are taken together with their intervening metal atom to form an optionally substituted 3-8 membered saturated ring having, in addition to the intervening metal atom, 0-4 heteroatoms independently selected from nitrogen, oxygen, or sulfur. In some embodiments, $R^{2'}$ and $R^{3'}$ are taken together with their intervening metal atom to form an optionally substituted 3-8 membered metallocycloalkane ring. In some embodiments, $R^{2'}$ and $R^{3'}$ are taken together with their intervening metal atom to form an optionally substituted 3-4 membered metallocycloalkane ring. In some embodiments, $R^{2'}$ and $R^{3'}$ are taken together with their intervening metal atom to form an optionally substituted metallacyclopropane ring. In some embodiments, $R^{2'}$ and $R^{3'}$ are taken together with their intervening metal atom to form an optionally substituted metallacyclobutane ring. In some embodiments, each ring carbon atom is independently optionally substituted. In some embodiments, each ring carbon atom is unsubstituted. In some embodiments, one or more ring carbon atoms are substituted.

In some embodiments, a provided catalyst or metal complex is:

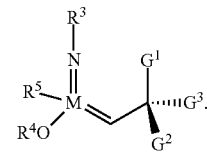

In some embodiments, a provided metal complex is

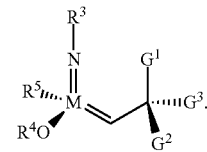

In some embodiments, a provided metal complex is

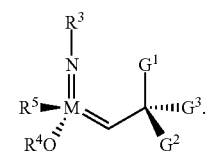

Exemplary embodiments for $G^1$, $G^2$, $G^3$, $R^3$, $R^4$, and $R^5$ are described below, which can be optionally substituted.

$G^1$-$G^3$=any alkyl (e.g., Me) or aryl (e.g., Ph)

$G^1$, $G^2$ and $G^3$ might be identical or any combination of the above

1. M=Mo or W
2. $R^3$=

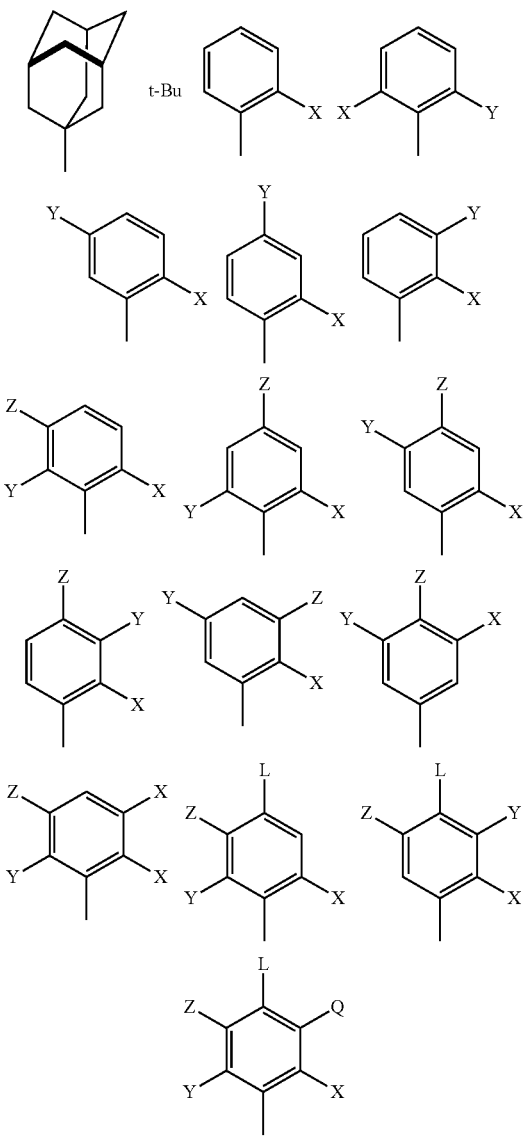

X, Y, Z, L and Q might be identical, or five different substituents, or any 2 (e.g., X=Y or Y=Z) or any 3 (e.g., X=Y=Z) might be identical, or only one might be different than the other four.

X, Y, Z, L and Q might be H, F, Cl, Br, I, Me, Et, or any other n-alkyl, i-Pr or any other i-alkyl, Cy or any other cycloalkyl or heterocyclic, t-Bu, adamantyl or any quaternary carbon containing substituent. X, Y, Z, L and Q might be $CF_3$, $C_2F_5$ or any linear, branched, cyclic or heterocyclic halogenated substituent.

3. $R^5$=

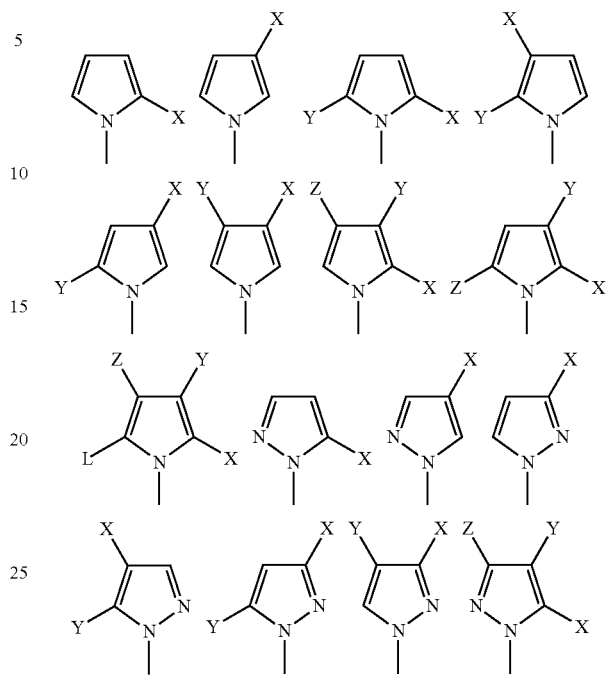

X, Y, Z and L might be identical, or four different substituents, or any 2 (e.g., X=Y or Y=Z) or any 3 (e.g., X=Y=Z) might be identical

4. $OR^4$=

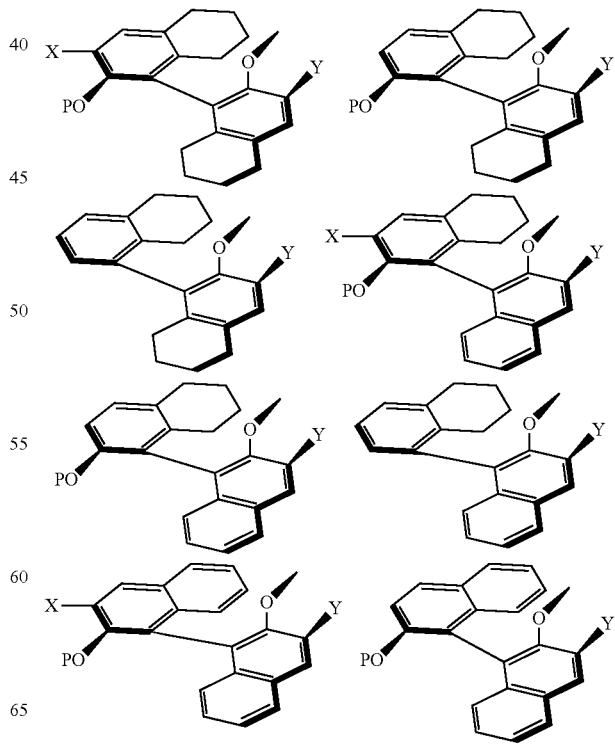

-continued

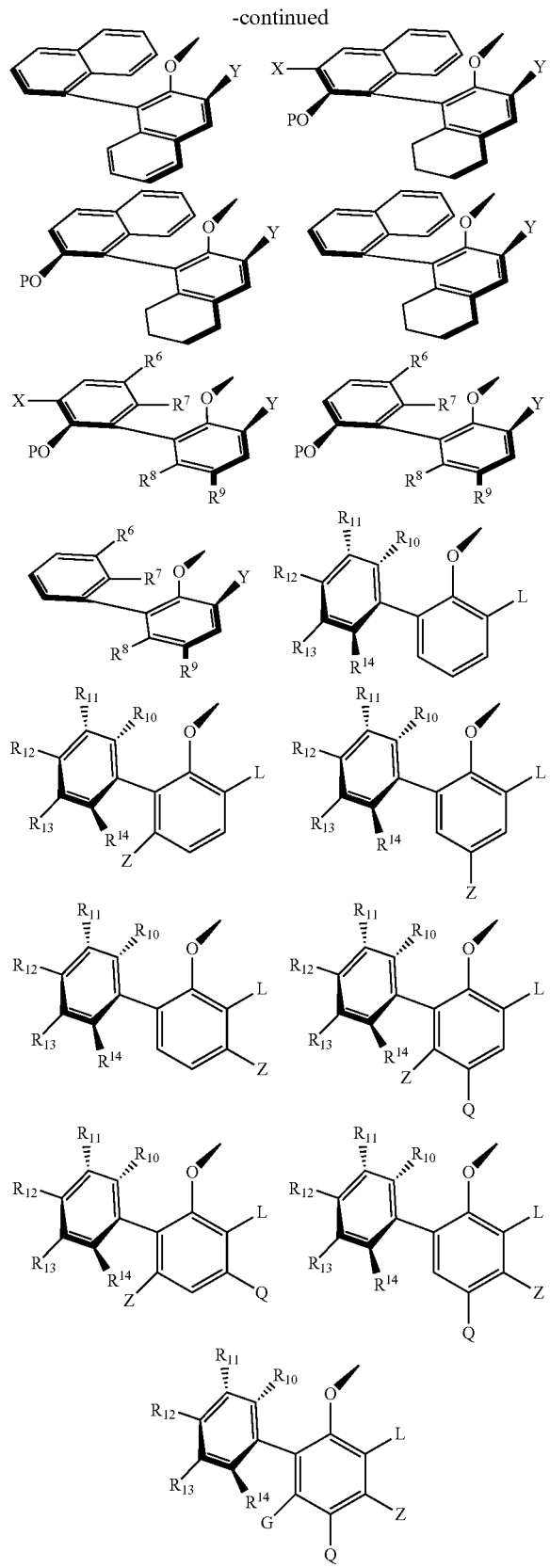

X might be the same or different from Y.
X and/or Y=H, F, Cl, Br, I, CF$_3$, or any linear or branched F-containing hydrocarbon, Me or any linear or branched alkyl, Ph, any mono-, di-, tri-, or tetra-substituted aryl (all isomers) with substituents being the same as for X/Y, 1- or 2-substituted naphthyl or any O-, N-, or S-containing heterocycle. X and/or Y might be S-based (sulfide, sulfoxide or sulfone).

R$^6$, R$^7$, R$^8$, R$^9$, R$^{10}$, R$^{11}$, R$^{12}$, R$^{13}$, and R$^{14}$=H, F, Cl, Br, I, CF$_3$, or any linear or branched hydrocarbon, Me, or any linear or branched alkyl, Ph, any mono-, di-, tri-, or tetra-substituted aryl (all isomers) with substituents, 1- or 2-substituted naphthyl or any O-, N-, or S-containing heterocycle. R$^6$, R$^7$, R$^8$, R$^9$, R$^{10}$, R$^{11}$, R$^{12}$, R$^{13}$, and R$^{14}$ might be S-based (sulfide, sulfoxide, or sulfone).

R$^6$, R$^7$, R$^8$, and R$^9$ might be identical or different in any possible combination. The same identification field may apply as indicated with X and Y above.

R$^{10}$, R$^{11}$, R$^{12}$, R$^{13}$ and R$^{14}$ might be identical or different in any possible combination. The same identification field may apply as indicated with X and Y above.

L might be Ph, any mono-, di-, tri-, or tetra-substituted aryl (all isomers) with substituents, 1- or 2-substituted naphthyl or any O-, N-, or S-containing heterocycle.

Z, Q, and G might be identical, or three different substituents, or any 2 (e.g., Z=Q or Q=G) might be identical.

Z, Q, and G might be H, F, Cl, Br, I, CF$_3$, or any linear or branched hydrocarbon, Me or any linear or branched alkyl, Ph, any mono-, di-, tri-, or tetra-substituted aryl (all isomers) with substituents, 1- or 2-substituted naphthyl or any O-, N-, or S-containing heterocycle. Z, Q, and G might be S-based (sulfide, sulfoxide or sulfone).

In some embodiments, each of G$^1$, G$^2$, and G$^3$ is independently R'. In some embodiments, each of G$^1$, G$^2$, and G$^3$ is independently an optionally substituted group selected from alkyl and aryl. In some embodiments, each of G$^1$, G$^2$, and G$^3$ is independently an optionally substituted group selected from alkyl and phenyl.

In some embodiments, when R$^3$ is part of an imido group as depicted above, R$^3$ is R'. In some embodiments, R$^3$ is optionally substituted tertiary aliphatic. In some embodiments, R$^3$ is optionally substituted tertiary alkyl such as tert-butyl. In some embodiments, R$^3$ is optionally substituted tertiary cycloalkyl. In some embodiments, R$^3$ is adamantyl. In some embodiments, R$^3$ is optionally substituted phenyl as depicted above. In some embodiments, R$^3$ is phenyl with 1, 2, 3, 4, or 5 substituents. In some embodiments, a substituent is X, Y, Z, L or Q. When multiple substituents are present, they can either all be the same, or some of them are the same, or each of them is different. In some embodiments, two or three substituents are identical. In some embodiments, four substituents are the same and are different from the fifth one.

As understood by a person having ordinary skill in the art, each of X, Y, Z, L and Q can independently be various suitable substituent groups.

In some embodiments, X is R$^s$. In some embodiments, X is R'. In some embodiments, X is optionally substituted C$_{1-6}$ aliphatic. In some embodiments, Y is optionally substituted C$_{1-6}$ cycloaliphatic. In some embodiments, Y is optionally substituted C$_{1-6}$ cycloalkyl. In some embodiments, X is optionally substituted C$_{1-6}$ aliphatic, wherein R$^s$ comprises one or more halogen. In some embodiments, X is optionally substituted C$_{1-6}$ aliphatic, wherein R$^s$ comprises one or more —F. In some embodiments, X is C$_{1-6}$ perfluoroaliphatic. In some embodiments, X is C$_{1-6}$ perfluoroalkyl. In some embodiments, X is —CF$_3$. In some embodiments, X is optionally substituted C$_{1-6}$ alkyl. In some embodiments, X is optionally substituted linear C$_{1-6}$ alkyl. In some embodiments, X is optionally substituted branched C$_{1-6}$ alkyl. In some embodiments, X is optionally substituted phenyl. In some embodiments, X is optionally substituted 8-10 membered bicyclic aryl. In some embodiments, X is optionally substituted 1-naphthyl. In some embodiments, X is optionally substituted 2-naphthyl. In some embodiments, X is 1-substituted naphthyl. In some embodiments, X is 2-substituted naphthyl. In some embodiments, X is optionally substituted 5-6 membered monocyclic heteroaryl ring having 1-4 heteroatoms independently selected from nitrogen, oxygen, or sulfur. In some embodiments, X is optionally substituted 8-10 membered bicyclic heteroaryl. In some embodiments, X is an optionally substituted 4-7 membered saturated or partially unsaturated heterocyclic ring having 1-3 heteroatoms independently selected from nitrogen, oxygen, or sulfur. In some embodiments, X is an optionally substituted 7-10 membered bicyclic saturated or partially unsaturated heterocyclic ring having 1-5 heteroatoms independently selected from nitrogen, oxygen, or sulfur. In some embodiments, X is selected from —SR', —S(O)R', —S(O)$_2$R', wherein each R' is independently as defined above and described herein.

In some embodiments, Y is R$^s$. In some embodiments, Y is R'. In some embodiments, Y is optionally substituted C$_{1-6}$ aliphatic. In some embodiments, Y is optionally substituted C$_{1-6}$ cycloaliphatic. In some embodiments, Y is optionally substituted C$_{1-6}$ cycloalkyl. In some embodiments, Y is optionally substituted C$_{1-6}$ aliphatic, wherein R$^s$ comprises one or more halogen. In some embodiments, Y is optionally substituted C$_{1-6}$ aliphatic, wherein R$^s$ comprises one or more —F. In some embodiments, Y is C$_{1-6}$ perfluoroaliphatic. In some embodiments, Y is C$_{1-6}$ perfluoroalkyl. In some embodiments, Y is —CF$_3$. In some embodiments, Y is optionally substituted C$_{1-6}$ alkyl. In some embodiments, Y is optionally substituted linear C$_{1-6}$ alkyl. In some embodiments, Y is optionally substituted branched C$_{1-6}$ alkyl. In some embodiments, Y is optionally substituted phenyl. In some embodiments, Y is optionally substituted 8-10 membered bicyclic aryl. In some embodiments, Y is optionally substituted 1-naphthyl. In some embodiments, Y is optionally substituted 2-naphthyl. In some embodiments, Y is 1-substituted naphthyl. In some embodiments, Y is 2-substituted naphthyl. In some embodiments, Y is optionally substituted 5-6 membered monocyclic heteroaryl ring having 1-4 heteroatoms independently selected from nitrogen, oxygen, or sulfur. In some embodiments, Y is optionally substituted 8-10 membered bicyclic heteroaryl. In some embodiments, Y is an optionally substituted 4-7 membered saturated or partially unsaturated heterocyclic ring having 1-3 heteroatoms independently selected from nitrogen, oxygen, or sulfur. In some embodiments, Y is an optionally substituted 7-10 membered bicyclic saturated or partially unsaturated heterocyclic ring having 1-5 heteroatoms independently selected from nitrogen, oxygen, or sulfur. In some embodiments, Y is selected from —SR', —S(O)R', —S(O)$_2$R', wherein each R' is independently as defined above and described herein.

In some embodiments, L is —Cl, —Br, or —I. In some embodiments, L is —Cl. In some embodiments, L is —Br. In some embodiments, L is —I. In some embodiments, L is R', wherein R' is not hydrogen.

In some embodiments, L is R', wherein R' is an optionally substituted cyclic group. In some embodiments, L is R', wherein R' is an optionally substituted aromatic group. In some embodiments, L is R', wherein R' is an optionally substituted tertiary group.

In some embodiments, L is an optionally substituted group selected from phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 4-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-10 membered bicyclic heteroaryl ring having 1-5 heteroatoms independently selected from nitrogen, oxygen, or sulfur. In some embodiments, L is an optionally substituted group selected from phenyl, an 8-10 membered bicyclic aryl ring, a 5-6 membered monocyclic heteroaryl ring having 1-4 heteroatoms independently selected from nitrogen, oxygen, or sulfur, a 4-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-10 membered bicyclic heteroaryl ring having 1-5 heteroatoms independently selected from nitrogen, oxygen, or sulfur. In some embodiments, L is an optionally substituted group selected from phenyl, an 8-10 membered bicyclic aryl ring, a 5-6 membered monocyclic heteroaryl ring having 1-4 heteroatoms independently selected from nitrogen, oxygen, or sulfur, or an 8-10 membered bicyclic heteroaryl ring having 1-5 heteroatoms independently selected from nitrogen, oxygen, or sulfur. In some embodiments, L is optionally substituted phenyl. In some embodiments, L is optionally substituted 8-10 membered bicyclic aryl ring. In some embodiments, L is optionally substituted 1-naphthyl. In some embodiments, L is optionally substituted 2-naphthyl. In some embodiments, L is 1-substituted naphthyl. In some embodiments, L is 2-substituted naphthyl. In some embodiments, L is optionally substituted 5-6 membered monocyclic heteroaryl. In some embodiments, L is optionally substituted 4-7 membered saturated or partially unsaturated heterocyclyl. In some embodiments, L is optionally substituted 8-10 membered bicyclic heteroaryl. In some embodiments, L is optionally substituted 7-10 membered bicyclic saturated or partially unsaturated heterocyclyl.

Z, Q and G can each independently be any suitable substituents. In some embodiments, each of Z, Q and G is independently a substituent as described herein for X and/or Y. In some embodiments, each of Z, Q and G is independently R$^s$. Z, Q and G can either be the same or different from one another.

R$^6$, R$^7$, R$^8$, R$^9$, R$^{10}$, R$^{11}$, R$^{12}$, R$^{13}$ and R$^{14}$ can each independently be any suitable substituents. In some embodiments, each of R$^6$, R$^7$, R$^8$, R$^9$, R$^{10}$, R$^{11}$, R$^{12}$, R$^{13}$ and R$^{14}$ is independently a substituent as described herein for X and/or Y. In some embodiments, each of R$^6$, R$^7$, R$^8$, R$^9$, R$^{10}$, R$^{11}$, R$^{12}$, R$^{13}$ and R$^{14}$ is independently R$^s$. R$^6$, R$^7$, R$^8$, R$^9$, R$^{10}$, R$^{11}$, R$^{12}$, R$^{13}$ and R$^{14}$ can either be the same or different from one another.

As understood by a person having ordinary skill in the art, P can be any suitable group, for example but not limited to any suitable protecting groups. In some embodiments, P is R$^s$.

In some embodiments, each of the variables is independently as described in US Patent Application Publication US2012/0323000, incorporated herein by reference, both individually and in combination.

Exemplary catalysts or metal complexes include but are not limited to those listed below:
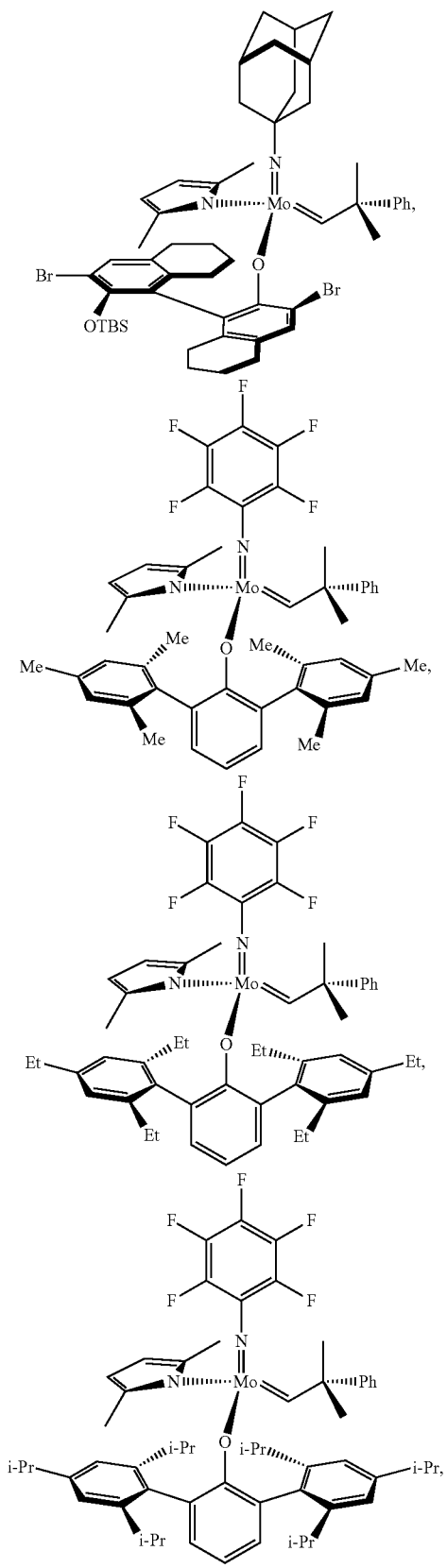
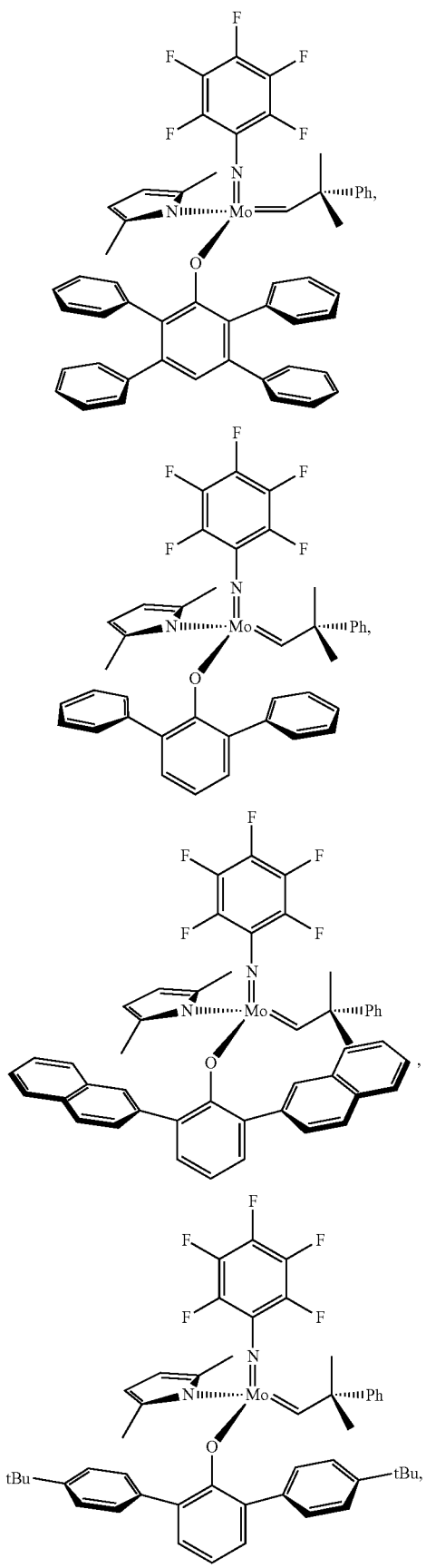

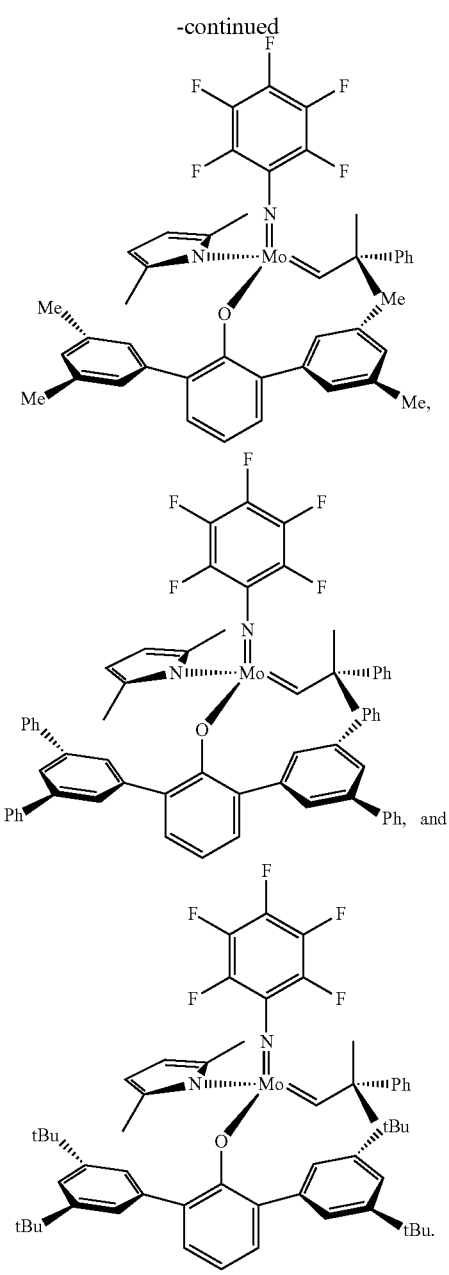

In some embodiments, the present disclosure provides methods for metathesis reactions. In some embodiments, the present disclosure provides a method, comprising:

reacting a first species comprising an olefin with a second species comprising an olefin in the presence of a catalyst or metal complex to provide at least one product comprising an olefin, wherein:

each carbon atom of the olefin in the first species is substituted with at least one halogen; and the olefin in the at least one product comprises a carbon atom from the first species and a carbon atom from the second species.

In some embodiments, the present disclosure provides a method for olefin metathesis, comprising providing a catalyst or metal complex has the structure of formula II-a or II-b. In some embodiments, the at least one product in a provided method has the structure of a product from the metathesis between the olefin of the first species and the olefin of the second species.

In some embodiments, a first species of a provided olefin metathesis method is an alkenyl halide, wherein each carbon of the alkene group is independently substituted with a halogen atom. In some embodiments, the two halogen atoms on the two carbon atoms of the double bond are cis. In some embodiments, the two halogen atoms on the two carbon atoms of the double bond are cis, and the at least one product comprises a carbon atom from the olefin of the first species and the halogen atom attached to the carbon atom, and the at least one product is produced with Z-selectivity. In some embodiments, the olefin in the first species is Z with respect to a halogen substituent on the first carbon atom of the olefin and a halogen substituent on the second carbon atom of the olefin. In some embodiments, the olefin in the first species is E with respect to a halogen substituent on the first carbon atom of the olefin and a halogen substituent on the second carbon atom of the olefin.

In some embodiments, the olefin in the first species is Z with respect to a halogen substituent on the first carbon atom of the olefin and a halogen substituent on the second carbon atom of the olefin. In some embodiments, a first species has the structure of

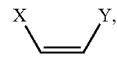

wherein each of X and Y is independently halogen. In some embodiments, each of X and Y is —Cl. In some embodiments, one of X and Y is —F and the other is —Cl. In some embodiments, one of X and Y is —F and the other is —Br. In some embodiments, the olefin of the second species comprises one or more substituents. In some embodiments, each substituent is independent $R^t$, wherein $R^t$ is an optionally substituted group selected from $C_{1-20}$ aliphatic, $C_{1-20}$ heteroaliphatic having 1-5 heteroatoms independently selected from boron, silicon, phosphorus, nitrogen, oxygen, or sulfur, phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from boron, silicon, phosphorus, nitrogen, oxygen, or sulfur, a 4-7 membered saturated or partially unsaturated heterocyclic ring having 1-5 heteroatoms independently selected from boron, silicon, phosphorus, nitrogen, oxygen, or sulfur, a 7-10 membered bicyclic saturated or partially unsaturated heterocyclic ring having 1-5 heteroatoms independently selected from boron, silicon, phosphorus, nitrogen, oxygen, or sulfur, or an 8-10 membered bicyclic heteroaryl ring having 1-5 heteroatoms independently selected from boron, silicon, phosphorus, nitrogen, oxygen, or sulfur. In some embodiments, a second species of a provided olefin metathesis method comprises a terminal olefin. In some embodiments, a second species has the structure of $R^t$—CH=CH$_2$. In some embodiments, a second species has the structure of $R^1$—CH=CH$_2$. In some embodiments, a second species has the structure of $R^1$—CH=CH$_2$, wherein $R^1$ is an optionally substituted group selected from $C_{1-20}$ aliphatic, $C_{1-20}$ heteroaliphatic having 1-3 heteroatoms independently selected from nitrogen, oxygen, or sulfur, phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 4-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-10 membered bicyclic heteroaryl ring having 1-5 heteroatoms independently selected from nitrogen, oxygen, or sulfur.

In some embodiments, a first species of a provided olefin metathesis method is an alkenyl halide, wherein each carbon of the alkene group is independently substituted with a halogen atom. In some embodiments, the two halogen atoms on the two carbon atoms of the double bond are cis. In some embodiments, the two halogen atoms on the two carbon atoms of the double bond are cis, and the at least one product comprises a carbon atom from the olefin of the first species and the halogen atom attached to the carbon atom, and the at least one product is produced with Z-selectivity. In some embodiments, the two halogen atoms on the two carbon atoms of the double bond are trans. In some embodiments, the two halogen atoms on the two carbon atoms of the double bond are trans, and the at least one product comprises a carbon atom from the olefin of the first species and the halogen atom attached to the carbon atom, and the at least one product is produced with E-selectivity.

In some embodiments, the olefin in the first species is E with respect to a halogen substituent on the first carbon atom of the olefin and a halogen substituent on the second carbon atom of the olefin. In some embodiments, a first species has the structure of

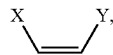

wherein each of X and Y is independently halogen. In some embodiments, a first species has the structure of

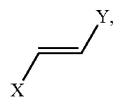

wherein each of X and Y is independently halogen. In some embodiments, each of X and Y is —Cl. In some embodiments, one of X and Y is —F and the other is —Cl. In some embodiments, one of X and Y is —F and the other is —Br.

In some embodiments, the olefin of the second species comprises one or more substituents. In some embodiments, each substituent is independent $R^t$, wherein $R^t$ is an optionally substituted group selected from $C_{1-20}$ aliphatic, $C_{1-20}$ heteroaliphatic having 1-5 heteroatoms independently selected from boron, silicon, phosphorus, nitrogen, oxygen, or sulfur, phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from boron, silicon, phosphorus, nitrogen, oxygen, or sulfur, a 4-7 membered saturated or partially unsaturated heterocyclic ring having 1-5 heteroatoms independently selected from boron, silicon, phosphorus, nitrogen, oxygen, or sulfur, a 7-10 membered bicyclic saturated or partially unsaturated heterocyclic ring having 1-5 heteroatoms independently selected from boron, silicon, phosphorus, nitrogen, oxygen, or sulfur, or an 8-10 membered bicyclic heteroaryl ring having 1-5 heteroatoms independently selected from boron, silicon, phosphorus, nitrogen, oxygen, or sulfur. In some embodiments, a second species of a provided olefin metathesis method comprises a terminal olefin. In some embodiments, a second species has the structure of $R^t$—CH=CH$_2$. In some embodiments, a second species has the structure of $R^1$—CH=CH$_2$. In some embodiments, a second species has the structure of $R^1$—CH=CH$_2$, wherein $R^1$ is an optionally substituted group selected from $C_{1-20}$ aliphatic, $C_{1-20}$ heteroaliphatic having 1-3 heteroatoms independently selected from nitrogen, oxygen, or sulfur, phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 4-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-10 membered bicyclic heteroaryl ring having 1-5 heteroatoms independently selected from nitrogen, oxygen, or sulfur.

In some embodiments, a provided exemplary method is selected from a reaction described below:

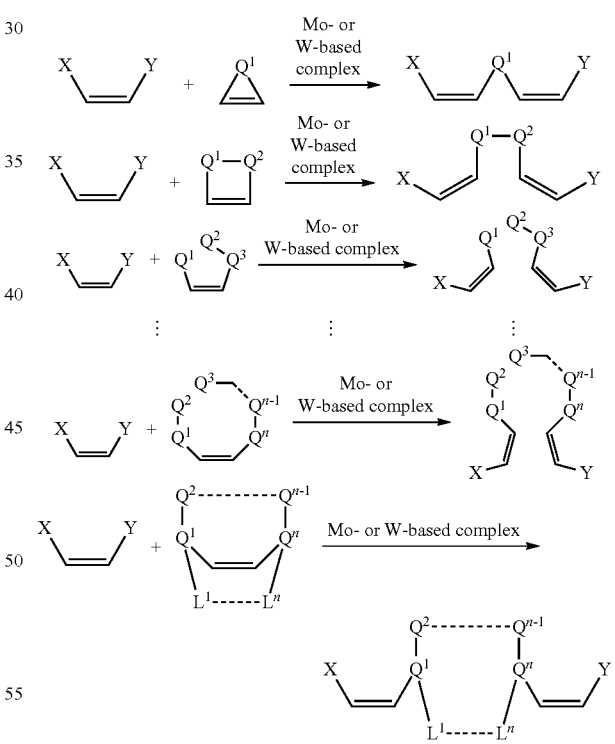

In some embodiments, X and Y might be identical or different; they may be H, F, Cl, Br, I; they must not be H at the same time. In some embodiments, each of X is —Cl.

In some embodiments, $Q^1, Q^2, Q^3, \ldots, Q^{n-1}, Q^n, L^1, L^2, L^3, \ldots, L^{n-1}, L^n$ might be any secondary carbon containing substituent, tertiary carbon containing substituent, quaternary carbon containing substituent, aromatic groups, or O-, N-, S-, Si-, B-, P-containing group, or heterocyclic substituent.

In some embodiments, n is an integer greater than 4. In some embodiments, n=4, 5, 6, . . . +∞. In some embodiments, n is 4-10. In some embodiments, n is 4-20. In some embodiments, n is 4-30. In some embodiments, n is 4-50. In some embodiments, n is 4-50 for Q.

In some embodiments, Z, Q, L might be any secondary carbon containing substituent, tertiary carbon containing substituent, quaternary carbon containing substituent, aromatic groups, O, N-, S-, Si-, B-, P-containing group, or heterocyclic substituent.

In some embodiments, m is an integer. In some embodiments, m=0, 1, 2, 3, . . . +∞. In some embodiments, m is 0-10. In some embodiments, m is 0-20.

In some embodiments, n is an integer. In some embodiments, n=0, 1, 2, 3, . . . +∞. In some embodiments, n is 0-10 for L. In some embodiments, n is 0-20 for L.

In some embodiments, a provided method is depicted below:

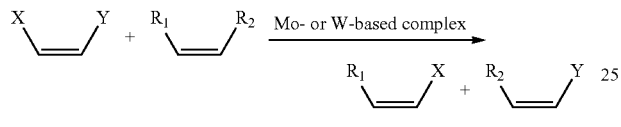

In some embodiments, a provided method is depicted below:

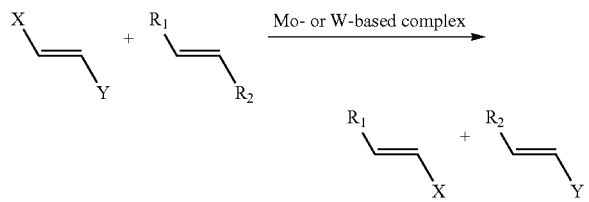

$R_1$ might be the same or different from $R_2$. X and/or Y=H, F, Cl, Br, I; they must not be H at the same time. In some embodiments, $R_1$, $R_2$=H or any linear or branched hydrocarbon, Me, or any linear or branched alkyl, Ph, any mono-, di-, tri-, or tetra-substituted aryl (all isomers) with substituents, 1- or 2-substituted naphthyl or any O-, N-, or S-containing heterocycle. In some embodiments, $R_1$, $R_2$ might be N-, S-, Si-, B-, P-based group, e.g, in some embodiments, the second species can be R'. In some embodiments, each of $R_1$ and $R_2$ is independently R'.

In some embodiments, provided methods provide regioselectivity when the first carbon atom of the olefin in the first species has a different halogen substituent than the second carbon atom of the olefin in the first species, and the first carbon atom of the olefin in the second species has different substituents than the second carbon atom of the olefin in the second species, in that, among all possible metathesis products, provided methods selectively provide products from one potential metathesis pathway. For example, the cross metathesis reaction depicted above with

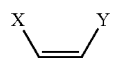

as the first species selectively produced

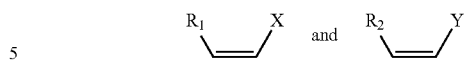

over

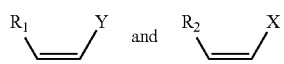

(or

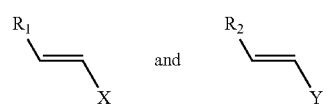

over

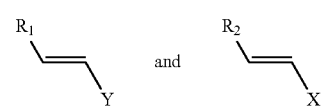

with

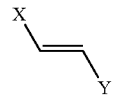

as the first species). In some embodiments, provided methods selectively provide a product comprising a double bond, wherein one carbon atom of the double bond is the first carbon atom of the olefin of the first species, wherein the halogen on the first carbon atom of the olefin of the first species is smaller than the halogen on the second carbon atom of the olefin of the first species, and the other carbon atom of the double bond is the first carbon atom of the olefin of the second species, wherein the substituent on the first carbon atom of the olefin of the second species is larger than the substituent on the second carbon atom of the olefin of the second species. In some embodiments, each olefin carbon atom maintains its substituents after the reaction into products. For example, in some embodiments, substituents on the first and second carbon atoms of the olefins in the first species and the second species do not change when such carbon atoms are re-arranged to form products. In some embodiments, a second species comprises a terminal olefin wherein the terminal double bond has only one unsubstituted carbon atom (=CH$_2$), and provided methods selectively provide a product by replacing the =CH$_2$ moiety with the first carbon atom of the olefin in the first species and its substituents, wherein the halogen on the first carbon atom of the olefin of the first species is smaller than the halogen on the second carbon atom of the olefin of the first species. For the above depicted reaction, in some embodiments, $R_1$ is sterically larger than $R_2$. In some embodiments, $R_2$ is hydrogen. In some embodiments, Y is sterically larger than X. In some embodiments, X is —F. In some embodiments, $R_1$ is sterically larger than $R_2$, and Y is sterically larger than X. In some embodiments, $R_2$ is hydrogen, X is —F, and Y is —Cl or —Br. In some embodiments, $R_2$ is hydrogen, X is —F, and Y is —Cl. In some embodiments, $R_2$ is hydrogen, X is —F, and Y is —Br. When X is —F and Y is —Cl or —Br, provided methods provide efficient synthesis of alkenyl fluoride. Such methods provide various benefits including but not limited to avoiding unstable and/or expensive substrates such as

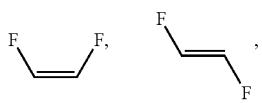

etc.

In some embodiments, each carbon atom of the double bond in the second species has the same substitution pattern. In some embodiments, each carbon atom of the double bond in the second species has the same set of substituents. In some embodiments, each carbon atom of the double bond in the second species is mono-substituted with the same substituent. In some embodiments, the second species is 1,2-disubstituted olefin. In some embodiments, a second species is $R^t$—CH=CH—$R^t$. In some embodiments, a second species is (Z)—$R^t$—CH=CH—$R^t$. In some embodiments, a second species is (E)-$R^t$—CH=CH-$R^t$. In some embodiments, the two $R^t$ are different. In some embodiments, a second species is asymmetric with respect to the center of its double bond. In some embodiments, the two $R^t$ are the same. In some embodiments, a second species is (E)-Ph-CH=CH-Ph. In some embodiments, a second species is symmetric with respect to the center of its double bond.

In some embodiments, the present disclosure provides a method, comprising:
  reacting a first species comprising an olefin with a second species comprising an alkyne in the presence of a catalyst or metal complex to provide at least one product comprising an olefin, wherein:
  each carbon atom of the olefin in the first species is substituted with at least one halogen; and
  the olefin in the at least one product comprises a carbon atom from the first species and a carbon atom from the second species.

In some embodiments, the present disclosure provides a method for enyne metathesis, comprising providing a catalyst or metal complex has the structure of formula II-a or II-b. In some embodiments, the at least one product in a provided method has the structure of a product from the metathesis between the olefin of the first species and the alkyne of the second species.

In some embodiments, a first species of a provided enyne metathesis method is an alkenyl halide, wherein each carbon of the alkene group is independently substituted with a halogen atom. In some embodiments, a first species has the structure of

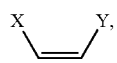

wherein each of X and Y is independently halogen. In some embodiments, each of X and Y is —Cl. In some embodiments, one of X and Y is —F and the other is —Cl. In some embodiments, one of X and Y is —F and the other is —Br. In some embodiments, a second species of a provided enyne metathesis method comprises an alkyne group. In some embodiments, a second species comprises a terminal alkyne.

In some embodiments, a second species has the structure of $R^1$—C≡CH. In some embodiments, a second species has the structure of $R^1$—C≡CH, wherein $R^1$ is an optionally substituted group selected from $C_{1-20}$ aliphatic, $C_{1-20}$ heteroaliphatic having 1-3 heteroatoms independently selected from nitrogen, oxygen, or sulfur, phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 4-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-10 membered bicyclic heteroaryl ring having 1-5 heteroatoms independently selected from nitrogen, oxygen, or sulfur. In some embodiments, a product comprises a conjugated diene. In some embodiments, a diene is substituted with one or more halogen. In some embodiments, a diene is useful as a material for organic synthesis, e.g., for Diels-Alder reaction.

In some embodiments, an exemplary provided method is depicted below:

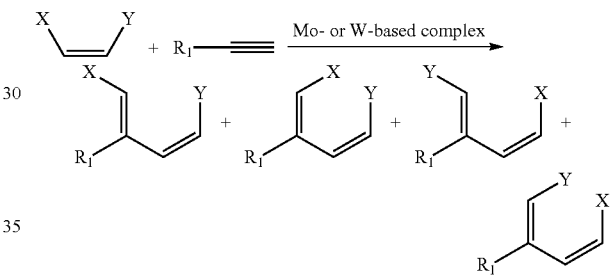

In some embodiments, X and/or Y=H, F, Cl, Br, I; they must not be H at the same time. In some embodiments, $R_1$=H or any linear or branched hydrocarbon, Me, or any linear or branched alkyl, Ph, any mono-, di-, tri-, or tetra-substituted aryl (all isomers) with substituents, 1- or 2-substituted naphthyl or any O-, N-, or S-containing heterocycle. $R^1$ might be N-, S-, Si-, B-, P-based group. In some embodiments, $R_1$ is $R^t$. In some embodiments, $R_1$ is R'.

In some embodiments, provided methods provide regioselectivity. In some embodiments, provided methods provide stereoselectivity. In some embodiments, provided methods provide regioselectivity and stereoselectivity. In some embodiments, provided methods provide regioselectivity and Z-selectivity. In some embodiments, provided methods provide regioselectivity and E-selectivity.

In some embodiments, a provided catalyst or metal complex, e.g., a compound of formula II-a, a compound of formula II-b, etc. is isolated. In some embodiments, when used as a solid, a provided catalyst or metal complex, e.g., a compound of formula II-a, a compound of formula II-b, etc. is purified and/or isolated. In some embodiments, when used in a solution, a provided catalyst or metal complex, e.g., a compound of formula II-a, a compound of formula II-b, etc. may not be isolated and may be generated in situ and used without isolation from a solution. In some embodiments, a provided catalyst or metal complex, e.g., a compound of formula II-a, a compound of formula II-b, etc. is added as substantially pure form as a solid and/or solution. In some embodiments, the purity is greater than 50% with respect to the metal in that, for example, 50% of the metal-containing compound in the solid and/or solution is a compound of formula II-, when a compound of formula II-a is used. In some embodiments, the purity is greater than 60%. In some embodiments, the purity is greater than 70%. In some embodiments, the purity is greater than 80%. In some embodiments, the purity is greater than 85%. In some embodiments, the purity is greater than 90%. In some embodiments, the purity is greater than 91%. In some embodiments, the purity is greater than 92%. In some embodiments, the purity is greater than 93%. In some embodiments, the purity is greater than 94%. In some embodiments, the purity is greater than 95%. In some embodiments, the purity is greater than 96%. In some embodiments, the purity is greater than 97%. In some embodiments, the purity is greater than 98%. In some embodiments, the purity is greater than 99%.

In some embodiments, the present disclosure provides a composition comprising

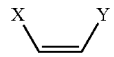

and a catalyst or metal complex having the structure of formula II-a or II-b. In some embodiments, the present disclosure provides a composition comprising

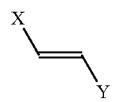

and a catalyst or metal complex having the structure of formula II-a or II-b. In some embodiments, the present disclosure provides a composition comprising a diene having the structure of formula I-a, and a catalyst or metal complex having the structure of formula II-a or II-b.

In some embodiments, the present disclosure provides a composition comprising a metal complex having the structure of formula II-a or II-b and a first species comprising an olefin, wherein each carbon atom of the olefin in the first species is substituted with at least one halogen. In some embodiments, the present disclosure provides a composition comprising a first species comprising an olefin, wherein each carbon atom of the olefin in the first species is substituted with at least one halogen, and one or more species selected from a metal complex comprising molybdenum or tungsten, $R^4OH$ or a salt thereof, and $R^5H$ or a salt thereof. In some embodiments, the present disclosure provides a composition comprising a first species comprising an olefin, wherein each carbon atom of the olefin in the first species is substituted with at least one halogen, and a metal complex comprising molybdenum or tungsten. In some embodiments, the present disclosure provides a composition comprising a first species comprising an olefin, wherein each carbon atom of the olefin in the first species is substituted with at least one halogen, and a species selected from $R^4OH$ or a salt thereof, and $R^5H$ or a salt thereof. In some embodiments, the present disclosure provides a composition comprising a first species comprising an olefin, wherein each carbon atom of the olefin in the first species is substituted with at least one halogen, and $R^4OH$ or a salt thereof. In some embodiments, the present disclosure provides a composition comprising a first species comprising an olefin, wherein each carbon atom of the olefin in the first species is substituted with at least one halogen, and $R^5H$ or a salt thereof. In some embodiments, the present disclosure provides a composition comprising a first species comprising an olefin, wherein each carbon atom of the olefin in the first species is substituted with at least one halogen, and a metal complex comprising molybdenum or tungsten, $R^4OH$ or a salt thereof, and $R^5H$ or a salt thereof. In some embodiments, $R^4OH$ or a salt thereof, and/or $R^5H$ or a salt thereof, is generated, or introduced, when preparing a metal complex, e.g., a metal complex of formula II-a, a metal complex of formula II-b, etc. In some embodiments, $R^4OH$ or a salt thereof, and/or $R^5H$ or a salt thereof, is generated when a metal complex, e.g., a metal complex of formula II-a, a metal complex of formula II-b, etc., degrades and/or is quenched when a methathesis reaction reaches a desired stage. In some embodiments, a first species is

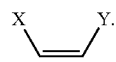

In some embodiments, a first species is

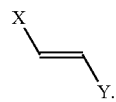

Y In some embodiments, X and Y are the same. In some embodiments, X and Y are different. In some embodiments, one of X and Y is —F, and the other is —Cl or —Br. In some embodiments, one of X and Y is —F, and the other is —Cl. In some embodiments, one of X and Y is —F, and the other is —Br. In some embodiments, a metal complex comprising molybdenum or tungsten has the structure of formula II-a or II-b. In some embodiments, a metal complex comprising molybdenum or tungsten has the structure of formula II-a. In some embodiments, a metal complex comprising molybdenum or tungsten has the structure of formula II-b. In some embodiments, a metal complex comprising molybdenum or tungsten is a compound when another metal complex, e.g., a metal complex of formula II-a, a metal complex of formula II-b, etc., degrades and/or is quenched when a metathesis reaction reaches a desired stage. Among other things, provided compositions are useful for preparing halogenated olefins with e.g., high efficiency, high regioselectivity, high stereoselectivity, etc.

In some embodiments, a provided composition comprises $CH_2=CHX$. In some embodiments, a provided composition comprises $CH_2=CHY$. In some embodiments, a provided composition comprises $CH_2=CHX$ and/or $CH_2=CHY$. In some embodiments, a provided composition comprises $CH_2=CHX$ or $CH_2=CHY$. In some embodiments, a provided composition comprises $CH_2=CHX$ and $CH_2=CHY$. In some embodiments, a provided composition comprises $CH_2=CHX$. In some embodiments, a provided composition comprises $CH_2=CHY$. In some embodiments, a provided composition comprises $CH_2=CHF$. In some embodiments, a provided composition comprises $CH_2=CHCl$. In some embodiments, a provided composition comprises $CH_2=CHBr$. In some embodiments, a provided composition comprises $CH_2=CHI$.

In some embodiments, a provided method generates $CH_2=CHX$. In some embodiments, a provided method generates $CH_2$=CHY. In some embodiments, a provided method generates $CH_2$=CHX and/or $CH_2$=CHY. In some embodiments, a provided method generates $CH_2$=CHX or $CH_2$=CHY. In some embodiments, a provided method generates $CH_2$=CHX and $CH_2$=CHY. In some embodiments, a provided method generates $CH_2$=CHX. In some embodiments, a provided method generates $CH_2$=CHY. In some embodiments, a provided method generates $CH_2$=CHF. In some embodiments, a provided method generates $CH_2$=CHCl. In some embodiments, a provided method generates $CH_2$=CHBr. In some embodiments, a provided method generates $CH_2$=CHI. In some embodiments, a provided method provides surprisingly high regioselectivity, and selectively generates one of $CH_2$=CHX and $CH_2$=CHY over the other, when E- or Z—CHX=CHY is used as a metathesis substrate. In some embodiments, $CH_2$=CHY is selectively generated over $CH_2$=CHX, wherein Y>X (e.g., as understood by a person having ordinary skill in the art, I>Br>Cl>F). In some embodiments, the selectivity is greater than about 1:1. In some embodiments, the selectivity is greater than about 2:1. In some embodiments, the selectivity is greater than about 3:1. In some embodiments, the selectivity is greater than about 4:1. In some embodiments, the selectivity is greater than about 5:1. In some embodiments, the selectivity is greater than about 6:1. In some embodiments, the selectivity is greater than about 7:1. In some embodiments, the selectivity is greater than about 8:1. In some embodiments, the selectivity is greater than about 9:1. In some embodiments, the selectivity is greater than about 10:1. In some embodiments, the selectivity is greater than about 20:1. In some embodiments, the selectivity is greater than about 30:1. In some embodiments, the selectivity is greater than about 40:1. In some embodiments, the selectivity is greater than about 50:1. In some embodiments, the selectivity is greater than about 60:1. In some embodiments, the selectivity is greater than about 70:1. In some embodiments, the selectivity is greater than about 80:1. In some embodiments, the selectivity is greater than about 90:1. In some embodiments, the selectivity is greater than about 100:1.

In some embodiments, a ligand is provided in a molar ratio of about 10:1, 9:1, 8:1, 7:1, 6:1, 5:1, 4:1, 3:1, 2:1, or 1:1 relative to the metal. In some embodiments, a ligand is provided in a molar ratio of about 0.9:1, 0.8:1, 0.7:1, 0.6:1, 0.5:1, 0.4:1, 0.3:1, 0.2:1, or 0.1:1 relative to the metal. In certain embodiments, a ligand is provided in a molar ratio of about 1:1 relative to the metal. One of skill in the art will appreciate that the optimal molar ratio of ligand to metal will depend on, inter alia, whether the ligand is mono- or polydentate. In some embodiments, a ligand or ligand precursor having the structure as described in formula II-a or II-b is provided in a molar ratio of about 1:1 to M. In some embodiments, —$OR^4$ is provided in a molar ratio of about 1:1 to M. In some embodiments, —$OR^4$ is provided in a molar ratio of about 2:1 to M. In some embodiments, —$OR^4$ is provided in a molar ratio of less than about 2:1 to M. In some embodiments, —$OR^4$ is provided in a molar ratio of less than about 1.9:1 to M. In some embodiments, —$OR^4$ is provided in a molar ratio of less than about 1.8:1 to M. In some embodiments, —$OR^4$ is provided in a molar ratio of less than about 1.7:1 to M. In some embodiments, —$OR^4$ is provided in a molar ratio of less than about 1.6:1 to M. In some embodiments, —$OR^4$ is provided in a molar ratio of less than about 1.5:1 to M. In some embodiments, —$OR^4$ is provided in a molar ratio of less than about 1.4:1 to M. In some embodiments, —$OR^4$ is provided in a molar ratio of less than about 1.3:1 to M. In some embodiments, —$OR^4$ is provided in a molar ratio of less than about 1.2:1 to M. In some embodiments, —$OR^4$ is provided in a molar ratio of less than about 1.1:1 to M. In some embodiments, —$OR^4$ is provided in a molar ratio of more than about 2:1 to M. In some embodiments, —$OR^4$ is provided in a molar ratio of more than about 1.9:1 to M. In some embodiments, —$OR^4$ is provided in a molar ratio of more than about 1.8:1 to M. In some embodiments, —$OR^4$ is provided in a molar ratio of more than about 1.7:1 to M. In some embodiments, —$OR^4$ is provided in a molar ratio of more than about 1.6:1 to M. In some embodiments, —$OR^4$ is provided in a molar ratio of more than about 1.5:1 to M. In some embodiments, —$OR^4$ is provided in a molar ratio of more than about 1.4:1 to M. In some embodiments, —$OR^4$ is provided in a molar ratio of more than about 1.3:1 to M. In some embodiments, —$OR^4$ is provided in a molar ratio of more than about 1.2:1 to M. In some embodiments, —$OR^4$ is provided in a molar ratio of more than about 1.1:1 to M.

Suitable conditions for performing provided methods generally employ one or more solvents. In certain embodiments, one or more organic solvents are used. Examples of such organic solvents include, but are not limited to, hydrocarbons such as benzene, toluene, and pentane, halogenated hydrocarbons such as dichloromethane, or polar aprotic solvents, such as ethereal solvents including ether, DME, tetrahydrofuran (THF), or dioxanes, or protic solvents, such as alcohols, or mixtures thereof. In certain embodiments, one or more solvents are deuterated.

In some embodiments, a single solvent is used. In certain embodiments, a solvent is benzene. In certain embodiments, a solvent is ether. In some embodiments, a solvent is a nitrile. In some embodiments, a solvent is acetonitrile.

In some embodiments, mixtures of two or more solvents are used, and in some cases may be preferred to a single solvent. In certain embodiments, the solvent mixture is a mixture of an ethereal solvent and a hydrocarbon. Exemplary such mixtures include, for instance, an ether/benzene mixture. In some embodiments, an exemplary mixture is a DME/Toluene mixture. In some embodiments, an exemplary mixture is DME/Toluene about 1:1. Solvent mixtures may be comprised of equal volumes of each solvent or may contain one solvent in excess of the other solvent or solvents. In certain embodiments wherein a solvent mixture is comprised of two solvents, the solvents may be present in a ratio of about 20:1, about 10:1, about 9:1, about 8:1, about 7:1, about 6:1, about 5:1, about 4:1, about 3:1, about 2:1, or about 1:1. In certain embodiments wherein a solvent mixture comprises an ethereal solvent and a hydrocarbon, the solvents may be present in a ratio of about 20:1, about 10:1, about 9:1, about 8:1, about 7:1, about 6:1, about 5:1, about 4:1, about 3:1, about 2:1, or about 1:1 ethereal solvent: hydrocarbon. In certain embodiments, the solvent mixture comprises a mixture of ether and benzene in a ratio of about 5:1. One of skill in the art would appreciate that other solvent mixtures and/or ratios are contemplated herein, that the selection of such other solvent mixtures and/or ratios will depend on the solubility of species present in the reaction (e.g., substrates, additives, etc.), and that experimentation required to optimized the solvent mixture and/or ratio would be routine in the art and not undue.

Suitable conditions, in some embodiments, employ ambient temperatures. In some embodiments, a suitable temperature is about 15° C., about 20° C., about 25° C., or about 30° C. In some embodiments, a suitable temperature is from about 15° C. to about 25° C. In certain embodiments, a suitable temperature is about 20° C., 21° C., 22° C., 23° C., 24° C., or 25° C.

In certain embodiments, a provided method is performed at elevated temperature. In some embodiments, a suitable temperature is from about 25° C. to about 110° C. In certain embodiments, a suitable temperature is from about 40° C. to about 100° C., from about 50° C. to about 100° C., from about 60° C. to about 100° C., from about 70° C. to about 100° C., from about 80° C. to about 100° C., or from about 90° C. to about 100° C. In some embodiments, a suitable temperature is about 80° C. In some embodiments, a suitable temperature is about 30° C. In some embodiments, a suitable temperature is about 40° C. In some embodiments, a suitable temperature is about 50° C. In some embodiments, a suitable temperature is about 60° C. In some embodiments, a suitable temperature is about 70° C. In some embodiments, a suitable temperature is about 80° C. In some embodiments, a suitable temperature is about 90° C. In some embodiments, a suitable temperature is about 100° C. In some embodiments, a suitable temperature is about 110° C.

In certain embodiments, a provided method is performed at temperature lower than ambient temperatures. In some embodiments, a suitable temperature is from about −100° C. to about 10° C. In certain embodiments, a suitable temperature is from about −80° C. to about 0° C. In certain embodiments, a suitable temperature is from about −70° C. to about 10° C. In certain embodiments, a suitable temperature is from about −60° C. to about 10° C. In certain embodiments, a suitable temperature is from about −50° C. to about 10° C. In certain embodiments, a suitable temperature is from about −40° C. to about 10° C. In certain embodiments, a suitable temperature is from about −30° C. to about 10° C. In some embodiments, a suitable temperature is below 0° C. In some embodiments, a suitable temperature is about −100° C. In some embodiments, a suitable temperature is about −90° C. In some embodiments, a suitable temperature is about −80° C. In some embodiments, a suitable temperature is about −70° C. In some embodiments, a suitable temperature is about −60° C. In some embodiments, a suitable temperature is about −50° C. In some embodiments, a suitable temperature is about −40° C. In some embodiments, a suitable temperature is about −30° C. In some embodiments, a suitable temperature is about −20° C. In some embodiments, a suitable temperature is about −10° C. In some embodiments, a suitable temperature is about 0° C. In some embodiments, a suitable temperature is about 10° C.

In some embodiments, a provided method is performed at different temperatures. In some embodiments, temperature changes in a provided method. In some embodiments, a provided method involves temperature increase from a lower suitable temperature to a higher suitable temperature. In some embodiments, a provided method comprises temperature increase from about −80° C., about −70° C., about −60° C., about −50° C., about −40° C., about −30° C., about −20° C., about −10° C., and about 0° C. to about 0° C., about 10° C., about 20° C., ambient temperature, about 22° C., about 25° C., about 30° C., about 40° C., about 50° C., about 60° C., about 70° C., about 80° C., about 90° C., about 100° C. and about 110° C. In some embodiments, a provided method comprises temperature increase from about −30° C. to 22° C. In some embodiments, a provided method comprises temperature decrease from a higher suitable temperature to a lower suitable temperature. In some embodiments, a provided method comprises temperature increase from about 110° C., about 100° C., about 90° C., about 80° C., about 70° C., about 60° C., about 50° C., about 40° C., about 30° C., about 25° C., about 22° C., ambient temperature, about 20° C., about 10° C., and about 0° C. to about 0° C., about −10° C., about −20° C., about −30° C., about −40° C., about −50° C., about −60° C., about −70° C., about −80° C., about −90° C., and about −100° C.

Suitable conditions typically involve reaction times of about 1 minute to about one or more days. In some embodiments, the reaction time ranges from about 0.5 hour to about 72 hours. In some embodiments, the reaction time ranges from about 0.5 hour to about 48 hours. In some embodiments, the reaction time ranges from about 0.5 hour to about 20 hours. In some embodiments, the reaction time ranges from about 0.5 hour to about 15 hours. In some embodiments, the reaction time ranges from about 1.0 hour to about 12 hours. In some embodiments, the reaction time ranges from about 1 hour to about 10 hours. In some embodiments, the reaction time ranges from about 1 hour to about 8 hours. In some embodiments, the reaction time ranges from about 1 hour to about 6 hours. In some embodiments, the reaction time ranges from about 1 hour to about 4 hours. In some embodiments, the reaction time ranges from about 1 hour to about 2 hours. In some embodiments, the reaction time ranges from about 2 hours to about 8 hours. In some embodiments, the reaction time ranges from about 2 hours to about 4 hours. In some embodiments, the reaction time ranges from about 2 hours to about 3 hours. In certain embodiments, the reaction time is about 1, 2, 3, 4, 5, 6, 7, 8, 9, 10, 11, 12, 24, 36, 48, 60, 72, 96 or 120 hours. In certain embodiments, the reaction time is about 1 hour. In certain embodiments, the reaction time is about 2 hours. In certain embodiments, the reaction time is about 3 hours. In certain embodiments, the reaction time is about 4 hours. In certain embodiments, the reaction time is about 5 hours. In certain embodiments, the reaction time is about 6 hours. In some embodiments, the reaction time is about 12 hours. In some embodiments, the reaction time is about 24 hours. In some embodiments, the reaction time is about 36 hours. In some embodiments, the reaction time is about 48 hours. In some embodiments, the reaction time is about 72 hours. In some embodiments, the reaction time is about 96 hours. In some embodiments, the reaction time is about 120 hours. In certain embodiments, the reaction time is less than about 1 hour. In certain embodiments, the reaction time is about 5, 10, 15, 20, 25, 30, 35, 40, 45, 50, or 55 minutes. In some embodiments, the reaction time is about 5 minutes. In some embodiments, the reaction time is about 10 minutes. In some embodiments, the reaction time is about 15 minutes. In some embodiments, the reaction time is about 20 minutes. In some embodiments, the reaction time is about 25 minutes. In some embodiments, the reaction time is about 30 minutes. In some embodiments, the reaction time is about 35 minutes. In some embodiments, the reaction time is about 40 minutes. In some embodiments, the reaction time is about 100 minutes. In some embodiments, the reaction time is about 110 minutes. In some embodiments, the reaction time is about 200 minutes. In some embodiments, the reaction time is about 300 minutes. In some embodiments, the reaction time is about 400 minutes.

In some embodiments, a provided metal complex compound, e.g. a compound of formula II-a or II-b or an active catalyst formed from a provided compound, is stable under metathesis conditions. In some embodiments, a provided compound, or an active catalyst formed from a provided compound, decomposes under metathesis conditions. In some embodiments, a provided compound, or an active catalyst formed from a provided compound, decomposes under metathesis conditions within about 1 hour. In some embodiments, a provided compound, or an active catalyst formed from a provided compound, decomposes under metathesis conditions within about 2 hours. In some embodiments, a provided compound, or an active catalyst formed from a provided compound, decomposes under metathesis conditions within about 6 hours. In some embodiments, a provided compound, or an active catalyst formed from a provided compound, decomposes under metathesis conditions within about 12 hours. In some embodiments, a provided compound, or an active catalyst formed from a provided compound, decomposes under metathesis conditions within about 24 hours. In some embodiments, a provided compound, or an active catalyst formed from a provided compound, decomposes under metathesis conditions within about 48 hours. In some embodiments, a provided compound, or an active catalyst formed from a provided compound, decomposes under metathesis conditions within about 96 hours.

Some embodiments may provide the ability to selectively synthesize, via a metathesis reaction, products having a Z or E configuration about a double bond. Some embodiments may provide the ability to selectively synthesize, via a metathesis reaction, products having a Z configuration about a double bond. Some embodiments may provide the ability to selectively synthesize, via a metathesis reaction, products having a E configuration about a double bond. In some embodiments, a method of the present disclosure provides the ability to synthesize compounds comprising a Z-olefin. In some embodiments, a method of the present disclosure provides the ability to synthesize compounds comprising a E-olefin. In some embodiments, such methods are useful when applied to a wide range of olefin substrates, including those having sterically small or large groups adjacent the olefin. In some embodiments, the substrate olefins are terminal olefins. In some embodiments, one of the substrate olefin is terminal olefin.

In some embodiments, the present disclosure provides methods for regioselective metathesis in that the methods selectively provide products via one of the possible metathesis pathways. In some embodiments, the present disclosure provides methods for regioselective synthesis of alkenyl fluoride using 1-bromo-2-fluoroethylene or 1-chloro-2-fluoroethylene. In some embodiments, provided methods further provide Z- or E-selectivity. Exemplary reactions are described below.

In some embodiments, the present disclosure provides a method for Z-selective metathesis reactions. In some embodiments, a provided method produces a double bond in a Z:E ratio greater than about 1:1, greater than about 2:1, greater than about 3:1, greater than about 4:1, greater than about 5:1, greater than about 6:1, greater than about 7:1, greater than about 8:1, greater than about 9:1, greater than about 95:5, greater than about 96:4, greater than about 97:3, greater than about 98:2, or, in some cases, greater than about 99:1, as determined using methods described herein (e.g., HPLC or NMR). In some cases, about 100% of the double bond produced in the metathesis reaction may have a Z configuration. The Z or cis selectivity may also be expressed as a percentage of product formed. In some cases, the product may be greater than about 50% Z, greater than about 60% Z, greater than about 70% Z, greater than about 80% Z, greater than about 90% Z, greater than about 95% Z, greater than about 96% Z, greater than about 97% Z, greater than about 98% Z, greater than about 99% Z, or, in some cases, greater than about 99.5% Z.

In some embodiments, the present disclosure provides a method for E-selective metathesis reactions. In some embodiments, a provided method produces a double bond in a E:Z ratio greater than about 1:1, greater than about 2:1, greater than about 3:1, greater than about 4:1, greater than about 5:1, greater than about 6:1, greater than about 7:1, greater than about 8:1, greater than about 9:1, greater than about 95:5, greater than about 96:4, greater than about 97:3, greater than about 98:2, or, in some cases, greater than about 99:1, as determined using methods described herein (e.g., HPLC or NMR). In some cases, about 100% of the double bond produced in the metathesis reaction may have a E configuration. The E or trans selectivity may also be expressed as a percentage of product formed. In some cases, the product may be greater than about 50% E, greater than about 60% E, greater than about 70% E, greater than about 80% E, greater than about 90% E, greater than about 95% E, greater than about 96% E greater than about 97% E, greater than about 98% E, greater than about 99% E, or, in some cases, greater than about 99.5% E.

In some embodiments, a provided method requires an amount of a provided compound (e.g., a metal complex having the structure of formula II-a or II-b) such that the loading is from about 0.01 mol % to about 20 mol % of the provided compound relative to substrate (e.g., a first or second double bond). In certain embodiments, a provided compound is used in an amount of between about 0.01 mol % to about 10 mol %. In certain embodiments, a provided compound is used in an amount of between about 0.01 mol % to about 6 mol %. In certain embodiments, a provided compound is used in an amount of between about 0.01 mol % to about 5 mol %. In certain embodiments, a provided compound is used in an amount of between about 0.01 mol % to about 4 mol %. In certain embodiments, a provided compound is used in an amount of between about 0.01 mol % to about 3 mol %. In certain embodiments, a provided compound is used in an amount of between about 0.01 mol % to about 1 mol %. In certain embodiments, a provided compound is used in an amount of between about 0.01 mol % to about 0.5 mol %. In certain embodiments, a provided compound is used in an amount of between about 0.01 mol % to about 0.2 mol %. In certain embodiments, a provided compound is used in an amount of about 0.05%, 0.1%, 0.2%, 0.5%, 1%, 2%, 3 mol %, 4 mol %, 5 mol %, 6 mol %, 7 mol %, 8 mol %, 9 mol %, or 10 mol %.

In some embodiments, a method of the present disclosure requires an amount of solvent such that the concentration of the reaction is between about 0.01 M and about 1 M. In some embodiments, the concentration of the reaction is between about 0.01 M and about 0.5 M. In some embodiments, the concentration of the reaction is between about 0.01 M and about 0.1 M. In some embodiments, the concentration of the reaction is between about 0.01 M and about 0.05 M. In some embodiments, the concentration of the reaction is about 0.01 M. In some embodiments, the concentration of the reaction is about 0.02 M. In some embodiments, the concentration of the reaction is about 0.03 M. In some embodiments, the concentration of the reaction is about 0.04 M. In some embodiments, the concentration of the reaction is about 0.05 M. In some embodiments, the concentration of the reaction is about 0.1 M. In some embodiments, the concentration of the reaction is about 0.3 M.

In some embodiments, a method of the present disclosure is performed at ambient pressure. In some embodiments, a method of the present disclosure is performed at reduced pressure. In some embodiments, a method of the present disclosure is performed at a pressure of less than about 20 torr. In some embodiments, a method of the present disclosure is performed at a pressure of less than about 15 torr. In some embodiments, a method of the present disclosure is performed at a pressure of less than about 10 torr. In some embodiments, a method of the present disclosure is performed at a pressure of about 9, 8, 7, 6, 5, 4, 3, 2, or 1 torr. In certain embodiments, a method of the present disclosure is performed at a pressure of about 7 torr. In certain embodiments, a method of the present disclosure is performed at a pressure of about 1 torr.

In some embodiments, a method of the present disclosure is performed at increased pressure. In some embodiments, a method of the present disclosure is performed at greater than about 1 atm. In some embodiments, a method of the present disclosure is performed at greater than about 2 atm. In some embodiments, a method of the present disclosure is performed at greater than about 3 atm. In some embodiments, a method of the present disclosure is performed at greater than about 5 atm. In some embodiments, a method of the present disclosure is performed at greater than about 10 atm. In some embodiments, a method of the present disclosure is performed at about 2 atm. In some embodiments, a method of the present disclosure is performed at about 3 atm. In some embodiments, a method of the present disclosure is performed at about 5 atm. In some embodiments, a method of the present disclosure is performed at about 10 atm.

In some embodiments, the present disclosure recognizes that ratios of metathesis substrates have impact on the reaction results, e.g., yield, regioselectivity, stereoselectivity (e.g., Z-selectivity, E-selectivity, etc.), etc. In some embodiments, provided technologies, e.g., compounds, methods, etc. provide high tolerance of molar ratio of substrates. In some embodiments, provided technologies deliver high yield and high selectivity (e.g., regioselectivity, stereoselectivity, chemoselectivity, etc., across a wide range of molar ratios of substrates. In some embodiments, the present disclosure demonstrates that when too much first species is used relative to a second species, product yield, regioselectivity and/or stereoselectivity may decrease. In some embodiments, the molar ratio of the first species to the second species is about 1:1. In some embodiments, the ratio is about 2:1. In some embodiments, the ratio is about 3:1. In some embodiments, the ratio is about 4:1. In some embodiments, the ratio is about 5:1. In some embodiments, the ratio is about 6:1. In some embodiments, the ratio is about 7:1. In some embodiments, the ratio is about 8:1. In some embodiments, the ratio is about 9:1. In some embodiments, the ratio is about 10:1. In some embodiments, the ratio is about 15:1. In some embodiments, the ratio is about 20:1. In some embodiments, the ratio is about 30:1. In some embodiments, the ratio is about 40:1. In some embodiments, the ratio is about 50:1. In some embodiments, the molar ratio of the first species to the second species is less than about 1:1. In some embodiments, the ratio is less than about 2:1. In some embodiments, the ratio is less than about 3:1. In some embodiments, the ratio is less than about 4:1. In some embodiments, the ratio is less than about 5:1. In some embodiments, the ratio is less than about 6:1. In some embodiments, the ratio is less than about 7:1. In some embodiments, the ratio is less than about 8:1. In some embodiments, the ratio is less than about 9:1. In some embodiments, the ratio is less than about 10:1. In some embodiments, the ratio is less than about 15:1. In some embodiments, the ratio is less than about 20:1. In some embodiments, the ratio is less than about 30:1. In some embodiments, the ratio is less than about 40:1. In some embodiments, the ratio is less than about 50:1. In some embodiments, the molar ratio of the first species to the second species is greater than about 1:1. In some embodiments, the ratio is greater than about 2:1. In some embodiments, the ratio is greater than about 3:1. In some embodiments, the ratio is greater than about 4:1. In some embodiments, the ratio is greater than about 5:1. In some embodiments, the ratio is greater than about 6:1. In some embodiments, the ratio is greater than about 7:1. In some embodiments, the ratio is greater than about 8:1. In some embodiments, the ratio is greater than about 9:1. In some embodiments, the ratio is greater than about 10:1. In some embodiments, the ratio is greater than about 15:1. In some embodiments, the ratio is greater than about 20:1. In some embodiments, the ratio is greater than about 30:1. In some embodiments, the ratio is greater than about 40:1. In some embodiments, the ratio is greater than about 50:1. In some embodiments, a ratio is within a range, wherein the lower end ratio is about 1:1, 2:1, 3:1, 4:1, 5:1, 6:1, 7:1, 8:1, 9:1, 10:1, 11:1, 12:1, 13:1, 14:1, 15:1, 20:1, 30:1, 40:1, or 50:1, and the higher end ratio is higher than the lower end ratio and is about 2:1, 3:1, 4:1, 5:1, 6:1, 7:1, 8:1, 9:1, 10:1, 11:1, 12:1, 13:1, 14:1, 15:1, 20:1, 30:1, 40:1, or 50:1. In some embodiments, the lower end ratio is selected from about 1:1, 2:1, or 3:1, and the higher end ratio is selected from 20:1, 30:1, 40:1, or 50:1.

In some embodiments, a provided catalyst or metal complex, or a reaction condition or selectivity, is independently as described in US Patent Application Publication US2012/0323000, incorporated herein by reference, both individually and in combination.

As mentioned above, provided compounds are useful for metathesis reactions. Exemplary such methods and reactions are described below.

It will be appreciated that, in certain embodiments, each variable recited is as defined above and described in embodiments, herein, both singly and in combination.

In some embodiments, the present disclosure provides the following examples:

E1. A method, comprising:

reacting a first species comprising an olefin with a second species comprising an alkyne in the presence of a catalyst or metal complex to provide at least one product comprising an olefin, wherein:

each carbon atom of the olefin in the first species is substituted with at least one halogen; and the olefin in the at least one product comprises a carbon atom from the first species and a carbon atom from the second species.

E2. The method of example E1, wherein the second species comprises a terminal alkyne.

E3. The method of example E2, wherein the second species has the structure of $R^1$—C≡CH, wherein $R^1$ is an optionally substituted group selected from $C_{1-20}$ aliphatic, $C_{1-20}$ heteroaliphatic having 1-3 heteroatoms independently selected from nitrogen, oxygen, or sulfur, phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 4-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-10 membered bicyclic heteroaryl ring having 1-5 heteroatoms independently selected from nitrogen, oxygen, or sulfur.

E4. The method of any one of the preceding examples, wherein the at least one product comprises a conjugated diene, wherein the diene comprising two carbon atoms from the olefin of the first species, and two carbon atoms from the alkyne in the second species.

E5. The method of example E4, wherein each of the two carbon atoms from the olefin of the first species is independently substituted with at least one halogen as in the first species.

E6. The method of any one of the preceding examples, wherein the reaction is an enyne metathesis.

E7. The method of any one of the preceding examples, wherein the first species has the structure of:

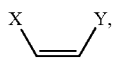

wherein each of X and Y is independently halogen.

E8. The method of example E7, wherein the second species has the structure of $R^1$—C≡CH, and the at least one product has a structure selected from:

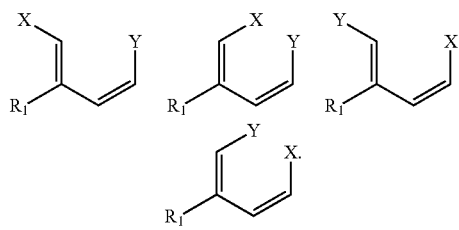

E9. A method, comprising:
reacting a first species comprising an olefin with a second species comprising an olefin in the presence of a catalyst or metal complex to provide at least one product comprising an olefin, wherein:
each carbon atom of the olefin in the first species is substituted with at least one halogen; and
the olefin in the at least one product comprises a carbon atom from the first species and a carbon atom from the second species.

E10. The method of example E9, wherein the olefin in the at least one product is formed via a metathesis reaction between the olefin in the first species and the olefin in the second species.

E11. The method of any one of the preceding examples, wherein each carbon atom of the double bond in the first species is substituted with no more than one halogen.

E12. The method of any one of the preceding examples, wherein the halogen substituent of the first carbon atom of the double bond in the first species and the halogen substituent of the second carbon atom of the double bond in the first species is cis.

E13. The method of any one of the preceding examples, wherein the halogen substituent of the first carbon atom of the double bond in the first species and the halogen substituent of the second carbon atom of the double bond in the first species is cis, and the olefin in the at least one product comprises a carbon atom from the first species and a carbon atom from the second species is produced with Z-selectivity.

E14. The method of any one of the preceding examples, wherein the first species has the structure of:

wherein each of X and Y is independently halogen.

E15. The method of any one of the preceding examples, wherein X and Y are the same.

E16. The method of any one of the preceding examples, wherein the first species is

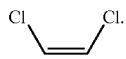

E17. The method of any one of examples E9-E14, wherein X and Y are different.

E18. The method of any one of examples E9-E14, wherein the first species is

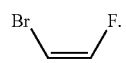

E19. The method of any one of the preceding examples, wherein the product is produced in a Z:E ratio greater than 80:20.

E20. The method of any one of the preceding examples, wherein the product is produced in a Z:E ratio greater than 85:15.

E21. The method of any one of the preceding examples, wherein the product is produced in a Z:E ratio greater than 90:10.

E22. The method of any one of the preceding examples, wherein the product is produced in a Z:E ratio greater than 95:5.

E23. The method of any one of the preceding examples, wherein the product is produced in a Z:E ratio greater than 98:2.

E24. The method of any one of examples E9-E11, wherein the halogen substituent of the first carbon atom of the double bond in the first species and the halogen substituent of the second carbon atom of the double bond in the first species is trans.

E25. The method of any one of examples E9-E11, wherein the halogen substituent of the first carbon atom of the double bond in the first species and the halogen substituent of the second carbon atom of the double bond in the first species is trans, and the olefin in the at least one product comprises a carbon atom from the first species and a carbon atom from the second species is produced with E-selectivity.

E26. The method of any one of examples E9-E11 and E24-E25, wherein the first species has the structure of:

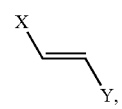

wherein each of X and Y is independently halogen.

E27. The method of any one of examples E9-E11 and E24-E26, wherein X and Y are the same.

E28. The method of any one of examples E9-E11 and E24-E26, wherein the first species is

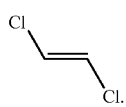

E29. The method of any one of examples E9-E11 and E24-E26, wherein X and Y are different.

E30. The method of any one of examples E9-E11 and E24-E26, wherein the first species is

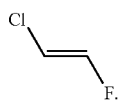

E31. The method of any one of examples E9-E11 and E24-E30, wherein the product is produced in a E:Z ratio greater than 80:20.

E32. The method of any one of examples E9-E11 and E24-E30, wherein the product is produced in a E:Z ratio greater than 85:15.

E33. The method of any one of examples E9-E11 and E24-E30, wherein the product is produced in a E:Z ratio greater than 90:10.

E34. The method of any one of examples E9-E11 and E24-E30, wherein the product is produced in a E:Z ratio greater than 95:5.

E35. The method of any one of examples E9-E11 and E24-E30, wherein the product is produced in a E:Z ratio greater than 98:2.

E36. The method of any one of the preceding examples, wherein the product is formed with greater than 80:20 regioselectivity.

E37. The method of any one of the preceding examples, wherein the product is formed with greater than 85:15 regioselectivity.

E38. The method of any one of the preceding examples, wherein the product is formed with greater than 90:10 regioselectivity.

E39. The method of any one of the preceding examples, wherein the product is formed with greater than 95:5 regioselectivity.

E40. The method of any one of the preceding examples, wherein the product is formed with greater than 98:2 regioselectivity.

E41. The method of any one of the preceding examples, wherein the product is formed with regioselectivity, wherein the at least one product is selectively produced and comprises a double bond, wherein one carbon atom of the double bond is the first carbon atom of the double bond of the first species, wherein the halogen on the first carbon atom of the double bond of the first species is smaller than the halogen on the second carbon atom of the double bond of the first species, and the other carbon atom of the double bond is the first carbon atom of the double bond of the second species, wherein the substituent on the first carbon atom of the double bond of the second species is larger than the substituent on the second carbon atom of the double bond of the second species.

E42. The method of any one of the preceding examples, wherein the carbon atoms of the double bond in the at least one product have the same substituents as in the first and second species.

E43. The method of any one of the preceding examples, wherein the halogen on the first carbon atom of the olefin of the first species is X, the halogen on the second carbon atom of the olefin of the first species is Y, and X<Y.

E44. The method of any one of the preceding examples, wherein the halogen on the first carbon atom of the olefin of the first species is —F.

E45. The method of any one of the preceding examples, wherein the halogen on the second carbon atom of the olefin of the first species is —Cl or —Br.

E46. The method of any one of the preceding examples, where in the second species comprises a terminal olefin.

E47. The method of any one of the preceding examples, wherein the second species is $R^t$—CH=CH$_2$.

E48. The method of any one of the preceding examples, wherein the at least one product is $R^t$—CH=CHX, and is regioselectively produced.

E49. The method of any one of the preceding examples, wherein the other metathesis product together with $R^t$—CH=CHX is CH=CHY, and is regioselectively produced.

E50. The method of any one of examples E36-E49, wherein the first species is

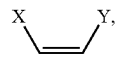

X is —F, Y is —Cl or —Br, and the at least one product is produced with Z-selectivity.

E51. The method of any one of examples E36-E49, wherein the first species is

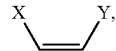

X is —F, Y is —Br, and the at least one product is produced with Z-selectivity.

E52. The method of any one of examples E36-E49, wherein the first species is

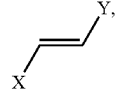

X is —F, Y is —Cl or —Br, and the at least one product is produced with E-selectivity.

E53. The method of any one of examples E36-E49, wherein the first species is

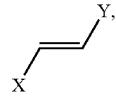

X is —F, Y is —Cl, and the at least one product is produced with E-selectivity.

E54. The method of any one of examples E46-E53, wherein the terminal olefin has the structure of $R^1$—CH=CH$_2$, wherein $R^1$ is an optionally substituted group selected from $C_{1-20}$ aliphatic, $C_{1-20}$ heteroaliphatic having 1-3 heteroatoms independently selected from nitrogen, oxygen, or sulfur, phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 4-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-10 membered bicyclic heteroaryl ring having 1-5 heteroatoms independently selected from nitrogen, oxygen, or sulfur.

E55. The method of any one of examples E9-E45, wherein the olefin in the second species is an internal olefin.

E56. The method of any one of examples E9-E45, wherein the olefin in the second species is an internal olefin within a ring.

E57. The method of any one of examples E9-E45 and E55-E56, wherein the reaction is ring-opening cross metathesis.

E58. The method of any one of examples E9-E54, wherein the reaction is not ring-opening cross metathesis.

E59. The method of any one of examples E9-E58, wherein the reaction is cross metathesis.

E60. The method of any one of the preceding examples, wherein the first species and the second species are different.

E61. The method of any one of the preceding examples, wherein the olefin in the at least one product comprises a carbon atom substituted with at least one halogen from the first species and a carbon atom from the second species.

E62. The method of example E61, wherein the at least one halogen is —Cl.

E63. The method of any one of the preceding examples, wherein the first and second species is independently a compound as exemplified.

E64. The method of any one of the preceding examples, wherein the catalyst or metal complex is of formula II-a:

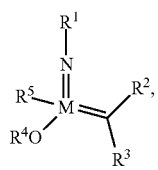

II-a wherein:

M is molybdenum or tungsten;

$R^1$ is an optionally substituted group selected from $C_{1-20}$ aliphatic, $C_{1-20}$ heteroaliphatic having 1-3 heteroatoms independently selected from nitrogen, oxygen, or sulfur, phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 4-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-10 membered bicyclic heteroaryl ring having 1-5 heteroatoms independently selected from nitrogen, oxygen, or sulfur; or $R^1$ is optionally substituted

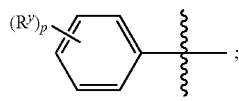

each of $R^2$ and $R^3$ is independently R', —OR', —SR', —N(R')$_2$, —OC(O)R', —SOR', —SO$_2$R', —SO$_2$N(R')$_2$, —C(O)N(R')$_2$, —NR'C(O)R', or —NR'SO$_2$R', provided that $R^2$ and $R^3$ are not simultaneously hydrogen;

$R^4$ is $R^7$, or an optionally substituted group selected from —Ar, $C_{1-20}$ aliphatic, $C_{1-20}$ heteroaliphatic having 1-3 heteroatoms independently selected from nitrogen, oxygen, or sulfur, phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 4-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-14 membered bicyclic or tricyclic heteroaryl ring having 1-5 heteroatoms independently selected from nitrogen, oxygen, or sulfur;

Ar is of the following formula:

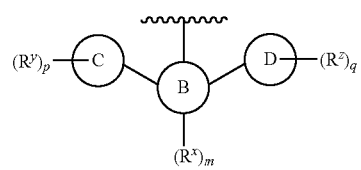

wherein:

m is 0-3;

Ring B is an optionally substituted group selected from phenyl or a 5-6 membered monocyclic heteroaryl ring having 1-4 heteroatoms independently selected from nitrogen, oxygen, or sulfur;

p and q are independently 0-6;

each of Ring C and Ring D is independently optionally substituted groups selected from phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 4-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-10 membered bicyclic heteroaryl ring having 1-5 heteroatoms independently selected from nitrogen, oxygen, or sulfur;

each of $R^x$, $R^y$, and $R^z$ is independently $R^s$;

$R^5$ is halogen, —OR$^6$, —OR$^7$, —N(R')$_2$, —NR'C(O)R', —NR'C(O)OR', —NR'C(O)N(R')$_2$, —NR'SO$_2$R', —NR'SO$_2$N(R')$_2$, or —NR'OR', or an optionally substituted group selected from a 5-6 membered monocyclic heteroaryl ring having at least one nitrogen and 0-3 heteroatoms independently selected from nitrogen, oxygen, or sulfur, a 4-7 membered saturated or partially unsaturated heterocyclic ring having at least one nitrogen and 0-2 heteroatoms independently selected from nitrogen, oxygen, or sulfur, a 7-10 membered bicyclic saturated or partially unsaturated heterocyclic ring having at least one nitrogen and 0-4 heteroatoms independently selected from nitrogen, oxygen, or sulfur, or an 8-10 membered bicyclic heteroaryl ring having at least one nitrogen and 0-4 heteroatoms independently selected from nitrogen, oxygen, or sulfur;

$R^6$ is an optionally substituted group selected from $C_{1-20}$ aliphatic, $C_{1-20}$ heteroaliphatic having 1-3 heteroatoms independently selected from nitrogen, oxygen, or sulfur, phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 4-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-14 membered bicyclic or tricyclic heteroaryl ring having 1-5 heteroatoms independently selected from nitrogen, oxygen, or sulfur; and each R' is independently hydrogen or an optionally substituted group selected from $C_{1-20}$ aliphatic, phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 4-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-10 membered bicyclic heteroaryl ring having 1-5 heteroatoms independently selected from nitrogen, oxygen, or sulfur, wherein:

two R' groups on the same nitrogen atom are optionally taken together with the nitrogen atom to form an optionally substituted 3-8 membered, saturated, partially unsaturated, or aryl ring having 1-4 heteroatoms independently selected from nitrogen, oxygen, or sulfur;

each $R^7$ is independently an optionally substituted group selected from —Ar', $C_{1-20}$ aliphatic, $C_{1-20}$ heteroaliphatic having 1-3 heteroatoms independently selected from nitrogen, oxygen, or sulfur, phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 4-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-14 membered bicyclic or tricyclic heteroaryl ring having 1-5 heteroatoms independently selected from nitrogen, oxygen, or sulfur; and two $R^7$ are optionally taken together with the oxygen atoms they are bound to form a bidentate ligand; and Ar' is of the following formula:

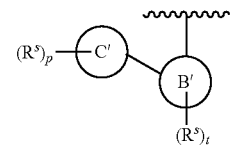

wherein:
t is 0-4;
p is 0-6;
each Ring B' and Ring C' is independently an optionally substituted group selected from phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 4-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-10 membered bicyclic heteroaryl ring having 1-5 heteroatoms independently selected from nitrogen, oxygen, or sulfur; and each $R^s$ is independently halogen, R', —OR', —SR', —S(O)R', —S(O)$_2$R', —OSi(R')$_3$, —N(R')$_2$, —NR'C(O)R', —NR'C(O)OR', —NR'C(O)N(R')$_2$, —NR'SO$_2$R', —NR'SO$_2$N(R')$_2$, or —NR'OR'.

E65. The method of any one of examples 1-63, wherein catalyst or the metal complex is of formula II-b:

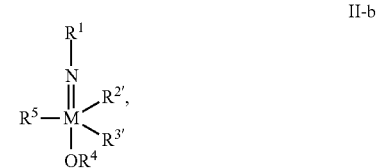

wherein:
$R^{2'}$ and $R^{3'}$ are taken together with their intervening metal atom to form an optionally substituted 3-8 membered saturated or partially unsaturated ring having, in addition to the intervening metal atom, 0-4 heteroatoms independently selected from nitrogen, oxygen, or sulfur; and
each of $R^1$, $R^4$ and $R^5$ is independently as defined in formula II-a.

E66. The method of any one of the preceding examples, wherein:
$R^1$ is an optionally substituted group selected from $C_{1-20}$ aliphatic, $C_{1-20}$ heteroaliphatic having 1-3 heteroatoms independently selected from nitrogen, oxygen, or sulfur, phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 4-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-10 membered bicyclic heteroaryl ring having 1-5 heteroatoms independently selected from nitrogen, oxygen, or sulfur;

each of $R^2$ and $R^3$ is independently R', —OR', —SR', —N(R')$_2$, —OC(O)R', —SOR', —SO$_2$R', —SO$_2$N(R')$_2$, —C(O)N(R')$_2$, —NR'C(O)R', or —NR'SO$_2$R', provided that $R^2$ and $R^3$ are not simultaneously hydrogen;

$R^4$ is $R^7$, or an optionally substituted group selected from —Ar, $C_{1-20}$ aliphatic, $C_{1-20}$ heteroaliphatic having 1-3 heteroatoms independently selected from nitrogen, oxygen, or sulfur, phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 4-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-14 membered bicyclic or tricyclic heteroaryl ring having 1-5 heteroatoms independently selected from nitrogen, oxygen, or sulfur;

Ar is of the following formula:

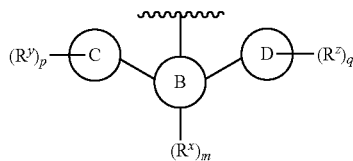

wherein:
  m is 0-3;
  Ring B is an optionally substituted group selected from phenyl or a 5-6 membered monocyclic heteroaryl ring having 1-4 heteroatoms independently selected from nitrogen, oxygen, or sulfur;
  p and q are independently 0-6;
  each of Ring C and Ring D is independently optionally substituted groups selected from phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 4-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-10 membered bicyclic heteroaryl ring having 1-5 heteroatoms independently selected from nitrogen, oxygen, or sulfur;
  each of $R^x$, $R^y$, and $R^z$ is independently halogen, —OR', —N(R')$_2$, —NR'C(O)R', —NR'C(O)OR', —NR'C(O)N(R')$_2$, —NR'SO$_2$R', —NR'SO$_2$N(R')$_2$, —NR'OR', or an optionally substituted group selected from $C_{1-20}$ aliphatic, $C_{1-20}$ heteroaliphatic having 1-3 heteroatoms independently selected from nitrogen, oxygen, or sulfur;
  $R^5$ is halogen, —OR$^6$, —OR$^7$, —N(R')$_2$, —NR'C(O)R', —NR'C(O)OR', —NR'C(O)N(R')$_2$, —NR'SO$_2$R', —NR'SO$_2$N(R')$_2$, or —NR'OR', or an optionally substituted group selected from a 5-6 membered monocyclic heteroaryl ring having at least one nitrogen and 0-3 heteroatoms independently selected from nitrogen, oxygen, or sulfur, a 4-7 membered saturated or partially unsaturated heterocyclic ring having at least one nitrogen and 0-2 heteroatoms independently selected from nitrogen, oxygen, or sulfur, a 7-10 membered bicyclic saturated or partially unsaturated heterocyclic ring having at least one nitrogen and 0-4 heteroatoms independently selected from nitrogen, oxygen, or sulfur, or an 8-10 membered bicyclic heteroaryl ring having at least one nitrogen and 0-4 heteroatoms independently selected from nitrogen, oxygen, or sulfur;

$R^6$ is an optionally substituted group selected from $C_{1-20}$ aliphatic, $C_{1-20}$ heteroaliphatic having 1-3 heteroatoms independently selected from nitrogen, oxygen, or sulfur, phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 4-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-14 membered bicyclic or tricyclic heteroaryl ring having 1-5 heteroatoms independently selected from nitrogen, oxygen, or sulfur; and each R' is independently hydrogen or an optionally substituted group selected from $C_{1-6}$ aliphatic, phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 4-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-10 membered bicyclic heteroaryl ring having 1-5 heteroatoms independently selected from nitrogen, oxygen, or sulfur, wherein:

two R' groups on the same nitrogen atom are optionally taken together with the nitrogen atom to form an optionally substituted 3-8 membered, saturated, partially unsaturated, or aryl ring having 1-4 heteroatoms independently selected from nitrogen, oxygen, or sulfur; and each $R^7$ is independently an optionally substituted group selected from —Ar', $C_{1-20}$ aliphatic, $C_{1-20}$ heteroaliphatic having 1-3 heteroatoms independently selected from nitrogen, oxygen, or sulfur, phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 4-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-14 membered bicyclic or tricyclic heteroaryl ring having 1-5 heteroatoms independently selected from nitrogen, oxygen, or sulfur; and two $R^7$ are optionally taken together with the oxygen atoms they are bound to form a bidentate ligand; and Ar' is of the following formula:

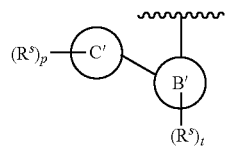

wherein:

t is 0-4;

p is 0-6;

each Ring B' and Ring C' is independently an optionally substituted group selected from phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 4-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-10 membered bicyclic heteroaryl ring having 1-5 heteroatoms independently selected from nitrogen, oxygen, or sulfur; and each $R^s$ is independently halogen, R', —OR', —SR', —S(O)R', —S(O)$_2$R', —OSi(R')$_3$, —N(R')$_2$, —NR' C(O)R', —NR' C(O)OR', —NR' C(O)N(R')$_2$, —NR'SO$_2$R', —NR'SO$_2$N(R')$_2$, or —NR'OR'.

E66. The method of any one of the preceding examples, wherein M is Mo.

E66a. The method of any one of the preceding examples, wherein M is W.

E67. The method of any one of the preceding examples, wherein $R^1$ is optionally substituted phenyl or optionally substituted C$_{1-20}$ aliphatic.

E67. The method of any one of the preceding examples, wherein $R^1$ is optionally substituted phenyl.

E68. The method of any one of the preceding examples, wherein $R^1$ is substituted phenyl comprising one or more electron-withdrawing groups.

E69. The method of any one of the preceding examples, wherein $R^1$ is $R^1$ is optionally substituted

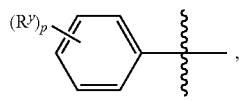

wherein p is not 0.

E70. The method of example E69, wherein each $R^y$ is independently halogen or optionally substituted C$_{1-10}$ haloalkyl.

E71. The method of example E69, wherein each $R^y$ is independently halogen or C$_{1-10}$ perfluoroalkyl.

E72. The method of any one of the preceding examples, wherein $R^1$ is

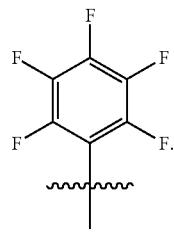

E73. The method of any one of examples E1-E66, wherein $R^1$ is optionally substituted C$_{1-20}$ aliphatic.

E73. The method of any one of examples E1-E66, wherein $R^1$ is optionally substituted C$_{1-20}$ aliphatic, and $R^1$ is a tertiary substituent.

E73a. The method of any one of examples E1-E66, wherein $R^1$ is adamantyl.

E74. The method of any one of the preceding examples, wherein one of $R^2$ and $R^3$ is hydrogen, and the other is optionally substituted C$_{1-6}$ aliphatic; or $R^{2'}$ and $R^{3'}$ are taken together with their intervening metal atom to form an optionally substituted 3-4 membered saturated or partially unsaturated ring having, in addition to the intervening metal atom, 0-4 heteroatoms independently selected from nitrogen, oxygen, or sulfur.

E75. The method of any one of the preceding examples, wherein one of $R^2$ and $R^3$ is hydrogen, and the other is optionally substituted C$_{1-6}$ aliphatic; or $R^{2'}$ and $R^{3'}$ are taken together with their intervening metal atom to form optionally substituted metallacyclopropane or metallacyclobutane.

E76. The method of any one of the preceding examples, wherein one of $R^2$ and $R^3$ is hydrogen, and the other is a tertiary substituent and is substituted C$_{1-6}$ alkyl; or $R^{2'}$ and $R^{3'}$ are taken together with their intervening metal atom to form metallacyclobutane.

E77. The method of any one of the preceding examples, wherein $R^4$ is optionally substituted group selected from phenyl, Ar' and Ar.

E77. The method of any one of the preceding examples, wherein $R^4$ is optionally substituted Ar'.

E78. The method of any one of the preceding examples, wherein $R^4$ is an optionally substituted group selected from:

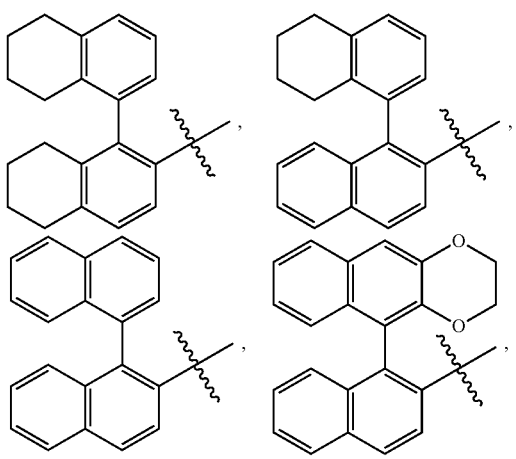

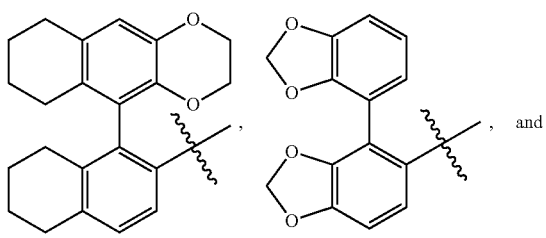, and

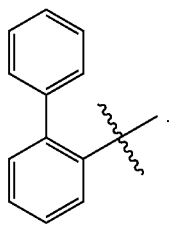 [SMILES: *c1ccccc1-c1ccccc1]

E78a. The method of any one of the preceding examples, wherein $R^4$ is optionally substituted

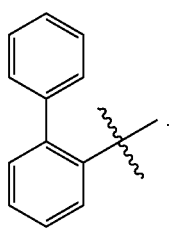.

E78b. The method of any one of the preceding examples, wherein $R^4$ is optionally substituted

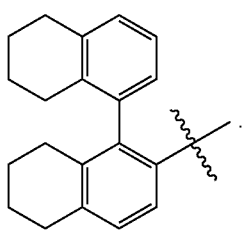 [SMILES: *c1ccc2c(c1-c1cccc3c1CCCC3)CCCC2].

E79. The method of any one of the preceding examples, wherein $R^4$ is optionally substituted Ar.

E80. The method of example E79, wherein Ar is

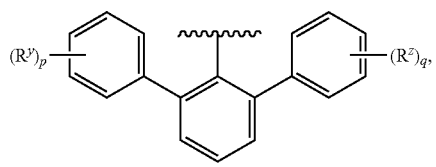

wherein each of $R^y$ and $R^z$ is independently $C_{1-6}$ alkyl.

E81. The method of example E79 or E80, wherein Ar is

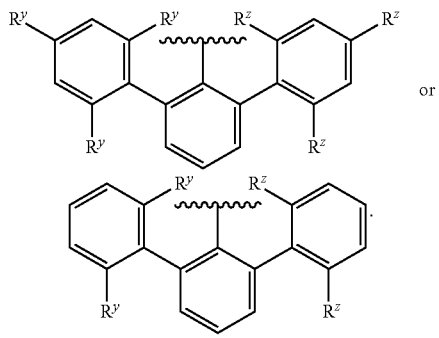 or

E82. The method of example E79 or E80, wherein Ar is

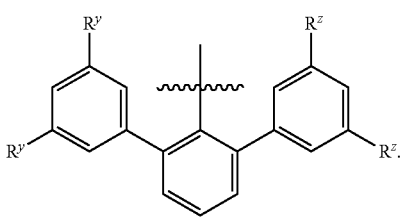.

E83. The method of any one of the preceding examples, wherein $R^4$ is optionally substituted

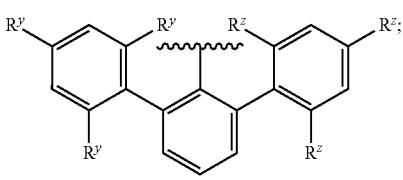.

E84. The method of any one of the preceding examples, wherein $R^4$ is optionally substituted phenyl.

E85. The method of any one of the preceding examples, wherein $R^4$ is substituted phenyl comprising a 2'- and a 6'-substituent.

E86. The method of any one of examples E1-E76, wherein:
 $R^4$ is —Ar;
 Ar is

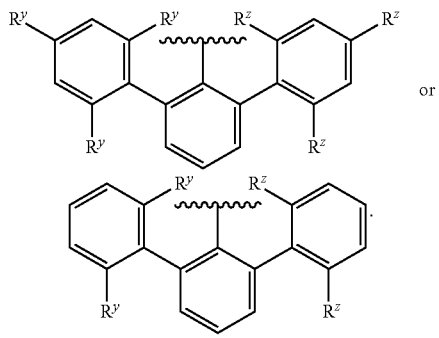;

each of $R^y$ and $R^z$ is independently optionally substituted $C_{1-20}$ aliphatic.

E87. The method of example E86, wherein each of $R^y$ and $R^z$ is methyl.

E88. The method of example E86, wherein each of $R^y$ and $R^z$ is ethyl.

E89. The method of any one of the preceding examples, wherein $R^4$ is selected from

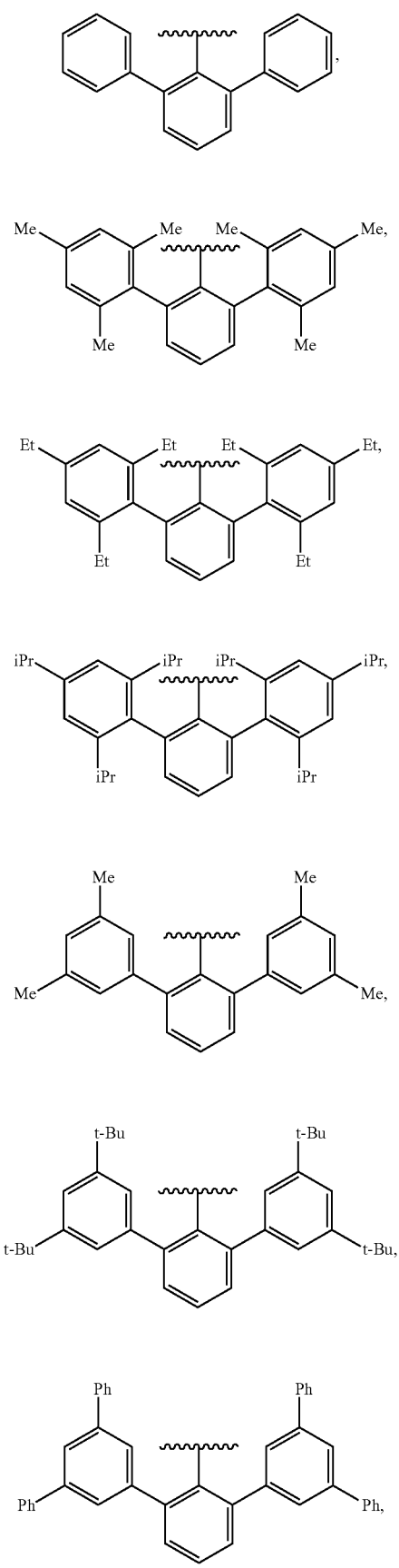

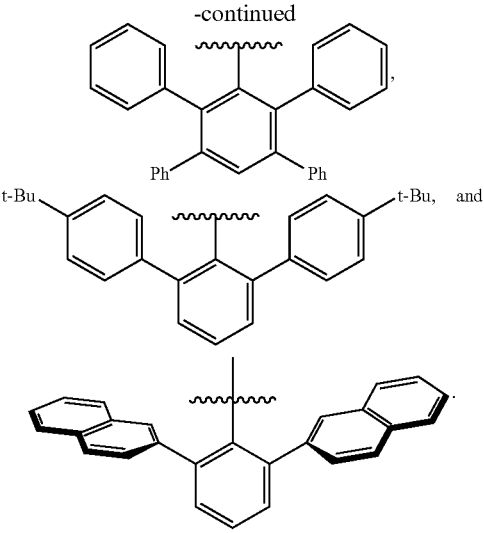

E90. The method of any one of the preceding examples, wherein $R^5$ is optionally substituted 5-6 membered heteroaryl having at least one nitrogen and 0-3 heteroatoms independently selected from nitrogen, oxygen, or sulfur, wherein the at least one nitrogen is bonded to M.

E91. The method of any one of the preceding examples, wherein $R^5$ is optionally substituted 1-pyrrolyl.

E92. The method of any one of the preceding examples, wherein $R^5$ is 1-pyrrolyl.

E93. The method of any one of the preceding examples, wherein $R^5$ is

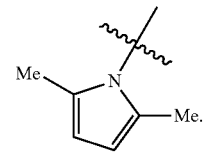

E94. The method of any one of the preceding examples, wherein the catalyst or metal complex is used in an amount of no more than about 15 mol % relative to the second species.

E95. The method of any one of the preceding examples, wherein the catalyst or metal complex is used in an amount of no more than about 10 mol % relative to the second species.

E96. The method of any one of the preceding examples, wherein the catalyst or metal complex is used in an amount of no more than about 5 mol % relative to the second species.

E97. The method of any one of the preceding examples, wherein the catalyst or metal complex is used in an amount of no more than about 3 mol % relative to the second species.

E98. The method of any one of the preceding examples, wherein the catalyst or metal complex is one exemplified in the present application.

E99. The method of any one of the preceding examples, wherein the catalyst or metal complex is

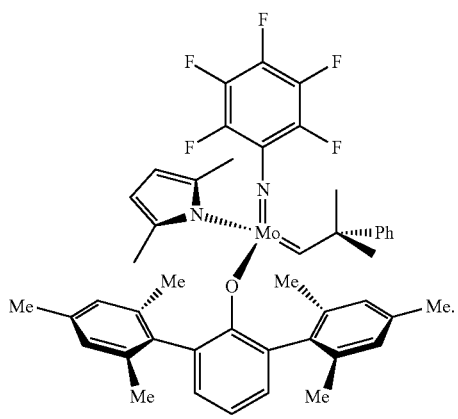

Mo-3

E100. The method of any one of examples E1-E98, wherein the catalyst or metal complex is:

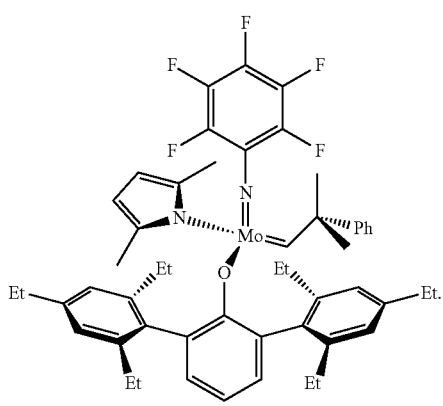

Mo-4

E101. The method of any one of examples E1-E98, wherein the catalyst or metal complex is:

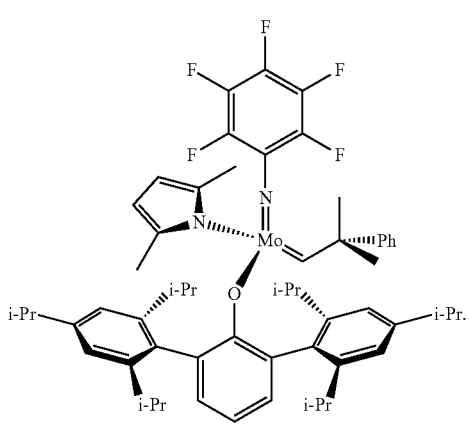

Mo-5

E102. The method of any one of examples E1-E98, wherein the catalyst or metal complex is:

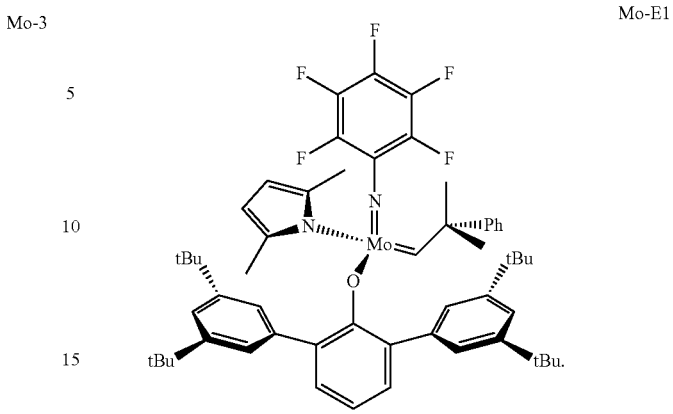

Mo-E1

E103. A compound of formula II-a or a compound of formula II-b.

E104. A compound having the structure of Mo-4 in example E100.

E104. A compound having the structure of Mo-E1 in example E102.

E105. A composition, comprising:
a first species comprising an olefin, wherein each carbon atom of the olefin in the first species is substituted with at least one halogen; and
a metal complex comprising Mo or W.

E106. The composition of example E105, wherein the first species has the structure of

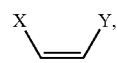

wherein each of X and Y is independently halogen.

E107. The composition of example E105, wherein the first species has the structure of

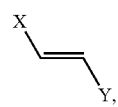

wherein each of X and Y is independently halogen.

E108. The composition of any one of examples E105-E107, wherein X and Y are different.

E109. The composition of any one of examples E105-E107, wherein X and Y are the same.

E110. The composition of any one of examples E105-E109, wherein X is —F, Y is —Cl or —Br.

E111. The composition of any one of examples E105-E109, wherein X is —F and Y is —Cl.

E112. The composition of any one of examples E105-E109, wherein X is —F and Y is —Br.

E113. The composition of any one of examples E105-E113, wherein the metal complex has the structure of formula II-a.

E114. The composition of any one of examples E105-E113, wherein the metal complex has the structure of formula II-b.

E114. The composition of any one of examples E105-E113, wherein the metal complex is as described in any one of E64-E104.

E115. The composition of any one of examples E105-E112, further comprising a second species comprising an olefin.

E116. The composition of any one of examples E105-E115, wherein the metal complex promotes a metathesis reaction between the first species and the second species.

E117. The composition of example E116, wherein the metathesis reaction provides regioselectivity.

E118. The composition of example E116 or E117, wherein the metathesis reaction provides Z-selectivity.

E119. The composition of example E116 or E117, wherein the metathesis reaction provides E-selectivity.

E120. The composition of any one of the preceding examples, comprising $R^4OH$ or a salt thereof.

E121. The composition of any one of the preceding examples, comprising $R^5H$ or a salt thereof.

E122. The composition of any one of the preceding examples, wherein the molar ratio of the first species and the metal complex is greater than about 2:1.

E123. The composition of any one of the preceding examples, wherein the molar ratio of the first species and the metal complex is greater than about 5:1.

E124. The composition of any one of the preceding examples, wherein the molar ratio of the first species and the metal complex is greater than about 10:1.

E125. The composition of any one of the preceding examples, wherein the molar ratio of the first species and the metal complex is greater than about 20:1.

E126. The composition of any one of the preceding examples, wherein the molar ratio of the first species and the metal complex is greater than about 30:1.

E127. The composition of any one of the preceding examples, wherein the molar ratio of the first species and the metal complex is greater than about 40:1.

E128. The composition of any one of the preceding examples, wherein the molar ratio of the first species and the metal complex is greater than about 50:1.

E129. The composition of any one of the preceding examples, comprising $CH_2$=CHY and/or $CH_2$=CHX.

E130. The composition of any one of the preceding examples, comprising $CH_2$=CHY and $CH_2$=CHX, wherein each of X and Y is independently halogen, X<Y, and the molar ratio of $CH_2$=CHY and $CH_2$=CHX is greater than 1:1.

E131. The composition of example E130, wherein the molar ratio of $CH_2$=CHY and $CH_2$=CHX is greater than 2:1.

E132. The composition of example E130, wherein the molar ratio of $CH_2$=CHY and $CH_2$=CHX is greater than 3:1.

E133. The composition of example E130, wherein the molar ratio of $CH_2$=CHY and $CH_2$=CHX is greater than 5:1.

E134. The composition of example E130, wherein the molar ratio of $CH_2$=CHY and $CH_2$=CHX is greater than 10:1.

E135. The composition of example E130, wherein the molar ratio of $CH_2$=CHY and $CH_2$=CHX is greater than 20:1.

E136. The composition of any one of examples E105-E135, comprising a metal complex comprising Mo or W, wherein the metal complex is a degradation product of a compound of formula II-a or II-b.

E137. The composition of any one of examples E105-E136, wherein the composition comprises no W.

E138. The composition of any one of examples E105-E136, wherein the composition comprises no Mo.

E139. A fluorinated compound derived from a bioactive molecule, wherein the bioactive molecule comprises a terminal olefin, and the fluorinated derivative comprises a terminal olefin comprising —CH=CHF derived from the terminal olefin of the bioactive molecule.

E140. The compound of example E139, wherein —CH=CHF has a Z configuration.

E141. The compound of example E139, wherein —CH=CHF has a E configuration.

E142. The compound of any one of examples E139-E141, wherein the bioactive molecule is an approved drug.

E142. The compound of any one of examples E139-E141, wherein the bioactive molecule is or was in clinical trial.

E143. The compound of any one of examples E139-E141, wherein the bioactive molecule is a natural product.

E144. A method for preparing a compound of any one of examples E139-E143, comprising a method of any one of examples E1-E102, wherein the second species is the bioactive molecule.

E145. A pharmaceutical composition, comprising a compound of any one of examples E139-E143, further comprising a pharmaceutically acceptable carrier.

EXEMPLIFICATION

Non-limiting examples were provided below.

Stereochemically defined alkenes are ubiquitous in natural occurring compounds and drugs and serve as substrates for numerous transformations in chemistry. Efficient protocols for the stereoselective preparation of olefins are highly desirable, particularly if they are promoted by catalysts that control the identity of the major product isomer. (Füstner, A. Science 2013, 341, 1357-1364.) Alkenyl halides rank as one of the most important classes of compounds in organic chemistry due to their occurrence in natural products as well as the immense applications associated. ((a) Guinchard, X.; Roulland, E. Synlett. 2011, 19, 2779-2788. (b) Stanforth, S. P. Vinyl and Aryl Halides in Comprehensive Organic Functional Group Transformations II (ed. Katritzky, A. R. & Taylor, R. J. K.) vol. 2 (Elsevier, 2004).) Traditional methods that afford Z-vinyl halides (e.g., Stork-Zhao olefination) (For a representative example, see: Stork, G.; Zhao, K. Tetrahedron Lett. 1989, 30, 2173-2174) and their corresponding E-diastereomers (e.g., Takai olefination) (For a representative example, see: Takai, K.; Nitta, K.; Utimoto, K. J. Am. Chem. Soc. 1986, 108, 7408-7410.) offer moderate to high levels of selectivity depending on the relative steric size of the substrates and reagents employed. Other routes of forming stereodefined vinyl halides frequently proceed though an organometallic precursor before conversion to the desired product with a halogen source. (For a representative example, see: Morrill, C.; Grubbs, R. H. J. Org. Chem. 2003, 68, 6031-6034.) Despite these advances, there is a persisting lack of catalytic protocols that directly furnish alkenyl halides efficiently and stereoselectively, particularly those that do not entail the generation of intermediates and stoichiometric waste. In some embodiments, the present disclosure recognizes that stereoselective catalytic olefin metathesis (OM) with an appropriate vinyl halide cross-partner can potentially provide a solution to the aforementioned challenge. However, previous reports have been limited to Ru-catalyzed protocols ((a) Sashuk, V.; Samojłowicz, C.; Szadkowska, A.; Grela, K. Chem. Commun. 2008, 2468-2470. (b) Macnaughtan, M. L.; Gary, J. B.; Gerlach, D. L.; Johnson, M. J. A.; Kampf, J. W. Organometallics 2009, 28, 2880-2887) which generally suffer from poor stereoselectivity (E/Z mixtures) and a narrow substrate range, likely as a result of the attenuated reactivity of the chloromethylidene species in OM and its susceptibility to various decomposition pathways. (Macnaughtan, M. L.; Johnson, M. J. A.; Kampf, J. W. J. Am. Chem. Soc. 2007, 129, 7708-7709.) Herein, the present disclosure demonstrates that, among other things, ring-opening/cross-metathesis (ROCM) (Ibrahem, I.; Yu, M.; Schrock, R. R.; Hoveyda, A. H. J. Am.

*Chem. Soc.* 2009, 131, 3844-3845) and cross-metathesis (CM) (Meek, S. J.; O'Brien, R. V.; Llaveria, J.; Schrock, R. R.; Hoveyda, A. H. *Nature* 2011, 471, 461-466) reactions involving suitable halogen-containing olefin cross-partners promoted by provided compounds, in some embodiments, molybdenum-based monoaryloxide monopyrrolide (MAP) complexes, can deliver Z-alkenyl halides with high efficiency and stereoselectivity.

We began by examining the ROCM reaction between Z-cyclooctene 1 and 2 equivalents of commercially available Z-1,2-dichloroethylene in the presence of 5 mol % of various Ru carbenes and Mo alkylidenes (Scheme 1).

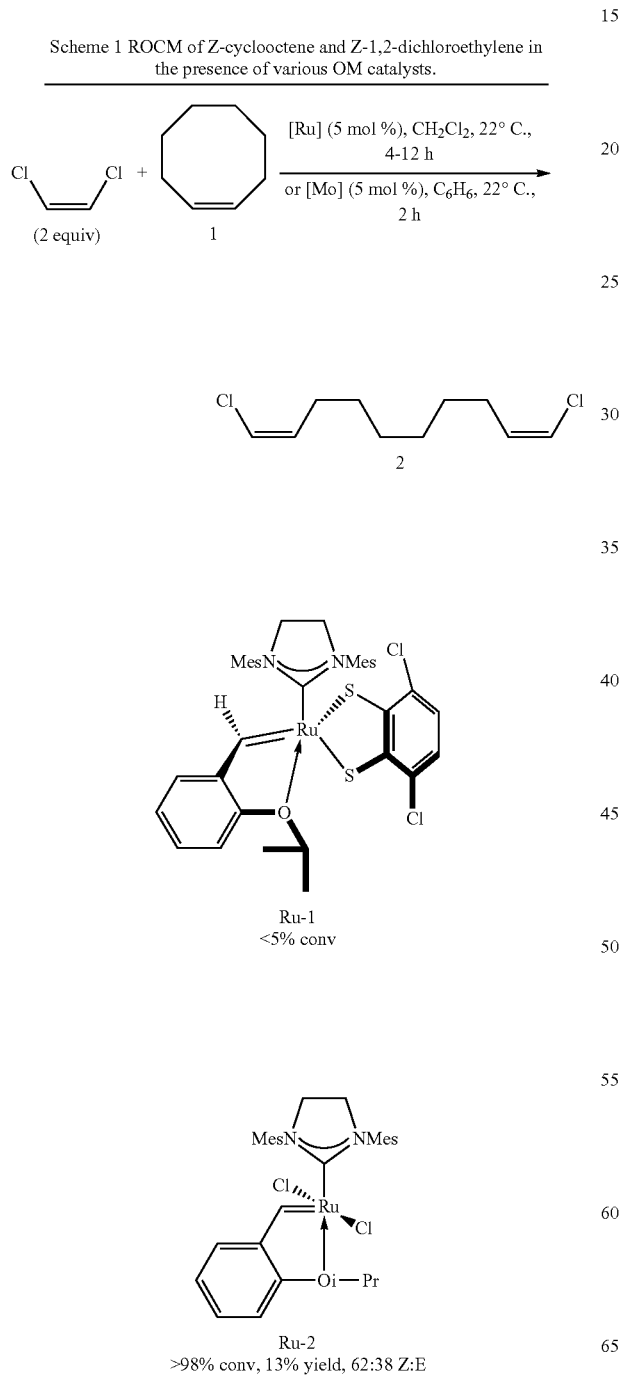

While ROCM was inefficient with Ru carbenes, Mo-based complexes Mo-2 and Mo-3 gave the desired product in moderate to good yields and Z-selectivities.

While there was minimal reaction with Ru-1 (Koh, M. J.; Khan, R. K. M.; Torker, S.; Yu, M.; Mikus, M.; Hoveyda, A. H., submitted) and significant ring-opening metathesis polymerization (ROMP) of 1 with Ru-2 (Garber, S. B.; Kingsbury, J. S.; Gray, B. L.; Hoveyda, A. H. *J. Am. Chem. Soc.* 2000, 122, 8168-8179) and Mo-1, (Meek, S. J.; O'Brien, R. V.; Llaveria, J.; Schrock, R. R.; Hoveyda, A. H. *Nature* 2011, 471, 461-466) both Mo-2 and Mo-3 furnished the desired ROCM product 3 in 75% yield (>98% Z-selectivity) and 63% yield (84% Z-selectivity) within 2 hours, respectively. We next assessed the ability of high oxidation-state alkylidenes to promote the more challenging CM of 8-bromo-1-octene 4 and Z-1,2-dichloroethylene (Scheme 2). 5 was obtained in 60% yield and complete Z-selectivity in the presence of 5 mol % of Mo-3 within 4 hours. In contrast, CM was less efficient with other Mo- and W-based catalysts, and metathesis homocoupling of 4 was observed to be a competitive side reaction in most cases. In some embodiments, the pentafluorophenylimido ligand of Mo-3 was partly responsible for promoting the CM reaction.

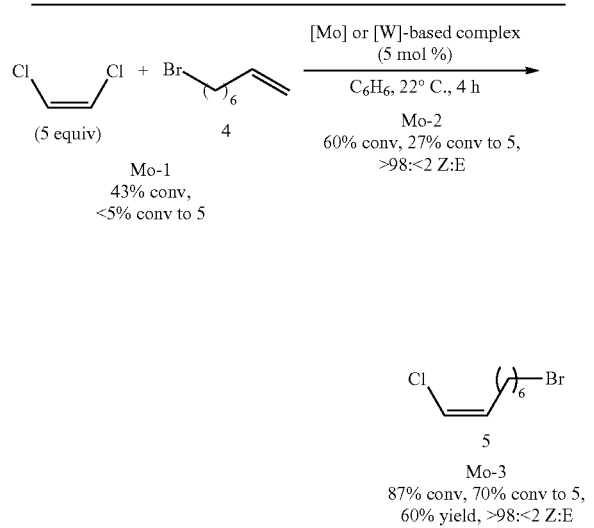

Scheme 2 CM of 8-bromo-1-octene and Z-1,2-dichloroethylene in the presence of various OM catalysts.

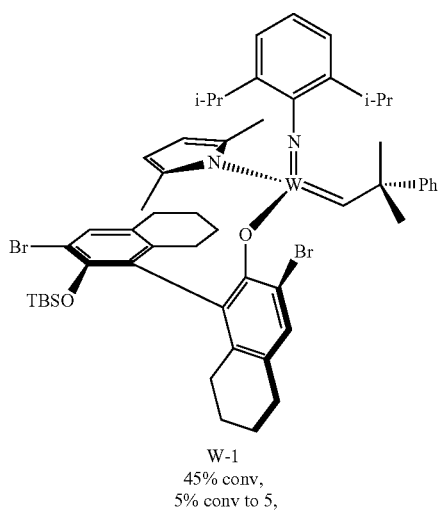

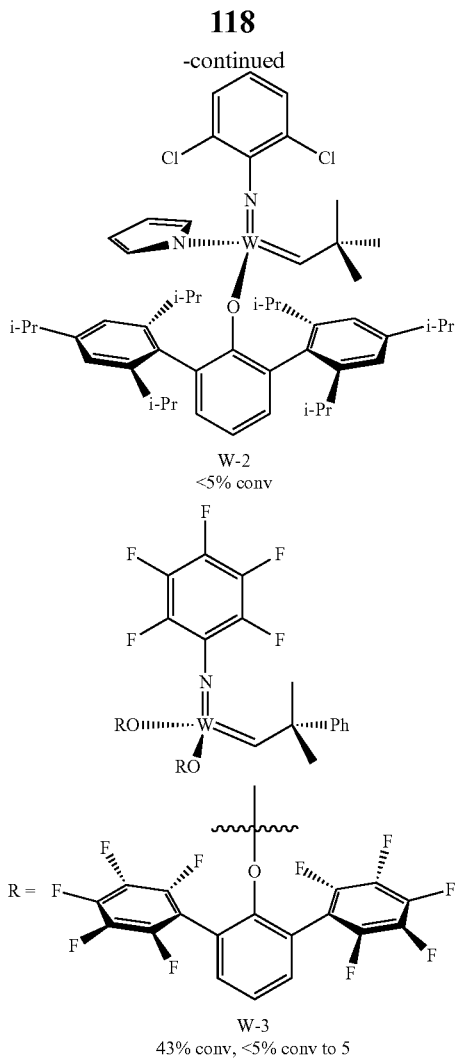

CM of 8-bromo-1-octene in the presence of excess Z-1,2-dichloroethylene was inefficient with W-based alkylidenes. Among the Mo-based complexes screened, best results were observed with Mo-3, which delivered the CM product in 50% yield and complete Z-selectivity.

Applicant recognizes that, in some embodiments, increasing the size of the aryloxide ligand on Mo-3 could potentially prolong catalyst lifetime and improve reaction efficiency. Mo-4 gave 5 in 75% yield and >98% Z-selectivity with minimal homocoupling side product. In some embodiments, without the intention to be limited by theory, Applicant notes that the greater steric bulk most likely increases catalyst longevity, allowing the homodimer of 4 to further participate in reaction to regenerate the propagating alkylidene species for CM with Z-1,2-dichloroethylene. CM with the sterically more encumbered Mo-5 complex proceeded to 62% conversion within 4 hours. Increasing the reaction time to 12 hours resulted in almost complete conversion and 5 was obtained in 84% yield, albeit with diminished Z-selectivity (93% Z) probably, without the intention to be limited by theory, as a result of post-metathesis isomerization. (Meek, S. J.; O'Brien, R. V.; Llaveria, J.; Schrock, R. R.; Hoveyda, A. H. *Nature* 2011, 471, 461-466) Applicant notes importance of tuning catalyst lifetime through ligand modification in order to achieve optimal results in efficiency and stereoselectivity. Lowering the catalyst loading of Mo-4 to 3 mol % was not detrimental for the reaction, and 5 was obtained in 77% yield and >98% Z-selectivity.

Scheme 3 CM of 8-bromo-1-octene and Z-1,2-dichloroethylene in the presence of various analogous of Mo-3.

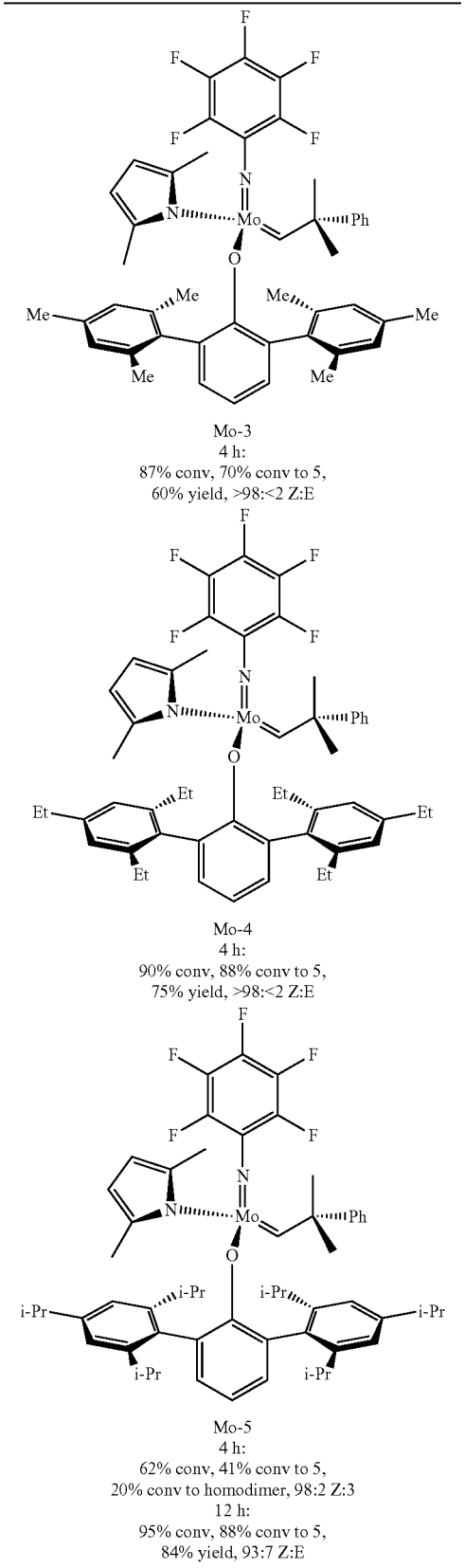

Mo-3
4 h:
87% conv, 70% conv to 5,
60% yield, >98:<2 Z:E

Mo-4
4 h:
90% conv, 88% conv to 5,
75% yield, >98:<2 Z:E

Mo-5
4 h:
62% conv, 41% conv to 5,
20% conv to homodimer, 98:2 Z:3
12 h:
95% conv, 88% conv to 5,
84% yield, 93:7 Z:E Exemplary optimal results were achieved with 5 mol % of Mo-4, which gave the desired CM product in 75% yield within 4 hours while preserving the high Z-selectivity. Reaction with the sterically more encumbered Mo-5 proceeded to give the product in greater yield (84%) but with plummeted stereoselectivity (93:7 Z:E) after 12 hours, likely as a result of post-metathesis isomerization during late stages of the transformation.

With the catalysts (Mo-3 and Mo-4) in hand, we proceeded to investigate the generality of the CM protocol with a myriad of functionalized terminal alkenes, including branched allylic olefins and those that contain heterocyclic and/or Lewis basic functionalities (Scheme 4). As demonstrated by examples herein, a broad scope of substrates can be used in provided methods. CM products were obtained in 41-80% yield and ≥97% Z-selectivity. The corresponding reactions with symmetric (14) and asymmetric (16 and 19) Z-1,2-disubstituted olefins were similarly efficient and Z-selective, generating the desired products in 79-91% yield and 94:6-97:3 Z:E ratios (Scheme 4). In addition, CM of vinyl-cyclohexane 21 with commercially available 1,2-dibromo-ethylene (64:36 Z:E ratio) was moderately efficient, affording 22 solely as the Z-isomer in 42% yield (Scheme 5).

Scheme 4 CM of Z-1,2-dichloroethylene with terminal alkenes and Z-1,2-disubstituted internal alkenes.

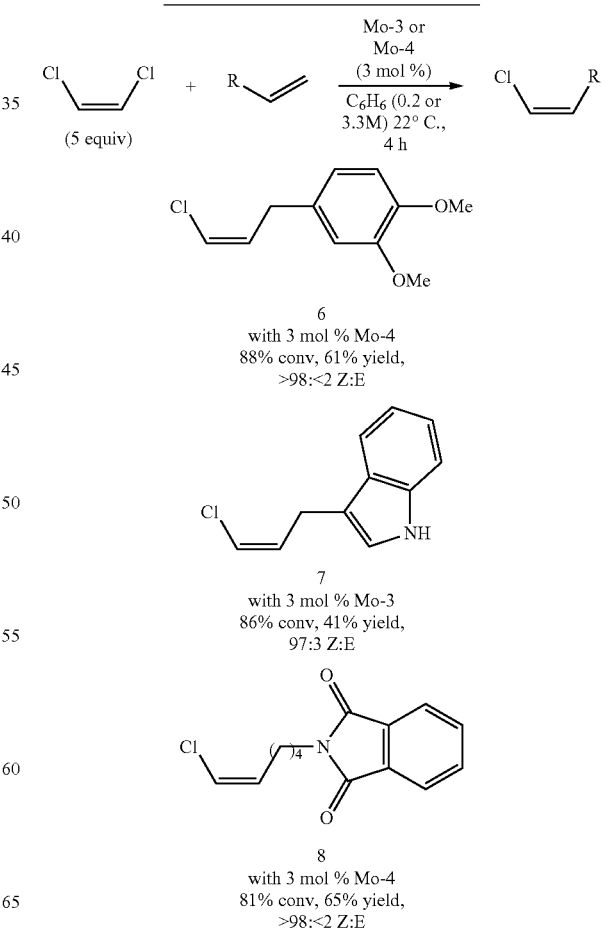

6
with 3 mol % Mo-4
88% conv, 61% yield,
>98:<2 Z:E 7
with 3 mol % Mo-3
86% conv, 41% yield,
97:3 Z:E 8
with 3 mol % Mo-4
81% conv, 65% yield,
>98:<2 Z:E

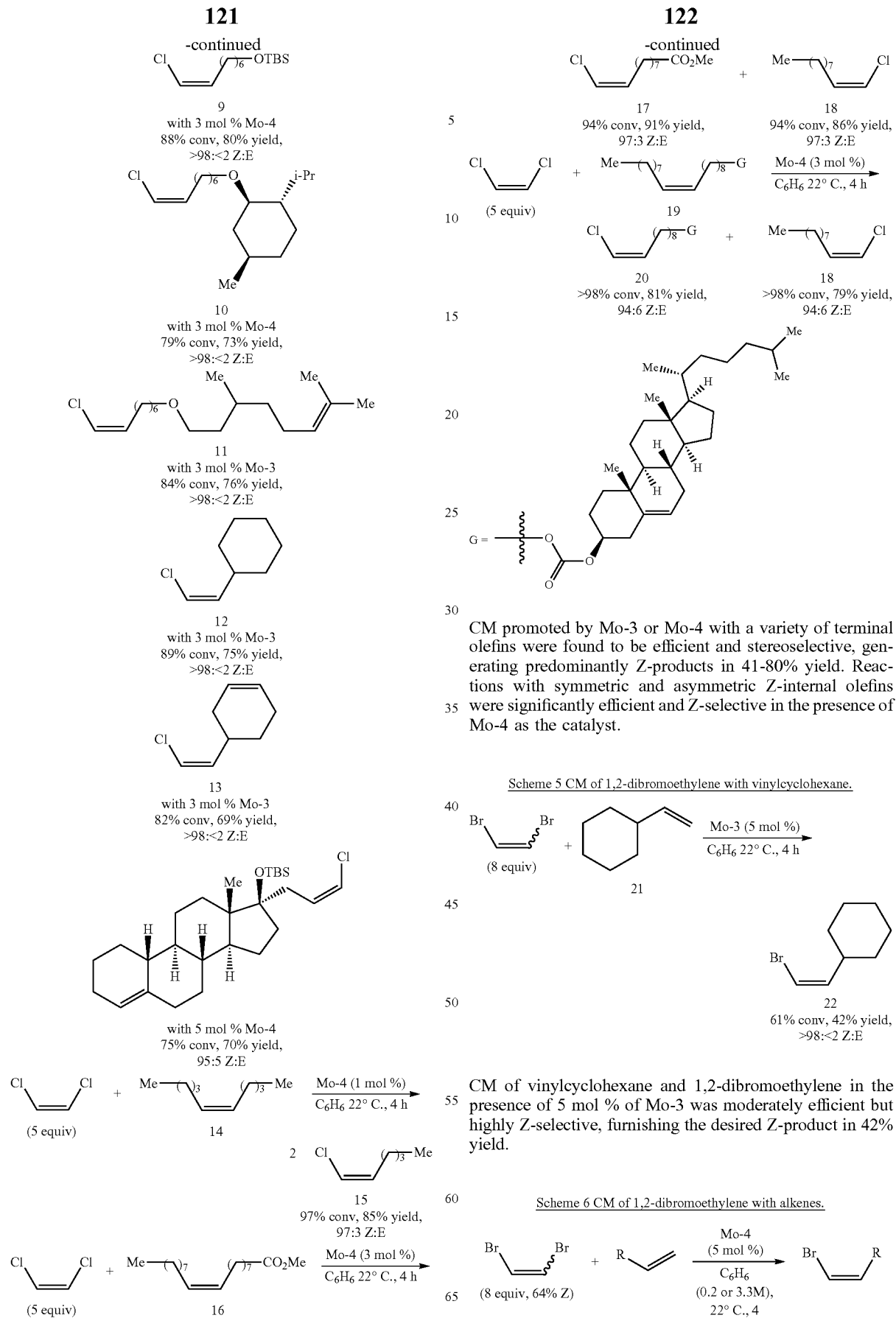

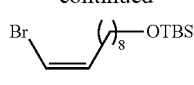

23
95% conv, 63% yield,
88:12 Z:E

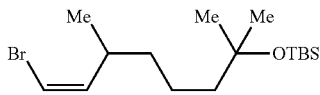

24
74% conv, 57% yield,
91:9 Z:E

The present disclosure, among other things, demonstrate that CM of 1,2-dibromoethylene with alkenes was efficient and Z-selective when using provided technologies. In some embodiments, as evidenced by the examples herein, when both a Z isomer and an E isomer of an alkene are present, provided compounds and methods selectively promotes reactions with the Z-isomer to produce a Z-product. In some embodiments, both the Z isomer and the E isomer of XCH=CHY are present, and provided compounds and methods selectively promotes reactions with the Z-isomer to produce a Z-product.

As described above, the present disclosure, among other things, also provides technologies, e.g., compound, methods, etc., for regioselective synthesis of olefins such as vinyl halides. In some embodiments, the present disclosure provides methods with both regioselectivity and stereoselectivity. In some embodiments, the present disclosure provides methods with both regioselectivity and Z-selectivity. Among other things, provided compounds and methods can provide alkenyl fluoride with unexpectedly high regioselectivity and/or Z-selectivity. Non-limiting examples are presented in Scheme 7.

Scheme 7 CM of Z-1-bromo-2-fluoroethylene with alkenes.

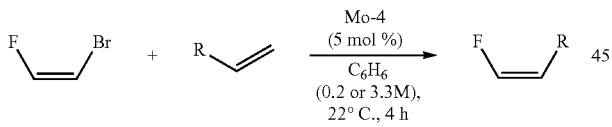

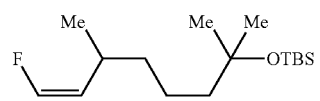

26.
>98% conv. 96:4 F:Br
70% yield (F), >98:<2 Z:E

R = OMe, >98% conv. 93.7 F:Br
71% yield (F), 95:5 Z:E

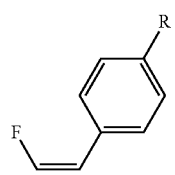

27.
R = Cl, 78% conv, 96:4 F:Br
64% yield (F), 97:3 Z:E

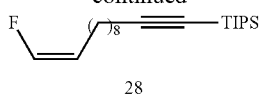

28
>98% conv, 72:28 F:Br
64% yield of fluoride,
>98:2 Z:E

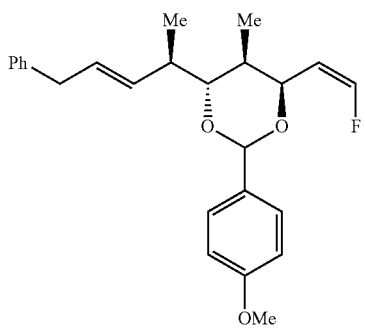

29
80% conv, >98:2 F:Br
63% yield of Fluoride,
>98:2 Z:E

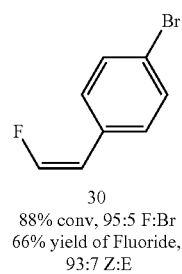

30
88% conv, 95:5 F:Br
66% yield of Fluoride,
93:7 Z:E

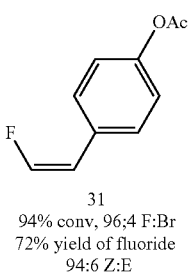

31
94% conv, 96;4 F:Br
72% yield of fluoride
94:6 Z:E

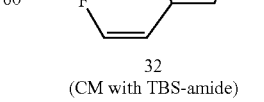 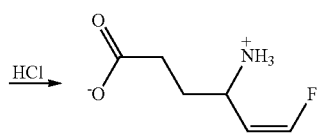

32
(CM with TBS-amide)
60% conv, >98:2 F:Br
55% overall yield of fluoride,
>98:2 Z:E GABA Inhibitor
with unique mode of action -continued

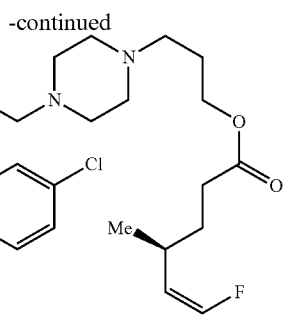

33
88% conv, 91:9 F:Br
78% yield of fluoride,
>98:2 Z:E
from perphenazine
anti-depressant

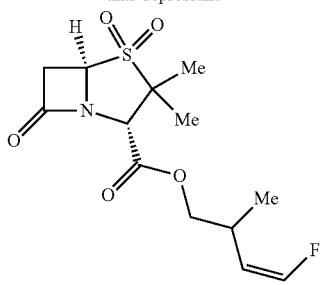

34
86% conv, >98:2 F:Br
80% yield of fluoride,
>98:2 Z:E
from sulbactam,
β-lactose inhibitor

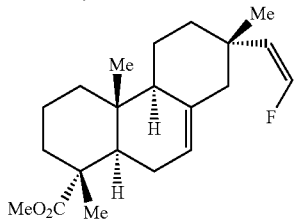

35
83% conv, 94:6 F:Br
70% yield of fluoride,
>98:2 Z:E
from isopimaric acid,
K channel activator Experimental Procedure for In Situ Preparation of Mo-Based MAP Complexes General Procedure for Preparation of Mo Complexes for NMR Analysis:

In a $N_2$-filled glove box, an oven-dried 4 mL vial equipped with a magnetic stir bar was charged with Mo bispyrrolide complex (Yuan, J.; Schrock, R. R.; Müller, P.; Axtell, J. C.; Dobereiner, G. E. *Organometallics* 2012, 31, 4650-4653) (1.00 equiv), phenol (Prepared in analogy to a previously reported procedure: Dickie, D. A; MacIntosh, I. S.; Ino, D. D.; He, Q.; Labeodan, O. A; Jennings, M. C.; Schatte, G.; Walsby, C. J.; Clyburne, J. A. C. *Can. J. Chem.* 2008, 86, 20-31) (1.00 equiv) and $C_6D_6$, resulting in a dark red solution. The vial was capped and the mixture was allowed to stir for 2 hours at 22° C., at which time it was transferred to a screw cap NMR tube by a pipette. The NMR tube was capped and sealed with Teflon tape. Note that for in situ generated complexes, only the diagnostic signals of the α carbon of the syn-alkylidenes are shown.

General Procedure for Preparation of Mo Complexes for Catalytic Reactions:

In a $N_2$-filled glove box, an oven-dried 4 mL vial equipped with a magnetic stir bar was charged with Mo bispyrrolide complex (1.00 equiv), phenol (1.00 equiv) and $C_6H_6$, resulting in a dark red solution. The vial was capped and the mixture was allowed to stir for 2 hours at 22° C., after which the catalyst solution was transferred to the reaction mixture by a syringe (dried at 65° C.).

2,6-(2,4,6-triethylphenyl)Phenol $^1$H NMR (400 MHz, CDCl$_3$): δ 7.09-7.06 (2H, m), 7.04-7.01 (5H, br s), 4.53 (1H, s), 2.67 (4H, q, J=7.6 Hz), 2.46-2.33 (8H, m), 1.29 (6H, t, J=7.6 Hz), 1.05 (12H, d, J=7.6 Hz).

Mo-3:

Following the general procedure, an oven-dried 4 mL vial equipped with a magnetic stir bar was charged with Mo bispyrrolide complex (59.8 mg, 0.1 mmol, 1.00 equiv), 2,6-Mes$_2$Phenol (Mes=2,4,6-Me$_3$C$_6$H$_2$) (33.0 mg, 0.1 mmol, 1.00 equiv) and $C_6H_6$ (1 mL), resulting in a dark red solution. The vial was capped and the mixture was allowed to stir for 2 hours at 22° C. $^1$H NMR (400 MHz, C$_6$D$_6$): δ 11.09 (1H, s).

Mo-4:

Following the general procedure, an oven-dried 4 mL vial equipped with a magnetic stir bar was charged with Mo bispyrrolide complex (59.8 mg, 0.1 mmol, 1.00 equiv), 2,6-(2,4,6-triethylphenyl)Phenol (41.5 mg, 0.1 mmol, 1.00 equiv) and $C_6H_6$ (1 mL), resulting in a dark red solution. The vial was capped and the mixture was allowed to stir for 2 hours at 22° C. $^1$H NMR (400 MHz, C$_6$D$_6$): δ 11.38 (1H, s).

Experimental Procedure for Z-Selective ROCM and CM

General Procedure:

In a $N_2$-filled glove box, an oven-dried 8 mL vial equipped with a magnetic stir bar was charged with alkene substrate (1.0 equiv) and Z-1,2-dichloroethylene (2.0-5.0 equiv). To this vessel, a solution of Mo-2, Mo-3 or Mo-4 in benzene (1-5 mol %) was added. The resulting solution was allowed to stir for 1-4 hours at 22° C., after which the reaction was quenched by addition of wet CDCl$_3$ (percent conversion is determined by 400 MHz $^1$H NMR analysis of the unpurified mixture). Purification was performed through silica gel chromatography.

(1Z,9Z)-1,10-dichloro-1,9-decadiene (2)

Following the general procedure, a solution of Mo-2 in benzene (0.1 M, 50 μL, 5.0 μmol, 5 mol %) was transferred by syringe to an oven-dried vial containing Z-1,2-dichloroethylene (19.4 mg, 0.2 mmol, 2.00 equiv), Z-cyclooctene (11.0 mg, 0.1 mmol, 1.00 equiv) and benzene (450 μL). The resulting solution was allowed to stir for 2 hours at 22° C. The reaction was quenched by addition of wet CDCl$_3$ and analysis of the unpurified mixture revealed >98% consumption of Z-cyclooctene. The resulting orange oil was purified by silica gel chromatography (100% hexanes) to afford 2 (15.6 mg, 0.0753 mmol, 75% yield) in >98:<2 Z:E ratio as colorless oil. $^1$H NMR (400 MHz, CDCl$_3$): Z-isomer (major): δ 6.01 (2H, dt, J=7.2, 1.6 Hz), 5.75 (2H, q, J=7.2 Hz), 2.22 (4H, qd, J=7.6, 1.6 Hz), 1.42-1.32 (8H, m).

(Z)-8-bromo-1-chloro-1-octene (5)

Following the general procedure, a solution of Mo-4 in benzene (0.1 M, 30 μL, 3.0 μmol, 3 mol %) was transferred by syringe to an oven-dried vial containing Z-1,2-dichloro-ethylene (48.5 mg, 0.5 mmol, 5.00 equiv), 8-bromo-1-octene (19.1 mg, 0.1 mmol, 1.00 equiv) and benzene (470 µL). The resulting solution was allowed to stir for 4 hours at 22° C. The reaction was quenched by addition of wet CDCl$_3$ and analysis of the unpurified mixture revealed 90% consumption of 8-bromo-1-octene. The resulting orange oil was purified by silica gel chromatography (100% hexanes) to afford 5 (17.4 mg, 0.0771 mmol, 77% yield) in >98:<2 Z:E ratio as colorless oil. $^1$H NMR (400 MHz, CDCl$_3$): Z-isomer (major): δ 6.02 (1H, dt, J=7.2, 1.6 Hz), 5.74 (1H, q, J=7.2 Hz), 3.41 (2H, t, J=6.8 Hz), 2.23 (2H, qd, J=7.2, 1.6 Hz), 1.86 (2H, m), 1.49-1.31 (6H, m).

(Z)-4-(3-chloroallyl)-1,2-dimethoxybenzene (6)

Following the general procedure, a solution of Mo-4 in benzene (0.1 M, 30 µL, 3.0 µmol, 3 mol %) was transferred by syringe to an oven-dried vial containing Z-1,2-dichloro-ethylene (48.5 mg, 0.5 mmol, 5.00 equiv) and 4-allyl-1,2-dimethoxybenzene (17.8 mg, 0.1 mmol, 1.00 equiv). The resulting solution was allowed to stir for 4 hours at 22° C. The reaction was quenched by addition of wet CDCl$_3$ and analysis of the unpurified mixture revealed 88% consumption of 4-allyl-1,2-dimethoxybenzene. The resulting orange oil was purified by silica gel chromatography (100% hexanes to 10% Et$_2$O in hexanes) to afford 6 (13.0 mg, 0.0611 mmol, 61% yield) in >98:<2 Z:E ratio as colorless oil. $^1$H NMR (400 MHz, CDCl$_3$): Z-isomer (major): δ 6.81 (1H, d, J=8.0 Hz), 6.77-6.72 (2H, m), 6.15 (1H, ddd, J=7.0, 2.0, 0.9 Hz), 5.95 (1H, q, J=7.1 Hz), 3.87 (3H, s), 3.86 (3H, s), 3.53 (2H, d, J=7.2 Hz).

(Z)-3-(3-chloroallyl)-1H-indole (7)

Following the general procedure, a solution of Mo-3 in benzene (0.1 M, 30 µL, 3.0 µmol, 3 mol %) was transferred by syringe to an oven-dried vial containing Z-1,2-dichloro-ethylene (48.5 mg, 0.5 mmol, 5.00 equiv) and 3-allyl-1H-indole (15.7 mg, 0.1 mmol, 1.00 equiv). The resulting solution was allowed to stir for 4 hours at 22° C. The reaction was quenched by addition of wet CDCl$_3$ and analysis of the unpurified mixture revealed 86% consumption of 3-allyl-1H-indole. The resulting orange oil was purified by silica gel chromatography (10% EtOAc in hexanes to 15% EtOAc in hexanes) to afford 7 (7.9 mg, 0.0412 mmol, 41% yield) in 97:3 Z:E ratio as colorless oil. $^1$H NMR (400 MHz, CDCl$_3$): Z-isomer (major): δ 7.95 (1H, brs), 7.62 (1H, d, J=7.6 Hz), 7.37 (1H, dt, J=7.6, 1.2 Hz), 7.21 (1H, td, J=7.6, 1.2 Hz), 7.14 (1H, td, J=7.2, 1.2 Hz), 7.03 (1H, m), 6.14 (1H, dt, J=7.2, 1.6 Hz), 6.03 (1H, q, J=7.2 Hz), 3.71 (2H, d, J=7.2 Hz).

(Z)-2-(6-chloro-5-hexenyl)isoindoline-1,3-dione (8)

Following the general procedure, a solution of Mo-4 in benzene (0.1 M, 30 µL, 3.0 µmol, 3 mol %) was transferred by syringe to an oven-dried vial containing Z-1,2-dichloro-ethylene (48.5 mg, 0.5 mmol, 5.00 equiv), 2-(5-hexenyl) isoindoline-1,3-dione (22.9 mg, 0.1 mmol, 1.00 equiv) and benzene (470 µL). The resulting solution was allowed to stir for 4 hours at 22° C. The reaction was quenched by addition of wet CDCl$_3$ and analysis of the unpurified mixture revealed 81% consumption of 2-(5-hexenyl)isoindoline-1,3-dione. The resulting orange oil was purified by silica gel chromatography (100% hexanes to 10% Et$_2$O in hexanes) to afford 8 (17.2 mg, 0.0652 mmol, 65% yield) in >98:<2 Z:E ratio as colorless oil. $^1$H NMR (400 MHz, CDCl$_3$): Z-isomer (major): δ 7.84 (1H, dd, J=5.5, 3.0 Hz), 7.71 (2H, dd, J=5.4, 3.1 Hz), 6.02 (1H, dt, J=7.1, 1.5 Hz), 5.73 (1H, q, J=7.2 Hz), 3.70 (2H, t, J=7.2 Hz), 2.28 (2H, qd, J=7.4, 1.5 Hz), 1.77-1.67 (2H, m), 1.52-1.44 (2H, m).

(Z)-tert-butyl(8-chloro-7-octenyloxy)dimethylsilane (9)

Following the general procedure, a solution of Mo-4 in benzene (0.1 M, 30 µL, 3.0 µmol, 3 mol %) was transferred by syringe to an oven-dried vial containing Z-1,2-dichloro-ethylene (48.5 mg, 0.5 mmol, 5.00 equiv), tert-butyldim-ethyl(7-octenyloxy)silane (24.2 mg, 0.1 mmol, 1.00 equiv) and benzene (470 µL). The resulting solution was allowed to stir for 4 hours at 22° C. The reaction was quenched by addition of wet CDCl$_3$ and analysis of the unpurified mixture revealed 88% consumption of tert-butyldimethyl(7-octeny-loxy)silane. The resulting orange oil was purified by silica gel chromatography (100% hexanes) to afford 9 (22.2 mg, 0.0802 mmol, 80% yield) in >98:<2 Z:E ratio as colorless oil. $^1$H NMR (400 MHz, CDCl$_3$): Z-isomer (major): δ 6.00 (1H, dd, J=7.0, 1.4 Hz), 5.74 (1H, qd, J=7.2, 2.2 Hz), 3.60 (2H, td, J=6.5, 2.2 Hz), 2.22 (2H, qd, J=7.0 Hz), 1.55-1.47 (2H, m), 1.44-1.29 (6H, m), 0.89 (9H, d, J=2.3 Hz), 0.04 (6H, d, J=2.3 Hz).

(1S,2R,4R)-2-((Z)-8-chloro-7-octenyloxy)-1-isopro-pyl-4-methylcyclohexane (10)

Following the general procedure, a solution of Mo-4 in benzene (0.1 M, 30 µL, 3.0 µmol, 3 mol %) was transferred by syringe to an oven-dried vial containing Z-1,2-dichloro-ethylene (48.5 mg, 0.5 mmol, 5.00 equiv), (1S,2R,4R)-1-isopropyl-4-methyl-2-(7-octenyloxy)cyclohexane (26.6 mg, 0.1 mmol, 1.00 equiv) and benzene (470 µL). The resulting solution was allowed to stir for 4 hours at 22° C. The reaction was quenched by addition of wet CDCl$_3$ and analy-sis of the unpurified mixture revealed 79% consumption of (1S,2R,4R)-1-isopropyl-4-methyl-2-(7-octenyloxy)cyclo-hexane. The resulting orange oil was purified by silica gel chromatography (100% hexanes to 5% Et$_2$O in hexanes) to afford 10 (22.1 mg, 0.0734 mmol, 73% yield) in >98:<2 Z:E ratio as colorless oil. $^1$H NMR (400 MHz, CDCl$_3$): Z-isomer (major): δ 6.00 (1H, d, J=7.0 Hz), 5.75 (1H, qd, J=7.2, 0.9 Hz), 3.65-3.57 (1H, m), 3.25 (1H, dd, J=15.8, 6.8 Hz), 2.99 (1H, td, J=10.4, 3.7 Hz), 2.26-2.17 (3H, m), 2.13-1.94 (2H, m), 1.68-1.53 (3H, m), 1.45-1.16 (11H, m), 0.91 (3H, d, J=6.7 Hz), 0.89 (3H, d, J=7.2 Hz), 0.77 (3H, d, J=7.0 Hz).

(Z)-1-chloro-8-(3,7-dimethyl-6-octenyloxy)-1-octene (11)

Following the general procedure, a solution of Mo-3 in benzene (0.1 M, 30 µL, 3.0 µmol, 3 mol %) was transferred by syringe to an oven-dried vial containing Z-1,2-dichloro-ethylene (48.5 mg, 0.5 mmol, 5.00 equiv), 8-(3,7-dimethyl-6-octenyloxy)-1-octene (26.6 mg, 0.1 mmol, 1.00 equiv) and benzene (470 µL). The resulting solution was allowed to stir for 4 hours at 22° C. The reaction was quenched by addition of wet CDCl$_3$ and analysis of the unpurified mixture revealed 84% consumption of 8-(3,7-dimethyl-6-octeny-loxy)-1-octene. The resulting orange oil was purified by silica gel chromatography (100% hexanes to 5% Et$_2$O in hexanes) to afford 11 (22.9 mg, 0.0761 mmol, 76% yield) in >98:<2 Z:E ratio as colorless oil. $^1$H NMR (400 MHz, CDCl$_3$): Z-isomer (major): δ 6.01 (1H, d, J=6.9 Hz), 5.74

(1H, qd, J=7.2, 2.3 Hz), 5.10 (1H, t, J=5.9 Hz), 3.45-3.35 (4H, m), 2.30-2.16 (2H, m), 2.09-1.88 (2H, m), 1.71-1.55 (3H, m), 1.68 (3H, s), 1.60 (3H, s), 1.47-1.08 (10H, m), 0.89 (3H, d, J=6.5 Hz).

(Z)-(2-chlorovinyl)cyclohexane (12)

Following the general procedure, a solution of Mo-3 in benzene (0.1 M, 30 µL, 3.0 µmol, 3 mol %) was transferred by syringe to an oven-dried vial containing Z-1,2-dichloroethylene (48.5 mg, 0.5 mmol, 5.00 equiv), vinylcyclohexane (11.0 mg, 0.1 mmol, 1.00 equiv) and benzene (470 µL). The resulting solution was allowed to stir for 4 hours at 22° C. The reaction was quenched by addition of wet $CDCl_3$ and analysis of the unpurified mixture revealed 89% consumption of vinylcyclohexane. The resulting orange oil was purified by silica gel chromatography (100% hexanes) to afford 12 (10.9 mg, 0.0754 mmol, 75% yield) in >98:<2 Z:E ratio as colorless oil. The spectral data for this compound were identical to those reported in the literature. (Miller, R. B.; McGarvey, G. J. Org. Chem. 1978, 43, 4424-4431.)

(Z)-4-(2-chlorovinyl)-1-cyclohexene (13)

Following the general procedure, a solution of Mo-3 in benzene (0.1 M, 30 µL, 3.0 µmol, 3 mol %) was transferred by syringe to an oven-dried vial containing Z-1,2-dichloroethylene (48.5 mg, 0.5 mmol, 5.00 equiv), 4-vinyl-1-cyclohexene (11.0 mg, 0.1 mmol, 1.00 equiv) and benzene (470 µL). The resulting solution was allowed to stir for 4 hours at 22° C. The reaction was quenched by addition of wet $CDCl_3$ and analysis of the unpurified mixture revealed 89% consumption of 4-vinyl-1-cyclohexene. The resulting orange oil was purified by silica gel chromatography (100% hexanes) to afford 13 (10.9 mg, 0.0754 mmol, 75% yield) in >98:<2 Z:E ratio as colorless oil. $^1$H NMR (400 MHz, $CDCl_3$): Z-isomer (major): δ 5.99 (1H, dd, J=7.1, 1.1 Hz), 5.74-5.62 (3H, m), 2.94-2.81 (1H, m), 2.20-2.05 (3H, m), 1.87-1.71 (2H, m), 1.50-1.42 (1H, m).

(Z)-1-chloro-1-hexene (15)

Following the general procedure, a solution of Mo-4 in benzene (0.1 M, 10 µL, 1.0 µmol, 1 mol %) was transferred by syringe to an oven-dried vial containing Z-1,2-dichloroethylene (48.5 mg, 0.5 mmol, 5.00 equiv) and Z-5-decene (14.0 mg, 0.1 mmol, 1.00 equiv). The resulting solution was allowed to stir for 2 hours at 22° C. The reaction was quenched by addition of wet $CDCl_3$ and analysis of the unpurified mixture revealed 97% consumption of Z-5-decene. The resulting orange oil was purified by silica gel chromatography (100% hexanes) to afford 15 (20.2 mg, 0.1703 mmol, 85% yield based on substrate stoichiometry) in 97:3 Z:E ratio as colorless oil. The spectral data for this compound were identical to those reported in the literature (Alami, M.; Crousse, B.; Ferri, F. J. Organomet. Chem. 2001, 624, 114-123.)

(Z)-methyl 10-chloro-9-decenoate (17) & (Z)-1-chloro-1-decene (18)

Following the general procedure, a solution of Mo-4 in benzene (0.1 M, 30 µL, 3.0 µmol, 3 mol %) was transferred by syringe to an oven-dried vial containing Z-1,2-dichloroethylene (48.5 mg, 0.5 mmol, 5.00 equiv), methyl oleate (29.7 mg, 0.1 mmol, 1.00 equiv) and benzene (470 µL). The resulting solution was allowed to stir for 4 hours at 22° C. The reaction was quenched by addition of wet $CDCl_3$ and analysis of the unpurified mixture revealed 94% consumption of methyl oleate. The resulting orange oil was purified by silica gel chromatography (100% hexanes to 10% $Et_2O$ in hexanes) to afford 17 (20.0 mg, 0.0914 mmol, 91% yield) in 97:3 Z:E ratio as colorless oil and 18 (15.0 mg, 0.0859 mmol, 86% yield) in 97:3 Z:E ratio as colorless oil. The spectral data for 18 were identical to those reported in the literature. (Okuyama, T.; Takino, T.; Sato, K.; Oshima, K.; Imamura, S.; Yamataka, H.; Asano, T.; Ochiai, M. Bull Chem. Soc. Jpn. 1998, 71, 243-257.) $^1$H NMR (400 MHz, $CDCl_3$) for 17: Z-isomer (major): δ 6.01 (1H, dd, J=7.1, 1.6 Hz), 5.74 (1H, q, J=7.1 Hz), 3.67 (3H, s), 2.30 (2H, t, J=7.5 Hz), 2.21 (2H, qd, J=7.2, 1.4 Hz), 1.67-1.58 (2H, m), 1.43-1.35 (2H, m), 1.34-1.30 (6H, m).

(Z)-10-chloro-9-decenyl (3S,8S,9S,10R,13R,14S,17R)-10,13-dimethyl-17-((R)-6-methyl-2-heptanyl)-2,3,4,7,8,9,10,11,12,13,14,15,16,17-tetradecahydro-1H-3-cyclopenta[a]phenanthrenyl carbonate (20) & (Z)-1-chloro-1-decene (18)

Following the general procedure, a solution of Mo-4 in benzene (0.1 M, 30 µL, 3.0 µmol, 3 mol %) was transferred by syringe to an oven-dried vial containing Z-1,2-dichloroethylene (48.5 mg, 0.5 mmol, 5.00 equiv), cholesteryl oleyl carbonate (68.1 mg, 0.1 mmol, 1.00 equiv) and benzene (470 µL). The resulting solution was allowed to stir for 4 hours at 22° C. The reaction was quenched by addition of wet $CDCl_3$ and analysis of the unpurified mixture revealed >98% consumption of cholesteryl oleyl carbonate. The resulting orange oil was purified by silica gel chromatography (100% hexanes to 5% $Et_2O$ in hexanes) to afford 20 (49.0 mg, 0.0812 mmol, 81% yield) in 94:6 Z:E ratio as colorless semi-solid and 18 (13.8 mg, 0.0790 mmol, 79% yield) in 94:6 Z:E ratio as colorless oil. The spectral data for 18 were identical to those reported in the literature. (Okuyama, T.; Takino, T.; Sato, K.; Oshima, K.; Imamura, S.; Yamataka, H.; Asano, T.; Ochiai, M. Bull Chem. Soc. Jpn. 1998, 71, 243-257.) $^1$H NMR (400 MHz, $CDCl_3$) for 20: Z-isomer (major): δ 6.01 (1H, d, J=7.1 Hz), 5.74 (1H, q, J=7.1 Hz), 5.39 (1H, d, J=4.9 Hz), 4.48 (1H, dt, J=10.2, 4.8 Hz), 4.11 (2H, t, J=6.7 Hz), 2.43-2.35 (2H, m), 2.26-2.16 (2H, m), 2.06-1.77 (6H, m), 1.70-1.61 (3H, m), 1.53-1.22 (22H, m), 1.17-1.04 (7H, m), 1.01 (3H, s), 0.91 (3H, d, J=6.5 Hz), 0.86 (6H, dd, J=6.6, 1.8 Hz), 0.68 (3H, s).

(Z)-(2-bromovinyl)cyclohexane (22)

Following the general procedure, a solution of Mo-3 in benzene (0.1 M, 30 µL, 3.0 µmol, 3 mol %) was transferred by syringe to an oven-dried vial containing 1,2-dibromoethylene (64:36 Z:E mixture, 148.7 mg, 0.8 mmol, 8.00 equiv), vinylcyclohexane (11.0 mg, 0.1 mmol, 1.00 equiv) and benzene (470 µL). The resulting solution was allowed to stir for 4 hours at 22° C. The reaction was quenched by addition of wet $CDCl_3$ and analysis of the unpurified mixture revealed 61% consumption of vinylcyclohexane. The resulting orange oil was purified by silica gel chromatography (100% hexanes) to afford 22 (7.9 mg, 0.0418 mmol, 42% yield) in >98:<2 Z:E ratio as colorless oil. The spectral data for this compound were identical to those reported in the literature. (Kuang, C.; Yang, Q.; Senboku, H.; Tokuda, M. Tetrahedron 2005, 61, 4043-4052.)

(Z)-((8-Bromooct-7-en-1-yl)oxy)(tert-butyl)dimethylsilane (23)

Following the general procedure, a solution of Mo-4 in benzene (0.1 M, 21 µL, 2.1 µmol, 5 mol %) was transferred by syringe to an oven-dried vial containing 1,2-dibromoethene (61.0 mg, 0.330 mmol, 8.00 equiv), tert-butyldimethyl(oct-7-en-1-yloxy)silane (10.0 mg, 0.0410 mmol, 1.00 equiv). The resulting solution was allowed to stir for 4 hours at 22° C. The reaction was quenched by addition of wet $CDCl_3$ and analysis of the unpurified mixture revealed 95% consumption of tert-butyldimethyl(oct-7-en-1-yloxy)silane. The resulting orange oil was purified by silica gel chromatography (2% $Et_2O$ in hexanes to 5% $Et_2O$ in hexanes) to afford 23 (8.3 mg, 0.0260 mmol, 63% yield) in 88:12 Z:E ratio as colorless oil. $^1$H NMR (400 MHz, $CDCl_3$): Z-isomer (major): δ 6.14 (1H, dt, J=7.2, 1.2 Hz), 6.08 (1H, q, J=6.8 Hz), 3.60 (2H, t, J=6.4 Hz), 2.19 (2H, q, J=7.2 Hz), 1.55-1.26 (8H, m), 0.90 (9H, s), 0.05 (6H, s).

(Z)-(8-Bromo-2,6-dimethyl-7-octen-2-yloxy)(tert-butyl)dimethylsilane (24)

Following the general procedure, a solution of Mo-4 in benzene (0.1 M, 18 μL, 1.8 μmol, 5 mol %) was transferred by syringe to an oven-dried vial containing 1,2-dibromoethene (55.0 mg, 0.296 mmol, 8.00 equiv) and tert-butyl(2,6-dimethyl-7-octen-2-yloxy)dimethylsilane (10.0 mg, 0.0370 mmol, 1.00 equiv). The resulting solution was allowed to stir for 4 hours at 22° C. The reaction was quenched by addition of wet $CDCl_3$ and analysis of the unpurified mixture revealed 71% consumption of tert-butyl(2,6-dimethyl-7-octen-2-yloxy)dimethylsilane. The resulting orange oil was purified by silica gel chromatography (100% hexanes) to afford 24 (7.4 mg, 0.0212 mmol, 57% yield) in 91:9 Z:E ratio as colorless oil. $^1$H NMR (400 MHz, $CDCl_3$): Z-isomer (major): δ 6.09 (1H, dd, J=7.0, 0.8 Hz), 5.85 (1H, dd, J=9.2, 7.0 Hz), 2.76-2.64 (1H, m), 1.39-1.31 (6H, m), 1.17 (6H, s), 0.99 (3H, d, J=6.7 Hz), 0.85 (9H, s), 0.06 (6H, s).

(Z)-tert-Butyl((8-fluoro-2,6-dimethyloct-7-en-2-yl)oxy)dimethylsilane (25)

Following the general procedure, a solution of Mo-4 in benzene (0.1 M, 25 μL, 2.5 μmol, 5 mol %) was transferred by syringe to an oven-dried vial containing Z-1-bromo-2-fluoroethene (31.3 mg, 0.251 mmol, 5.00 equiv) and tert-butyl(2,6-dimethyl-7-octen-2-yloxy)dimethylsilane (13.5 mg, 0.0499 mmol, 1.00 equiv). The resulting solution was allowed to stir for 2 hours at 22° C. The reaction was quenched by addition of wet $CDCl_3$ and analysis of the unpurified mixture revealed >98% consumption of tert-butyl(2,6-dimethyl-7-octen-2-yloxy)dimethylsilane that resulted in the formation of a mixture of F- and Br-alkenes (F:Br=96:4). The resulting orange oil was purified by silica gel chromatography (100% hexanes) to afford 25 (10.1 mg, 0.0350 mmol, 70% yield) in >98:<2 Z:E ratio as colorless oil. $^1$H NMR (600 MHz, $CDCl_3$): Z-isomer (major): δ 6.41 (1H, ddd, J=86.0, 4.8, 0.8 Hz), 4.52 (1H, ddd, J=43.9, 9.8, 4.8 Hz), 2.73-2.63 (m, 1H), 1.46-1.19 (6H, m), 1.18 (3H, s), 1.17 (3H, s), 0.99 (d, J=6.8 Hz, 3H), 0.85 (s, 9H), 0.06 (s, 6H).

(Z)-1-(2-Fluorovinyl)-4-methoxybenzene (26)

Following the general procedure, a solution of Mo-4 in benzene (0.1 M, 25 μL, 2.5 μmol, 5 mol %) was transferred by syringe to an oven-dried vial containing Z-1-bromo-2-fluoroethene (62.5 mg, 0.500 mmol, 10.0 equiv) and 4-methoxystyrene (6.8 mg, 0.0507 mmol, 1.00 equiv). The resulting solution was allowed to stir for 4 hours at 22° C. The reaction was quenched by addition of wet $CDCl_3$ and analysis of the unpurified mixture revealed >98% consumption of 4-methoxystyrene that resulted in the formation of a mixture of F- and Br-alkenes (F:Br=93:7). The resulting orange oil was purified by silica gel chromatography (20:1 hexanes/$Et_2O$) to afford 26 (5.4 mg, 0.0355 mmol, 71% yield) in 95:5 Z:E ratio as pale yellow oil. The spectral data for this compound were identical to those reported in the literature. (Zhu, L.; Ni, C.; Zhao, Y.; Hu, J. Tetrahedron 66, 5089-5100 (2010).)

(Z)-1-Chloro-4-(2-fluorovinyl)benzene (27)

Following the general procedure, a solution of Mo-4 in benzene (0.1 M, 36 μL, 3.6 μmol, 5 mol %) was transferred by syringe to an oven-dried vial containing Z-1-bromo-2-fluoroethene (90.2 mg, 0.722 mmol, 10.0 equiv) and 4-chlorostyrene (10.0 mg, 0.0722 mmol, 1.00 equiv). The resulting solution was allowed to stir for 4 hours at 22° C. The reaction was quenched by addition of wet $CDCl_3$ and analysis of the unpurified mixture revealed 78% consumption of 4-chlorostyrene that resulted in the formation of a mixture of F- and Br-alkenes (96:4 F:Br). The resulting orange oil was purified by silica gel chromatography (100% hexanes to 2% $Et_2O$ in hexanes) to afford 27 (7.2 mg, 0.0460 mmol, 64% yield) in 97:3 Z:E ratio as colorless oil. The spectral data for this compound were identical to those reported in the literature. (Emet, T.; Maulitz, A. H.; Wurthwein, E.-U.; Haufe, G. J. Chem. Soc., Perkin Trans 1. 1929-1938 (2001).)

tert-Butyl(((8R,9S,10R,13S,14S,17R)-17-((Z)-3-chloroallyl)-13-methyl-2,3,6,7,8,9,10,11,12,13,14,15,16,17-tetradecahydro-1H-cyclopenta[a]phenanthren-17-yl)oxy)dimethylsilane Following the general procedure, a solution of Mo-4 in benzene (0.1 M, 25 μL, 2.5 μmol, 5 mol %) was transferred by syringe to an oven-dried vial containing Z-1,2-dichloroethene (24.3 mg, 0.251 mmol, 5.00 equiv) and (((8R,9S,10R,13S,14S,17R)-17-allyl-13-methyl-2,3,6,7,8,9,10,11,12,13,14,15,16,17-tetradecahydro-1H-cyclopenta[a]phenanthren-17-yl)oxy) (tert-butyl)dimethylsilane (20.7 mg, 0.0499 mmol, 1.00 equiv). The resulting solution was allowed to stir for 4 hours at 22° C. The reaction was quenched by addition of wet $CDCl_3$ and analysis of the unpurified mixture revealed 75% consumption of (((8R,9S,10R,13S,14S,17R)-17-allyl-13-methyl-2,3,6,7,8,9,10,11,12,13,14,15,16,17-tetradecahydro-1H-cyclopenta[a]phenanthren-17-yl)oxy) (tert-butyl)dimethylsilane. The resulting orange oil was purified by silica gel chromatography (100% hexanes) to afford the product (15.7 mg, 0.0349 mmol, 70% yield) in 95:5 Z:E ratio as off-white solid. $^1$H NMR (400 MHz, $C_6D_6$): Z-isomer (major): δ 5.97 (1H, q, J=6.6 Hz), 5.81 (1H, dt, J=7.1, 1.9 Hz), 5.49 (1H, bs), 2.60 (1H, ddd, J=16.4, 6.1, 1.2 Hz), 2.47 (1H, ddd, J=16.2, 6.6, 2.1 Hz), 2.30-2.22 (1H, m), 2.10-0.80 (32H, m), 0.63-0.51 (1H, m), 0.12 (3H, s), 0.09 (3H, s).

(Z)-(10-Fluorodec-9-en-1-yn-1-yl)triisopropylsilane (28)

Following the general procedure, a solution of Mo-4 in benzene (0.1 M, 30 μL, 3.0 μmol, 3 mol %) was transferred by syringe to an oven-dried vial containing Z-1-bromo-2-fluoroethene (62.5 mg, 0.500 mmol, 5.00 equiv) and 9-decen-1-ynyltriisopropylsilane (29.3 mg, 0.100 mmol, 1.00 equiv). The resulting solution was allowed to stir for 4 hours at 22° C. The reaction was quenched by addition of wet CDCl₃ and analysis of the unpurified mixture revealed >98% consumption of 9-decen-1-ynyltriisopropylsilane that resulted in the formation of a mixture of F- and Br-alkenes (F:Br=72:28). The resulting orange oil was purified by silica gel chromatography (100% hexanes) to afford 28 in 74:26 F:Br (70% F-alkene by mass) and >98:<2 Z:E ratio (28.3 mg, 0.0638 mmol, 64% yield) as colorless oil. ¹H NMR (600 MHz, CDCl₃: Z-isomer (major): δ 6.44 (F-alkene, 1H, ddt, J=86.0, 4.7, 1.5 Hz), 6.17-6.04 (Br-alkene, 2H, m), 4.71 (F-alkene, 1H, dtd, J=43.5, 7.6, 4.7 Hz), 2.29-2.04 (4H, m), 1.59-1.20 (8H, m), 1.12-0.97 (21H, m).

(4R,5S,6S)-4-((Z)-2-Fluorovinyl)-2-(4-methoxyphenyl)-5-methyl-6-((S,E)-5-phenylpent-3-en-2-yl)-1,3-dioxane (29)

Following the general procedure, a solution of Mo-4 in benzene (0.1 M, 40 μL, 4.0 μmol, 10 mol %) was transferred by syringe to an oven-dried vial containing Z-1-bromo-2-fluoroethene (25.0 mg, 0.200 mmol, 5.00 equiv) and (4R,5S,6R)-2-(4-methoxyphenyl)-5-methyl-4-((R,E)-5-phenylpent-3-en-2-yl)-6-vinyl-1,3-dioxane (15.1 mg, 0.0399 mmol, 1.00 equiv). The resulting solution was allowed to stir for 4 hours at 22° C. The reaction was quenched by addition of wet CDCl₃ and analysis of the unpurified mixture revealed 80% consumption of (4R,5S,6R)-2-(4-methoxyphenyl)-5-methyl-4-((R,E)-5-phenylpent-3-en-2-yl)-6-vinyl-1,3-dioxane that resulted in the exclusive formation of F-alkene. The resulting orange oil was purified by preparative thin layer chromatography (1:8 EtOAc/hexanes) to afford 29 (10.0 mg, 0.0252 mmol, 63% yield) with >98:<2 Z:E ratio as off-white solid. ¹H NMR (500 MHz, CDCl₃): Z-isomer (major): δ 7.41 (2H, d, J=8.7 Hz), 7.33-7.27 (4H, m), 7.22-7.15 (2H, m), 6.89 (2H, d, J=8.7 Hz), 6.66 (1H, ddd, J=84.2, 4.9, 1.1 Hz), 5.75 (1H, s), 5.74-5.65 (1H, m), 5.60 (1H, dt, J=15.3, 6.6 Hz), 5.40 (1H, ddd, J=40.8, 9.6, 5.0 Hz), 5.06 (1H, dd, J=9.8, 5.6 Hz), 3.81 (3H, s), 3.55 (1H, dd, J=10.6, 2.1 Hz), 3.38 (2H, d, J=6.4 Hz), 2.51-2.41 (1H, m), 2.34-2.24 (1H, m), 1.40-1.19 (4H, m), 1.16 (3H, d, J=7.0 Hz), 0.73 (3H, d, J=7.0 Hz).

(Z)-1-Bromo-4-(2-fluorovinyl)benzene (30)

Following the general procedure, a solution of Mo-4 in benzene (0.1 M, 27 μL, 2.7 μmol, 5 mol %) was transferred by syringe to an oven-dried vial containing Z-1-bromo-2-fluoroethene (68.3 mg, 0.546 mmol, 10.0 equiv) and 4-bromostyrene (10.0 mg, 0.0546 mmol, 1.00 equiv). The resulting solution was allowed to stir for 4 hours at 22° C. The reaction was quenched by addition of wet CDCl₃ and analysis of the unpurified mixture revealed 88% consumption of 4-bromostyrene that resulted in the formation of a mixture of F- and Br-alkenes (95:5 F:Br). The resulting orange oil was purified by silica gel chromatography (100% hexanes to 2% Et₂O in hexanes) to afford 30 (7.2 mg, 0.0358 mmol, 66% yield) in 93:7 Z:E ratio as colorless oil. The spectral data for this compound were identical to those reported in the literature. (Zhu, L.; Ni, C.; Zhao, Y.; Hu, J. *Tetrahedron* 66, 5089-5100 (2010).)

(Z)-4-(2-Fluorovinyl)phenyl acetate (31)

Following the general procedure, a solution of Mo-4 in benzene (0.1 M, 25 μL, 2.5 μmol, 5 mol %) was transferred by syringe to an oven-dried vial containing Z-1-bromo-2-fluoroethene (62.5 mg, 0.500 mmol, 10.0 equiv) and 4-acetoxystyrene (8.1 mg, 0.0499 mmol, 1.00 equiv). The resulting solution was allowed to stir for 4 hours at 22° C. The reaction was quenched by addition of wet CDCl₃ and analysis of the unpurified mixture revealed 84% consumption of 4-acetoxystyrene that resulted in the formation of a mixture of F- and Br-alkenes (F:Br=96:4). The resulting orange oil was purified by silica gel chromatography (10:1 hexanes/Et₂O) to afford 31 (6.5 mg, 0.0361 mmol, 72% yield) in 94:6 Z:E ratio as pale yellow oil. ¹H NMR (600 MHz, CDCl₃): Z-isomer (major): δ 7.52 (2H, d, J=8.6 Hz), 7.07 (2H, d, J=8.7 Hz), 6.65 (1H, dd, J=82.6, 5.4 Hz), 5.60 (1H, dd, J=44.3, 5.4 Hz), 2.30 (3H, s).

(Z)-5-(2-Fluorovinyl)pyrrolidin-2-one (32)

Following the general procedure, a solution of Mo-4 in benzene (0.1 M, 89 μL, 8.9 μmol, 10 mol %) was transferred by syringe to an oven-dried vial containing Z-1-bromo-2-fluoroethene (55.4 mg, 0.444 mmol, 5.00 equiv) and 1-(tert-butyldimethylsilyl)-5-vinylpyrrolidin-2-one (20.0 mg, 0.0887 mmol, 1.00 equiv). The resulting solution was allowed to stir for 12 hours at 40 OC. The reaction was quenched by addition of wet CDCl₃ and analysis of the unpurified mixture revealed 60% consumption of 1-(tert-butyldimethylsilyl)-5-vinylpyrrolidin-2-one that resulted in the exclusive formation of F-alkene (>98:<2 F:Br). The mixture was concentrated and the unpurified residue was re-dissolved in MeOH (1.0 mL) and treated with an aqueous 1.0 M solution of HCl (0.25 mL). The solution was allowed to stir for 2 hours at 22° C. The solution was diluted with EtOAc (2 mL) and H₂O (2 mL) and the organic layer was separated. The aqueous layer was further extracted with EtOAc (3×2 mL), the organic layers were combined and dried over MgSO₄. The volatiles were removed to afford yellow oil, which was purified by silica gel chromatography (30% EtOAc in hexanes to 100% EtOAc) to afford 32 (6.3 mg, 0.0488 mmol, 55% yield over two steps) with >98:<2 Z:E ratio as pale yellow oil. The spectral data for this compound were identical to those reported in the literature. (Kolb, M.; Barth, J.; Heydt, J.-G.; Jung, M. J. *J. Med. Chem.* 2007, 30, 267-272.)

(S,Z)-2-(4-(3-(2-Chloro-10H-phenothiazin-10-yl)propyl)piperazin-1-yl)ethyl 6-fluoro-4-methyl-5-hexenoate (33)

Following the general procedure, a solution of Mo-4 in benzene (0.1 M, 10 μL, 1.0 μmol, 5 mol %) was transferred by syringe to an oven-dried vial containing Z-1-bromo-2-fluoroethene (12.0 mg, 0.0970 mmol, 5.00 equiv), (S)-2-(4-(3-(2-chloro-10H-phenothiazin-10-yl)propyl)piperazin-1-yl)ethyl 4-methylhex-5-enoate (10.0 mg, 0.0200 mmol, 1.00 equiv) and benzene (40 μL). The resulting solution was allowed to stir for 4 hours at 22° C. The reaction was quenched by addition of wet CDCl₃ and analysis of the unpurified mixture revealed 88% consumption of (S)-2-(4-(3-(2-chloro-10H-phenothiazin-10-yl)propyl)piperazin-1-yl)ethyl 4-methylhex-5-enoate that resulted in the formation of a mixture of F- and Br-alkenes (91:9 F:Br). The resulting orange oil was purified by silica gel chromatography (5% MeOH in CH₂Cl₂) to afford 33 (8.3 mg, 0.0156 mmol, 78% yield) with >98:<2 Z:E ratio as colorless oil. ¹H NMR (400 MHz, CDCl₃): Z-isomer (major): δ 7.15 (1H, t, J=7.6 Hz), 7.11 (1H, d, J=7.6 Hz), 7.01 (1H, d, J=8.0 Hz), 6.94-6.84 (4H, m), 6.44 (1H, dd, J=85.6, 4.8 Hz), 4.51 (1H, dq, J=43.2, 4.8 Hz), 4.18 (2H, t, J=6.4 Hz), 3.89 (2H, t, J=6.8 Hz), 2.71-2.28 (15H, m), 1.94 (2H, quint, J=7.2 Hz), 1.76-1.68 (1H, m), 1.55-1.47 (1H, m), 1.02 (3H, d, J=6.8 Hz).

(Z)-4-Fluoro-2-methyl-3-butenyl (2S,5R)-3,3-dimethyl-7-oxo-4-thia-1-azabicyclo[3.2.0]heptane-2-carboxylate 4,4-dioxide (34)

Following the general procedure, a solution of Mo-4 in benzene (0.1 M, 10 µL, 1.0 µmol, 5 mol %) was transferred by syringe to an oven-dried vial containing Z-1-bromo-2-fluoroethene (20.7 mg, 0.166 mmol, 5.00 equiv) and 2-methyl-3-butenyl (2S,5R)-3,3-dimethyl-7-oxo-4-thia-1-azabicyclo[3.2.0]heptane-2-carboxylate 4,4-dioxide (10.0 mg, 0.0332 mmol, 1.00 equiv). The resulting solution was allowed to stir for 4 hours at 22° C. The reaction was quenched by addition of wet CDCl$_3$ and analysis of the unpurified mixture revealed 86% consumption of 2-methyl-3-butenyl (2S,5R)-3,3-dimethyl-7-oxo-4-thia-1-azabicyclo[3.2.0]heptane-2-carboxylate 4,4-dioxide that resulted in the exclusive formation of F-alkene (>98:<2 F:Br). The resulting orange oil was purified by silica gel chromatography (10% Et$_2$O in hexanes to 40% Et$_2$O in hexanes) to afford 34 (8.5 mg, 0.0266 mmol, 80% yield) with >98:<2 Z:E ratio as yellow oil. $^1$H NMR (400 MHz, CDCl$_3$): Z-isomer (major): δ 6.51 (1H, dd, J=84.4, 4.6 Hz), 4.64-4.59 (1H, m), 4.62 (1H, ddd, J=41.8, 9.5, 4.6 Hz), 4.43-4.37 (1H, m), 4.20-3.98 (2H, m), 3.53-3.42 (2H, m), 3.17-3.03 (1H, m), 1.62 (3H, s), 1.42 (3H, s), 1.08 (3H, d, J=3.3 Hz).

Methyl (1R,4aR,4bS,7S,10aR)-7-((Z)-2-fluorovinyl)-1,4a,7-trimethyl-1,2,3,4,4a,4b,5,6,7,8,10,10a-dodecahydrophenanthrene-1-carboxylate (35)

Following the general procedure, a solution of Mo-4 in benzene (0.1 M, 27 µL, 2.7 µmol, 10 mol %) was transferred by syringe to an oven-dried vial containing Z-1-bromo-2-fluoroethene (16.2 mg, 0.130 mmol, 5.00 equiv) and isopimaric acid methyl ester (8.2 mg, 0.0259 mmol, 1.00 equiv). The resulting solution was allowed to stir for 4 hours at 22° C. The reaction was quenched by addition of wet CDCl$_3$ and analysis of the unpurified mixture revealed 83% consumption of isopimaric acid methyl ester that resulted in the formation of a mixture of F- and Br-alkenes (F:Br=94:6). The resulting orange oil was purified by silica gel chromatography (1:1 hexanes/benzene to 20:1 hexanes/Et$_2$O) to afford 35 (6.4 mg, 0.0191 mmol, 70% yield) in >98:<2 Z:E ratio as colorless oil. $^1$H NMR (400 MHz, CDCl$_3$): Z-isomer (major): δ 6.26 (1H, dd, J=85.0, 5.4 Hz), 5.35-5.28 (1H, m), 4.49 (1H, dd, J=50.1, 5.4 Hz), 3.64 (3H, s), 2.13 (2H, d, J=2.1 Hz), 2.05-1.66 (6H, m), 1.65-1.45 (6H, m), 1.44-1.28 (1H, m), 1.26 (3H, d, J=0.7 Hz), 1.18-1.05 (1H, m), 1.02 (3H, s), 0.89 (3H, m).

As described previously, in some embodiments, the present disclosure provides technologies for E-selective synthesis of olefins. In some embodiments, the present disclosure provides technologies for E-selective synthesis of vinyl halides. In some embodiments, the present disclosure provides methods with both regioselectivity and E-selectivity. Among other things, provided compounds and methods can provide alkenyl fluoride with unexpectedly high regioselectivity and/or E-selectivity.

Stereochemically defined alkenes are ubiquitous in natural occurring compounds and drugs and serve as substrates for numerous transformations in chemistry. Efficient protocols for the stereoselective preparation of olefins are highly desirable, particularly if they are promoted by catalysts that control the identity of the major product isomer. (Füstner, A. *Science* 2013, 341, 1357-1364.) Alkenyl halides rank as one of the most valuable classes of compounds in organic chemistry due to their occurrence in natural products as well as the immense applications associated. ((a) Guinchard, X.; Roulland, E. *Synlett*. 2011, 19, 2779-2788. (b) Stanforth, S. P. *Vinyl and Aryl Halides in Comprehensive Organic Functional Group Transformations II* (ed. Katritzky, A. R. & Taylor, R. J. K.) vol. 2 (Elsevier, 2004).) Traditional methods that afford E-alkenyl halides (e.g. Takai olefination) ((For a representative example, see: Takai, K.; Nitta, K.; Utimoto, K. *J. Am. Chem. Soc.* 1986, 108, 7408-7410) offer certain levels of selectivity depending on the relative steric size of the substrates, reagents and conditions employed. Other routes of preparing these compounds frequently proceed though multi-step synthesis routes. (For a representative example, see: Morrill, C.; Grubbs, R. H. *J. Org. Chem.* 2003, 68, 6031-6034.) There is a persisting lack of catalytic one-step protocols that directly furnish E-alkenyl halides efficiently and stereoselectively, particularly those that do not entail the generation of unnecessary intermediates and stoichiometric waste. Added to this problem is the inherent preference for 1,2-disubstituted halogenated olefins to exist as equilibrium mixtures of E/Z isomers, with the Z-diastereomer being thermodynamically more favored in several cases. (Craig, N. C.; Piper, L. G.; Wheeler, V. L. *J. Phys. Chem.* 1971, 75, 1453-1460.) Stereoselective catalytic olefin metathesis (OM), in some embodiments, with an appropriate halogen-containing cross-partner, could potentially provide a solution to the aforementioned dilemma. However, previous reports have been limited to Ru-catalyzed protocols ((a) Sashuk, V.; Samojłowicz, C.; Szadkowska, A.; Grela, K. *Chem. Commun.* 2008, 2468-2470. (b) Macnaughtan, M. L.; Gary, J. B.; Gerlach, D. L.; Johnson, M. J. A.; Kampf, J. W. *Organometallics* 2009, 28, 2880-2887.) which generally suffer from poor stereoselectivity (E/Z mixtures) and a narrow substrate range, in some cases as a result of the attenuated reactivity of the chloromethylidene species in OM and its susceptibility to various decomposition pathways. (Macnaughtan, M. L.; Johnson, M. J. A.; Kampf, J. W. *J. Am. Chem. Soc.* 2007, 129, 7708-7709.) The present disclosure recognizes that developing a catalyst-controlled kinetically E-selective OM protocol in the context of alkenyl halides is a compelling challenge. In some embodiments, the present disclosure present efficient and in some embodiments kinetically, E-selective cross-metathesis (CM) reactions involving suitable halogen-containing olefin reagents promoted by provided compounds, for example, a compound of formula II-a, a compound of formula II-b, etc. In some embodiments, provided compounds are molybdenum-based monoaryloxide monopyrrolide (MAP) complexes.

We began by examining the CM of 4-methoxystyrene and 10 equivalents of commercially available E-1,2-dichloroethene (E-DCE) in the presence of 3 mol % of Mo-E1 to afford alkenyl chloride E1 (Scheme E1). A direct comparison can be made with the Ru-catalyzed results previously reported in the literature. ((a) Sashuk, V.; Samojłowicz, C.; Szadkowska, A.; Grela, K. *Chem. Commun.* 2008, 2468-2470. (b) Macnaughtan, M. L.; Gary, J. B.; Gerlach, D. L.; Johnson, M. J. A.; Kampf, J. W. *Organometallics* 2009, 28, 2880-2887.)

Scheme E1 CM of 4-methoxystyrene and E-DCE in the presence of Ru-1 and the recently developed complex Mo-E1.

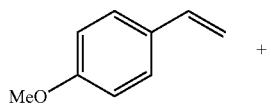

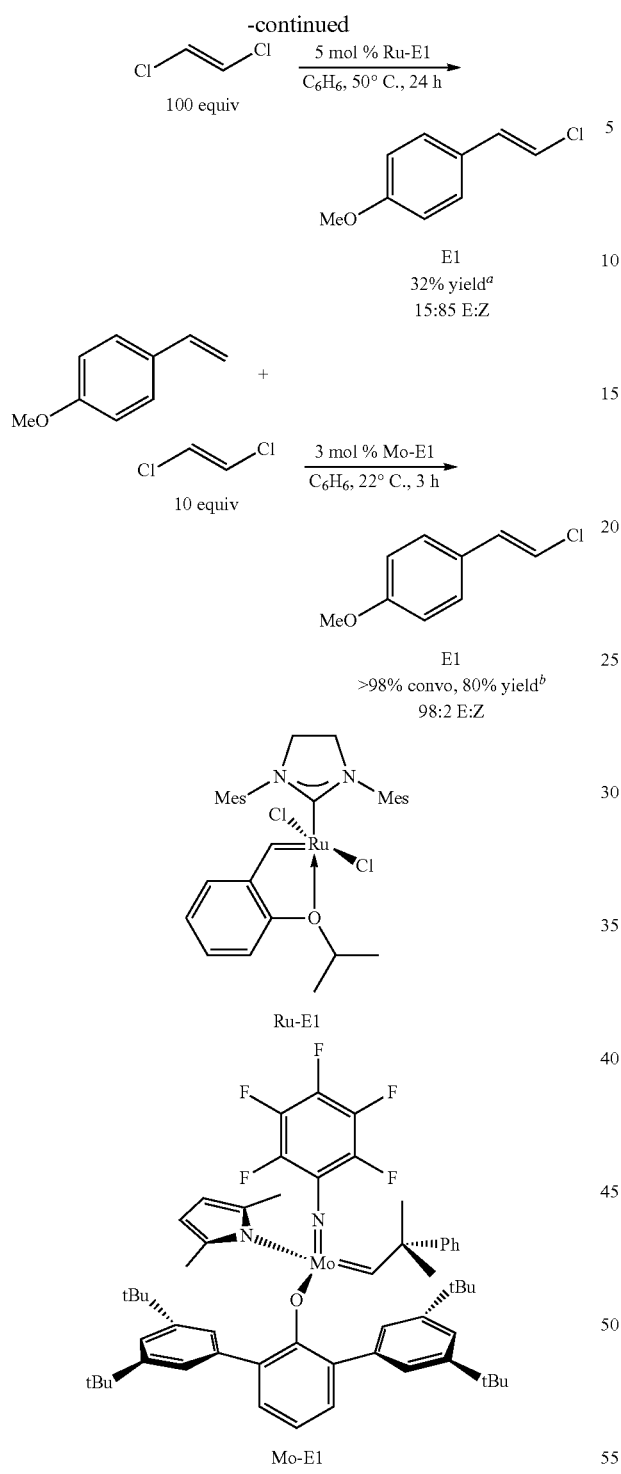
<sup>a</sup>Yield was determined by GC.
<sup>b</sup>Isolated yield.
Other provided metal complexes work as well:
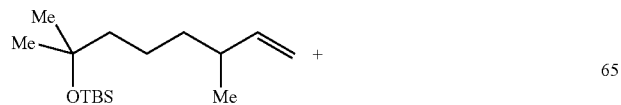
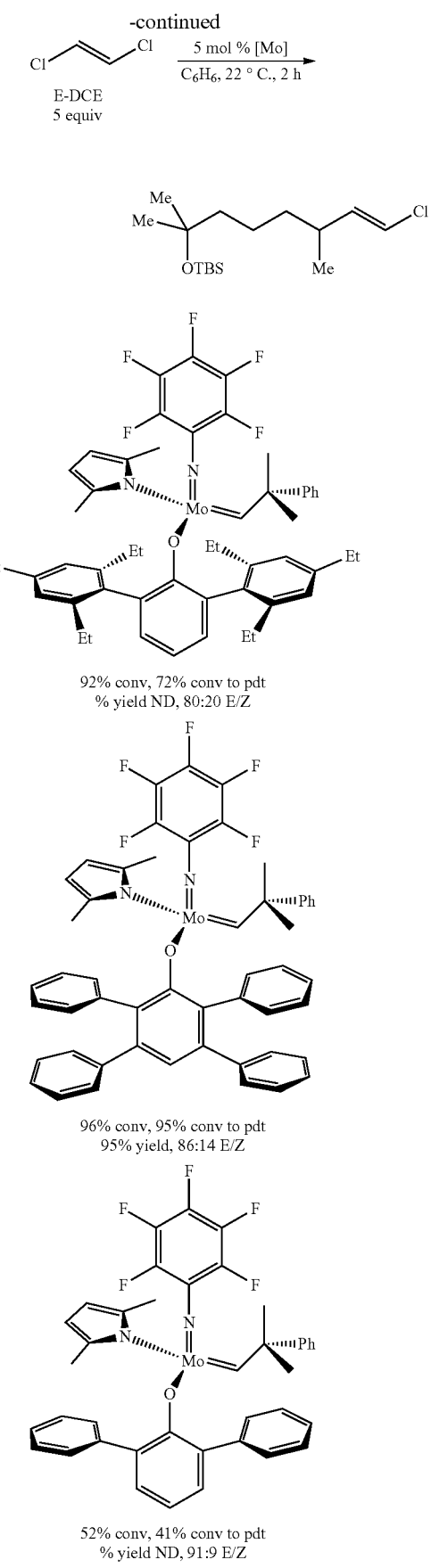

-continued

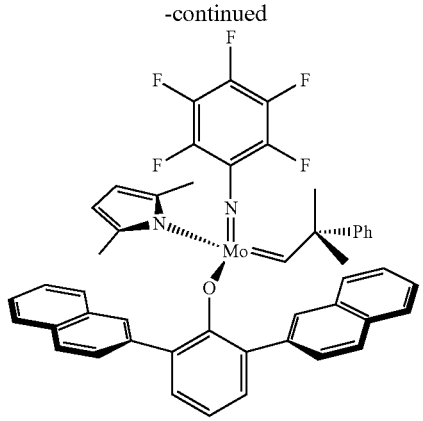

54% conv, 25% conv to pdt
% yield ND, 91:9 E/Z

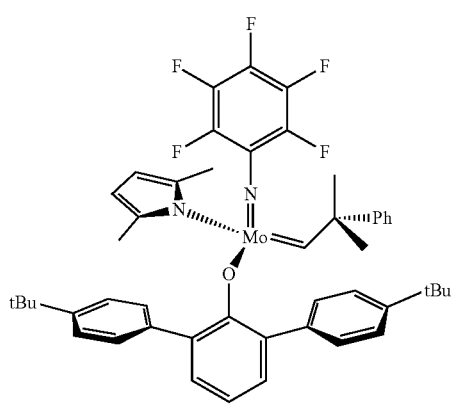

84% conv, 79% conv to pdt
77% yield, 90:10 E/Z

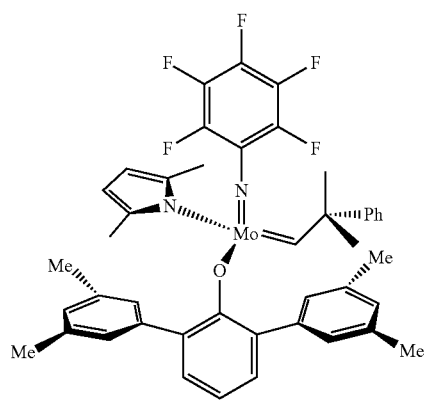

78% conv, 70% conv to pdt
% yield ND, 90:10 E/Z

-continued

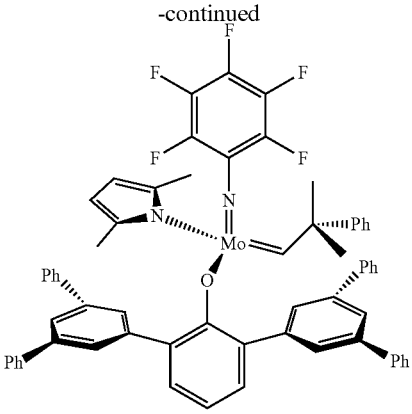

50% conv, 35% conv to pdt
% yield ND, 85:15 E/Z

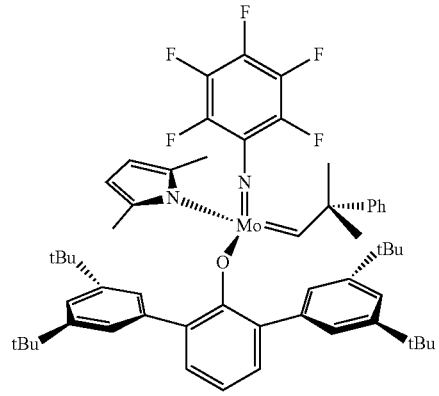

>98% conv, 93% conv to pdt
98% yield, 89:11 E/Z
with 20 equiv E-DCE
98% yield, 93:7 E/Z While less than desired efficiency (32% GC yield) and moderate stereoselectivity (15:85 E:Z) was obtained from Ru-E1 under forcing conditions (24 hours at 50 OC), Mo-E1 and other exemplary provided compound furnished the desired product in good yield with unexpectedly high E stereoselectivity (up to >98% E-isomer) in much shorter reaction time at ambient temperature (3 hours at 22° C.). Furthermore, the Mo-catalyzed reactions were highly efficient; a lower catalyst loading can be used to achieve complete consumption of the starting aryl alkene.

As exemplified herein, a broad scope of olefins (in some embodiments, second species in provided methods) can be used. For example, CM of a variety of olefins including e.g., aryl, heteroaryl, alkyl, etc., proceeded with high efficiency, high yield and high selectivity. In some embodiments, with 3.0-5.0 mol % of Mo-E1, CM products were obtained in 59-94% yield in 93:7 to >98:2 E:Z ratio (Scheme E2).

Scheme E2
a. CM of various alkenes and E-DCE in the presence of Mo-E1.

a. CM between various olefins and E-DCE to acess E-alkenyl chlorides

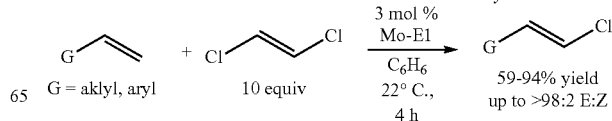

G = aklyl, aryl     10 equiv     3 mol % Mo-E1
C₆H₆
22° C.,
4 h
59-94% yield
up to >98:2 E:Z -continued

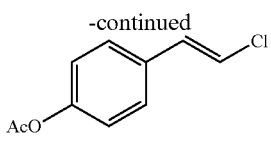

E2
\>98% conv, 75% yield
\>98:2 E:Z

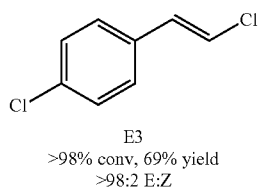

E3
\>98% conv, 69% yield
\>98:2 E:Z

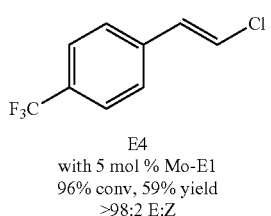

E4
with 5 mol % Mo-E1
96% conv, 59% yield
\>98:2 E:Z

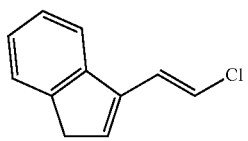

E5
2 h
\>98% conv, 85% yield
\>98:2 E:Z

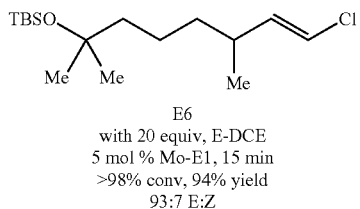

E6
with 20 equiv, E-DCE
5 mol % Mo-E1, 15 min
\>98% conv, 94% yield
93:7 E:Z b. Efficient CM between two trans-1,2-disubstituted olefins

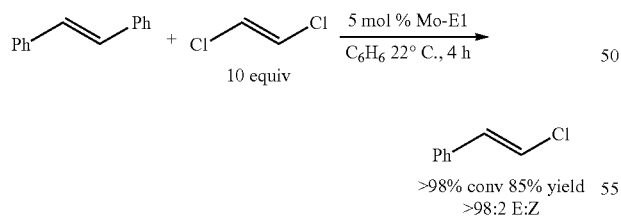

\>98% conv 85% yield
\>98:2 E:Z

Excellent stereoselectivities were observed in all cases. A slightly higher catalyst loading was necessary to obtain synthetically useful yields in the cases of highly electron-deficient aryl olefins such as 4-trifluoromethylstyrene. b. CM of trans-stilbene with E-DCE. Efficient CM between trans-stilbene, generally unreactive substrate in CM due to its steric bulk and electron-deficiency.

Electron-rich (e.g., E1, E2, E5, and E6) as well as electron-poor (e.g., E3 and E4) olefins serve well as substrates in the above transformations. In some embodiments, a slightly higher catalyst loading was required for 4-trifluoromethylstyrene. Among other things, complex Mo-E1 is able to efficiently react with trans-stilbene to afford trans-β-chlorostyrene in excellent yield and stereoselectivity.

As described, provided technologies, among other things, provide regioselectivity, for example, when a first species has different halogen substituents on the two carbon atoms of its olefin double bond. In some embodiments, the present disclosure provides technologies for regioselective and stereoselective synthesis of vinyl fluorides. As shown in Scheme E-3, the present disclosure, among other things, provides access to high-value alkenyl fluorides with surprisingly high selectivity, in some embodiments, as single E-isomers. Again, a broad scope of alkenes can be used as substrate, including aryl alkenes, heteroaryl alkenes, etc. Sterically encumbered a-branched alkyl olefins can also be efficiently transformed to the corresponding E-alkenyl fluorides (e.g., E9 and E10). The efficient reaction between the methyl ester derivative of isopimaric acid (Imaizumi, Y.; Sakamoto, K.; Yamada, A.; Hotta, A.; Ohya, S.; Muraki, K.; Uchiyama, M.; Ohwada, T. *Mol. Pharmacol.* 2002, 62, 836-846) (potassium channel activator) and 5 equivalents of E-CFE affording E-E10 in 74% yield as a single diastereomer highlights CM as an economical catalytic strategy for site- and stereoselective late-stage fluorination (Campbell, M. G.; Ritter, T. *Org. Process Res. Dev.* 2014, 18, 474-480) in alkene-tethered natural products and/or pharmaceuticals.

Scheme E3 CM of various alkenes and E-CFE in the presence of Mo-E2.

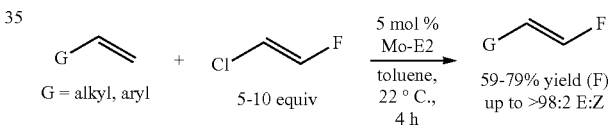

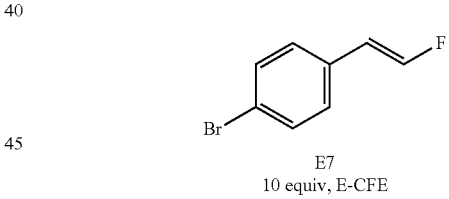

E7
10 equiv, E-CFE
\>98% conv, 89:11 F/Cl
59% yield (F), \>98:2 E:Z (F)

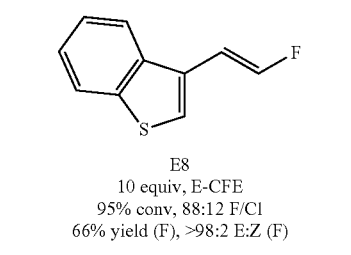

E8
10 equiv, E-CFE
95% conv, 88:12 F/Cl
66% yield (F), \>98:2 E:Z (F)

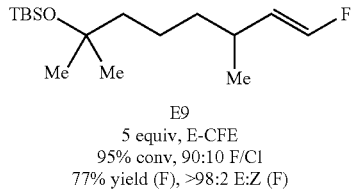

E9
5 equiv, E-CFE
95% conv, 90:10 F/Cl
77% yield (F), \>98:2 E:Z (F)

-continued

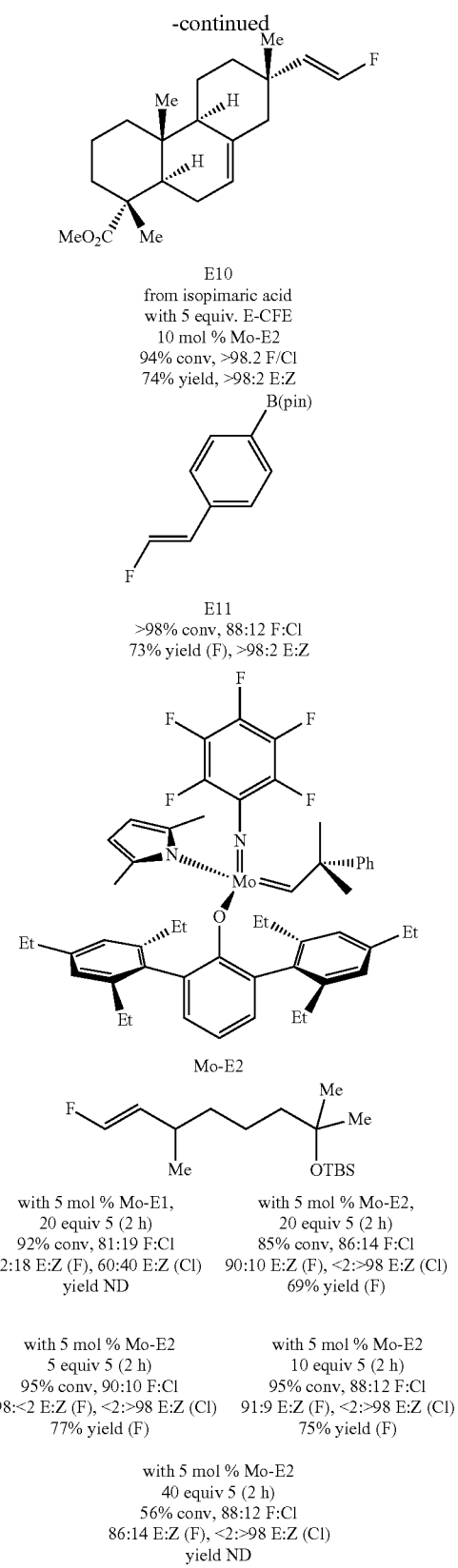

E10
from isopimaric acid
with 5 equiv. E-CFE
10 mol % Mo-E2
94% conv, >98.2 F/Cl
74% yield, >98:2 E:Z E11
>98% conv, 88:12 F/Cl
73% yield (F), >98:2 E:Z Mo-E2 with 5 mol % Mo-E1,
20 equiv 5 (2 h)
92% conv, 81:19 F/Cl
82:18 E:Z (F), 60:40 E:Z (Cl)
yield ND with 5 mol % Mo-E2,
20 equiv 5 (2 h)
85% conv, 86:14 F:Cl
90:10 E:Z (F), <2:>98 E:Z (Cl)
69% yield (F)

with 5 mol % Mo-E2
5 equiv 5 (2 h)
95% conv, 90:10 F:Cl
>98:<2 E:Z (F), <2:>98 E:Z (Cl)
77% yield (F)

with 5 mol % Mo-E2
10 equiv 5 (2 h)
95% conv, 88:12 F:Cl
91:9 E:Z (F), <2:>98 E:Z (Cl)
75% yield (F)

with 5 mol % Mo-E2
40 equiv 5 (2 h)
56% conv, 88:12 F:Cl
86:14 E:Z (F), <2:>98 E:Z (Cl)
yield ND As demonstrated in examples herein, provided technologies, among other things, provide high functional group tolerance, mild reaction conditions, high efficiency, and/or high selectivity, e.g., regioselectivity, Z/E-selectivity, chemoselectivity, etc. In some embodiments, when a substrate comprises a terminal olefin and an internal olefin, provide technologies selectively promote reactions at the terminal olefin. In some embodiments, when a substrate comprises an olefin and an alkyne, provided technologies selectively promote reactions at the olefin. In some embodiments, when a substrate comprises a terminal olefin and an alkyne, provided technologies selectively promote reactions at the terminal olefin.

Exemplary Procedure for In Situ Preparation of Mo-Based MAP Complexes

General Procedure for Preparation of Mo Complexes for NMR Analysis:

In a $N_2$-filled glove box, an oven-dried 4 mL vial equipped with a magnetic stir bar was charged with Mo bis-pyrrolide complex (Yuan, J.; Schrock, R. R.; Müller, P.; Axtell, J. C.; Dobereiner, G. E. *Organometallics* 2012, 31, 4650-4653) (1.00 equiv), phenol (Prepared in analogy to previously reported procedures: (a) Barder, T. E.; Walker, S. D.; Martinelli, J. R.; Buchwald, S. L. *J. Am. Chem. Soc.* 2005, 127, 4685-4696. (b) Radlauer, M. R.; Day, M. W.; Agapie, T. *Organometallics* 2012, 31, 2231-2243) (1.00 equiv) and $C_6D_6$, resulting in a dark red solution.

The vial was capped and the mixture was allowed to stir for 2 hours at 22° C., at which time it was transferred to a screw cap NMR tube by a pipette. The NMR tube was capped and sealed with Teflon tape. In some embodiments, for in situ generated complexes, the diagnostic signals of the α carbon of the syn-alkylidenes were evaluated.

General Procedure for Preparation of Mo Complexes for Catalytic Reactions:

In a $N_2$-filled glove box, an oven-dried 4 mL vial equipped with a magnetic stir bar was charged with Mo bis-pyrrolide complex (1.00 equiv), phenol (1.00 equiv) and $C_6H_6$, resulting in a dark red solution. The vial was capped and the mixture was allowed to stir for 2 hours at 22° C., after which the catalyst solution was transferred to the reaction mixture by a syringe (dried at 65° C.).

2,6-Bis(3,5-di-tert-butylphenyl)phenol $^1$H NMR (600 MHz, CDCl$_3$): δ 7.45 (2H, t, J=1.8 Hz), 7.39 (4H, d, J=1.8 Hz), 7.30 (2H, d, J=7.5 Hz), 7.06 (1H, t, J=7.6 Hz), 5.55 (1H, s), 1.36 (36H, s). Mo-E1: Following the general procedure, an oven-dried 4 mL vial equipped with a magnetic stir bar was charged with Mo bispyrrolide complex (59.7 mg, 0.100 mmol, 1.00 equiv), 2,6-bis(3,5-di-tert-butylphenyl)phenol (47.1 mg, 0.100 mmol, 1.00 equiv) and $C_6H_6$ (1.0 mL), resulting in a dark red solution. The vial was capped and the mixture was allowed to stir for 2 hours at 22° C. $^1$H NMR (400 MHz, $C_6D_6$): δ 11.88 (1H, s).

Experimental Procedure for E-Selective CM

General Procedure:

In a $N_2$-filled glove box, an oven-dried 4 mL vial equipped with a magnetic stir bar was charged with alkene substrate (1.0 equiv) and E-1,2-dichloroethene (10-20 equiv) or E-1-chloro-2-fluoroethene (5-10 equiv). To this vessel, a solution of provided compound, e.g., Mo-E1 or Mo-E2 (3.0-10.0 mol %), was added. The resulting solution was allowed to stir for 15 minutes-4 hours at 22° C., after which the reaction was quenched by addition of wet CDCl$_3$ (percent conversion was determined by 400 or 600 MHz $^1$H NMR analysis of the unpurified mixture). Purification was performed through silica gel chromatography.

(E)-1-(2-Chlorovinyl)-4-methoxybenzene (E1)

Following the general procedure, a solution of Mo-E1 in benzene (0.1 M, 30 μL, 3.0 mol, 3 mol %) was transferred by syringe to an oven-dried vial containing E-1,2-dichloroethene (96.9 mg, 1.0 mmol, 10.0 equiv) and 4-methoxystyrene (13.4 mg, 0.100 mmol, 1.00 equiv). The resulting solution was allowed to stir for 3 hours at 22° C. The reaction was quenched by addition of wet $CDCl_3$ and analysis of the unpurified mixture revealed >98% consumption of 4-methoxystyrene. The resulting orange oil was purified by silica gel chromatography (50:1 hexanes/$Et_2O$) to afford E1 (13.5 mg, 0.0801 mmol, 80% yield) in >98:2 E:Z ratio as off-white solid. $^1H$ NMR (400 MHz, $CDCl_3$): δ 7.23 (2H, d, J=8.3 Hz), 6.86 (2H, d, J=8.8 Hz), 6.77 (1H, d, J=13.6 Hz), 6.50 (1H, d, J=13.6 Hz), 3.81 (3H, s).

(E)-4-(2-Chlorovinyl)phenyl acetate (E2)

Following the general procedure, a solution of Mo-E1 in benzene (0.1 M, 24 μL, 2.4 mol, 3 mol %) was transferred by syringe to an oven-dried vial containing E-1,2-dichloroethene (77.6 mg, 0.8 mmol, 10.0 equiv) and 4-acetoxystyrene (13.0 mg, 0.0800 mmol, 1.00 equiv). The resulting solution was allowed to stir for 4 hours at 22° C. The reaction was quenched by addition of wet $CDCl_3$ and analysis of the unpurified mixture revealed >98% consumption of 4-acetoxystyrene. The resulting orange oil was purified by silica gel chromatography (10:1 hexanes/$Et_2O$) to afford E2 (11.8 mg, 0.0600 mmol, 75% yield) in >98:2 E:Z ratio as off-white solid. $^1H$ NMR (400 MHz, $CDCl_3$): δ 7.30 (2H, d, J=8.8 Hz), 7.06 (2H, d, J=8.9 Hz), 6.81 (1H, d, J=13.7 Hz), 6.60 (1H, dd, J=13.7 Hz), 2.30 (4H, s).

(E)-1-Chloro-4-(2-chlorovinyl)benzene (E3)

Following the general procedure, a solution of Mo-E1 in benzene (0.1 M, 40 μL, 4.0 mol, 5 mol %) was transferred by syringe to an oven-dried vial containing E-1,2-dichloroethene (77.6 mg, 0.800 mmol, 10.0 equiv) and 4-chlorostyrene (11.1 mg, 0.0800 mmol, 1.00 equiv). The resulting solution was allowed to stir for 4 hours at 22° C. The reaction was quenched by addition of wet $CDCl_3$ and analysis of the unpurified mixture revealed >98% consumption of 4-chlorostyrene. The resulting orange oil was purified by silica gel chromatography (100% hexanes) to afford E3 (9.6 mg, 0.0555 mmol, 69% yield) in >98:2 E:Z ratio as off-white solid. $^1H$ NMR (400 MHz, $CDCl_3$): δ 7.58 (4H, d, J=7.8 Hz), 7.40 (2H, d, J=8.0 Hz), 6.87 (2H, d, J=13.7 Hz), 6.76 (2H, d, J=13.7 Hz).

(E)-1-(2-Chlorovinyl)-4-(trifluoromethyl)benzene (E4)

Following the general procedure, a solution of Mo-E1 in benzene (0.1 M, 30 μL, 3.0 mol, 5 mol %) was transferred by syringe to an oven-dried vial containing E-1,2-dichloroethene (58.1 mg, 0.600 mmol, 10.0 equiv) and 4-trifluoromethylstyrene (10.3 mg, 0.0600 mmol, 1.00 equiv). The resulting solution was allowed to stir for 4 hours at 22° C. The reaction was quenched by addition of wet $CDCl_3$ and analysis of the unpurified mixture revealed >98% consumption of 4-trifluoromethylstyrene. The resulting orange oil was purified by silica gel chromatography (100% hexanes) to afford E4 (7.3 mg, 0.0353 mmol, 59% yield) in >98:2 E:Z ratio as colorless oil. $^1H$ NMR (400 MHz, $CDCl_3$): δ 7.30 (2H, d, J=8.5 Hz), 7.23 (2H, d, J=8.8 Hz), 6.79 (1H, d, J=13.6 Hz), 6.63 (1H, d, J=13.7 Hz).

(E)-3-(2-Chlorovinyl)-1H-indole (E5)

Following the general procedure, a solution of Mo-E1 in benzene (0.1 M, 30 μL, 3.0 mmol, 5 mol %) was transferred by syringe to an oven-dried vial containing E-1,2-dichloroethene (58.1 mg, 0.600 mmol, 10.0 equiv) and 3-vinyl-1H-indole (8.6 mg, 0.0600 mmol, 1.00 equiv). The resulting solution was allowed to stir for 2 hours at 22° C. The reaction was quenched by addition of wet $CDCl_3$ and analysis of the unpurified mixture revealed >98% consumption of 3-vinyl-1H-indole. The resulting orange oil was purified by silica gel chromatography (5:1 hexanes/$Et_2O$) to afford E5 (9.1 mg, 0.0512 mmol, 85% yield) in >98:2 E:Z ratio as slightly yellow solid. $^1H$ NMR (400 MHz, $CDCl_3$): δ 8.12 (1H, s), 7.73 (1H, ddt, J=7.8, 1.4, 0.8 Hz), 7.41-7.33 (1H, m), 7.29-7.14 (3H, m), 6.99 (1H, dd, J=13.6, 0.6 Hz), 6.64 (1H, dd, J=13.7, 0.5 Hz).

(E)-tert-Butyl((8-chloro-2,6-dimethyloct-7-en-2-yl)oxy)dimethylsilane (E6)

Following the general procedure, a solution of Mo-E1 in benzene (0.1 M, 25 μL, 2.5 μmol, 5 mol %) was transferred by syringe to an oven-dried vial containing E-1,2-dichloroethene (96.9 mg, 1.00 mmol, 20.0 equiv) and tert-butyl ((2,6-dimethyloct-7-en-2-yl)oxy)dimethylsilane (13.5 mg, 0.0500 mmol, 1.00 equiv). The resulting solution was allowed to stir for 15 minutes at 22° C. The reaction was quenched by addition of wet $CDCl_3$ and analysis of the unpurified mixture revealed >98% consumption of tert-butyl ((2,6-dimethyloct-7-en-2-yl)oxy)dimethylsilane. The resulting orange oil was purified by silica gel chromatography (100% pentane) to afford E6 (11.4 mg, 0.0374 mmol, 94% yield) in 93:7 E:Z ratio as colorless oil. $^1H$ NMR (600 MHz, $CDCl_3$): E-isomer (major): δ 5.91 (1H, dd, J=13.3, 0.9 Hz), 5.78 (1H, d, J=13.2, 8.4 Hz), 1.39-1.24 (6H, m), 1.17 (6H, s), 1.00 (3H, d, J=6.7 Hz), 0.85 (9H, s), 0.06 (6H, s).

(E)-1-Bromo-4-(2-fluorovinyl)benzene (E7)

Following the general procedure, a solution of Mo-E2 in benzene (0.1 M, 25 μL, 2.5 μmol, 5 mol %) was transferred by syringe to an oven-dried vial containing a solution of E-1-chloro-2-fluoroethene in toluene (2.36 M, 218 μL, 0.514 mmol, 10.0 equiv) and 4-bromostyrene (9.4 mg, 0.0514 mmol, 1.00 equiv). The resulting solution was allowed to stir for 2 hours at 22° C. The reaction was quenched by addition of wet $CDCl_3$ and analysis of the unpurified mixture revealed >98% consumption of 4-bromostyrene that resulted in the formation of a mixture of F- and Cl-alkenes (89:11 F:Cl). The resulting red oil was purified by silica gel chromatography (100% hexanes) to afford E7 (6.1 mg, 0.0303 mmol, 59% yield) in >98:2 E:Z ratio as colorless oil. $^1H$ NMR (400 MHz, $CDCl_3$): δ 7.41 (2H, d, J=8.4 Hz), 7.15 (1H, dd, J=82.6, 11.4 Hz), 7.10 (2H, d, J=8.6 Hz), 6.32 (1H, dd, J=18.9, 11.4 Hz).

(E)-3-(2-Fluorovinyl)benzo[b]thiophene (E8)

Following the general procedure, a solution of Mo-E2 in benzene (0.1 M, 31 μL, 3.1 μmol, 5 mol %) was transferred by syringe to an oven-dried vial containing a solution of E-1-chloro-2-fluoroethene in toluene (2.36 M, 264 L, 0.624 mmol, 10.0 equiv) and 3-vinylbenzo[b]thiophene (10.0 mg, 0.0624 mmol, 1.00 equiv). The resulting solution was allowed to stir for 2 hours at 22° C. The reaction was quenched by addition of wet $CDCl_3$ and analysis of the unpurified mixture revealed 95% consumption of 3-vinylbenzo[b]thiophene that resulted in the formation of a mixture of F- and Cl-alkenes (88:12 F:Cl). The resulting red oil was purified by silica gel chromatography (2% $Et_2O$/ hexanes) to afford E8 (7.3 mg, 0.0410 mmol, 66% yield) in >98:<2 E:Z ratio as colorless oil. $^1$H NMR (400 MHz, CDCl$_3$): δ 7.89-7.85 (1H, m), 7.80-7.76 (1H, m), 7.45-7.36 (2H, m), 7.30 (1H, s), 7.23 (1H, dd, J=83.5, 11.3 Hz), 6.63 (1H, ddd, J=18.1, 11.3, 1.0 Hz).

(E)-tert-Butyl(8-fluoro-2,6-dimethyl-7-octen-2-yloxy)dimethylsilane (E9)

Following the general procedure, a solution of Mo-E2 in benzene (0.1 M, 18 μL, 1.8 μmol, 5 mol %) was transferred by syringe to an oven-dried vial containing a solution of E-1-chloro-2-fluoroethene in toluene (2.36 M, 78 μL, 0.185 mmol, 5.00 equiv) and tert-butyl(2,6-dimethyl-7-octen-2-yloxy)dimethylsilane (10.0 mg, 0.0370 mmol, 1.00 equiv). The resulting solution was allowed to stir for 2 hours at 22° C. The reaction was quenched by addition of wet CDCl$_3$ and analysis of the unpurified mixture revealed 95% consumption of tert-butyl(2,6-dimethyl-7-octen-2-yloxy)dimethylsilane that resulted in the formation of a mixture of F- and Cl-alkenes (90:10 F:Cl). The resulting red oil was purified by silica gel chromatography (100% pentane) to afford E9 (8.2 mg, 0.0284 mmol, 77% yield) in >98:<2 E:Z ratio as colorless oil. $^1$H NMR (400 MHz, CDCl$_3$): δ 6.48 (1H, ddd, J=86.3, 11.1, 0.8 Hz), 5.22 (1H, ddd, J=20.0, 11.1, 9.0 Hz), 2.05 (1H, qt, J=10.9, 7.3 Hz), 2.01-1.99 (1H, m), 1.37-1.23 (6H, m), 1.17 (6H, s), 1.00 (3H, s), 0.85 (9H, s), 0.05 (6H, s).

Methyl (1R,4aR,4bS,7S,10aR)-7-((E)-2-fluorovinyl)-1,4a,7-trimethyl-1,2,3,4,4a,4b,5,6,7,8,10,10a-dodecahydrophenanthrene-1-carboxylate (E10)

Following the general procedure, a solution of Mo-E2 in benzene (0.1 M, 14 μL, 1.4 μmol, 10 mol %) was transferred by syringe to an oven-dried vial containing a solution of E-1-chloro-2-fluoroethene in toluene (2.36 M, 30 μL, 0.0711 mmol, 5.00 equiv) and isopimaric acid methyl ester (4.5 mg, 0.0142 mmol, 1.00 equiv). The resulting solution was allowed to stir for 2 hours at 22° C. The reaction was quenched by addition of wet CDCl$_3$ and analysis of the unpurified mixture revealed 94% consumption of isopimaric acid methyl ester that resulted in the exclusive formation of F-alkene (>98:<2 F:Cl). The resulting red oil was purified by silica gel chromatography (1:1 benzene/hexanes then 10:1 hexanes/Et$_2$O) to afford E10 (3.5 mg, 0.0105 mmol, 74% yield) in >98:2 E:Z ratio as colorless oil. $^1$H NMR (400 MHz, CDCl$_3$): δ 6.47 (1H, dd, J=86.1, 11.2 Hz), 5.37 (1H, dd, J=22.8, 11.2 Hz), 5.32-5.28 (1H, m), 3.64 (3H, s), 2.14-0.63 (25H, m).

(E)-2-(4-(2-Fluorovinyl)phenyl-4,4,5,5-tetramethyl-1,3,2-dioxaborolane (E11)

Following the general procedure, a solution of Mo-E2 in benzene (0.1 M, 22 μL, 2.2 μmol, 5 mol %) was transferred by syringe to an oven-dried vial containing a solution of E-1-chloro-2-fluoroethene in toluene (2.36 M, 184 μL, 0.435 mmol, 10.0 equiv) and 4,4,5,5-tetramethyl-2-(4-vinylphenyl)-1,3,2-dioxaborolane (10.0 mg, 0.0435 mmol, 1.00 equiv). The resulting solution was allowed to stir for 2 hours at 22° C. The reaction was quenched by addition of wet CDCl$_3$ and analysis of the unpurified mixture revealed >98% consumption of tert-butyl(2,6-dimethyl-7-octen-2-yloxy)dimethylsilane that resulted in the formation of a mixture of F- and Cl-alkenes (88:12 F:Cl). The resulting red oil was purified by silica gel chromatography (2% Et$_2$O/hexanes) to afford E11 (7.9 mg, 0.0318 mmol, 73% yield) in >98:<2 E:Z ratio as colorless oil. $^1$H NMR (400 MHz, CDCl$_3$): δ 7.74 (2H, d, J=8.0 Hz), 7.25 (2H, d, J=8.3 Hz), 7.22 (1H, dd, J=83.0, 11.4 Hz), 6.39 (1H, dd, J=19.3, 11.3 Hz), 1.34 (12H, s).

As demonstrated above, provided technologies can use complex compounds with various functional groups as substrates, and provide high yield and selectivity, e.g., regioselectivity, Z/E-selectivity, etc. In some embodiments, the present disclosure provides a method for preparing a fluorinated derivative of a bioactive molecule. In some embodiments, a bioactive molecule is the second species in a provided method. In some embodiments, a second species is a bioactive molecule. In some embodiments, a bioactive molecule comprises an olefin. In some embodiments, a bioactive molecule comprises a terminal olefin. In some embodiments, a bioactive molecule comprises a terminal olefin, and the derivatization step converts the =CH$_2$ moiety of the terminal olefin into =CHF. In some embodiments, the present disclosure provides a method for preparing a fluorinated derivative of a bioactive molecule, wherein the bioactive molecule comprises a terminal olefin, and the derivatization step converts the =CH$_2$ moiety of the terminal olefin into =CHF with Z-selectivity. In some embodiments, the present disclosure provides a method for preparing a fluorinated derivative of a bioactive molecule, wherein the bioactive molecule comprises a terminal olefin, and the derivatization step converts the =CH$_2$ moiety of the terminal olefin into =CHF with E-selectivity. In some embodiments, a bioactive molecule is an approved drug. In some embodiments, a bioactive molecule is a compound in clinical trial. In some embodiments, a bioactive molecule is a natural product. As understood by a person having ordinary skill in the art, fluorinated derivatives can have one or more improved properties. In some embodiments, the present disclosure provides a fluorinated derivative of a bioactive molecule comprising a terminal olefin, wherein the fluorinated derivative comprises a —CH=CHF moiety. In some embodiments, the double bond in —CH=CHF has a Z configuration. In some embodiments, the double bond in —CH=CHF has a E configuration. In some embodiments, the present disclosure provides pharmaceutical compositions comprising a fluorinated derivative of a bioactive molecule and a pharmaceutically acceptable carrier.

While several embodiments of the present disclosure have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present disclosure. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present disclosure is/are used. Those skilled in the art will recognize, or be able to ascertain using no more than routine experimentation, many equivalents to the specific embodiments of the disclosure described herein. It is, therefore, to be understood that the foregoing embodiments are presented by way of example only and that, within the scope of the appended claims and equivalents thereto, the disclosure may be practiced otherwise than as specifically described and claimed. The present disclosure is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present disclosure.

The invention claimed is:

1. A method, comprising:
reacting a first species comprising an olefin with a second species comprising an olefin in the presence of a catalyst or metal complex to provide at least one product comprising an olefin, wherein:
each carbon atom of the olefin in the first species is substituted with at least one halogen; and
the olefin in at least one product comprises a carbon atom from the first species and a carbon atom from the second species; and
wherein the catalyst or metal complex is of formula II-a:

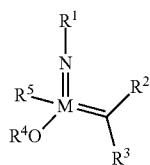

wherein:
M is molybdenum or tungsten;
R¹ is an optionally substituted group selected from $C_{1-20}$ aliphatic, $C_{1-20}$ heteroaliphatic having 1-3 heteroatoms independently selected from nitrogen, oxygen, or sulfur, phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 4-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-10 membered bicyclic heteroaryl ring having 1-5 heteroatoms independently selected from nitrogen, oxygen, or sulfur; or R' is optionally substituted

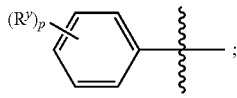

each of R² and R³ is independently R', —OR', —SR', —N(R')₂, —OC(O)R', —SOR', —SO₂R', —SO₂N(R')₂, —C(O)N(R')₂, —NR'C(O)R', or —NR'SO₂R', provided that R² and R³ are not simultaneously hydrogen;
R⁴ is R⁷, or an optionally substituted group selected from —Ar, $C_{1-20}$ aliphatic, $C_{1-20}$ heteroaliphatic having 1-3 heteroatoms independently selected from nitrogen, oxygen, or sulfur, phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 4-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-14 membered bicyclic or tricyclic heteroaryl ring having 1-5 heteroatoms independently selected from nitrogen, oxygen, or sulfur;
Ar is of the following formula:

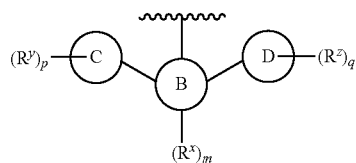

wherein:
m is 0-3;
Ring B is an optionally substituted group selected from phenyl or a 5-6 membered monocyclic heteroaryl ring having 1-4 heteroatoms independently selected from nitrogen, oxygen, or sulfur;
p and q are independently 0-6;
each of Ring C and Ring D is independently optionally substituted groups selected from phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 4-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-10 membered bicyclic heteroaryl ring having 1-5 heteroatoms independently selected from nitrogen, oxygen, or sulfur;
each of $R^x$, $R^y$, and $R^z$ is independently $R^s$;
R⁵ is halogen, —OR⁶, —OR', —N(R')₂, —NR'C(O)R', —NR'C(O)OR', —NR'C(O)N(R')₂, —NR'SO₂R', —NR'SO₂N(R')₂, or —NR'OR', or an optionally substituted group selected from a 5-6 membered monocyclic heteroaryl ring having at least one nitrogen and 0-3 heteroatoms independently selected from nitrogen, oxygen, or sulfur, a 4-7 membered saturated or partially unsaturated heterocyclic ring having at least one nitrogen and 0-2 heteroatoms independently selected from nitrogen, oxygen, or sulfur, a 7-10 membered bicyclic saturated or partially unsaturated heterocyclic ring having at least one nitrogen and 0-4 heteroatoms independently selected from nitrogen, oxygen, or sulfur, or an 8-10 membered bicyclic heteroaryl ring having at least one nitrogen and 0-4 heteroatoms independently selected from nitrogen, oxygen, or sulfur;
R⁶ is an optionally substituted group selected from $C_{1-20}$ aliphatic, $C_{1-20}$ heteroaliphatic having 1-3 heteroatoms independently selected from nitrogen, oxygen, or sulfur, phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 4-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-14 membered bicyclic or tricyclic heteroaryl ring having 1-5 heteroatoms independently selected from nitrogen, oxygen, or sulfur; and each R' is independently hydrogen or an optionally substituted group selected from $C_{1-20}$ aliphatic, phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 4-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-10 membered bicyclic heteroaryl ring having 1-5 heteroatoms independently selected from nitrogen, oxygen, or sulfur, wherein:

two R' groups on the same nitrogen atom are optionally taken together with the nitrogen atom to form an optionally substituted 3-8 membered, saturated, partially unsaturated, or aryl ring having 1-4 heteroatoms independently selected from nitrogen, oxygen, or sulfur;

each $R^7$ is independently an optionally substituted group selected from —Ar', $C_{1-20}$ aliphatic, $C_{1-20}$ heteroaliphatic having 1-3 heteroatoms independently selected from nitrogen, oxygen, or sulfur, phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 4-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-14 membered bicyclic or tricyclic heteroaryl ring having 1-5 heteroatoms independently selected from nitrogen, oxygen, or sulfur; and two $R^7$ are optionally taken together with the oxygen atoms they are bound to form a bidentate ligand; and Ar' is of the following formula:

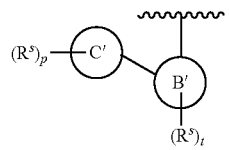

wherein:
t is 0-4;
p is 0-6;
each Ring B' and Ring C' is independently an optionally substituted group selected from phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 4-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-10 membered bicyclic heteroaryl ring having 1-5 heteroatoms independently selected from nitrogen, oxygen, or sulfur; and each $R^s$ is independently halogen, R', —OR', —SR', —S(O)R', —S(O)$_2$R', —OSi(R')$_3$, —N(R')$_2$, —NR'C(O)R', —NR'C(O)OR', —NR'C(O)N(R')$_2$, —NR'SO$_2$R', —NR'SO$_2$N(R')$_2$, or —NR'OR'.

2. A method, comprising:
reacting a first species comprising an olefin with a second species comprising an alkyne in the presence of a catalyst or metal complex to provide at least one product comprising an olefin, wherein:
each carbon atom of the olefin in the first species is substituted with at least one halogen; and
the olefin in at least one product comprises a carbon atom from the first species and a carbon atom from the second species; and
wherein the catalyst or metal complex is of formula II-a:

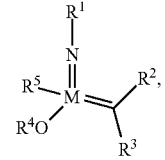

wherein:
M is molybdenum or tungsten;
$R^1$ is an optionally substituted group selected from $C_{1-20}$ aliphatic, $C_{1-20}$ heteroaliphatic having 1-3 heteroatoms independently selected from nitrogen, oxygen, or sulfur, phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 4-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-10 membered bicyclic heteroaryl ring having 1-5 heteroatoms independently selected from nitrogen, oxygen, or sulfur; or $R^1$ is optionally substituted

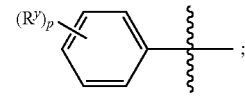

each of R² and R³ is independently R', —OR', —SR', —N(R')₂, —OC(O)R', —SOR', —SO₂N(R')₂, —C(O)N(R')₂, —NR'C(O)R', or —NR'SO₂R', provided that R² and R³ are not simultaneously hydrogen;

R⁴ is R⁷, or an optionally substituted group selected from —Ar, $C_{1-20}$ aliphatic, $C_{1-20}$ heteroaliphatic having 1-3 heteroatoms independently selected from nitrogen, oxygen, or sulfur, phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 4-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-14 membered bicyclic or tricyclic heteroaryl ring having 1-5 heteroatoms independently selected from nitrogen, oxygen, or sulfur;

Ar is of the following formula:

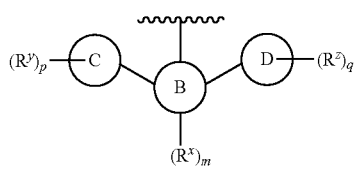

wherein:
  m is 0-3;
  Ring B is an optionally substituted group selected from phenyl or a 5-6 membered monocyclic heteroaryl ring having 1-4 heteroatoms independently selected from nitrogen, oxygen, or sulfur;
  p and q are independently 0-6;
  each of Ring C and Ring D is independently optionally substituted groups selected from phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 4-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-10 membered bicyclic heteroaryl ring having 1-5 heteroatoms independently selected from nitrogen, oxygen, or sulfur;
  each of $R^x$, $R^y$, and $R^z$ is independently $R^s$;

R⁵ is halogen, —OR⁶, —OR⁷, —N(R')₂, —NR'C(O)R', —NR'C(O)OR', —NR'C(O)N(R')₂, —NR'SO₂R', —NR'SO₂N(R')₂, or —NR'OR', or an optionally substituted group selected from a 5-6 membered monocyclic heteroaryl ring having at least one nitrogen and 0-3 heteroatoms independently selected from nitrogen, oxygen, or sulfur, a 4-7 membered saturated or partially unsaturated heterocyclic ring having at least one nitrogen and 0-2 heteroatoms independently selected from nitrogen, oxygen, or sulfur, a 7-10 membered bicyclic saturated or partially unsaturated heterocyclic ring having at least one nitrogen and 0-4 heteroatoms independently selected from nitrogen, oxygen, or sulfur, or an 8-10 membered bicyclic heteroaryl ring having at least one nitrogen and 0-4 heteroatoms independently selected from nitrogen, oxygen, or sulfur;

R⁶ is an optionally substituted group selected from $C_{1-20}$ aliphatic, $C_{1-20}$ heteroaliphatic having 1-3 heteroatoms independently selected from nitrogen, oxygen, or sulfur, phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 4-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-14 membered bicyclic or tricyclic heteroaryl ring having 1-5 heteroatoms independently selected from nitrogen, oxygen, or sulfur; and each R' is independently hydrogen or an optionally substituted group selected from $C_{1-20}$ aliphatic, phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 4-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-10 membered bicyclic heteroaryl ring having 1-5 heteroatoms independently selected from nitrogen, oxygen, or sulfur, wherein:
  two R' groups on the same nitrogen atom are optionally taken together with the nitrogen atom to form an optionally substituted 3-8 membered, saturated, partially unsaturated, or aryl ring having 1-4 heteroatoms independently selected from nitrogen, oxygen, or sulfur;

each R⁷ is independently an optionally substituted group selected from —Ar', $C_{1-20}$ aliphatic, $C_{1-20}$ heteroaliphatic having 1-3 heteroatoms independently selected from nitrogen, oxygen, or sulfur, phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 4-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-14 membered bicyclic or tricyclic heteroaryl ring having 1-5 heteroatoms independently selected from nitrogen, oxygen, or sulfur; and two R⁷ are optionally taken together with the oxygen atoms they are bound to form a bidentate ligand; and Ar' is of the following formula:

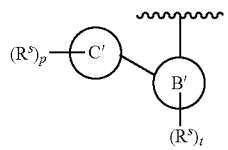

wherein:
t is 0-4;
p is 0-6;
each Ring B' and Ring C' is independently an optionally substituted group selected from phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 4-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-10 membered bicyclic heteroaryl ring having 1-5 heteroatoms independently selected from nitrogen, oxygen, or sulfur; and
each $R^s$ is independently halogen, R', —OR', —SR', —S(O)R', —S(O)$_2$R', —OSi(R')$_3$, —N(R')$_2$, —NR'C(O)R', —NR'C(O)OR', —NR'C(O)N(R')$_2$, —NR'SO$_2$R', —NR'SO$_2$N(R')$_2$, or —NR'OR'.

3. The method of claim 1, wherein the olefin in at least one product is formed via a metathesis reaction between the olefin in the first species and the olefin in the second species; and
the halogen substituent of the first carbon atom of the double bond in the first species and the halogen substituent of the second carbon atom of the double bond in the first species is cis, and the olefin in the at least one product comprises a carbon atom from the first species and a carbon atom from the second species is produced with Z-selectivity.

4. The method of claim 3, wherein the first species has the structure of:

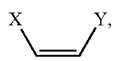

wherein each of X and Y is independently halogen; and
wherein the product is produced in a Z:E ratio greater than 80:20.

5. The method of claim 1, wherein the olefin in at least one product is formed via a metathesis reaction between the olefin in the first species and the olefin in the second species; and
the halogen substituent of the first carbon atom of the double bond in the first species and the halogen substituent of the second carbon atom of the double bond in the first species is trans, and the olefin in the at least one product comprises a carbon atom from the first species and a carbon atom from the second species is produced with E-selectivity.

6. The method of claim 5, wherein the first species has the structure of:

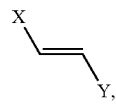

wherein each of X and Y is independently halogen; and
wherein the product is produced in a E:Z ratio greater than 80:20.

7. The method of claim 4, comprising reacting the first species with the second species via a metathesis reaction between the olefin of the first species and the olefin of the second species with regioselectivity to provide as products:
CH$_2$=CHY; and
at least one product comprising an olefin wherein the olefin comprising =CHX, over CH$_2$=CHX and a product comprising an olefin wherein the olefin comprising =CHY, wherein X is smaller than Y.

8. The method of claim 7, wherein X is —F.

9. The method of claim 8, wherein the regioselectivity is greater than 80:20.

10. The method of claim 6, comprising reacting the first species with the second species via a metathesis reaction between the olefin of the first species and the olefin of the second species with regioselectivity to provide as products:
CH$_2$=CHY; and
at least one product comprising an olefin wherein the olefin comprising =CHX, over CH$_2$=CHX and a product comprising an olefin wherein the olefin comprising =CHY, wherein X is smaller than Y.

11. The method of claim 10, wherein X is —F.

12. The method of claim 11, wherein the regioselectivity is greater than 80:20.

13. The method of claim 9, wherein the second species is $R^t$—CH=CH$_2$, and at least one product is (Z)$R^t$—CH=CHF.

14. The method of claim 12, wherein the second species is $R^t$—CH=CH$_2$, and at least one product is (Z)$R^t$—CH=CHF.

15. The method of claim 1, wherein $R^1$ is optionally substituted adamantyl, or $R^1$ is substituted phenyl comprising one or more electron-withdrawing substituents, wherein each electron-withdrawing substituent is independently halogen or substituted C$_{1-6}$ alkyl comprising one or more halogen.

16. The method of claim 15, wherein $R^1$ is

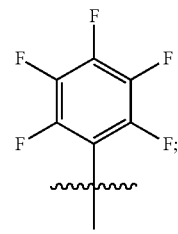 [SMILES: *c1c(F)c(F)c(F)c(F)c1F]

$R^4$ is optionally substituted

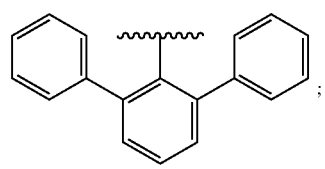 [SMILES: *c1c(-c2ccccc2)cccc1-c1ccccc1]

and
R⁵ is optionally substituted
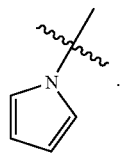 [SMILES: *n1cccc1]
\* \* \* \* \*

UNITED STATES PATENT AND TRADEMARK OFFICE
CERTIFICATE OF CORRECTION

Page 1 of 1

PATENT NO. : 9,850,268 B2
APPLICATION NO. : 14/933741
DATED : December 26, 2017
INVENTOR(S) : Amir H. Hoveyda et al.

It is certified that error appears in the above-identified patent and that said Letters Patent is hereby corrected as shown below:

In the Specification

Column 44, Line 33 reads, ". . . 3,5-dimethphenyl. . . ." which should read, ". . . 3,5-dimethylphenyl. . . ."

Column 65, Line 2 reads, ". . . the structure of N . . ." which should read, ". . . the structure of . . ."

Column 86, Line 17 reads, ". . . methathesis reaction . . ." which should read, ". . . metathesis reaction . . ."

Column 86, Line 32 reads, "Y In some embodiments, . . ." which should read, "In some embodiments, . . ."

Signed and Sealed this
Twenty-fourth Day of July, 2018

Andrei Iancu
*Director of the United States Patent and Trademark Office*